(12) United States Patent
Keefe et al.

(10) Patent No.: US 12,037,350 B2
(45) Date of Patent: Jul. 16, 2024

(54) COMPOSITIONS AND METHODS FOR THE PREVENTION AND/OR TREATMENT OF MITOCHONDRIAL DISEASE, INCLUDING FRIEDREICH'S ATAXIA

(71) Applicant: Stealth BioTherapeutics Inc., Needham, MA (US)

(72) Inventors: Dennis Keefe, Bedford, MA (US); Guozhu Zheng, Lexington, MA (US)

(73) Assignee: STEALTH BIOTHERAPEUTICS INC., Needham, MA (US)

( * ) Notice: Subject to any disclaimer, the term of this patent is extended or adjusted under 35 U.S.C. 154(b) by 127 days.

(21) Appl. No.: 17/221,463

(22) Filed: Apr. 2, 2021

(65) Prior Publication Data

US 2021/0317146 A1  Oct. 14, 2021

Related U.S. Application Data

(60) Provisional application No. 63/004,639, filed on Apr. 3, 2020.

(51) Int. Cl.
*C07F 7/08* (2006.01)
*C07C 43/23* (2006.01)
*C07C 50/28* (2006.01)

(52) U.S. Cl.
CPC .............. *C07F 7/081* (2013.01); *C07C 43/23* (2013.01); *C07C 50/28* (2013.01)

(58) Field of Classification Search
CPC .. A61P 27/02; A61P 9/00; C07F 7/081; C07C 50/28
See application file for complete search history.

(56) References Cited

U.S. PATENT DOCUMENTS

| | | | |
|---|---|---|---|
| 6,133,322 | A | 10/2000 | Rustin et al. |
| 7,432,305 | B2 | 10/2008 | Miller et al. |
| 7,470,798 | B2 | 12/2008 | Wang et al. |
| 8,314,153 | B2 | 11/2012 | Miller et al. |
| 8,716,486 | B2 | 5/2014 | Hinman et al. |
| 8,716,527 | B2 | 5/2014 | Hinman et al. |
| 9,399,612 | B2 | 7/2016 | Miller |
| 9,663,485 | B2 | 5/2017 | Marugan et al. |
| 9,932,286 | B2 | 4/2018 | Miller et al. |
| 10,071,978 | B2 | 9/2018 | Wesson et al. |
| 10,105,325 | B2 | 10/2018 | Miller et al. |
| 10,189,830 | B2 | 1/2019 | Hinman et al. |
| 10,703,701 | B2 | 7/2020 | Hinman et al. |
| 2005/0065149 | A1 | 3/2005 | Wang et al. |
| 2006/0281809 | A1 | 12/2006 | Miller et al. |
| 2013/0345312 | A1 | 12/2013 | Jankowski et al. |

FOREIGN PATENT DOCUMENTS

| | | |
|---|---|---|
| EP | 2 332 534 | 6/2011 |
| EP | 2 424 513 | 3/2012 |
| EP | 2 605 769 | 6/2013 |
| WO | WO-2006/130775 | 12/2006 |
| WO | WO-2007/100652 | 9/2007 |
| WO | WO-2011/025785 | 3/2011 |
| WO | WO-2012/022467 | 2/2012 |
| WO | WO-2012/022468 | 2/2012 |
| WO | WO-2012/068552 | 5/2012 |
| WO | WO-2012/170773 | 12/2012 |
| WO | WO-2014/011047 A1 | 1/2014 |
| WO | WO-2014/039862 | 3/2014 |
| WO | WO-2014/078573 | 5/2014 |
| WO | WO-2014/145116 | 9/2014 |
| WO | WO-2015/183963 | 12/2015 |
| WO | WO-2017/087795 | 5/2017 |
| WO | WO-2017/106803 | 6/2017 |
| WO | WO-2017/123822 | 7/2017 |
| WO | WO-2018/191732 | 10/2018 |
| WO | WO 2018/191732 | * 10/2018 ........... A61K 31/122 |
| WO | WO-2018/191789 | 10/2018 |
| WO | WO-2019/118878 | 6/2019 |

OTHER PUBLICATIONS

Yu (Biochemistry, 1982, 21, 4096-4101).*
Yang (The Journal of Biological Chemistry; vol. 266, No. 31, pp. 20863-20869; 1991).*
Guo (Chem. Eur. J. 2019, 25, 7259-7264).*
Daniel et al. "Novel Short-Chain Quinones to Treat Vision Loss in a Rat Model of Diabetic Retinopathy," International Journal of Molecular Sciences, vol. 22 (2021) (pp. 1-17).
International Search Report and Written Opinion on PCT PCT/US2021/025558 dated Jul. 9, 2021 (15 pages).
Walter, L, et al, Three classes of ubiquinone analogs regulate the mitochondrial permeability transition pore through a common site, Journal of Biological Chemistry, American Society for Biochemistry and Molecular Biology, US, vol. 275, No. 38, Sep. 22, 2000, pp. 29521-29527.
Abeti et al., "Calcium Deregulation: Novel Insights to Understand Friedreich's Ataxia Pathophysiology", Frontiers in Cellular Neuroscience. vol. 12 Article 264 pp. 1-13 (published Oct. 2, 2018) doi: 10.3389/fncel.2018.00264.
Bodmer, et al., "Pharmacokinetics and metabolism of idebenone in healthy male subjects," Eur J Clin Pharmacol, 2009, vol. 65, pp. 493-501. DOI 10.1007/s00228-008-0596-1.
C. Varricchio et al., "The ying and yang of idebenone: Not too little, not too much—cell death in NQO1 deficient cells and the mouse retina", Free Radical Biology and Medicine, https://doi.org/10.1016/j.freeradbiomed.2019.11.030.

(Continued)

*Primary Examiner* — Pancham Bakshi
(74) *Attorney, Agent, or Firm* — Foley & Lardner LLP

(57) ABSTRACT

The disclosure provides therapeutic compounds, compositions (e.g., therapeutic agents or medicaments) and methods for preventing or treating mitochondrial disease such as Friedreich's ataxia in a mammalian subject, reducing risk factors, signs and/or symptoms associated with mitochondrial disease, such as Friedreich's ataxia, and/or reducing the likelihood or severity of mitochondrial disease such as Friedreich's ataxia. The disclosure further provides novel intermediates for the production of said therapeutic compositions. In some instances, the intermediates may themselves by therapeutic agents or prodrugs of therapeutic agents (e.g. reduced forms of the therapeutic compounds).

6 Claims, 22 Drawing Sheets

(56) References Cited

OTHER PUBLICATIONS

Erb et al. "Features of Idebenone and Related Short-Chain Quinones that Rescue ATP Levels under Conditions of Impaired Mitochondrial Complex I", PLoS ONE Apr. 2012 vol. 7 Issue 4 pp. 1-8 e36153.
Gousiadou et al., "Computational Analysis of LOX1 Inhibition Identifies Descriptors Responsible for Binding Selectivity" ACS Omega 2018, 3, 2261-2272.
Haefeli et al. "NQO1-Dependent Redox Cycling of Idebenone: Effects on Cellular Redox Potential and Energy Levels", PLoS ONE, vol. 6, Issue 3, e17963, Mar. 2011.
Hausse et al., "Idebenone and reduced cardiac hypertrophy in Friedreich's ataxia" Heart. 2002;87:346-349.
Hinman et al., "Vitamin E hydroquinone is an endogenous regulator of ferroptosis via redox control of 15-lipoxygenase", PLOS ONE. Aug. 15, 2018 pp. 1-22 https://doi.org/10.1371/journal.pone.0201369.
Imounan et al., "Clinical and Genetic Study of Friedreich's Ataxia and Ataxia with Vitamin E Deficiency in 44 Moroccan Families", World Journal of Neuroscience, 4, 299-305 (2014) http://dx.doi.org/10.4236/wjns.2014.44033.
International Search Report and Written Opinion on PCT PCT/US2020/054107 dated Mar. 16, 2021 (30 pages).
Invitation to Pay Additional Fees, and Where Applicable, Protest Fee in International Patent Application No. PCT/US2020/054107 dated Jan. 12, 2021.
Jabbari et al., "O-prenylated 3-carboxycoumarins as a novel class of 15-LOX-1 inhibitors" PLOS ONE. pp. 1-21 Feb. 9, 2017 DOI:10.1371/journal.pone.0171789.
Jaber, et al. "Idebenone and Neuroprotection: Antioxidant, Prooxidant, or Electron Carrier?" J Bioenerg Biomembr., Apr. 2015, vol. 47(0), pp. 111-118. doi:10.1007/s10863-014-9571-y.
Jauslin et al., "A cellular model for Friedreich Ataxia reveals small-molecule glutathione peroxidase mimetics as novel treatment strategy", Human Molecular Genetics, 2002, vol. 11, No. 24 3055-3063.
Kahn-Kirby et al. "Targeting ferroptosis: A novel therapeutic strategy for the treatment of mitochondrial disease-related epilepsy", PLoS ONE 14(3): e0214250. Mar. 28, 2019 https://doi.org/10.1371/journal.pone.0214250.
Lutz F. Tietze et al., "Enantioselective Synthesis of the Chromane Moiety of Vitamin E", European Journal of Organic Chemistry, vol. 1999, No. 5, May 1, 1999 (May 1, 1999), pp. 1075-1084, XP055760513, DE ISSN: 1434-193X, DOI: 10.1002/(SICI)1099-0690(199905)1999:5<1075 ::AID-EJOC1075>3.0.CO;2-I compound 19.
Lynch et al. "A Phase 3, Double-blind, Placebo-Controlled Trial of Idebenone in Friedreich Ataxia", Arch Neurol. 2010;67(8):941-947.
Nunez et al., "Discovery two potent and new inhibitors of 15-lipoxygenase: (E)-3-((3,4-dihydroxybenzylidene) amino)-7-hydroxy-2H-chromen-2-one and (E)-O-(4-(((7-hydroxy-2-oxo-2H-chromen-3-yl) imino)methine) phenyl)dimethylcarbamothioate", Med Chem Res. (2017) 26:2707-2717 DOI 10.1007/s00044-017-1968-9.
Pallast et al., "12/15-Lipoxygenase targets neuronal mitochondria under oxidative stress", J Neurochem. Nov. 2009 ; 111(3): 882-889. doi:10.1111/j.1471-4159.2009.06379.x.
Parkinson et al., "Co-enzyme Q10 and idebenone use in Friedreich's ataxia", J. Neurochem. (2013) 126 (Suppl. 1), 125-141 doi: 10.1111/jnc.12322.
Petrillo et al., "Targeting NRF2 for the Treatment of Friedreich's Ataxia: A Comparison among Drugs", Int. J. Mol. Sci. 2019, 20, 5211; doi:10.3390/ijms20205211.
Sadeghian et al., "15-Lipoxygenase inhibitors: a patent review", Expert Opin. Ther. Patents. (2015) 26(1) pp. 1-24 DOI: 10.1517/13543776.2016.1113259.
Sekimoto M et al., "Asymmetric syntheses of daedalin A and quercinol and their tyrosinase inhibitory activity", Biorganic & Medicinal Chemistry Letters, Elsevier, Amsterdam, NL, vol. 20, No. 3, Feb. 1, 2010 (Feb. 1, 2010), pp. 1063-1064, XP026861868, ISSN: 0960-894X [retrieved on Dec. 11, 2009] compound 15, p. 1064.
Stealth Biotherapeutics (*company presentation*) Leading Mitochondrial Medicine. Nov. 2019.
Stealth Biotherapeutics Corp. Form 20-F (Annual and Transition Report (foreign private issuer)). Filed Apr. 1, 2020 for the Period Ending Dec. 31, 2019. EDGAR Online, a division of Donnelley Financial Solutions.
Tadokoro et al., "Mitochondria-dependent ferroptosis plays a pivotal role in doxorubicin cardiotoxicity", JCI Insight. 2020;5(9): e132747. https://doi.org/10.1172/jci.insight.132747.
V. Giorgio, et al., "The idebenone metabolite QS10 restores electron transfer in complex I and coenzyme Q defects," BBA—Bioenergetics 1859, 2018, pp. 901-908. https://doi.org/10.1016/j.bbabio.2018.04.006.
Vafai SB et al., "Natural Product Screening Reveals NaphthoquinoneComplex I Bypass Factors", PLoS ONE 11(9): e0162686. doi:10.1371/journal.pone.0162686 (Sep. 13, 2016).
Worth et al. "Stable isotopes and LC-MS for monitoring metabolic disturbances in Friedreich's ataxia platelets", Bioanalysis. (2015) 7(15), 1843-1855.
Xingui Liu et al., "Synthesis and Liver Microsomal Metabolic Stability Studies of a Fluorine-Substituted [delta]-Tocotrienol Derivative", Chemmedchem, vol. 15, No. 6, Jan. 19, 2020 (Jan. 19, 2020), pp. 506-516, XP055760690, DE ISSN: 1860-7179, DOI: 10.1002/cmdc.201900676 the whole document compounds DT3-F2, 31.
Zesiewicz et al., "Double-blind, randomized and controlled trial of EPI-743 in Friedreich's ataxia", Neurodegener. Dis. Manag. Jul. 27, 2018 10.2217/nmt-2018-0013 ISSN:1758-2024.
Zhao et al. "Peptide SS-31 upregulates frataxin expression and improves the quality of mitochondria: implications in the treatment of Friedreich ataxia", Scientific Reports. 7:9840 pp. 1-11 Aug. 29, 2017 DOI:10.1038/s41598-017-10320-2.
International Preliminary Report on Patentability on PCT PCT/US2020/054107 dated Apr. 14, 2022.
International Preliminary Report on Patentability on PCT PCT/US2021/025558 dated Oct. 13, 2022.
Foreign Action on CN 202180040296.8, dated Jan. 12, 2024.
Jinbo Hu et al., "Rapid Deoxyfluorination of Alcohols with 4-Chloro-N-tosylbenzene-1-Sulfonimidoyl Fluoride (SulfoxFluor) at Room Temperature", Chemistry—A European Journal, 201901176, Dec. 31, 2019.
Foreign Office Action on CA 3176909 dated Feb. 14, 2024.
Lagishetti et al. "Construction of Bridged-Ring-Fused Naphthalenone Derivatives Through an Unexpected Zn(OTf)2-Catalyzed Cascade Transformation", Org. Lett. 2019, 21, pp. 5301-5304.
Office Action on CN 202180040296.8 dated Mar. 1, 2024.
Sekimoto et al. "Asymmetric syntheses of daedalin A and quercinol and their tyrosinase inhibitory activity", Bioorganic & Medicinal Chemistry Letters 20, (2010), pp. 1063-1064.
Zhao et al. "Toward a Total Synthesis of Divergolide A; Synthesis of the Amido Hydroquinone Core and the C10-C15 Fragment", SYNLETT, 2012, 23, pp. 2845-2849.

* cited by examiner

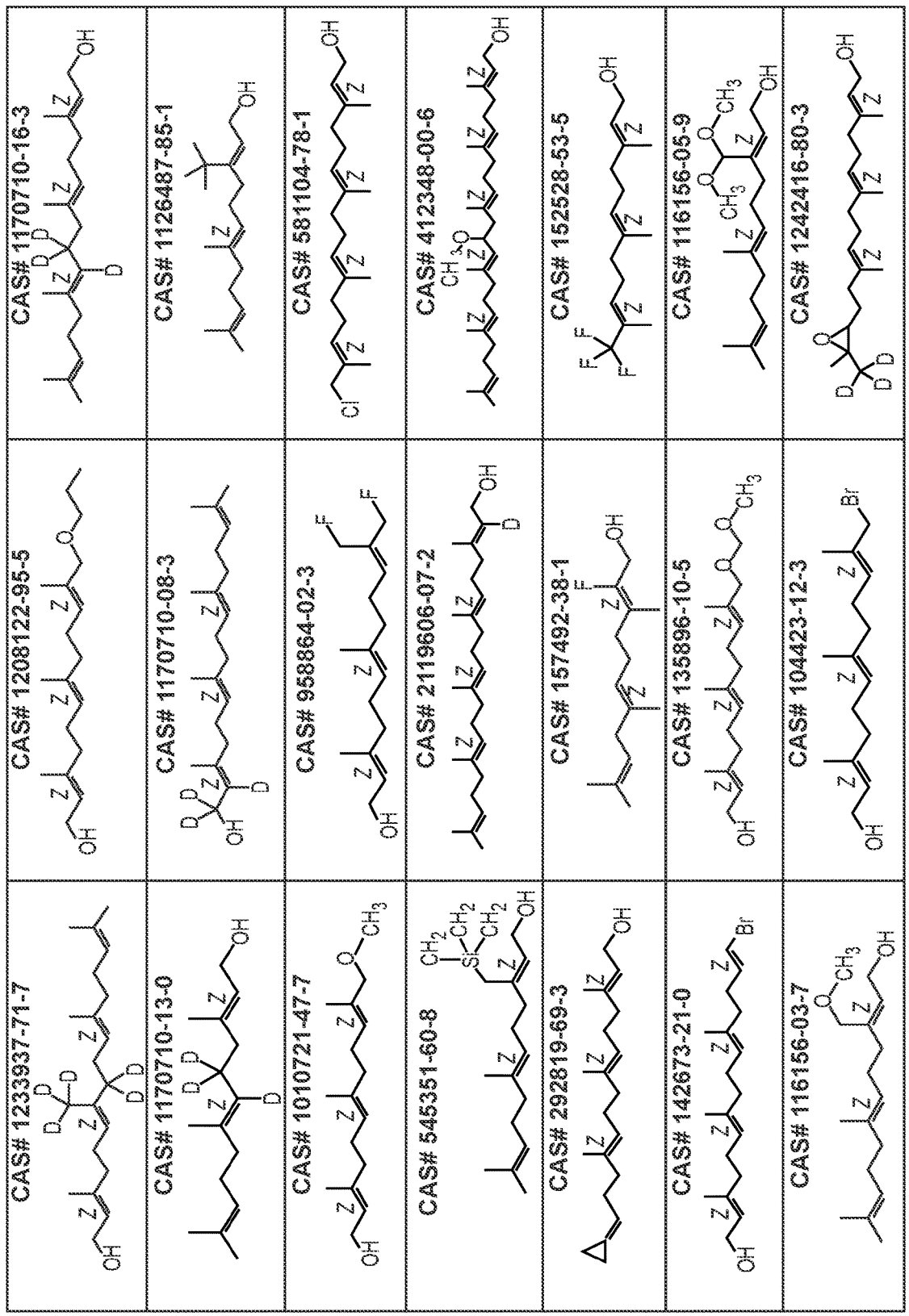
FIG. 8 (Cont. 3)

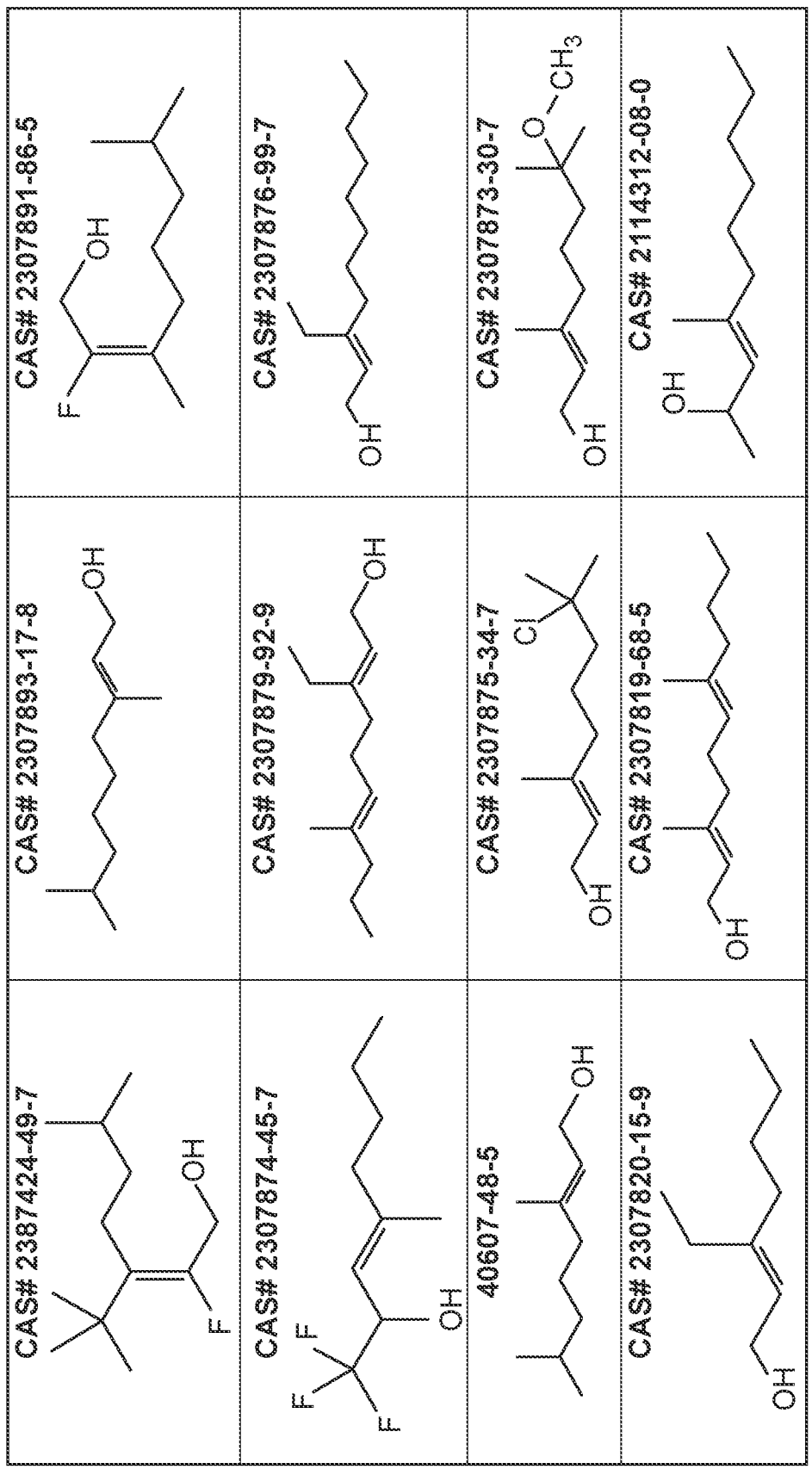
FIG. 8 (Cont. 4)

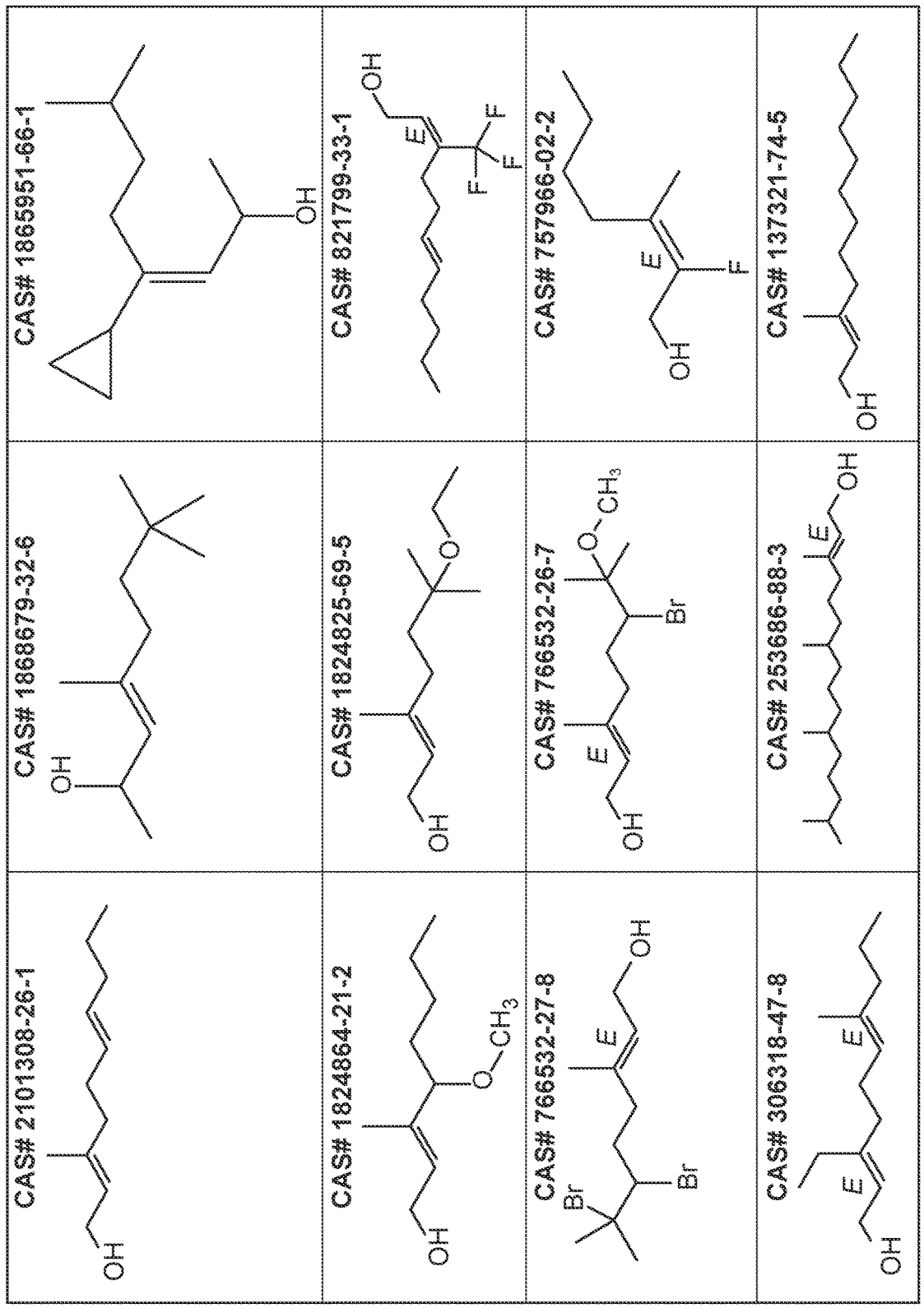
FIG. 8 (Cont. 5)

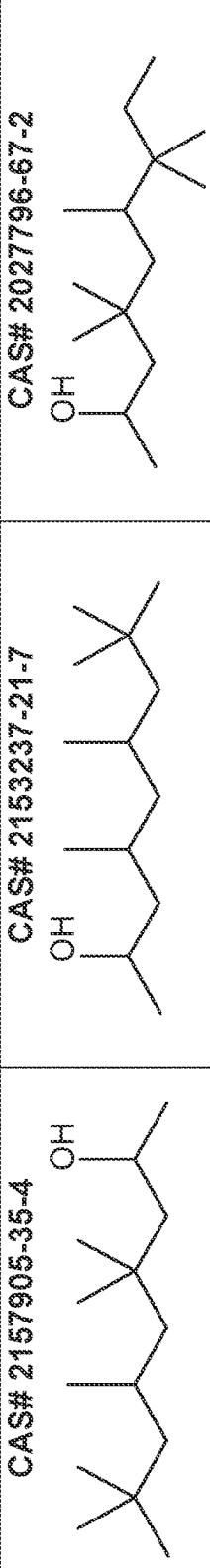
FIG. 8 (Cont. 8)

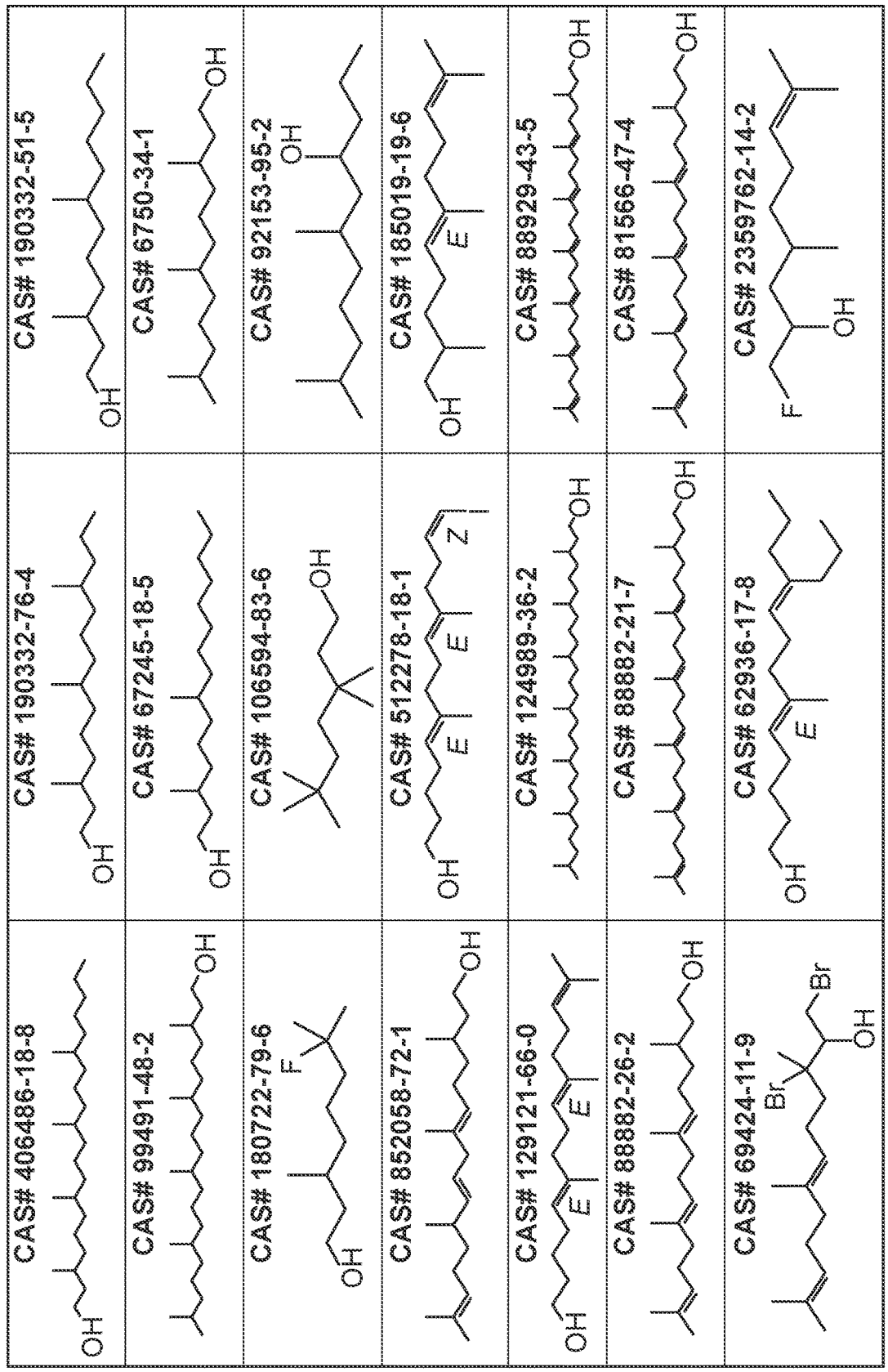
FIG. 8 (Cont. 9)

FIG. 8 (Cont. 10)

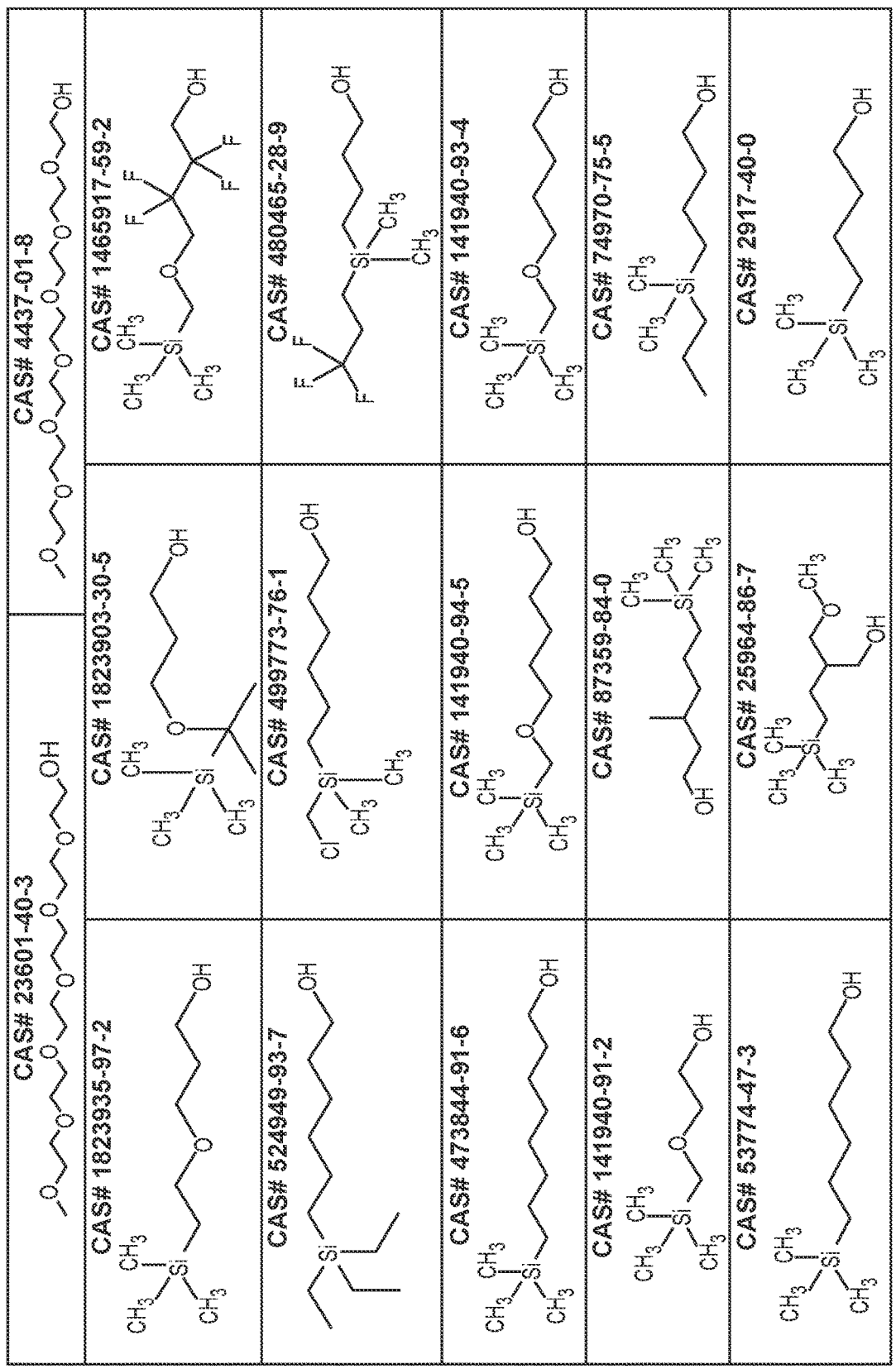
FIG. 8 (Cont. 11)

FIG. 9 (Cont.)

COMPOSITIONS AND METHODS FOR THE PREVENTION AND/OR TREATMENT OF MITOCHONDRIAL DISEASE, INCLUDING FRIEDREICH'S ATAXIA

CROSS REFERENCE TO RELATED APPLICATIONS

This application claims the benefit of and priority to U.S. Provisional Appl. No. 63/004,639 filed on Apr. 3, 2020, the contents of which is incorporated herein by reference in its entirety for any and all purposes.

TECHNICAL FIELD

The present application relates generally to compositions and methods for preventing, ameliorating and/or treating mitochondrial disease, such as Friedreich's ataxia, and/or reducing the severity of such diseases. Furthermore, the present application relates to: 1) methods for the preparation of novel therapeutic compounds and related intermediates (e.g., chromanes (benzodihydropyrans), quinones, hydroquinones, benzoquinones and hydroxybenzoquinones) and/or 2) administering an effective amount of a novel compound disclosed herein (itself or as formulated), alone or in combination with one or more other agents, to a subject suffering from a mitochondrial disease such as Friedreich's ataxia.

INTRODUCTION

The following description is provided to assist the understanding of the reader. None of the information provided or references cited is admitted as being prior art to the compositions and methods disclosed herein.

Friedreich's ataxia (FA) is a fatal, monogenic, autosomal recessive disease caused by mutations in the gene encoding the nuclear encoded mitochondrial protein frataxin. Tissues in both the peripheral and central nervous systems are affected in FA, and include the dentate nucleus, Clark's column, spinocerebellar tract and dorsal root ganglia. Progressive degeneration of these tissues leads to a worsening ataxia which for most patients ends in loss of independent ambulation by the third decade of life.

The FXN gene encodes the protein frataxin. Frataxin is an iron binding protein responsible for forming iron-sulfur clusters. One result of frataxin deficiency is mitochondrial iron overload.

Frataxin is a highly conserved iron binding protein. Human frataxin is synthesized as a 210 amino acid precursor that is imported to the mitochondria via the mitochondrial targeting signal contained in the N-terminus. The frataxin precursor is subsequently cleaved to a mature 14 kDa protein (residues 81-210).

Frataxin binds both $Fe^{2+}$ and $Fe^{3+}$ ions in an electrostatic manner and functions as an iron chaperone during Fe—S cluster assembly. Frataxin directly binds to the central Fe—S cluster assembly complex, which is composed of Nfs1 enzyme and Isu scaffold protein. Nfs1 is a cysteine desulfurase used in the synthesis of sulfur bioorganic derivatives and Isu is the transient scaffold protein on which the Fe—S cluster assembles. Frataxin increases the efficiency of Fe—S cluster formation, which is required to activate the mitochondrial Kreb cycle enzyme aconitase. Frataxin also plays a role in mitochondrial iron storage and heme biosynthesis by incorporating mitochondrial iron into protoporphyrin (PIX).

Loss of frataxin function results in the disruption of iron-sulfur cluster biosynthesis, mitochondrial iron overload, oxidative stress, impaired aerobic electron transport chain respiration and cell death in the brain, spinal cord, dorsal root ganglia and heart. Studies have also shown that frataxin protects dopaminergic neuronal cells against MPTP-induced toxicity in a mouse model of Parkinson's disease.

Ferroptosis is an iron-dependent type of cell death that is biochemically distinct from apoptosis and typically accompanied by a large amount of iron accumulation and lipid peroxidation during the cell death process. Ferroptosis-inducing factors can directly or indirectly affect glutathione peroxidase through different pathways, resulting in a decrease in antioxidant capacity and accumulation of lipid reactive oxygen species (ROS) in cells, ultimately leading to oxidative cell death. Recent studies have shown that ferroptosis is closely related to the pathophysiological processes of many diseases, such as tumors, nervous system diseases, ischemia-reperfusion injury, kidney injury, and blood diseases. Decreased expression of frataxin (FXN) is associated with mitochondrial dysfunction, mitochondrial iron accumulation, and increased oxidative stress. Recent studies have shown that frataxin, which modulates iron homeostasis and mitochondrial function, is a key regulator of ferroptosis. As such, ferroptosis as has been identified as a therapeutic target for Friedreich's ataxia. As described above, ferroptosis is associated with glutathione depletion and production of lipid peroxides, which are generated by lipoxygenase enzymes such as lipoxygenase-15. Accordingly, targeting lipoxygenase-15 provides a therapeutic target for Friedreich's ataxia.

Mitochondrial iron overload leads to impaired intra-mitochondrial metabolism and a defective mitochondrial respiratory chain. A defective mitochondrial respiratory chain leads to increased free radical generation and oxidative damage, which may be considered as mechanisms that compromise cell viability. Some evidence suggests that frataxin might detoxify ROS via activation of glutathione peroxidase and elevation of thiols. (See e.g., Calabrese et al., Journal of the Neurological Sciences, 233(1): 145-162 (June 2005)).

Friedreich's ataxia occurs when the FXN gene contains amplified intronic GAA repeats. The mutant FXN gene contains expanded GAA triplet repeats in the first intron; in a few pedigrees, point mutations have also been detected. Since the defect is located in an intron, which is removed from the mRNA transcript between transcription and translation, the mutated FXN gene does not result in the production of abnormal proteins. Instead, the mutation causes gene silencing, i.e., the mutation decreases the transcription of the gene.

Symptoms typically begin between the ages of 5 and 15 years, although they sometimes appear in adulthood. The first symptom to appear is usually gait ataxia, or difficulty walking. The ataxia gradually worsens and slowly spreads to the arms and the trunk. There is often loss of sensation in the extremities, which may spread to other parts of the body. Other features include loss of tendon reflexes, especially in the knees and ankles. Most people with Friedreich's ataxia develop scoliosis, which often requires surgical intervention for treatment. Dysarthria (slowness and slurring of speech) develops and can get progressively worse. Many individuals with later stages of Friedreich's ataxia develop hearing and vision loss.

Heart disease often accompanies Friedreich's ataxia, such as hypertrophic cardiomyopathy, myocardial fibrosis (formation of fiber-like material in the muscles of the heart), and cardiac (heart) failure. Heart rhythm abnormalities such as tachycardia (fast heart rate) and heart block (impaired conduction of cardiac impulses within the heart) are also common. Other symptoms that may occur include chest pain, shortness of breath, and heart palpitations.

Many patients with Friedreich's ataxia will exhibit a slow decline in visual acuity in later stages of the disease. The most common ophthalmic manifestation of Friedreich's ataxia is optic neuropathy. In some cases, severe/catastrophic visual loss is experienced.

About 20 percent of people with Friedreich's ataxia develop carbohydrate intolerance and 10 percent develop diabetes. Most individuals with Friedreich's ataxia tire very easily and find that they require more rest and take a longer time to recover from common illnesses such as colds and flu.

The rate of progression varies from person to person. Generally, within 10 to 20 years after the appearance of the first symptoms, the person is confined to a wheelchair, and in later stages of the disease individuals may become completely incapacitated. Friedreich's ataxia can shorten life expectancy, and heart disease is the most common cause of death.

The five enzyme complexes (i.e. Complex I, Complex II, Complex III, Complex IV and Complex V) of the oxidative phosphorylation (OXPHOS) system are located in the mitochondrial membrane and Complex I deficiency leading to decreased levels (and decreased production) of adenosine triphosphate (ATP) is believed to be associated with Friedreich's ataxia. Indeed, it has been suggested that decreased frataxin expression in the cells of Friedreich's ataxia patients increases the pool of non-bioavailable iron within the cell, thereby leading to free radical generation, increased oxidative damage to the cell and decreased Complex I activity and associated decreases in intracellular ATP generation (Heidari et al., Complex I and ATP Content Deficiency in Lymphocytes from Friedreich's Ataxia, Can. J. Neurol. Sci. 2009: 36: 26-31).

There is no known cure for Friedreich's ataxia. Generally, therapies involve treatment of the symptoms. Because patients with Friedreich's ataxia are at a risk of developing heart disease, they are often prescribed medications such as beta blockers, ACE inhibitors and/or diuretics. Because it is believed that damage caused by oxidative stress is involved in the progression of Friedreich's ataxia, antioxidants such as vitamin E, idebenone and coenzyme Q10 are often co-administered to persons diagnosed or suspected of having Friedrich's ataxia. These compounds have been used in various clinical trials.

Currently, EPI-743 (a benzoquinone compound also known as vatiquinone) is currently recruiting a phase 2/3 clinical trial for the treatment of Friedreich's ataxia. Vatiquinone is believed to reduce oxidative stress and improve mitochondrial function.

Omaveloxolone is a second generation synthetic oleanane triterpenoid that is believed to exhibit antioxidative and anti-inflammatory activity. Omaveloxolone was used in a now completed phase 2 clinical trial for treatment of Friedreich's ataxia.

Several other therapies for the treatment of Friedreich's ataxia are currently in clinical trials but there are no FDA approved drugs. Hence, there remains a need for better drug candidates to address the needs of patients diagnosed with Friedreich's ataxia.

BRIEF DESCRIPTION OF THE DRAWINGS

FIG. 8 is a listing of various possible known alcohols that are useful in the production of bromides identified in FIGS. 1A, 1B, 1C, 2A, 2B, 2C, 3A, 3B, 3C, 4A, 4B, 4C, 5A and 5B as illustrated by general formulas 209, 209A, 209B, 219, 219a, 219b, 229, 229a, 229b, 239, 239a, 239b, 309a and 309b.

DETAILED DESCRIPTION

I. Chemical Definitions

Figure 1A:
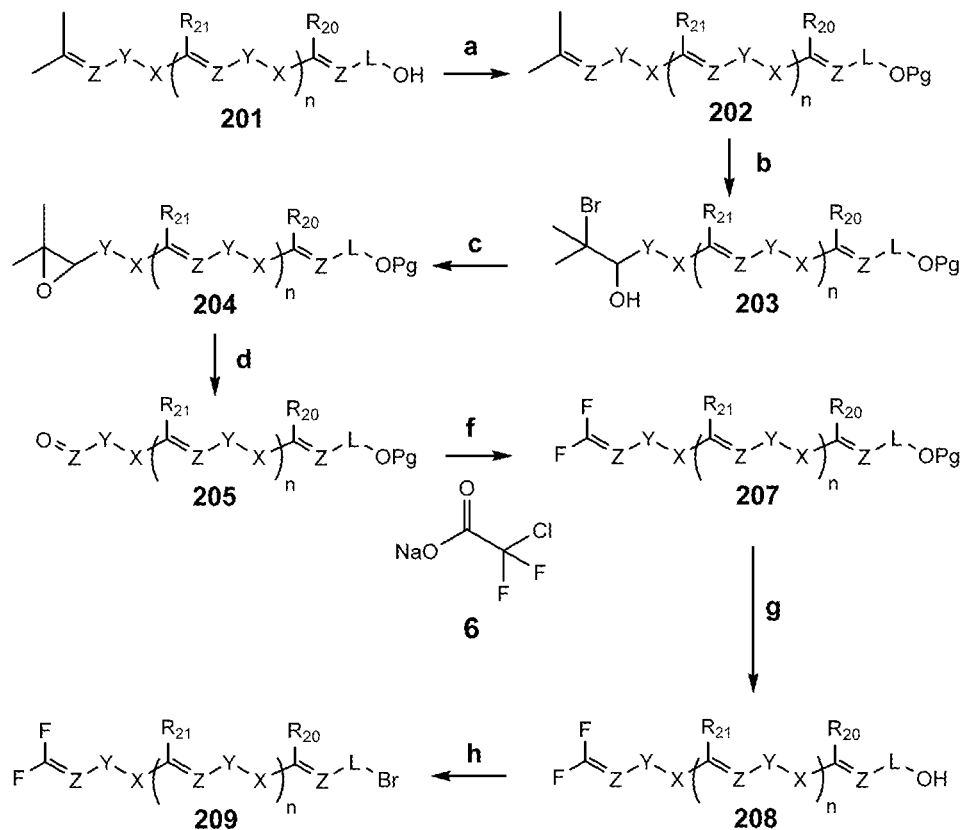
FIG. 1A is an illustration of a chemical scheme for the production of novel bis-fluorinated tail-group intermediates used in the production of the therapeutic compositions disclosed herein.

Definitions of specific functional groups and chemical terms are described in more detail below. The chemical elements are identified in accordance with the Periodic Table of the Elements, GAS version, Handbook of Chemistry and Physics, 7Sh Ed., inside cover. Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5th Edition, John Wiley & Sons, Inc., New York, 2001; Larock, Comprehensive Organic Transformations, VCH Publishers, Inc., New York, 1989; and Carruthers, Some Modern Methods of Organic Synthesis, 3rd Edition, Cambridge University Press, Cambridge, 1987.

The abbreviations used herein have their conventional meaning within the chemical and biological arts. The chemical structures and formulae set forth herein are intended to comply with the standard rules of chemical valency known in the chemical arts. When a range of values is listed, it is intended to encompass each value and subrange within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_5$, $C_3$-$C_4$, $C_4$-$C_6$, $C_4$-$C_5$, and $C_5$-$C_6$ alkyl. When a group or moiety is referred to as "substituted", one or more of the hydrogen atoms of the group has been replaced with a substituent. Possible "substituents" include, for example, one or more: (i) deuterium (D), fluorine (F), chlorine (Cl), bromine (Br) or iodine (I) atoms (individually each of F, Cl, Br and I is a "halogen" and collectively F, Cl, Br and I are "halogens"; or (ii) methyl, ethyl, propyl, trichloromethyl, trifluoromethyl, carbonyl (i.e., C=O), nitrile (i.e., —C≡N), hydroxyl or protected hydroxyl (i.e., —OH or —OPg, wherein Pg is a protecting group), alkoxy (i.e., —OR") nitro (i.e., —NO$_2$) groups or amino (in protected or unprotected form, i.e., —NH$_2$ or —NHPg, wherein Pg is a protecting group), each independently chosen for each possible position for substitution of a hydrogen atom. Other substituents are contemplated, such as azide, alkyl, aralkyl, alkenyl, alkynyl, cycloalkyl, alkoxy, nitro, sulfhydryl, imino, amido, phosphonate, phosphinate, carboxyl, silyl, ether, sulfonyl, sulfonamido, ketone, aldehyde, ester, heterocyclyl, aromatic or heteroaromatic moieties, fluoroalkyl (such as fluoromethyl, difluoromethyl and trifluoromethyl), cyano, or the like. A group or moiety that is not substituted is unsubstituted.

Certain compounds of the present application can exist in unsolvated forms as well as solvated forms, including hydrated forms. Solvated forms can exist, for example, because it is difficult or impossible to remove all the solvent from the compound post synthesis. In general, the solvated forms are equivalent to unsolvated forms and are encompassed within the scope of the present application. Certain compounds of the present application may exist in multiple crystalline or amorphous forms. Certain compounds of the present application may exist in various tautomeric forms. Certain compounds of the present application may exist in various salt forms. In general, all physical forms are equivalent for the uses contemplated by the present application and are intended to be within the scope of the present application.

As used herein "alkoxy" is one example of a heteroalkyl group and refers to an alkyl, cycloalkyl, heteroalkyl or cycloheteroalkyl group linked to a terminal oxygen of general formula:

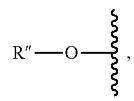

wherein R" is the alkyl, cycloalkyl, heteroalkyl or cycloheteroalkyl group and ⌇ identifies the bond that forms the point of attachment of the alkoxy group to another compound or moiety. Each instance of an alkoxy group may be independently optionally unsubstituted (an "unsubstituted alkoxy") or substituted (a "substituted alkoxy") with one or more substituents. For example, the substituent can be a halogen such as fluorine. A few non-limiting examples of fluorine substituted alkoxy groups used herein include: fluoromethoxy ("—OCH$_2$F"), difluoromethoxy ("—OCHF$_2$") and trifluoromethoxy ("—OCF$_3$").

As used herein, "alkyl" refers to a radical of a straight-chain or branched saturated hydrocarbon group having from 1 to 20 carbon atoms ("$C_1$-$C_{20}$ alkyl"). In some embodiments, an alkyl group has 1 to 12 carbon atoms ("$C_1$-$C_{12}$ alkyl"). In some embodiments, an alkyl group has 1 to 10 carbon atoms ("$C_1$-$C_{10}$ alkyl"). In some embodiments, an alkyl group has 1 to 8 carbon atoms ("$C_1$-$C_8$ alkyl"). In some embodiments, an alkyl group has 1 to 6 carbon atoms ("$C_1$-$C_6$ alkyl"). In some embodiments, an alkyl group has 1 to 5 carbon atoms ("$C_1$-$C_5$ alkyl"). In some embodiments, an alkyl group has 1 to 4 carbon atoms ("$C_1$-$C_4$ alkyl"). In some embodiments, an alkyl group has 1 to 3 carbon atoms ("$C_1$-$C_3$ alkyl"). In some embodiments, an alkyl group has 1 to 2 carbon atoms ("$C_1$-$C_2$ alkyl"). In some embodiments, an alkyl group has 1 carbon atom ("$C_1$ alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of higher order alkyl groups (e.g. $C_1$-$C_{12}$) include n-heptyl ($C_7$), n-octyl ($C_8$), nonyl ($C_9$), decyl ($C_{10}$), undecyl ($C_{11}$) and dodecyl ($C_{12}$) and the like. Each instance of an alkyl group may be independently optionally unsubstituted (an "unsubstituted alkyl") or substituted (a "substituted alkyl") with one or more substituents; e.g., for instance from 1 to 5 substituents, 1 to 4 substituents, 1 to 3 substituents, 1 to 2 substituents or just 1 substituent. For example, the substituent can be a halogen such as fluorine. A few non-limiting examples of substituted alkyl groups used herein include: fluoromethyl ("—CH$_2$F"), difluoromethyl ("—CHF$_2$") and trifluoromethyl ("—CF$_3$"). The term "alkyl" is also intended to refer to those compounds wherein one or more methylene groups in the alkyl chain can be replaced by a heteroatom such as O or Si.

As used herein, "alkenyl" refers to a radical of a straight-chain or branched hydrocarbon group having from 2 to 12 carbon atoms, one or more carbon-carbon double bonds, and no triple bonds ("C$_2$-C$_{12}$ alkenyl"). In some embodiments, an alkenyl group has 1-10 carbon atoms ("C$_2$-C$_{10}$alkenyl"). In some embodiments, an alkenyl group has 2 to 8 carbon atoms ("C$_2$-C$_8$ alkenyl"). In some embodiments, an alkenyl group has 2 to 6 carbon atoms ("C$_2$-C$_6$ alkenyl"). In some embodiments, an alkenyl group has 2 to 5 carbon atoms ("C$_2$-C$_5$ alkenyl"). In some embodiments, an alkenyl group has 2 to 4 carbon atoms ("C$_2$-C$_4$ alkenyl"). In some embodiments, an alkenyl group has 2 to 3 carbon atoms ("C$_2$-C$_3$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_2$-C$_4$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_2$-C$_6$ alkenyl groups include the aforementioned C$_2$-C$_4$ alkenyl groups as well as pentenyl (C$_5$), pentadienyl (C$_5$), hexenyl (C$_6$), and the like. Additional examples of alkenyl include heptenyl (C$_1$), octenyl (C$_8$), octatrienyl (C$_8$), and the like. Each instance of an alkenyl group may be independently optionally unsubstituted (an "unsubstituted alkenyl") or substituted (a "substituted alkenyl") with one or more substituents; e.g., for instance from 1 to 5 substituents, 1 to 4 substituents, 1 to 3 substituents, 1 to 2 substituents or just 1 substituent. For example, the substituent can be a halogen such as fluorine.

As used herein, the term "alkynyl" refers to a radical of a straight-chain or branched hydrocarbon group having from 2 to 12 carbon atoms, one or more carbon-carbon triple bonds ("C$_2$-C$_{12}$ alkynyl"). In some embodiments, an alkynyl group has 2 to 10 carbon atoms ("C$_2$-C$_{10}$ alkynyl"). In some embodiments, an alkynyl group has 2 to 8 carbon atoms ("C$_2$-C$_8$ alkynyl"). In some embodiments, an alkynyl group has 2 to 6 carbon atoms ("C$_2$-C$_6$ alkynyl"). In some embodiments, an alkynyl group has 2 to 5 carbon atoms ("C$_2$-C$_5$ alkynyl"). In some embodiments, an alkynyl group has 2 to 4 carbon atoms ("C$_2$-C$_4$ alkynyl"). In some embodiments, an alkynyl group has 2 to 3 carbon atoms ("C$_2$-C$_3$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_2$-C$_4$ alkynyl groups include ethynyl (C$_2$), 1-propynyl (C$_3$), 2-propynyl (C$_3$), 1-butynyl (C$_4$), 2-butynyl (C$_4$), and the like. Each instance of an alkynyl group may be independently optionally unsubstituted (an "unsubstituted alkynyl") or substituted (a "substituted alkynyl") with one or more substituents; e.g., for instance from 1 to 5 substituents, 1 to 4 substituents, 1 to 3 substituents, 1 to 2 substituents or just 1 substituent. For example, the substituent can be a halogen such as fluorine.

As used herein, "aprotic solvent" refers to an organic solvent that has no O—H or N—H bonds. Non-limiting examples of aprotic solvents include: acetonitrile (abbreviated as ACN or MeCN), tetrahydrofuran (THF), dioxane, dichloromethane (DCM), diethyl ether (Et$_2$O), ethyl acetate (EtOAc), N,N-dimethylformamide (DMF) and dimethylsulfoxide (DMSO).

As used herein, "aryl" (sometimes abbreviated as "Ar") refers to a radical of a monocyclic or polycyclic (e.g, bicyclic or tricyclic) 4n+2 aromatic ring system (e.g, having 6, 10, or 14 π electrons shared in a cyclic array) having 6-14 ring carbon atoms and zero heteroatoms provided in the aromatic ring system ("C$_6$-C$_{14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). An aryl group may be described as, e.g., a C$_6$-C$_{10}$-membered aryl, wherein the term "membered" refers to the non-hydrogen ring atoms within the moiety. Aryl groups include phenyl, naphthyl, indenyl, and tetrahydronaphthyl. Each instance of an aryl group may be independently optionally unsubstituted (an "unsubstituted aryl") or substituted, (a "substituted aryl") with one or more substituents; e.g, for instance from 1 to 5 substituents, 1 to 4 substituents, 1 to 3 substituents, 1 to 2 substituents or just 1 substituent. For example, the substituent can be a halogen such as fluorine or chlorine. In some embodiments, the aromatic ring may be substituted at one or more ring positions with one or more substituents, such as halogen, azide, alkyl, aralkyl, alkenyl, alkynyl, cycloalkyl, hydroxyl or protected hydroxyl (i.e., —OH or —OPg, wherein Pg is a protecting group), alkoxy (i.e., —OR), nitro, amino (in protected or unprotected form, i.e., —NH$_2$ or —NHPg, wherein Pg is a protecting group), sulfhydryl, imino, amido, phosphonate, phosphinate, carbonyl, carboxyl, silyl, ether, sulfonyl, sulfonamido, ketone, aldehyde, ester, heterocyclyl, aromatic or heteroaromatic moieties, fluoroalkyl (such as trifluoromethyl, difluoromethyl and trifluoromethyl), cyano, or the like. An aryl group is sometimes referred to as an aromatic group (or aromatic moiety).

As used herein, the term "arylalkyl" refers to a radical of an aryl or heteroaryl group (which aryl or heteroaryl group may be substituted or unsubstituted) that is attached to a (C$_1$-C$_{20}$)alkyl group (which alkyl group may be substituted or unsubstituted) via an alkylene linker. The term "arylalkyl" refers to a group that may be substituted or unsubstituted. The term "arylalkyl" is also intended to refer to those compounds wherein one or more methylene groups in the alkyl chain of the arylalkyl group can be replaced by a heteroatom such as O, N, P, Si, and S, and wherein the nitrogen, phosphorus and sulfur atoms may optionally be oxidized and the nitrogen heteroatom may optionally be quaternized with one or more appended alkyl and/or aryl groups. Arylalkyl groups include for example, benzyl (in substituted or unsubstituted form).

As used herein, the term "arylheteroalkyl" refers to a radical of aryl group (which aryl group may be substituted or unsubstituted) linked to a non-cyclic stable straight or branched chain, or combinations thereof, alkyl group including at least one carbon atom and at least one heteroatom selected from the group consisting of O, N, P, Si, and S, and wherein the nitrogen, phosphorus and sulfur atoms may optionally be oxidized, and the nitrogen heteroatom may optionally be quaternized with one or more appended alkyl and/or aryl groups.

As used herein, the term "benzyl group" refers to a group of formula:

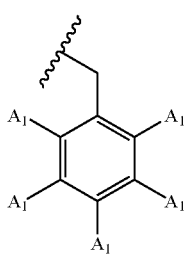

wherein each $A_1$ is independently H, D, F, Cl, Br, I, —$CH_3$, —$OCH_3$, —$CF_2CH_3$, —$OCF_2CH_3$, chloromethyl, dichloromethyl, trichloromethyl, fluoromethyl, difluoromethyl, trifluoromethyl, nitrile (—C≡N), hydroxyl/phenol (i.e., —OH or —OPg, wherein Pg is a protecting group) or nitro (—$NO_2$). If each $A_1$ is H, then the benzyl group is unsubstituted. If at least one $A_1$ is not H, then the benzyl group is substituted.

As used herein, the term "carbocyclic ring" or "carbocycle" refers to a ring formed by linked carbon atoms. A carbocyclic ring may be independently optionally unsubstituted (e.g. an "unsubstituted cycloalkyl") or substituted (e.g. a "substituted cycloalkyl") with one or more substituents. For example, the substituent can be a halogen such as fluorine. A cycloalkyl group comprises a carbocyclic ring. An aryl group such as benzene comprises a carbocyclic ring. A carbocyclic ring can comprise 3 carbon atoms (a "$C_3$ carbocycle"), 4 carbon atoms (a "$C_4$ carbocycle"), 5, carbon atoms (a "$C_5$ carbocycle"), 6 carbon atoms (a "$C_6$ carbocycle"), 7 carbon atoms (a "$C_7$ carbocycle") or 8 carbon atoms (a "$C_8$ carbocycle"). A carbocyclic ring can be aromatic and therefore comprise 6 carbon atoms (a "$C_6$ carbocycle"), 10 carbon atoms (a "$C_{10}$ carbocycle") or 14 carbon atoms (a "$C_{14}$ carbocycle").

As used herein, "chiral chromatography" refers to the use of a chiral column (i.e. chiral stationary phase) for the separation of racemic, and sometimes diastereomeric, mixtures to obtain an optically enriched or optically pure product from the chromatographic separation.

As used herein, "cycloalkyl" refers to a radical of a non-aromatic cyclic hydrocarbon group having from 3 to 12 ring carbon atoms ("$C_3$-$C_{12}$ cycloalkyl"). In some embodiments, a cycloalkyl group has 3 to 10 ring carbon atoms ("$C_3$-$C_{10}$ cycloalkyl"). In some embodiments, a cycloalkyl group has 3 to 8 ring carbon atoms ("$C_3$-$C_8$ cycloalkyl"). In some embodiments, a cycloalkyl group has 3 to 6 ring carbon atoms ("$C_3$-$C_6$ cycloalkyl"). In some embodiments, a cycloalkyl group has 4 to 6 ring carbon atoms ("$C_4$-$C_6$ cycloalkyl"). In some embodiments, a cycloalkyl group has 5 to 6 ring carbon atoms ("$C_5$-$C_6$ cycloalkyl"). In some embodiments, a cycloalkyl group has 5 to 7 ring carbon atoms ("$C_5$-$C_7$ cycloalkyl"). In some embodiments, a cycloalkyl group has 6 to 7 ring carbon atoms ("$C_6$-$C_7$ cycloalkyl"). A cycloalkyl group maybe described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_7$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), and cycloheptatrienyl ($C_7$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_7$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. Non-limiting examples of bicyclic cycloalkyl groups include 1-ethylbicyclo[1.1.1]pentane, 1-ethylbicyclo[2.2.2]octane and (3r,5r,7r)-1-ethyladamantane. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally unsubstituted (an "unsubstituted cycloalkyl") or substituted (a "substituted cycloalkyl") with one or more substituents. For example, the substituent can be a halogen such as fluorine.

As used herein, "cycloheteroalkyl" refers to a radical of a cycloalkyl group comprising at least one heteroatom (wherein the heteroatom is substituted in the ring for a carbon atom) selected from the group consisting of O, N, P, Si, and S, and wherein the nitrogen, phosphorus and sulfur atoms may optionally be oxidized, and the nitrogen heteroatom may optionally be quaternized with appended alkyl and/or aryl groups. The heteroatom(s) O, N, P, S, and Si may be placed at any position of the cycloheteroalkyl group but generally each heteroatom is linked to at least two carbon atoms of the cycloalkyl group.

As used herein, the term "heteroalkyl" refers to a radical of a non-cyclic stable straight or branched chain, or combinations thereof, including at least one carbon atom and at least one heteroatom selected from the group consisting of O, N, P, Si, and S, and wherein the nitrogen, phosphorus and sulfur atoms may optionally be oxidized, and the nitrogen heteroatom may optionally be quaternized with appended alkyl and/or aryl groups. The heteroatom(s) O, N, P, S, and Si may be placed at any position of the heteroalkyl group but generally each heteroatom is linked to at least two carbon atoms of the cycloalkyl group. Exemplary heteroalkyl groups include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —$CH_2$—$CH_2$—P(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, and —O—$CH_2$—$CH_3$. Up to two heteroatoms may be consecutive, such as, for example, —$CH_2$—NH—$OCH_3$, —$CH_2CH_2$—S—S—$CH_2CH_3$ and —$CH_2$—O—Si($CH_3$)$_3$. Each instance of heteroalkyl group may be independently optionally unsubstituted (an "unsubstituted heteroalkyl") or substituted (a "substituted heteroalkyl") with one or more substituents; e.g., for instance from 1 to 5 substituents, 1 to 4 substituents, 1 to 3 substituents, 1 to 2 substituents or just 1 substituent. For example, the substituent can be a halogen such as fluorine.

As used herein, the term "heteroaryl" refers to a radical of an aromatic heterocycle that comprises 1, 2, 3 or 4 heteroatoms selected, independently of the others, from nitrogen, sulfur and oxygen. As used herein, the term "heteroaryl" refers to a group that may be substituted or unsubstituted. For example, the substituent can be a halogen such as fluorine. A heteroaryl may be fused to one or two rings, such as a cycloalkyl, an aryl, or a second heteroaryl ring. The point of attachment of a heteroaryl to a molecule may be on the heteroaryl, cycloalkyl, heterocycloalkyl or aryl ring, and the heteroaryl group may be attached through carbon or a heteroatom. Examples of heteroaryl groups include imidazolyl, furyl, pyrrolyl, thienyl, thiazolyl, isoxazolyl, isothiazolyl, thiadiazolyl, oxadiazolyl, pyridinyl, pyrimidyl, pyrazinyl, pyridazinyl, quinolyl, isoquinolinyl, indazolyl, benzoxazolyl, benzisooxazolyl, benzofuryl, benzothiazolyl, indolizinyl, imidazopyridinyl, pyrazolyl, triazolyl, oxazolyl, tetrazolyl, benzimidazolyl, benzoisothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidyl, pyrazolo[3,4]pyrimidyl or benzo(b)thienyl, each of which can be optionally substituted. The aromatic heterocycle may be substituted at one or more ring positions with one or more substituents, such as halogen, azide, alkyl, aralkyl, alkenyl, alkynyl, cycloalkyl, hydroxyl or protected hydroxyl (i.e., —OH or —OPg, wherein Pg is a protecting group), alkoxy (i.e., —OR), nitro, amino (in protected or unprotected form, i.e., —NH$_2$ or —NHPg, wherein Pg is a protecting group), sulfhydryl, imino, amido, phosphonate, phosphinate, carbonyl, carboxyl, silyl, ether, sulfonyl, sulfonamido, ketone, aldehyde, ester, heterocyclyl, aromatic or heteroaromatic moieties, fluoroalkyl (such as trifluoromethyl), cyano, or the like. A heteroaryl group is sometimes referred to as a heteroaromatic group (or moiety).

As used herein, the term "heterocyclic ring" or "heterocycle" refers to a ring of atoms of at least two different elements, one of which is carbon. Additional reference is made to: Oxford Dictionary of Biochemistry and Molecular Biology, Oxford University Press, Oxford, 1997 as evidence that the term "heterocyclic ring" is a term well-established in field of organic chemistry. A heterocyclic ring can be aliphatic (e.g. tetrahydrofuran) or aromatic (e.g. pyridine). A heterocyclic ring can be substituted or unsubstituted.

As used herein, the term "hydrate" refers to a compound which is associated with water. The number of the water molecules contained in a hydrate of a compound may be (or may not be) in a definite ratio to the number of the compound molecules in the hydrate.

As used herein, the term "pharmaceutically acceptable salt" refers to a salt of a therapeutically active compound that can be prepared with relatively nontoxic acids or bases, depending on the particular substituents found on the compounds described herein. When compounds of the present application contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present application contain relatively basic functionalities, acid addition salts can be obtained by contacting the neutral form of such compounds with a sufficient amount of the desired acid, either neat or in a suitable inert solvent. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-methylmorpholine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine (NEt$_3$), trimethylamine, tripropylamine, tromethamine and the like, such as where the salt includes the protonated form of the organic base (e.g., [HNEt$_3$]$^+$). Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g, acetic, butyric, formic, propionic and trifluoroacetic acids), amino acids (e.g, aspartic and glutamic acids), aromatic carboxylic acids (e.g, benzoic, p-chlorobenzoic, diphenylacetic, gentisic, hippuric, and triphenylacetic acids), aromatic hydroxyl acids (e.g, o-hydroxybenzoic, p-hydroxybenzoic, 1-hydroxynaphthalene-2-carboxylic and 3-hydroxynaphthalene-2-carboxylic acids), ascorbic, dicarboxylic acids (e.g, fumaric, maleic, oxalic and succinic acids), glucuronic, mandelic, mucic, nicotinic, orotic, pamoic, pantothenic, sulfonic acids (e.g, benzenesulfonic, camphorsulfonic, edisylic, ethanesulfonic, isethionic, methanesulfonic, naphthalenesulfonic, naphthalene-1,5-disulfonic, naphthalene-2,6-disulfonic and p-toluenesulfonic acids (PTSA)), xinafoic acid, and the like. In some embodiments, the pharmaceutically acceptable counterion is selected from the group consisting of acetate, benzoate, besylate, bromide, camphorsulfonate, chloride, chlorotheophyllinate, citrate, ethanedisulfonate, fumarate, gluceptate, gluconate, glucoronate, hippurate, iodide, isethionate, lactate, lactobionate, laurylsulfate, malate, maleate, mesylate, methylsulfate, naphthoate, sapsylate, nitrate, octadecanoate, oleate, oxalate, pamoate, phosphate, polygalacturonate, succinate, sulfate, sulfosalicylate, tartrate, tosylate, and trifluoroacetate. In some embodiments, the salt is a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt, a maleate salt, a trifluoroacetate salt, a hydrochloride salt, or a tosylate salt. Also included are salts of amino acids such as arginate and the like, and salts of organic acids such as glucuronic or galactunoric acids and the like (see, e.g., Berge et al, Journal of Pharmaceutical Science 66: 1-19 (1977)). Certain specific compounds of the present application may contain both basic and acidic functionalities that allow the compounds to be converted into either base or acid addition salts or exist in zwitterionic form. These salts may be prepared by methods known to those skilled in the art. Other pharmaceutically acceptable carriers known to those of skill in the art are suitable for the present technology.

As used herein, the term "protecting group" or "Pg" refers to a chemical group that is reacted with, and bound to (at least for some period of time), a functional group in a molecule to prevent said functional group (e.g. —OH, —NH$_2$, —SH) from participating in reactions of the molecule but which chemical group can subsequently be removed to thereby regenerate said functional group. Additional reference is made to: Oxford Dictionary of Biochemistry and Molecular Biology, Oxford University Press, Oxford, 1997 as evidence that protecting group is a term well-established in field of organic chemistry. Further reference is made to Greene's Protective Groups in Organic Synthesis, Fourth Edition, 2007, John Wiley & Sons, Inc.

which is known as a primary reference for researching the suitability of various protecting groups (e.g., protecting groups (i.e., Pg) for hydroxyl or amine groups) for organic synthesis reactions.

As used herein, the term "solvate" refers to forms of the compound that are associated with a solvent, usually by a solvolysis reaction. This physical association may include hydrogen bonding. Conventional solvents include water, methanol, ethanol, isopropanol, acetic acid, ethyl acetate, acetone, hexane(s), DMSO, THF, diethyl ether, and the like As used herein, the term "tautomer" refers to compounds that are interchangeable forms of a particular compound structure, and that vary in the displacement of hydrogen atoms and electrons. Thus, two structures may be in equilibrium through the movement of n electrons and an atom (usually H). For example, enols and ketones are tautomers because they are rapidly interconverted by treatment with either acid or base. Tautomeric forms may be relevant to the attainment of the optimal chemical reactivity and biological activity of a compound of interest.

II. Other Definitions

It is to be appreciated that certain aspects, modes, embodiments, variations and features of the technology are described below in various levels of detail in order to provide a substantial understanding of the present application. The definitions of certain terms as used in this specification are provided below. Unless defined otherwise, all technical and scientific terms used herein generally have the same meaning as commonly understood by one of ordinary skill in the art to which this technology belongs.

As used in this specification and the appended claims, the singular forms "a", "an" and "the" include plural references unless the content clearly dictates otherwise. For example, reference to "a cell" includes a combination of two or more cells, and the like.

As used herein, the "administering" or the "administration" of an agent (i.e. therapeutic agent) or drug to a subject includes any route of introducing or delivering to a subject a compound to perform its intended function. Administration may be carried out by any suitable route, such as oral administration. Administration can be carried out subcutaneously. Administration can be carried out intravenously. Administration can be carried out intraocularly. Administration can be carried out systemically. Alternatively, administration may be carried out topically, intranasally, intraperitoneally, intradermally, ophthalmically, intrathecally, intracerebroventricularly, iontophoretically, transmucosally, intravitreally, or intramuscularly. Administration includes self-administration and the administration by another.

As used herein the terms "carrier" and "pharmaceutically acceptable carrier" refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, silica particles (nanoparticles or microparticles) urea, and the like. In addition, auxiliary, stabilizing, thickening, lubricating, flavoring, and coloring agents may be used. Other examples of suitable pharmaceutical carriers are described in *Remington's Pharmaceutical Sciences* by E. W. Martin, herein incorporated by reference in its entirety.

As used herein, the phrase "delaying the onset of" refers to, in a statistical sample, postponing, hindering, or causing one or more symptoms of a disorder, symptom, condition or indication to occur more slowly than normal in a treated sample relative to an untreated control sample.

As used herein, the term "effective amount" refers to a quantity sufficient to achieve a desired therapeutic and/or prophylactic effect, e.g., an amount that reduces, ameliorates, prevents or delays the onset of the physiological symptoms of mitochondrial disease, such as Friedreich's ataxia. In the context of therapeutic or prophylactic applications, in some embodiments, the amount of a composition administered to the subject will depend on the type and severity of the disease and on the characteristics of the individual, such as general health, age, sex, body weight and tolerance to drugs. In some embodiments, it will also depend on the degree, severity and type of disease. The skilled artisan will be able to determine appropriate dosages depending on these and other factors. The compositions can also be administered in combination with one or more additional therapeutic compounds (a so called "co-administration" where, for example, the additional therapeutic compounds could be administered simultaneously, sequentially or by separate administration). The one or more additional therapeutic compounds could be, for example, a beta blocker, ACE inhibitor and/or diuretic used to treat a patient experiencing at risk of heart disease or heart failure. The one or more additional therapeutic compounds could be, for example, a Szeto-Schiller peptide such as SS-20 or SS-31 (a.k.a. elamipretide or bendavia).

In the methods described herein, therapeutic compounds, or pharmaceutically acceptable salts, stereoisomers, mixtures of stereoisomers, tautomers, hydrates, and/or solvates thereof, may be administered to a subject having one or more signs, symptoms, or risk factors of mitochondrial disease such as Friedreich's ataxia; e.g., muscle weakness, especially in the arms and legs, loss of coordination, motor control impairment, vision impairment, hearing impairment, slurred speech, curvature of the spine, diabetes, heart and/or ophthalmic conditions or disorders. For example, a "therapeutically effective amount" of therapeutic compound includes levels at which the presence, frequency, or severity of one or more signs, symptoms, or risk factors of mitochondrial disease such as Friedreich's ataxia are reduced or eliminated. In some embodiments, a therapeutically effective amount reduces or ameliorates the physiological effects of a mitochondrial disease such as Friedreich's ataxia, and/or the risk factors of the mitochondrial disease (e.g. Friedreich's ataxia), and/or delays the progression or onset of the mitochondrial disease (e.g. Friedreich's ataxia).

As used herein, "inhibit" or "inhibiting" means to reduce by an objectively measurable amount or degree compared to control. In one embodiment, inhibit or inhibiting means reduce by at least a statistically significant amount compared to control. In one embodiment, inhibit or inhibiting means reduce by at least 5 percent compared to control. In various individual embodiments, inhibit or inhibiting means reduce by at least 2, 3, 4, 5, 10, 15, 20, 25, 30, 33, 40, 50, 60, 67, 70, 75, 80, 90, 95, or 99 percent compared to control.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this definition.

As used herein, a "subject" refers to a living animal. In various embodiments, a subject is a mammal. In various embodiments, a subject is a non-human mammal, including, without limitation, a mouse, rat, hamster, guinea pig, rabbit, sheep, goat, cat, dog, pig, minipig, horse, cow, or non-human primate. In certain embodiments, the subject is a human.

As used herein, the terms "treating" or "treatment" or "alleviation" refers to therapeutic treatment, wherein the object is to reduce, alleviate or slow down (lessen) the targeted pathologic condition or disorder. By way of example, but not by way of limitation, a subject is successfully "treated" for a mitochondrial disease (e.g. Friedreich's ataxia) if, after receiving an effective amount of the compounds of the present application or a pharmaceutically acceptable salt thereof, such as hydrochloride, acetate, citrate, trifluoroacetate, benzoate, oxalate or mesylate salt, stereoisomers, mixtures of stereoisomers, tautomers, hydrates, and/or solvates thereof, according to the methods described herein, the subject shows observable and/or measurable reduction in or absence of one or more signs and symptoms of the mitochondrial disease (e.g. Friedreich's ataxia), such as but not limited to, e.g., muscle weakness, especially in the arms and legs, loss of coordination, motor control impairment, vision impairment, hearing impairment, slurred speech, curvature of the spine, diabetes, heart and/or ophthalmic conditions or disorders. It is also to be appreciated that the various modes of treatment of medical conditions as described are intended to mean "substantial," which includes total but also less than total treatment, and wherein some biologically or medically relevant result is achieved. Treating Friedreich's ataxia, as used herein, in some embodiments, also refers to treating the signs and symptoms related to reduced frataxin activity or frataxin expression levels characteristic of Friedreich's ataxia.

As used herein, "prevention" or "preventing" of a disease or condition, e.g., a mitochondrial disease such as Friedreich's ataxia refers to results that, in a statistical sample, exhibit a reduction in the occurrence of the disorder or condition in the treated sample relative to an untreated control sample, or exhibit a delay in the onset of one or more symptoms of the disorder or condition relative to the untreated control sample. Such prevention is sometimes referred to as a prophylactic treatment. As used herein, preventing mitochondrial disease (e.g. Friedreich's ataxia) includes preventing or delaying the onset of, preventing, delaying, or slowing the progression or advancement of mitochondrial disease (e.g. Friedreich's ataxia). As used herein, prevention of Friedreich's ataxia also includes preventing a recurrence of one or more signs or symptoms of Friedreich's ataxia.

III. Chiral/Stereochemistry Considerations

Compounds described herein can comprise one or more asymmetric centers, and thus can exist in various isomeric forms, e.g, enantiomers and/or diastereomers (i.e., stereoisomers). Chiral centers in illustrated structures (including the claims) may be identified herein by use of an asterisk (*). For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The disclosure of the present application additionally encompasses compounds described herein as individual isomers substantially free of other isomers, and alternatively, as mixtures of various isomers.

As used herein, a pure enantiomeric compound is substantially free from other enantiomers or stereoisomers of the compound (i.e., in enantiomeric excess); as purity is a relative term in the sense that it is exceedingly difficult to achieve 100% purity. In other words, an "S" form of the compound is substantially free from the "R" form of the compound and is, thus, in enantiomeric excess of the "R" form. With respect to amino acids (which are more commonly described in terms of "D" and "L" enantiomer, it is to be understood that for a "D"-amino acid the configuration is "R" and for an "L"-amino acid, the configuration is "S". In some embodiments, 'substantially free', refers to: (i) an aliquot of an "R" form compound that contains less than 2% "S" form; or (ii) an aliquot of an "S" form compound that contains less than 2% "R" form. The term "enantiomerically pure" or "pure enantiomer" denotes that the compound comprises more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the particularly identified enantiomer (e.g. as compared with the other enantiomer). In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure "R" form compound can comprise, for example, about 90% excipient and about 10% enantiomerically pure "R" form compound. In certain embodiments, the enantiomerically pure "R" form compound in such compositions can, for example, comprise, at least about 95% by weight "R" form compound and at most about 5% by weight "S" form compound, by total weight of the compound. For example, a pharmaceutical composition comprising enantiomerically pure "S" form compound can comprise, for example, about 90% excipient and about 10% enantiomerically pure "S" form compound. In certain embodiments, the enantiomerically pure "S" form compound in such compositions can, for example, comprise, at least about 95% by weight "S" form compound and at most about 5% by weight "R" form compound, by total weight of the enantiomers of the compound. In certain embodiments, the active ingredient can be formulated with little or no excipient or carrier.

IV. Pharmaceutical Compositions, Routes of Administration, and Dosing

In some embodiments, the present application is directed to a pharmaceutical composition. In some embodiments, the composition comprises a compound of the present application and a pharmaceutically acceptable carrier. In certain embodiments, the pharmaceutical composition comprises a plurality of compounds of the present application and a pharmaceutically acceptable carrier. The pharmaceutical composition can be a medicament.

In certain embodiments, a pharmaceutical composition of the present application further comprises at least one additional therapeutic agent other than a compound or compounds of the present application. The at least one additional therapeutic agent can be an agent useful in the treatment of mitochondrial disease, such as Friedreich's ataxia. Thus, in some embodiments, pharmaceutical compositions of the present application can be prepared, for example, by combining one or more compounds of the present application with a pharmaceutically acceptable carrier and, optionally, one or more additional therapeutical agents.

Pharmaceutical compositions of the present application contain an effective amount of a therapeutic compound (or compounds) as described herein and may optionally be disbursed in a pharmaceutically acceptable carrier. The components of the pharmaceutical compositions also are capable of being commingled with the compounds of the present application, and with each other, in a manner such that there is no interaction which would substantially impair the desired pharmaceutical efficiency.

As stated above, an "effective amount" refers to any amount of the active compound (or compounds; alone or as formulated) that is sufficient to achieve a desired biological effect. Combined with the teachings provided herein, by choosing among the various active compounds and weighing factors such as potency, relative bioavailability, patient body weight, severity of adverse side-effects and mode of administration, an effective prophylactic (i.e. preventative) or therapeutic treatment regimen can be planned which does not cause substantial unwanted toxicity and yet is effective to treat the particular condition or disease of a particular subject. The effective amount for any particular indication can vary depending on such factors as the disease or condition being treated, the particular compound of the present application being administered, the size of the subject, or the severity of the disease or condition. The effective amount may be determined during pre-clinical trials and/or clinical trials by methods familiar to physicians and clinicians. One of ordinary skill in the art can empirically determine the effective amount of a particular compound of the present application and/or other therapeutic agent(s) without necessitating undue experimentation. A maximum dose may be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein. A dose may be administered by oneself, by another or by way of a device (e.g. a pump).

For any compound described herein the therapeutically effective amount can be initially determined from animal models. A therapeutically effective dose can also be determined from human data for compounds which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

Compounds (alone or as formulated in a pharmaceutical composition) for use in therapy or prevention can be tested in suitable animal model systems. Suitable animal model systems include, but are not limited to, rats, mice, chicken, cows, monkeys, rabbits, pigs, minipigs and the like, prior to testing in human subjects. In vivo testing, any of the animal model system known in the art can be used prior to administration to human subjects.

Dosage, toxicity and therapeutic efficacy of any therapeutic compounds, compositions (e.g. formulations or medicaments), other therapeutic agents, or mixtures thereof can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

In some embodiments, an effective amount of a therapeutic compound disclosed herein sufficient for achieving a therapeutic or prophylactic effect, can range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In some embodiments, a single dosage of a therapeutic compound disclosed herein ranges from 0.001-10,000 micrograms per kg body weight. In some embodiments, a therapeutic compound disclosed herein dissolved or suspended in a carrier range from 0.2 to 2000 micrograms per delivered milliliter.

An exemplary treatment regime can entail administration once per day, twice per day, trice per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regimen.

In some embodiments, a therapeutically effective amount of a therapeutic compound disclosed herein may be defined as a concentration of compound existing at the target tissue of $10^{12}$ to $10^{6}$ molar, e.g., approximately $10^{7}$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g, oral, systemic, topical, subcutaneous, parenteral infusion or transdermal application)

In some embodiments, intravenous or subcutaneous administration of a compound (alone or as formulated) may typically be from 0.01 µg/kg/day to 20 mg/kg/day. In some embodiments, intravenous or subcutaneous administration of a compound (alone or as formulated) may typically be from 0.01 µg/kg/day to 100 µg/kg/day. In some embodiments, intravenous or subcutaneous administration of a compound (alone or as formulated) may typically be from 0.1 µg/kg/day to 1 mg/kg/day. In some embodiments, intravenous or subcutaneous administration of a compound (alone or as formulated) may typically be from 10 µg/kg/day to 2 mg/kg/day. In some embodiments, intravenous or subcutaneous administration of a compound (alone or as formulated) may typically be from 500 µg/kg/day to 5 mg/kg/day. In some embodiments, intravenous or subcutaneous administration of a compound (alone or as formulated) may typically be from 1 mg/kg/day to 20 mg/kg/day. In some embodiments, intravenous or subcutaneous administration of a compound (alone or as formulated) may typically be from 1 mg/kg/day to 10 mg/kg/day.

Generally, daily oral doses of a compound (alone or as formulated) will be, for human subjects, from about 0.01 micrograms/kg per day to 100 milligrams/kg per day. In some embodiments, daily oral doses of a compound (alone or as formulated) will be, for human subjects, from about 1 milligrams/kg per day to 100 milligrams/kg per day or from about 10 milligrams/kg per day to 75 milligrams/kg per day or It is expected that oral doses of a compound (alone or as formulated) in the range of 0.1 to 50 milligrams/kg, in one or more administrations per day, will yield therapeutic results. Dosage may be adjusted appropriately to achieve desired drug levels, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of the compound.

For use in therapy, an effective amount of the compound (alone or as formulated) can be administered to a subject by any mode that delivers the compound to the desired surface. Administering a pharmaceutical composition may be accomplished by any means known to the skilled artisan. Routes of administration include but are not limited to oral, topical, intranasal, systemic, intravenous, subcutaneous, intraperitoneal, intradermal, intraocular, ophthalmical, intrathecal, intracerebroventricular, iontophoretical, transmucosal, intravitreal, or intramuscular administration. Administration includes self-administration, the administration by another and administration by a device.

The formulations of the present application can be administered in pharmaceutically acceptable solutions, which may routinely contain pharmaceutically acceptable concentrations of salt, (e.g. NaCl or sodium phosphate), buffering agents, preservatives, compatible carriers, adjuvants, and optionally other therapeutic ingredients.

A therapeutic compound disclosed herein can be delivered to the subject in a formulation or medicament (i.e. a pharmaceutical composition). Formulations and medicaments can be prepared by, for example, dissolving or suspending a therapeutic compound disclosed herein in water or a carrier (i.e. a pharmaceutically acceptable carrier). For example, the formulations and medicaments of the present application can be administered in pharmaceutically acceptable solutions, which may routinely contain pharmaceutically acceptable concentrations of salt, buffering agents, preservatives, compatible carriers, adjuvants, and optionally other therapeutic ingredients.

The pharmaceutical compositions (e.g. a formulation or medicament) can include a carrier, which can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Solutions or suspensions (e.g. a formulation or medicament) used for parenteral, intradermal, subcutaneous or intraocular application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided alone or in a kit containing all necessary equipment (e.g., vials of drug, vials of diluent, syringes and needles) for a treatment course (e.g, 2, 3, 4, 5, 6, 7 days or more of treatment).

Systemic formulations include those designed for administration by injection, e.g, subcutaneous, intravenous, intramuscular, intrathecal or intraperitoneal injection, as well as those designed for transdermal, transmucosal oral or pulmonary administration.

For intravenous and other parenteral routes of administration, a compound of the present application can be formulated as a lyophilized preparation, as a lyophilized preparation of liposome-intercalated or -encapsulated active compound, as a lipid complex in aqueous suspension, or as a salt complex. Lyophilized formulations are generally reconstituted in suitable aqueous solution, e.g, in sterile water or saline, shortly prior to administration.

Pharmaceutical compositions (e.g. a formulation or medicament) suitable for injection can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). A composition for administration by injection will generally be sterile and should be fluid to the extent that easy syringability exists. It should be stable under the conditions of manufacture and storage and must be preserved against the contaminating action of microorganisms such as bacteria and fungi.

Sterile injectable solutions (e.g. a formulation or medicament) can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, that contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

The therapeutic compounds or pharmaceutical compositions, when it is desirable to deliver them systemically, may be formulated for parenteral administration by injection, e.g., by bolus injection or continuous infusion (for example by IV injection or via a pump to meter the administration over a defined time). Formulations for injection may be presented in unit dosage form, e.g, in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical compositions for parenteral administration include aqueous solutions of the active compounds in water-soluble form. Additionally, suspensions of the therapeutic compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the therapeutic compounds to allow for the preparation of highly concentrated solutions.

For oral administration, the compounds can be formulated readily by combining the active compound(s) with pharmaceutically acceptable carriers well known in the art. Such carriers enable the compounds of the present application to be formulated as tablets, pills, dragees, capsules, liquids, gels, syrups, slurries, suspensions and the like, for oral ingestion by a subject to be treated. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel®, or corn starch; a lubricant such as magnesium stearate or sterates; a glidant such as colloidal silicon dioxide; a sweetening agent such as sucrose or saccharin; or a flavoring agent such as peppermint, methyl salicylate, or orange flavoring.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above may be chemically modified so that oral delivery of the derivative is efficacious. Generally, the chemical modification contemplated is the attachment of at least one moiety to the therapeutic agent(s), ingredient(s), and/or excipient(s), where said moiety permits (a) inhibition of acid hydrolysis; and (b) uptake into the blood stream from the stomach or intestine. Also desired is the increase in overall stability of the therapeutic agent(s), ingredient(s), and/or excipient(s) and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. For pharmaceutical usage, as indicated above, polyethylene glycol (PEG) moieties of various molecular weights are suitable.

For the formulation of the therapeutic agent(s), ingredient(s), and/or excipient(s), the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the present application (or derivative) or by release of the biologically active material beyond the stomach environment, such as in the intestine.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic compound or pharmaceutical composition can be included in the formulation as fine multiparticulates in the form of granules or pellets of particle size about 1-2 mm. The formulation of the material for capsule administration could also be as a powder, lightly compressed plugs or even as tablets. The therapeutic compound or pharmaceutical composition could be prepared by compression.

Colorants and flavoring agents may all be included. For example, the compound or pharmaceutical composition of the present application (or derivative) may be formulated and then further contained within an edible product, such as a refrigerated beverage containing colorants and flavoring agents.

One may dilute or increase the volume of the therapeutic compound or pharmaceutical composition with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo®, Emdex®, STARCH 1500®, Emcompress® and Avicel®.

Disintegrants may be included in the formulation of the therapeutic compound or composition into a solid dosage form. Materials used as disintegrates include but are not limited to starch, including the commercial disintegrant based on starch, Explotab. Sodium starch glycolate, Amberlite®, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, karaya gum or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol (PEG) of various molecular weights, Carbowax™ 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic compound or composition into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the present application or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For topical administration, the compound may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

For administration by inhalation, compounds or compositions (e.g. medicament) for use according to the present application may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In some embodiments, the formulation, medicament or therapeutic compound can be delivered in the form of an aerosol spray from a pressurized container or dispenser, which contains a suitable propellant, e.g., a gas such as carbon dioxide, or a nebulizer. Such methods include those described in U.S. Pat. No. 6,468,798. In the case of a pressurized aerosol the dosage unit may be determined by providing a valve to deliver a metered amount. In the case of a pressurized aerosol the dosage unit may be determined by providing a valve to deliver a metered amount. For example, capsules and cartridges of e.g., gelatin for use in an inhaler or insufflator may be formulated containing a powder mix of the therapeutic compound and a suitable powder base such as lactose or starch.

Nasal delivery of a therapeutic compound or pharmaceutical composition of the present application is also contemplated. Nasal delivery allows the passage of a therapeutic compound or pharmaceutical composition of the present application to the blood stream directly after administering the therapeutic compound or pharmaceutical composition to the nose, without the necessity for deposition of the product in the lung. Formulations for nasal delivery include those with dextran or cyclodextran.

For nasal administration, a useful device is a small, hard bottle to which a metered dose sprayer is attached. In some embodiments, the metered dose is delivered by drawing the pharmaceutical composition of the present application solution into a chamber of defined volume, which chamber has an aperture dimensioned to aerosolize and aerosol formulation by forming a spray when a liquid in the chamber is compressed. The chamber is compressed to administer the therapeutic compound or pharmaceutical composition. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the therapeutic compound or pharmaceutical composition.

Alternatively, the therapeutic compound or pharmaceutical composition may be in powder form for constitution with a suitable vehicle, e.g., sterile pyrogen-free water, before use. Also contemplated herein is pulmonary delivery of the compounds disclosed herein (or salts thereof). The compound or pharmaceutical composition is delivered to the lungs of a mammal while inhaling and traverses across the lung epithelial lining to the blood stream. Other reports of inhaled molecules include Adjei et al., *Pharm Res* 7:565-569 (1990); Adjei et al., *IntJ Pharmaceutics* 63:135-144 (1990) (leuprolide acetate); Braquet et al., *J Cardiovasc Pharmacol* 13(suppl. 5): 143-146 (1989) (endothelin-1); Hubbard et al., *Annal Int Med* 3:206-212 (1989) (α1-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colorado, March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor; incorporated by reference). A method and composition for pulmonary delivery of drugs for systemic effect is described in U.S. Pat. No. 5,451,569 (incorporated by reference), issued Sep. 19, 1995 to Wong et al.

Contemplated for use in the practice of this technology are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this technology are the Ultravent™ nebulizer, manufactured by Mallinckrodt, Inc., St. Louis, Mo.; the Acorn II® nebulizer, manufactured by Marquest Medical Products, Englewood, Colo.; the Ventolin® metered dose inhaler, manufactured by Glaxo Inc., Research Triangle Park, North Carolina; and the Spinhaler® powder inhaler, manufactured by Fisons Corp., Bedford, Mass.

All such devices require the use of formulations suitable for the dispensing of the compounds of the present application. Typically, each formulation is specific to the type of device employed and may involve the use of an appropriate propellant material, in addition to the usual diluents, adjuvants and/or carriers useful in therapy. Also, the use of liposomes, microcapsules, microspheres, nanoparticles, nanospheres, inclusion complexes, or other types of carriers is contemplated. Chemically modified compound of the present application may also be prepared in different formulations depending on the type of chemical modification or the type of device employed.

Formulations suitable for use with a nebulizer, either jet or ultrasonic, can, for example, comprise a compound of the present application (or derivative) dissolved in water at a concentration of about 0.01 to 50 mg of biologically active compound per mL of solution. The formulation may also include a buffer and a simple sugar (e.g., for inhibitor stabilization and regulation of osmotic pressure). The nebulizer formulation may also contain a surfactant, to reduce or prevent surface induced aggregation of the compound of the present application caused by atomization of the solution in forming the aerosol.

Formulations for use with a metered-dose inhaler device may generally comprise a finely divided powder containing the compound of the present application (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device may comprise a finely divided dry powder containing compound of the present application (or derivative) and may also include a bulking agent, such as lactose, sorbitol, sucrose, or mannitol in amounts which facilitate dispersal of the powder from the device, e.g., 50 to 90% by weight of the formulation. The compound of the present application (or derivative) can advantageously be prepared in particulate or nanoparticulate form with an average particle size of less than 10 micrometers (μm), most preferably 0.5 to 5 μm, for most effective delivery to the deep lung.

Nasal delivery of a pharmaceutical composition of the present application is also contemplated. Nasal delivery allows the passage of a pharmaceutical composition of the present application to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present application solution into a chamber of defined volume, which chamber has an aperture dimensioned to aerosolize and aerosol formulation by forming a spray when a liquid in the chamber is compressed. The chamber is compressed to administer the pharmaceutical composition of the present application. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, optionally with an added preservative. Said formulations could be delivered from an IV bag, injected via syringe or via a pen injector device. The formulations/compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g, sterile pyrogen-free water, before use.

The compounds may also be formulated in rectal or vaginal compositions such as suppositories or retention enemas, e.g., containing conventional suppository bases such as cocoa butter or other glycerides.

For ophthalmic or intraocular indications, any suitable mode of delivering the therapeutic compounds or pharmaceutical compositions to the eye or regions near the eye can be used. For ophthalmic formulations generally, see Mitra (ed.), *Ophthalmic Drug Delivery Systems*, Marcel Dekker, Inc., New York, N.Y. (1993) and also Havener, W. H., *Ocular Pharmacology*, C. V. Mosby Co., St. Louis (1983). Nonlimiting examples of pharmaceutical compositions suitable for administration in or near the eye include, but are not limited to, ocular inserts, minitablets, and topical formulations such as eye drops, ointments, and in situ gels. In one embodiment, a contact lens is coated with a pharmaceutical composition comprising a therapeutic compound disclosed herein. In some embodiments, a single dose comprises from between 0.1 ng to 5000 µg, 1 ng to 500 µg, or 10 ng to 100 µg of the therapeutic compounds or pharmaceutical compositions administered to the eye.

Eye drops can comprise a sterile liquid formulation that can be administered directly to the eye. In some embodiments, eye drops comprise at least one therapeutic compound disclosed herein and may further comprise one or more preservatives. In some embodiments, the optimum pH for eye drops equals that of tear fluid and is about 7.4.

In situ gels are viscous liquids, showing the ability to undergo sol-to-gel transitions when influenced by external factors, such as appropriate pH, temperature, and the presence of electrolytes. This property causes slowing of drug drainage from the eyeball surface and increase of the active ingredient bioavailability. Polymers commonly used in in situ gel formulations include, but are not limited to, gellan gum, poloxamer, silicone containing formulations and cellulose acetate phthalate. In some embodiments, the therapeutic compound is formulated into an in-situ gel (as the pharmaceutical composition).

For topical ophthalmic administration, therapeutic compound or pharmaceutical composition may be formulated as solutions, gels, ointments, creams, suspensions, etc. as are well-known in the art. Ointments are semisolid dosage forms for external use such as topical use for the eye or skin. In some embodiments, ointments comprise a solid or semi-solid hydrocarbon base of melting or softening point close to human core temperature. In some embodiments, an ointment applied to the eye decomposes into small drops, which stay for a longer time period in conjunctival sac, thus increasing bioavailability.

Ocular inserts are solid or semisolid dosage forms without disadvantages of traditional ophthalmic drug forms. They are less susceptible to defense mechanisms like outflow through nasolacrimal duct, show the ability to stay in conjunctival sac for a longer period, and are more stable than conventional dosage forms. They also offer advantages such as accurate dosing of one or more therapeutic compounds, slow release of one or more therapeutic compounds with constant speed and limiting of one or more therapeutic compounds' systemic absorption. In some embodiments, an ocular insert comprises one or more therapeutic compounds as disclosed herein and one or more polymeric materials. The polymeric materials can include, but are not limited to, methylcellulose and its derivatives (e.g., hydroxypropyl methylcellulose (HPMC)), ethylcellulose, polyvinylpyrrolidone (PVP K-90), polyvinyl alcohol, chitosan, carboxymethyl chitosan, gelatin, and various mixtures of the aforementioned polymers. An ocular insert can comprise silica. An ocular insert can comprise can comprise liposomes, nanoparticles or microparticles of degradable or biodegradable polymer (as described in more detail below).

Minitablets are biodegradable, solid drug forms, that transit into gels after application to the conjunctival sac, thereby extending the period of contact between active ingredient (i.e. the therapeutic compound disclosed herein) and the eyeball surface, which in turn increases a therapeutic compounds' bioavailability. The advantages of minitablets include easy application to conjunctival sac, resistance to defense mechanisms like tearing or outflow through nasolacrimal duct, longer contact with the cornea caused by presence of mucoadhesive polymers, and gradual release of the active ingredient from the formulation in the place of application due to the swelling of the outer carrier layers. Minitablets can comprise one or more of the therapeutic compounds disclosed herein and one or more polymers. Nonlimiting examples of polymers suitable for use in in a minitablet formulation include cellulose derivatives, like hydroxypropyl methylcellulose (HPMC), hydroxyethyl cellulose (HEC), sodium carboxymethyl cellulose, ethyl cellulose, acrylates (e.g., polyacrylic acid and its cross-linked forms), Carbopol® or carbomer, chitosan, and starch (e.g., drum-dried waxy maize starch). In some embodiments, minitablets further comprise one or more excipients. Nonlimiting examples of excipients include mannitol and magnesium stearate.

The ophthalmic or intraocular formulations and medicaments may contain non-toxic auxiliary substances such as antibacterial components which are non-injurious in use, for example, thimerosal, benzalkonium chloride, methyl and propyl paraben, benzyldodecinium bromide, benzyl alcohol, or phenyl ethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

In some embodiments, the viscosity of the ocular formulation comprising one or more therapeutic compounds is increased to improve contact with the cornea and bioavailability in the eye. Viscosity can be increased by the addition of hydrophilic polymers of high molecular weight which do not diffuse through biological membranes and which form three-dimensional networks in the water. Nonlimiting examples of such polymers include polyvinyl alcohol, poloxamers, hyaluronic acid, carbomers, and polysaccharides, cellulose derivatives, gellan gum, and xanthan gum.

In some embodiments, the ocular formulation can be injected into the eye, for example as a sol-gel. In some embodiments, the ocular formulation is a depot formulation such as a controlled release formulation. Such controlled release formulation may comprise particles, such as microparticles or nanoparticles.

In addition to the formulations described above, a therapeutic compound disclosed herein may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms can, for example, be aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions can be suitable for use in a variety of drug delivery systems. For a brief review of methods for drug delivery, see Langer R, *Science* 249:1527-33 (1990).

The therapeutic agent(s), including specifically but not limited to a compound of the present application, may be provided in particles. Particles as used herein means nanoparticles or microparticles (or in some instances larger particles) which can consist in whole or in part of the compound of the present application or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the present application in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, polyethylene glycols (PEGs), polyvinylalcohols (PVAs), poly(methyl methacrylates), poly(ethyl methacrylates), poly(butylmethacrylate), poly(isobutyl methacrylate), poly(lactic-co-glycolic) acid (PLGA), poly(hexylmethacrylate), poly(isodecyl methacrylate), poly(lauryl methacrylate), poly (phenyl methacrylate), poly(methyl acrylate), poly (isopropyl acrylate), poly(isobutyl acrylate), poly(octadecyl acrylate) and poly(s-caprolactone) or mixtures of two or more of the foregoing.

A therapeutic compound or other therapeutic agent or mixtures thereof can be formulated in a carrier system. The carrier can be a colloidal system. The carrier or colloidal system can be a liposome, a phospholipid bilayer vehicle. In one embodiment, therapeutic compound or other therapeutic agent or mixtures thereof can be encapsulated in a liposome while maintaining integrity of the therapeutic compound or other therapeutic agent or mixtures thereof. One skilled in the art would appreciate that there are a variety of methods to prepare liposomes. (See Lichtenberg, et al., *Methods Biochem. Anal,* 33:337-462 (1988); Anselem, et al., *Liposome Technology,* CRC Press (1993)). Liposomal formulations can delay clearance and increase cellular uptake (See Reddy, *Ann. Pharmacother.,* 34(7-8):915-923 (2000)). For example, an active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic compound or other therapeutic agent or mixtures thereof can be embedded in the polymer matrix, while maintaining integrity of the composition. The polymer can be a microparticle or nanoparticle that encapsulates the therapeutic agent or agents. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or poly lactic/glycolic acid (PLGA). The polymeric matrices can be prepared and isolated in a variety of forms and sizes, including microspheres and nanospheres. Polymer formulations can lead to prolonged duration of therapeutic effect. (See Reddy, *Ann. Pharmacother.,* 34(7-8):915-923 (2000)). A polymer formulation for human growth hormone (hGH) has been used in clinical trials. (See Kozarich and Rich, *Chemical Biology,* 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compound or other therapeutic agent or mixtures thereof are prepared with carriers that will protect the therapeutic compound, other therapeutic agent or mixtures thereof against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compound(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant or depot formulation may be particularly suitable for treatment of chronic conditions. The term "implant" and "depot formulation" is intended to include a single composition (such as a mesh) or composition comprising multiple components (e.g. a fibrous mesh constructed from several individual pieces of mesh material) or a plurality of individual compositions where the plurality remains localized and provide the long-term sustained release occurring from the aggregate of the plurality of compositions. "Long-term" release, as used herein, means that the implant or depot formulation is constructed and arranged to deliver therapeutic or prophylactic levels of the active ingredient for at least 2 days. In some embodiments, the implant or depot formulation is constructed and arranged to deliver therapeutic or prophylactic levels of the active ingredient for at least 7 days. In some embodiments, the implant or depot formulation is constructed and arranged to deliver therapeutic or prophylactic levels of the active ingredient for at least 14 days. In some embodiments, the implant or depot formulation is constructed and arranged to deliver therapeutic or prophylactic levels of the active ingredient for at least 30 days. In some embodiments, the implant or depot formulation is constructed and arranged to deliver therapeutic or prophylactic levels of the active ingredient for at least 60 days. In some embodiments, the implant or depot formulation is constructed and arranged to deliver therapeutic or prophylactic levels of the active ingredient for at least 90 days. In some embodiments, the implant or depot formulation is constructed and arranged to deliver therapeutic or prophylactic levels of the active ingredient for at least 180 days. In some embodiments, the implant or depot formulation is constructed and arranged to deliver therapeutic or prophylactic levels of the active ingredient for at least one year. In some embodiments, the implant or depot formulation is constructed and arranged to deliver therapeutic or prophylactic levels of the active ingredient for 15-30 days. In some embodiments, the implant or depot formulation is constructed and arranged to deliver therapeutic or prophylactic levels of the active ingredient for 30-60 days. In some embodiments, the implant or depot formulation is constructed and arranged to deliver therapeutic or prophylactic levels of the active ingredient for 60-90 days. In some embodiments, the implant or depot formulation is constructed and arranged to deliver therapeutic or prophylactic levels of the active ingredient for 90-120 days. In some embodiments, the implant or depot formulation is constructed and arranged to deliver therapeutic or prophylactic levels of the active ingredient for 120-180 days. In some embodiments, the long-term sustained release implants or depot formulation are well-known to those of ordinary skill in the art and include some of the release systems described above. In some embodiments, such implants or depot formulation can be administered surgically. In some embodiments, such implants or depot formulation can be administered topically or by injection.

It will be understood by one of ordinary skill in the relevant arts that other suitable modifications and adaptations to the compositions and methods described herein are readily apparent from the description of the present technology contained herein in view of information known to the ordinarily skilled artisan, and may be made without departing from the scope of the present application or any embodiment thereof.

V. Compounds & Compositions Useful for Treating Mitochondrial Disease (e.g., Friedreich's Ataxia) and Intermediates Related Thereto (a) Therapeutic Compounds (i.e. Agents)

In some embodiments, the present application pertains to novel compounds and compositions (comprising said compounds) useful for treating mitochondrial disease such as Friedreich's ataxia in a mammalian subject. Said compounds and compositions can be formulated in any way suitable for administration to the subject. Various possible modes of administration have been previously discussed. Said compounds and compositions can, for example, be formulated as a tablet (for oral administration) or in solution for subcutaneous injection or intravenous injection. In some embodiments, said compounds and compositions can be used to prepare medicaments.

In some embodiments, the present application pertains to compounds represented by the formula A-B, or pharmaceutically acceptable salts, stereoisomers, mixtures of stereoisomers, tautomers, hydrates, and/or solvates thereof, wherein A is a head-group of formula 1 or 2:

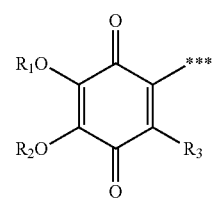

-continued

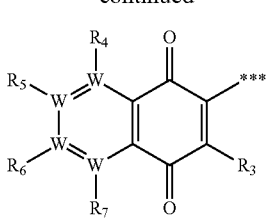

2 and B is a tail-group of formula 3, 4, 5, 6, 7, 8, 9, 10, or 11:

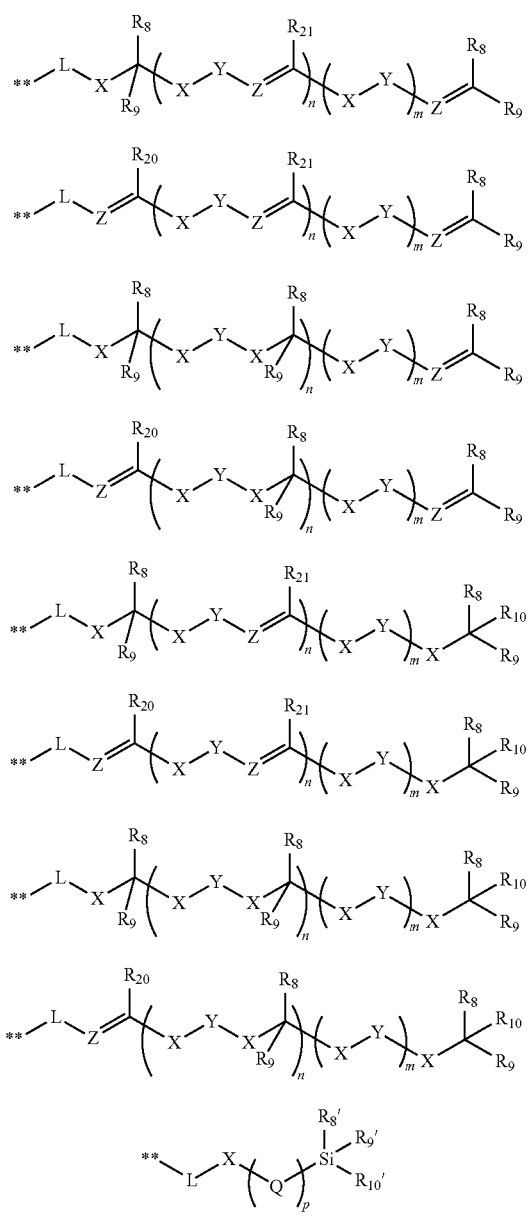

wherein, each Q is independently a group of formula —$(CR_{12}R_{13})$—, O or $Si(CH_3)_2$, provided that each O and each $Si(CH_3)_2$ is not directly bonded to O or $Si(CH_3)_2$; each of $R_1$ and $R_2$ is independently H, D, or $C_1$-$C_6$ alkyl, or $R_1$ and $R_2$ together form a 5-membered heterocyclic ring or a 6-membered heterocyclic ring; $R_3$ is independently H, D, F, Cl, Br, I, $C_1$-$C_6$ alkyl or $C_1$-$C_6$ alkoxy; each W is independently C (carbon) or N (nitrogen) and wherein for each use of W=W, the bond between each W can be a single bond or double bond and further provided that if a single bond, each C (carbon) atom will have a hydrogen atom linked hereto in addition to one of $R_4$, $R_5$, $R_6$ or $R_7$; and where (i) if W is C (carbon), each of $R_4$, $R_5$, $R_6$ and $R_7$ attached thereto is independently H, D, F, Cl, Br, I, $C_1$-$C_6$ alkyl or $C_1$-$C_6$ alkoxy, and (ii) if W is N (nitrogen), each of $R_4$, $R_5$, $R_6$ and $R_7$ attached thereto is independently absent or selected from H, D or $C_1$-$C_6$ alkyl; L is absent or —$(CR_{12}R_{13})$—; each X is independently a group of formula —$(CR_{12}R_{13})$—; each Y is independently absent or a group of formula —$(CR_{12}R_{13})$—; each Z is independently a group of formula —$(CR_{14})$—; each of $R_8$ and $R_9$ is independently H, D, F, Cl, Br, I, $C_1$-$C_4$ alkyl or $C_1$-$C_8$ alkoxy, or taken together, the $R_8$ and $R_9$, of a group of the formula —$(CR_8R_9)$—, —$(CR_8R_9)$ or —$(CR_8R_9R_{10})$, form a 3-, 4-, 5-, 6- or 7-membered carbocyclic or heterocyclic ring; each $R_8'$, $R_9'$ and $R_{10}'$ is independently Cl, Br, I, $C_1$-$C_4$ alkyl or $C_1$-$C_4$ alkoxy, or taken together $R_8'$ and RC form a 3-, 4-, 5-, 6- or 7-membered carbocyclic or heterocyclic ring; $R_{10}$ is H, D, F, Cl, Br, I, $C_1$-$C_6$ alkyl or $C_1$-$C_6$ alkoxy; each $R_{12}$, $R_{13}$ and $R_{14}$ is independently H, D, F, Cl, Br, I, $C_1$-$C_8$ alkyl, $C_1$-$C_8$ alkoxy, $C_3$-$C_6$ cycloalkyl, $C_1$-$C_6$ alkenyl, $C_1$-$C_6$ alkynyl, $C_1$-$C_6$ heteroalkyl, $C_6$-$C_{14}$ aryl or —$NR_{22}R_{23}$, or taken together, the $R_{12}$ and $R_{13}$, of a group of the formula —$(CR_{12}R_{13})$—, form a 3-, 4-, 5-, 6- or 7-membered carbocyclic or heterocyclic ring; $R_{20}$ is H, D, F, $C_1$-$C_{12}$ alkyl or $C_3$-$C_6$ cycloalkyl; each $R_{21}$ is independently H, D, F, Cl, Br, I, or $C_1$-$C_4$ alkyl; each of $R_{22}$ and $R_{23}$ is independently H, D, $C_1$-$C_4$ alkyl, or taken together, the $R_{22}$ and $R_{23}$, of the group of formula —$NR_{22}R_{23}$, form a 3-, 4-, 5-, 6- or 7-membered carbocyclic or heterocyclic ring; m is 0 or 1; n is an integer from 0 to 12, inclusive (i.e., 0, 1, 2, 3, 4, 5, 6, 7, 8, 9, 10, 11, or 12); p is an integer from 0 to 20, inclusive (i.e., 0, 1, 2, 3, 4, 5, 6, 7, 8, 9, 10, 11, 12, 13, 14, 15, 16, 17, 18, 19 or 20); and * indicates the point of attachment of A to B and  indicates the point of attachment of B to A; and further provided that:
(i) at least one of $R_8$, $R_9$, or $R_{10}$: (a) is F, or (b) is a group that comprises at least one fluorine atom; or (ii) at least one $R_8$ and $R_9$, of a group of the formula —$(CR_8R_9)$—, —$(CR_8R_9)$ or —$(CR_8R_9R_{10})$, taken together forms a 3-, 4-, 5-, 6- or 7-membered carbocyclic or heterocyclic ring; or (iii) the compound of formula A-B has a calculated Log D of 2 to 7, inclusive. In some embodiments, if B is 7, then n cannot be 0. In some embodiments, B is 9, each of m and n is independently 0 or 1, provided that if m+n=2, then L is absent, and at least one of $R_8$, $R_9$, or $R_{10}$ is F. In some embodiments, B is 9, m+n=0, 1 or 2, provided that if m+n=2, then L is absent and each of $R_8$, $R_9$, and $R_{10}$ is F.

Any combination of head-group 1 and 2 (i.e. "A") with tail-group 3, 4, 5, 6, 7, 8, 9, 10, or 11 (i.e. "B") is permissible. In some embodiments, A is 1 and B is 3, 4, 9 or 10. In some embodiments, A is 1 and B is 5, 6, 7 or 8. In some embodiments, A is 1 and B is 3, 5, 7 or 9. In some embodiments, A is 1 and B is 4, 6, 8 or 10. In some embodiments, A is 1 and B is 11. In some embodiments, A is 2 and B is 3, 4, 9 or 10. In some embodiments, A is 2 and B is 5, 6, 7 or 8. In some embodiments, A is 2 and B is 3, 5, 7 or 9. In some embodiments, A is 2 and B is 4, 6, 8 or 10. In some embodiments, A is 2 and B is 11. In some embodiments, A is 1 and B is 3. In some embodiments, A is 1 and B is 4. In some embodiments, A is 1 and B is 5. In some embodiments, A is 1 and B is 6. In some embodiments, A is 1 and B is 7. In some embodiments, A is 1 and B is 8. In some embodiments, A is 1 and B is 9. In some embodiments, A is 1 and B is 10. In some embodiments, A is 1 and B is 11. In some embodiments, A is 2 and B is 3. In some embodiments, A is 2 and B is 4. In some embodiments, A is 2 and B is 5. In some embodiments, A is 2 and B is 6. In some embodiments, A is 2 and B is 7. In some embodiments, A is 2 and B is 8. In some embodiments, A is 2 and B is 9. In some embodiments, A is 2 and B is 10. In some embodiments, A is 2 and B is 11.

Generally for the compound A-B, any combination of head-group 1 with tail-group 3, 4, 5, 6, 7, 8, 9, 10, or 11, in combination with any possible value for m and n is permissible; provided that: (i) if B is 3, one of m or n is 1; (ii) if B is 5, m is not 0; (iii) if B is 7, then n is not 0; (iv) if B is 9, then m+n=0 or 1; and in some embodiments, $R_8$, $R_9$ and $R_{10}$ are selected from H, D, F, —$CH_3$, $CH_2F$, $CHF_2$ and $CF_3$. For example, in some embodiments, A is 1, B is 3, m is 1 and n is 0, or A is 1, B is 3, m is 0 and n is 1, or A is 1, B is 3, m is 1 and n is 1. In some embodiments, A is 1, B is 4, m is 0 and n is 0, or A is 1, B is 4, m is 1 and n is 0, or A is 1, B is 4, m is 1 and n is 1, or A is 1, B is 4, m is 0 and n is 1. In some embodiments, A is 1, B is 5, m is 1 and n is 0, or A is 1, B is 5, m is 1 and n is 1. In some embodiments, A is 1, B is 6, m is 0 and n is 0, or A is 1, B is 6, m is 1 and n is 0, or A is 1, B is 6, m is 1 and n is 1, or A is 1, B is 6, m is 0 and n is 1. In some embodiments, A is 1, B is 7, m is 0 and n is 1, or A is 1, B is 7, m is 1 and n is 1. In some embodiments, A is 1, B is 8, m is 0 and n is 0, or A is 1, B is 8, m is 1 and n is 0, or A is 1, B is 8, m is 1 and n is 1, or A is 1, B is 8, m is 0 and n is 1. In some embodiments, A is 1, B is 9, m is 0 and n is 0, or A is 1, B is 9, m is 1 and n is 0, or A is 1, B is 9, m is 0 and n is 1. In some embodiments, A is 1, B is 10, m is 0 and n is 0, or A is 1, B is 10, m is 1 and n is 0, or A is 1, B is 10, m is 1 and n is 1, or A is 1, B is 10, m is 0 and n is 1.

In some embodiments (i.e. any of the forgoing recited embodiments of A-B), the group represented by L is absent. In some embodiments (i.e. any of the forgoing recited embodiments of A-B), the group represented by L is —$(CR_{12}R_{13})$—. In some embodiments, L is —$(CH_2)$—, —$(CD_2)$-, —(CHF)—, —$(CF_2)$—, —$(CH(CH_3))$—, —$(CD(CD_3))$-, —$(CF(CH_3))$—, —$(CH(CF_3))$—, —$(CF(CF_3))$—, —$(C(CH_3)_2)$—, —$(C(CD_3)_2)$-, —$(C(CF_3)_2)$—, —(CH(OCH_3))—, —(CD(OCD_3))-, —(CF(OCH_3))—, —(CH(OCF_3))—, —(CF(OCF_3))—, —$(C(OCH_3)_2)$—, —$(C(OCD_3)_2)$-, —$(C(OCF_3)_2)$—, —$(C(CH_3)(CF_3))$—, —$(C(CD_3)(CF_3))$—, —$(CH(CH_2CH_3))$—, —$(CD(CD_2CD_3))$-, —$(CF(CH_2CH_3))$—, —$(CH(CH_2CF_3))$—, —$(CH(CF_2CF_3))$—, —$(CF(CF_2CF_3))$—, —$(C(CH_2CH_3)_2)$—, —$(C(CD_2CD_3)_2)$— or —$(C(CF_2CF_3)_2)$—. In some embodiments, L is —$(CH_2)$—, —$(CD_2)$-, —$(CF_2)$—, —(CH(CH_3))—, —(CD(CD_3))-, —$(CF(CF_3))$—, —$(C(CH_3)_2)$—, —$(C(CD_3)_2)$-, —$(C(CF_3)_2)$—, —(CH(OCH_3))—, —(CD(OCD_3))-, —(CF(OCF_3))— or —$(C(OCH_3)_2)$—. In some embodiments, L is —$(CH_2)$—, —$(CD_2)$-, —(CHF)—, —$(CF_2)$—, —(CH(CH_3))—, —(CF(CF_3))—, —$(C(CH_3)_2)$— or —$(C(CF_3)_2)$—. In some embodiments, L is —$(CH_2)$—, —$(CD_2)$- or —$(CF_2)$—. In some embodiments, L is —$(CH_2)$—. In some embodiments, L is —$(CD_2)$-. In some embodiments, L is —$(CF_2)$—. In some embodiments, L is —(CHF)—. In some embodiments, L is —$(CR_{12}R_{13})$— and wherein taken together $R_{12}$ and $R_r$, form a 3-, 4-, 5-, 6- or 7-membered carbocyclic or heterocyclic ring.

In some embodiments of the compound represented by A-B, each X and each Y is independently —$(CH_2)$—, —$(CD_2)$-, —(CHF)—, —$(CF_2)$—, —(CH(CH_3))—, —(CD(CD_3))-, —(CF(CH_3))—, —(CH(CF_3))—, —(CF(CF_3))—, —$(C(CH_3)_2)$—, —$(C(CD_3)_2)$-, —$(C(CF_3)_2)$—, —(CH(OCH_3))—, —(CD(OCD_3))-, —(CF(OCH_3))—, —(CH(OCF_3))—, —(CF(OCF_3))—, —$(C(OCH_3)_2)$—, —$(C(OCD_3)_2)$-, —$(C(OCF_3)_2)$—, —$(C(CH_3)(CF_3))$—, —$(C(CD_3)(CF_3))$—, —$(CH(CH_2CH_3))$—, —$(CD(CD_2CD_3))$-, —$(CF(CH_2CH_3))$—, —$(CH(CH_2CF_3))$—, —$(CH(CF_2CF_3))$—, —$(CF(CF_2CF_3))$—, —$(C(CH_2CH_3)_2)$—, —$(C(CD_2CD_3)_2)$— or —$(C(CF_2CF_3)_2)$—. In some embodiments, each X and each Y is independently —$(CH_2)$—, —$(CD_2)$-, —$(CF_2)$—, —(CH(CH_3))—, —(CD(CD_3))-, —(CF(CF_3))—, —$(C(CH_3)_2)$—, —$(C(CD_3)_2)$-, —$(C(CF_3)_2)$—, —(CH(OCH_3))—, —(CD(OCD_3))-, —(CF(OCF_3))— or —$(C(OCH_3)_2)$—. In some embodiments, each X and each Y is independently —$(CH_2)$—, —$(CD_2)$-, —(CHF)—, —$(CF_2)$—, —(CH(CH_3))—, —(CF(CF_3))—, —$(C(CH_3)_2)$— or —$(C(CF_3)_2)$—. In some embodiments, each X and each Y is independently —$(CH_2)$—, —$(CD_2)$- or —$(CF_2)$—. In some embodiments, each X and each Y is —$(CH_2)$—. In some embodiments, each X and each Y is —$(CD_2)$-. In some embodiments, each X and each Y is —$(CF_2)$—. In some embodiments, each X and each Y is —(CHF)—. In some embodiments, at least one X or one Y is —$(CD_2)$-, —$(CF_2)$— or —(CHF)—. In some embodiments, at least one of X and Y is —$(CR_{12}R_{13})$—, wherein taken together $R_{12}$ and $R_{13}$ form a 3-, 4-, 5-, 6- or 7-membered carbocyclic or heterocyclic ring. In some embodiments, each X and Y is —$(CR_{12}R_{13})$—, wherein taken together each $R_{12}$ and $R_{13}$, with respect to each group of formula —$(CR_{12}R_{13})$—, form a 3-, 4-, 5-, 6- or 7-membered carbocyclic or heterocyclic ring.

In some embodiments of the compound represented by A-B, each X is —$(CH_2)$—. In some embodiments, each X is —$(CD_2)$-. In some embodiments, each X is —$(CF_2)$—. In some embodiments, each X is —(CHF)—. In some embodiments, each Y is —$(CH_2)$—. In some embodiments, each Y is —$(CD_2)$-. In some embodiments, each Y is —$(CF_2)$—. In some embodiments, each Y is —(CHF)—. In some embodiments, at least one X is —$(CD_2)$-, —$(CF_2)$— or —(CHF)—. In some embodiments, at least one X or one Y is —$(CD_2)$-, —$(CF_2)$— or —(CHF)—.

In some embodiments of the compound represented by A-B, each Z is independently —(CH)—, —(CD)-, —(CF)— or —$(C(CH_3))$—. In some embodiments, each Z is —(CH)—. In some embodiments, each Z is —(CD)-. In some embodiments, each Z is —(CF)—. In some embodiments, each Z is —$(C(CH_3))$—. In some embodiments, at least one Z is —(CD)- or —(CF)—.

In some embodiments of the compound represented by A-B, each Q is a group of formula —$(CR_{12}R_{13})$—. In some embodiments, each Q is a group of formula —$(CH_2)$—. In some embodiments, p is >2 and at least one Q is O and the other Qs are —$(CH_2)$—. In some embodiments, p is >2 and the group represented by -$(Q)_p$- comprises at least one ethylene glycol moiety (i.e. at least one group of formula —$OCH_2CH_2$—). In some embodiments, p is >3 and the group represented by -$(Q)_p$- comprises at least one propylene glycol moiety (i.e. at least one group of formula —$OCH_2CH_2CH_2$—). In some embodiments, the group represented by -$(Q)_p$- is a group of formula —$(OCH_2CH_2)_s$—, wherein s is 1, 2, 3, 4, 5 or 6. In some embodiments, the group represented by -$(Q)_p$- is a group of formula —$(OCH_2CH_2CH_2)_t$—, wherein t is 1, 2, 3, or 4.

In some embodiments of the compound represented by A-B, wherein A is 1, each of $R_a$ and $R_2$ is independently H, D, —$CH_3$, —$CD_3$, —$CH_2F$, —$CHF_2$, —$CF_3$, —$CH_2CH_3$, —$CH(CH_3)_2$, —$CD_2CD_3$, —$CD(CD_3)_2$, —$CF_2CH_3$, —$CF(CH_3)_2$, —$CH_2CF_3$, —$CH(CF_3)_2$, —$CF_2CF_3$, —$CF(CF_3)_2$, —$C(CH_3)_3$, —$C(CD_3)_3$, —$C(CF_3)_3$, —$C(CH_3)_2(CF_3)$, —C(CH₃)(CF₃)₂, —CH₂CH₂CH₃, —CH(CH₂CH₃)₂, —CD₂CD₂CD₃, —CD(CD₂CD₃)₂, —CF₂CH₂CH₃, —CF(CH₂CH₃)₂, —CH₂CF₂CF₃, —CH(CF₂CF₃)₂, —CF₂CF₂CF₃, —CF(CF₂CF₃)₂, or —OCH₂CH₂CH₃; and R₃ is H, D, Cl, F, —CH₃, —OCH₃, —CD₃, —OCD₃, —CH₂F, —OCH₂F, —CHF₂, —OCHF₂, —CF₃, —OCF₃, —CH₂CH₃, —CH(CH₃)₂, —CD₂CD₃, —CD(CD₃)₂, —CF₂CH₃, —CF(CH₃)₂, —CH₂CF₃, —CH(CF₃)₂, —CF₂CF₃, —CF(CF₃)₂, —C(CH₃)₃, —C(CD₃)₃, —C(CF₃)₃, —OCH₂CH₃, —OCH(CH₃)₂, —OCD₂CD₃, —OCD(CD₃)₂, —OCF₂CH₃, —OCF(CH₃)₂, —OCH₂CF₃, —OCF₂CF₃, —OCH(CF₃)₂, —OCF₂(CF₃), —OCF(CF₃)₂, —OC(CH₃)₃, —OC(CD₃)₃, —OC(CF₃)₃, —C(CH₃)₂(CF₃), —C(CH₃)(CF₃)₂, —OC(CH₃)₂(CF₃), —OC(CH₃)(CF₃)₂, —CH₂CH₂CH₃, —CH(CH₂CH₃)₂, —CD₂CD₂CD₃, —CD(CD₂CD₃)₂, —CF₂CH₂CH₃, —CF(CH₂CH₃)₂, —CH₂CF₂CF₃, —CH(CF₂CF₃)₂, —CF₂CF₂CF₃, —CF(CF₂CF₃)₂, —OCH₂CH₂CH₃, —OCH(CH₂CH₃)₂, —OCD₂CD₂CD₃, —OCD(CD₂CD₃)₂, —OCF₂CH₂CH₃, —OCF(CH₂CH₃)₂, —OCH₂CF₂CF₃, —OCH(CF₂CF₃)₂, —OCF₂CF₂CF₃ or —OCF(CF₂CF₃)₂. In some embodiments wherein A is 1, each of R₁ and R₂ is independently H, D, —CH₃, —CD₃, —CH₂F, —CHF₂, —CF₃, —C(CH₃)₃, —C(CD₃)₃, —C(CF₃)₃, —CH₂CH₃, or —CH(CH₃)₂; and R₃ is H, D, Cl, F, —CH₃, —OCH₃, —CD₃, —OCD₃, —CH₂F, —CHF₂, —CF₃, —OCF₃, —C(CH₃)₃, —C(CD₃)₃, —C(CF₃)₃, —OC(CH₃)₃, —OC(CD₃)₃, —OC(CF₃)₃, —CH₂CH₃, —OCH₂CH₃, or —CH(CH₃)₂. In some embodiments, wherein A is 1, each of R₁ and R₂ is independently and H, —CH₃, —CH₂F, —CHF₂, —CF₃, —C(CH₃)₃, —C(CF₃)₃, —CH₂CH₃, or —CH(CH₃)₂; and R₃ is H, F, —CH₃, —OCH₃, —CH₂F, —CHF₂, —CF₃, —OCF₃, —C(CH₃)₃, —C(CF₃)₃, —CH₂CH₃, —OCH₂CH₃, or —CH(CH₃)₂. In some embodiments wherein A is 1, each of R₁ and R₂ is H, —CH₃, or —CF₃; and R₃ is H, F, —CH₃, —OCH₃, —CF₃ or —OCF₃. In some embodiments wherein A is 1, each of R₁ and R₂ is —CH₃ or —CH₂CH₃; and R₃ is H, F, or —CH₃. In some embodiments wherein A is 1, each of R₁ and R₂ is —CH₃; and R₃ is H. In some embodiments wherein A is 1, each of R₁ and R₂ is —CH₃; and R₃ is F. In some embodiments wherein A is 1, each of R₁ and R₂ is —CH₃; and R₃ is —CH₃. In some embodiments wherein A is 1, each of R₁ and R₂ is —CH₃; and R₃ is —OCH₃. In some embodiments wherein A is 1, at least one of R₁, R₂ and R₃ comprises at least one fluorine atom. In some embodiments wherein A is 1, each of R₁ and R₂ is —CH₃; R₃ is H, F, CH₃ or —OCH₃ and at least one of R₈ and R₉ comprises a fluorine atom. In some embodiments wherein A is 1, each of R₁ and R₂ is —CH₃; R₃ is H, F, CH₃ or —OCH₃ and each of R₈ and R₉ comprises a fluorine atom. In some embodiments wherein A is 1, each of R₁ and R₂ is —CH₃; R₃ is H, F, CH₃ or —OCH₃ and each of R₈, R₉ and R₁₀ comprises a fluorine atom. In some embodiments wherein A is 1: (i) at least one of R₁, R₂ and R₃ comprises at least one fluorine atom; and/or (ii) at least one of R₈ and R₉ comprises a fluorine atom. In some embodiments wherein A is 1, each of R₁ and R₂ is —CH₃; R₃ is H, F, CH₃ or —OCH₃ and each of R₈ and R₉ is a fluorine atom. In some embodiments wherein A is 1, each of R₁ and R₂ is —CH₃; R₃ is H, F, CH₃ or —OCH₃ and each of R₈, R₉ and R₁₀ is a fluorine atom. In some embodiments wherein A is 1, each of R₁ and R₂ is —CH₃; R₃ is H, F, CH₃ or —OCH₃ and one of R₈, R₉ and R₁₀ is a fluorine atom and the others are hydrogen atoms. In some embodiments wherein A is 1, each of R₁ and R₂ is —CH₃; R₃ is H, F, CH₃ or —OCH₃ and two of R₈, R₉ and R₁₀ are a fluorine atoms and the other(s) is/are a hydrogen atom. In some embodiments wherein A is 1, each of R₁ and R₂ is —CH₃; R₃ is H, F, CH₃ or —OCH₃ and each R₈, R₉ and R₁₀ is a fluorine atom.

In some embodiments of the compound represented by A-B, wherein A is 1, (i) R₃ is H, D, Cl, F, —CH₃, —OCH₃, —CD₃, —OCD₃, —CF₃, —OCF₃, —C(CH₃)₃, —C(CD₃)₃, —C(CF₃)₃, —OC(CH₃)₃, —OC(CD₃)₃, —OC(CF₃)₃, —CH₂CH₃, —OCH₂CH₃, or —CH(CH₃)₂; and (ii) each of R₁ and R₂ is —CH₃, or taken together form a 5-, or 6-membered heterocyclic ring. In some embodiments wherein A is 1, (i) R₃ is H, D, F, —CH₃, —OCH₃, —CF₃ or —OCF₃; and (ii) R₁ and R₂ taken together form a 5-, or 6-membered heterocyclic ring. In some embodiments wherein A is 1; (i) R₃ is H, F, —CH₃, or —OCH₃, and (ii) R₁ and R₂ taken together form a 5-, or 6-membered heterocyclic ring. In some embodiments wherein A is 1; (i) R₃ is H; and (ii) R₁ and R₂ taken together form a 5-, or 6-membered heterocyclic ring. In some embodiments wherein A is 1; (i) R₃ is —CH₃; and (ii) R₁ and R₂ taken together form a 5-, or 6-membered heterocyclic ring. In some embodiments of the compound represented by A-B, wherein A is 1; (i) R₃ is —OCH₃; and (ii) R₁ and R₂ taken together form a 5-, or 6-membered heterocyclic ring. In some embodiments of the compound represented by A-B, wherein A is 1; (i) R₃ is F; and (ii) R₁ and R₂ taken together form a 5-, or 6-membered heterocyclic ring.

In some embodiments of the compound represented by A-B, A is a head-group of formula 1A, or 1B:

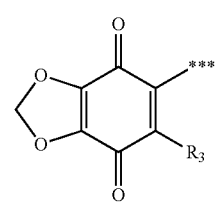

1A

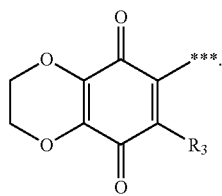

1B

In some embodiments of 1A or 1B, R₃ is H, F, —CH₃ or —OCH₃. In some embodiments of 1A or 1B, R₃ is H. In some embodiments of 1A or 1B, R₃ is F. In some embodiments of 1A or 1B, R₃ is —CH₃. In some embodiments of 1A or 1B, R₃ is —OCH₃.

In some embodiments of the compound represented by A-B, wherein A is 2, R₃ is H, D, F, Cl, —CH₃, —OCH₃, —CD₃, —OCD₃, —CH₂F, —OCH₂F, —CHF₂, —OCHF₂, —CF₃, —OCF₃, —CH₂CH₃, —CH(CH₃)₂, —CD₂CD₃, —CD(CD₃)₂, —CF₂CH₃, CF(CH₃)₂, —CH₂CF₃, —CH(CF₃)₂, —CF₂CF₃, —CF(CF₃)₂, —C(CH₃)₃, —C(CD₃)₃, —C(CF₃)₃, —OCH₂CH₃, —OCH(CH₃)₂, —OCD₂CD₃, —OCD(CD₃)₂, —OCF₂CH₃, —OCF(CH₃)₂, —OCH₂CF₃, —OCF₂CF₃, —OCH(CF₃)₂, —OCF₂(CF₃), —OCF(CF₃)₂, —OC(CH₃)₃, —OC(CD₃)₃, —OC(CF₃)₃, —C(CH₃)₂(CF₃), —C(CH₃)(CF₃)₂, —OC(CH₃)₂(CF₃), —OC(CH₃)(CF₃)₂, —CH₂CH₂CH₃, —CH(CH₂CH₃)₂, —CD₂CD₂CD₃, —CD(CD₂CD₃)₂, —CF₂CH₂CH₃, —CF(CH₂CH₃)₂, —CH₂CF₂CF₃, —CH(CF₂CF₃)₂, —CF₂CF₂CF₃, —CF(CF₂CF₃)₂, —OCH₂CH₂CH₃, —OCH(CH₂CH₃)₂, —OCD$_2$CD$_2$CD$_3$, —OCD(CD$_2$CD$_3$)$_2$, —OCF$_2$CH$_2$CH$_3$, —OCF(CH$_2$CH$_3$)$_2$, —OCH$_2$CF$_2$CF$_3$, —OCH(CF$_2$CF$_3$)$_2$, —OCF$_2$CF$_2$CF$_3$ or —OCF(CF$_2$CF$_3$)$_2$; and where if W is C (carbon), each of R$_4$, R$_5$, R$_6$ and R$_7$ attached thereto can be independently H, D, F, Cl, Br, I, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, or —CH(CH$_3$)$_2$, and where if W is N (nitrogen), each of R$_4$, R$_5$, R$_6$ and R$_7$ attached thereto can be independently absent or is H, D, methyl, ethyl, isopropyl or t-butyl. In some embodiments wherein A is 2, R$_3$ is H, D, Cl, F, —CH$_3$, —OCH$_3$, —CD$_3$, —OCD$_3$, —CH$_2$F, —CHF$_2$, —CF$_3$, —OCF$_3$, —C(CH$_3$)$_3$, —C(CD$_3$)$_3$, —C(CF$_3$)$_3$, —OC(CH$_3$)$_3$, —OC(CD$_3$)$_3$, —OC(CF$_3$)$_3$, —CH$_2$CH$_3$, —OCH$_2$CH$_3$, or —CH(CH$_3$)$_2$; and where if W is C (carbon), each of R$_4$, R$_5$, R$_6$ and R$_7$ attached thereto is independently H, D, F, Cl, —CH$_3$, —OCH$_3$, —CH$_2$F, —CHF$_2$, —CF$_3$, —OCF$_3$, —CH$_2$CH$_3$, or —CH(CH$_3$)$_2$, and where if W is N (nitrogen), each of R$_4$, R$_5$, R$_6$ and R$_7$ attached thereto is independently absent or is H, D, methyl or ethyl. In some embodiments wherein A is 2, R$_3$ is H, F, —CH$_3$, —OCH$_3$, —CF$_3$, or —OCF$_3$; and where if W is C (carbon), each of R$_4$, R$_5$, R$_6$ and R$_7$ attached thereto is independently H, F, —CH$_3$, —OCH$_3$, —CF$_3$, or —OCF$_3$, and where if W is N (nitrogen), each of R$_4$, R$_5$, R$_6$ and R$_7$ attached thereto is independently absent or is H, or methyl. In some embodiments wherein A is 2, each W is C (carbon) and each of R$_4$, R$_5$, R$_6$ and R$_7$ is independently H, D, Cl, F, —CH$_3$, —OCH$_3$, —CH$_2$F, —CHF$_2$, —CF$_3$ or —OCF$_3$. In some embodiments wherein A is 2, each W is C (carbon) and each of R$_4$, R$_5$, R$_6$ and R$_7$ is independently H, F, —CH$_3$, —OCH$_3$, —CF$_3$ or —OCF$_3$. In some embodiments wherein A is 2, each W is C (carbon) and each of R$_4$, R$_5$, R$_6$ and R$_7$ is independently H, F, —CH$_3$, or —OCH$_3$. In some embodiments wherein A is 2, each W is C (carbon) and each of R$_4$, R$_5$, R$_6$ and R$_7$ is H. In some embodiments wherein A is 2, each W is C (carbon) and each of R$_4$, R$_5$, R$_6$ and R$_7$ is F. In some embodiments wherein A is 2, each W is C (carbon) and each of R$_4$, R$_5$, R$_6$ and R$_7$ is —CH$_3$.

In some embodiments of the compound represented by A-B, each R$_8$ and R$_9$ is independently H, D, F, Cl, Br, I, —CH$_3$, —CD$_3$, —CH$_2$F, —CHF$_2$, —CF$_3$, —CH$_2$CH$_3$, —CH(CH$_3$)$_2$, —CD$_2$CD$_3$, —CD(CD$_3$)$_2$, —CF$_2$CH$_3$, —CF(CH$_3$)$_2$, —CH$_2$CF$_3$, —CH(CH$_2$F)$_2$, —CH(CF$_3$)$_2$, —CF$_2$CF$_3$, —CF(CF$_3$)$_2$, —C(CH$_3$)$_3$, —C(CD$_3$)$_3$, —C(CF$_3$)$_3$, —C(CH$_3$)$_2$(CF$_3$), —C(CH$_3$)(CF$_3$)$_2$, —CH$_2$CH$_2$CH$_3$, —CH(CH$_3$)CH$_3$, —CD$_2$CD$_2$CD$_3$, —CD(CD$_2$CD$_3$)$_2$, —CF$_2$CH$_2$CH$_3$, —CF(CH$_2$CH$_3$)$_2$, —CH$_2$CF$_2$CF$_3$, —CH(CF$_2$CF$_3$)$_2$, —CF$_2$CF$_2$CF$_3$ or —CF(CF$_2$CF$_3$)$_2$. In some embodiments of the compound represented by A-B, each R$_8$ and R$_9$ is independently H, F, —CH$_3$, —CH$_2$F, —CHF$_2$, —CF$_3$, —CH$_2$CH$_3$, —CH(CH$_3$)$_2$, —CF$_2$CH$_3$, —CH$_2$CF$_3$, —CH(CF$_3$)$_2$, —CF$_2$CF$_3$, —CF(CF$_3$)$_2$, —C(CH$_3$)$_3$, —C(CF$_3$)$_3$, —CH$_2$CH$_2$CH$_3$, —CH(CH$_2$F)$_2$, —CH(CH$_2$CH$_3$)$_2$, —CF$_2$CF$_2$CF$_3$ or —CF(CF$_2$CF$_3$)$_2$. In some embodiments of the compound represented by A-B, each R$_8$ and R$_9$ is independently H, F, —CH$_3$, —CF$_3$, —CH$_2$CH$_3$, —CH(CH$_3$)$_2$, —CH(CH$_2$F)$_2$, —CH(CF$_3$)$_2$, —CF$_2$CF$_3$, —CF(CF$_3$)$_2$, —C(CH$_3$)$_3$ or —C(CF$_3$)$_3$. In some embodiments of the compound represented by A-B, each R$_8$ and R$_9$ is independently H, F, —CH$_3$, —CF$_3$, —CH$_2$CH$_3$ or —CH(CH$_2$F)$_2$. In some embodiments of the compound represented by A-B, each R$_8$ and R$_9$ is independently H, F, —CH$_3$, —CH$_2$F, —CHF$_2$, or —CF$_3$. In some embodiments of the compound represented by A-B, each R$_8$ and R$_9$ is H. In some embodiments of the compound represented by A-B, each R$_8$ and R$_9$ is F. In some embodiments of the compound represented by A-B, one of R$_8$ and R$_9$ is F and the other(s) of R$_8$ and R$_9$ is/are H. In some embodiments of the compound represented by A-B, each R$_8$ and R$_9$ is —CH$_3$. In some embodiments of the compound represented by A-B, each R$_8$ and R$_9$ is —CH$_2$F. In some embodiments of the compound represented by A-B, each R$_8$ and R$_9$ is —CF$_3$. In some embodiments of the compound represented by A-B, at least one of R$_8$ and R$_9$ is —CF$_3$. In some embodiments of the compound represented by A-B, at least one of R$_8$ and R$_9$ is F. In some embodiments of the compound represented by A-B, at least one of R$_8$ and R$_9$ is —CH$_2$F.

In some embodiments of the compound represented by A-B, at least one R$_8$ and R$_9$, of a group of the formula —(CR$_8$R$_9$)—, —(CR$_8$R$_9$) or —(CR$_8$R$_9$R$_{10}$), taken together form a 3-, 4-, 5-, 6- or 7-membered carbocyclic or heterocyclic ring selected from a group of formula 31, 32, 33, 34, 35, 36, 37, 38, 39, 40, 41, 42, 43, 44, 45, 46 and 47:

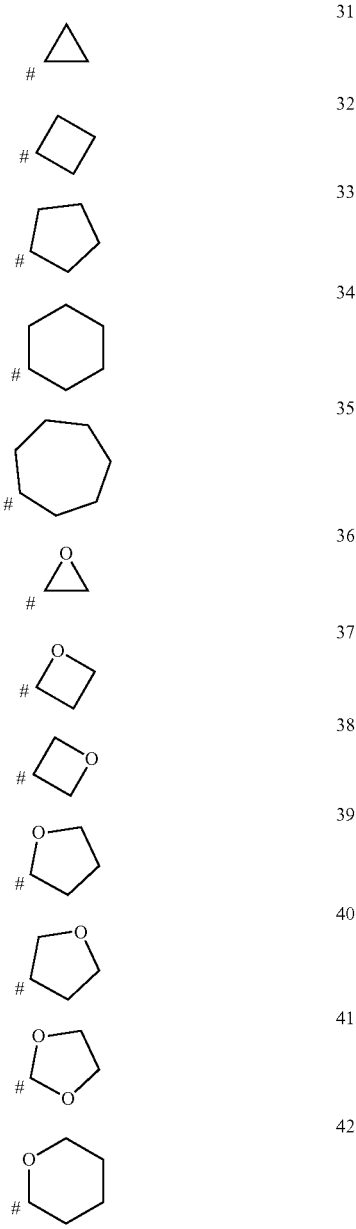

-continued

43 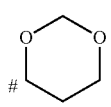

44 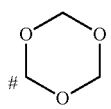

45 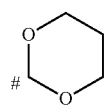

46 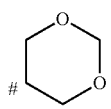

47 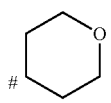

wherein # indicates the point of attachment of the carbocycle or heterocycle to the remainder of the compound. In some embodiments of the compound represented by A-B, each $R_8$ and $R_9$, of a group of the formula —$(CR_8R_9)$—, —$(CR_8R_9)$ or —$(CR_8R_9R_{10})$, taken together form a 3-, 4-, 5-, 6- or 7-membered carbocyclic or heterocyclic ring selected from a group of formula 31, 32, 33, 34, 35, 36, 37, 38, 39, 40, 41, 42, 43, 44, 45, 46 and 47:

31 

32 

33 

34 

35 

36 

37 

38 

-continued

39 

40 

41 

42 

43 

44 

45 

46 

47 

wherein # indicates the point of attachment of the carbocycle or heterocycle to the remainder of the compound. In some embodiments of the compound represented by A-B, each $R_8$ and $R_9$, of a group of the formula —$(CR_8R_9)$ or —$(CR_8R_9R_{10})$, taken together form a 3-, 4-, 5-, 6- or 7-membered carbocyclic or heterocyclic ring selected from a group of formula 31, 32, 33, 34, 35, 36, 37, 38, 39, 40, 41, 42, 43, 44, 45, 46 and 47:

31 

32 

33 

34 

-continued

| | |
|---|---|
| 35 | 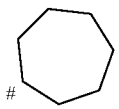 |
| 36 |  |
| 37 | 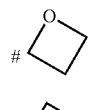 |
| 38 |  |
| 39 | 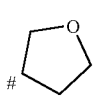 |
| 40 |  |
| 41 | 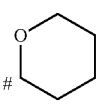 |
| 42 | 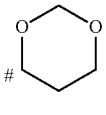 |
| 43 | 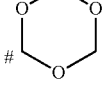 |
| 44 | 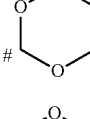 |
| 45 | 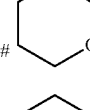 |
| 46 |  |
| 47 |  | wherein # indicates the point of attachment of the carbocycle or heterocycle to the remainder of the compound.

In some embodiments, each $R_8'$, $R_9'$ and $R_{10}'$ is independently a $C_1$-$C_4$ alkyl. In some embodiments, each $R_8'$, $R_9'$ and $R_{10}'$ is independently a $C_1$-$C_4$ alkoxy. In some embodiments, each $R_8'$, $R_9'$ and $R_{10}'$ is independently methyl, ethyl or t-butyl. In some embodiments, each $R_8'$, $R_9'$ and $R_{10}'$ is methyl. In some embodiments, each $R_8'$, $R_9'$ and $R_{10}'$ is methoxy. In some embodiments, each $R_8'$, $R_9'$ and $R_{10}'$ is ethyl. In some embodiments, each $R_8'$, $R_9'$ and $R_{10}'$ is t-butyl. In some embodiments, taken together $R_8'$ and $R_9'$ form a 4-, 5-, or 6-membered carbocyclic or heterocyclic ring.

In some embodiments of the compound A-B, $R_{10}$ is H, D, F, —$CH_3$, —$OCH_3$, —$CD_3$, —$OCD_3$, —$CH_2F$, —$OCH_2F$, —$CHF_2$, —$OCHF_2$, —$CF_3$, —$OCF_3$, —$CH_2CH_3$, —$CH(CH_3)_2$, —$CD_2CD_3$, —$CD(CD_3)_2$, —$CF_2CH_3$, $CF(CH_3)_2$, —$CH_2CF_3$, —$CH(CF_3)_2$, —$CF_2CF_3$, —$CF(CF_3)_2$, —$C(CH_3)_3$, —$C(CD_3)_3$, —$C(CF_3)_3$, —$OCH_2CH_3$, —$OCH(CH_3)_2$, —$OCD_2CD_3$, —$OCF_2CF_3$, —$OCD(CD_3)_2$, —$OCF_2(CF_3)$, —$OCF(CF_3)_2$, —$OC(CH_3)_3$, —$OC(CD_3)_3$, —$OC(CF_3)_3$, —$C(CH_3)_2(CF_3)$, —$C(CH_3)(CF_3)_2$, —$OC(CH_3)_2(CF_3)$, —$OC(CH_3)(CF_3)_2$, —$CH_2CH_2CH_3$, —$CH(CH_2CH_3)_2$, —$CD_2CD_2CD_3$, —$CD(CD_2CD_3)_2$, —$CF_2CF_2CF_3$, —$CF(CF_2CF_3)_2$, —$C(CH_2CH_3)_3$, —$C(CD_2CD_3)_3$, —$C(CF_2CF_3)_3$, —$OCH_2CH_2CH_3$, —$OCH(CH_2CH_3)_2$, —$OCD_2CD_2CD_3$, —$OCD(CD_2CD_3)_2$, —$OCF_2CF_2CF_3$ or —$OCF(CF_2CF_3)_2$. In some embodiments of the compound A-B, $R_{10}$ is H, D, F, —$CH_3$, —$OCH_3$, —$CD_3$, —$OCD_3$, —$CH_2F$, —$OCH_2F$, —$CHF_2$, —$OCHF_2$, —$CF_3$, —$OCF_3$, —$CH_2CH_3$ or —$CH(CH_3)_2$. In some embodiments of the compound A-B, $R_{10}$ is H, D, F, —$CH_3$, —$CH_2F$, —$CHF_2$, or —$CF_3$. In some embodiments of the compound A-B, $R_{10}$ is $R_{10}$ is H, F, —$CH_3$, —$OCH_3$, —$CF_3$ or —$OCF_3$. In some embodiments of the compound A-B, $R_{10}$ is H, D or F. In some embodiments of the compound A-B, $R_{10}$ is —$CH_3$ or —$CF_3$. In some embodiments of the compound A-B, $R_{10}$ is H or —$CH_3$. In some embodiments of the compound A-B, $R_{10}$ is H or —$CF_3$. In some embodiments of the compound A-B, $R_{10}$ is H. In some embodiments of the compound A-B, $R_{10}$ is D. In some embodiments of the compound A-B, $R_{10}$ is F. In some embodiments of the compound A-B, $R_{10}$ is —$CH_3$. In some embodiments of the compound A-B, $R_{10}$ is —$OCH_3$. In some embodiments of the compound A-B, $R_{10}$ is absent.

In some embodiments of the compound A-B, each instance of $R_{12}$, $R_{13}$ or $R_{14}$ is independently H, D, F, —$CH_3$, —$OCH_3$, —$CD_3$, —$OCD_3$, —$CH_2F$, —$OCH_2F$, —$CHF_2$, —$OCHF_2$, —$CF_3$, —$OCF_3$, —$CH_2CH_3$, —$CH(CH_3)_2$, —$CH_2CH_2CH_3$, —$CH(CH_2CH_3)_2$, —$C(CH_3)_3$, —$OCH_2CH_3$, —$OCH(CH_3)_2$, —$OCH_2CH_2CH_3$, —$OCH(CH_2CH_3)_2$, or —$OC(CH_3)_3$. In some embodiments of the compound A-B, each instance of $R_{12}$, $R_{13}$ or $R_{14}$ is independently H, D, F, —$CH_3$, —$OCH_3$, —$CD_3$, —$OCD_3$, —$CH_2F$, —$OCH_2F$, —$CHF_2$, —$OCHF_2$, —$CF_3$, —$OCF_3$, —$CH_2CH_3$ or —$CH(CH_3)_2$. In some embodiments of the compound A-B, each instance of $R_{12}$, $R_{13}$ or $R_{14}$ is independently H, D, F, —$CH_3$, —$OCH_3$, —$CD_3$, —$OCD_3$, —$CH_2F$, —$OCH_2F$, —$CHF_2$, —$OCHF_2$, —$CF_3$ or —$OCF_3$. In some embodiments of the compound A-B, each instance of $R_{12}$, $R_{13}$ and $R_{14}$ is independently H, F, —$CH_3$, —$OCH_3$, —$CF_3$, —$OCF_3$, —$CH_2CH_3$ or —$OCH_2CH_3$. In some embodiments of the compound A-B, each instance of $R_{12}$, $R_{13}$ or $R_{14}$ is independently H, D, F, —$CH_3$, —$CD_3$ or —$CF_3$. In some embodiments of the compound A-B, each instance of $R_{12}$, $R_{13}$ or $R_{14}$ is independently H, D, F or —$CH_3$. In some embodiments of the compound A-B, each instance of $R_{12}$, $R_{13}$ or $R_{14}$ is independently H, or F. In some embodiments of the compound A-B, each instance of $R_{12}$, $R_{13}$ or $R_{14}$ is H. In some embodiments of the compound A-B, each instance of $R_{12}$, $R_{13}$ or $R_{14}$ is D. In some embodiments of the compound A-B, each instance of $R_{12}$, $R_{13}$ or $R_{14}$ is F. In some embodiments of the compound A-B, each instance of $R_{12}$, $R_{13}$ or $R_{14}$ is —$CH_3$. In some embodiments of the compound A-B, each instance of $R_{12}$, $R_{13}$ and $R_{14}$ is independently H, F, —$CH_3$, —$OCH_3$, —$CF_3$, —$OCF_3$, —$CH_2CH_3$ or —$OCH_2CH_3$; provided however that for at least one group of formula —(CR$_{12}$R$_{13}$)—, taken together R$_{12}$ and R$_{13}$ form a 3-, 4-, 5-, 6- or 7-membered carbocyclic or heterocyclic ring.

In some embodiments of the compound A-B, R$_{20}$ is H, D, F, —CH$_3$, —CD$_3$, —CH$_2$F, —CHF$_2$, —CF$_3$, —CH$_2$CH$_3$, —CH$_2$CH$_2$CH$_3$, —CH(CH$_3$)$_2$, —C(CH$_3$)$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CH$_2$CH$_2$CH$_2$CH$_2$CH$_2$CH$_2$CH$_3$, —CH$_2$CH$_2$CH$_2$CH$_2$CH$_2$CH$_2$CH$_2$CH$_3$, —CH$_2$CH$_2$CH$_2$CH$_2$CH$_2$CH$_2$CH$_2$CH$_2$CH$_3$ or —CH$_2$CH$_2$CH$_2$CH$_2$CH$_2$CH$_2$CH$_2$CH$_2$CH$_2$CH$_3$. In some embodiments of the compound A-B, R$_{20}$ is H, D, F, —CH$_3$, —CD$_3$, —CH$_2$F, —CHF$_2$, —CF$_3$, —CH$_2$CH$_3$, —CH$_2$CH$_2$CH$_3$, —CH(CH$_3$)$_2$ or —C(CH$_3$)$_3$. In some embodiments of the compound A-B, R$_{20}$ is H, D, F, —CH$_3$, —CD$_3$, —CH$_2$F, —CHF$_2$ or —CF$_3$. In some embodiments of the compound A-B, R$_{20}$ is H, D, F, —CH$_3$, —CD$_3$, —CH$_2$F, —CHF$_2$ or —CF$_3$. In some embodiments of the compound A-B, R$_{20}$ is H, D, F, or —CH$_3$. In some embodiments of the compound A-B, R$_{20}$ is —CH$_3$, —CD$_3$, —CH$_2$F, —CHF$_2$ or —CF$_3$. In some embodiments of the compound A-B, R$_{20}$ is H, F or —CH$_3$. In some embodiments of the compound A-B, R$_{20}$ is H. In some embodiments of the compound A-B, R$_{20}$ is —CH$_3$. In some embodiments of the compound A-B, R$_{20}$ is —CF$_3$. In some embodiments of the compound A-B, R$_{20}$ is F.

In some embodiments of the compound A-B, each R$_{21}$ is independently H, D, F, —CH$_3$, —CD$_3$, —CH$_2$F, —CHF$_2$, —CF$_3$, —CH$_2$CH$_3$, —CH$_2$CH$_2$CH$_3$, —CH(CH$_3$)$_2$, —CH$_2$CH$_2$CH$_2$CH$_3$ or —C(CH$_3$)$_3$. In some embodiments of the compound A-B, each R$_{21}$ is independently H, D, F, —CH$_3$, —CD$_3$, —CH$_2$F, —CHF$_2$ or —CF$_3$. In some embodiments of the compound A-B, each R$_{21}$ is independently H, F, —CH$_3$ or —CF$_3$. In some embodiments of the compound A-B, each R$_{21}$ is independently H, F, or —CH$_3$. In some embodiments of the compound A-B, each R$_{21}$ is —CH$_3$. In some embodiments of the compound A-B, each R$_{21}$ is H. In some embodiments of the compound A-B, each R$_{21}$ is F.

In some embodiments of the compound A-B, m is 0. In some embodiments of the compound A-B, m is 1. In some embodiments of the compound A-B, n is 0. In some embodiments of the compound A-B, n is 1. In some embodiments of the compound A-B, both n and m are 0. In some embodiments of the compound A-B, one of n and m is 0 and the other is 1. In some embodiments of the compound A-B, both n and m are 1. In some embodiments of the compound A-B, (i) m is 0 and n is 0; (ii) m is 0 and n is 1, 2 or 3; or (iii) m is 1 and n is 0, 1, 2 or 3.

In some embodiments of the compound A-B, n is 0, 1, 2, 3, 4, 5, 6, 7 or 8. In some embodiments of the compound A-B, n is 0, 1, 2, 3, 4, 5 or 6. In some embodiments of the compound A-B, n is 0, 1, 2, 3 or 4. In some embodiments of the compound A-B, n is 2. In some embodiments of the compound A-B, n is 3. In some embodiments of the compound A-B, n is 4. In some embodiments of the compound A-B, n is 5. In some embodiments of the compound A-B, n is 6. In some embodiments of the compound A-B, n is 7. In some embodiments of the compound A-B, n is 8. In some embodiments of the compound A-B, n is 9. In some embodiments of the compound A-B, n is 10. In some embodiments of the compound A-B, n is 11. In some embodiments of the compound A-B, n is 12.

In some embodiments of the compound A-B, p is 0, 1, 2, 3, 4, 5, 6, 7, 8, 9, 10, 11, 12, 13, 14 or 15. In some embodiments of the compound A-B, p is 0, 1, 2, 3, 4, 5, 6, 7, 8, 9, 10, 11 or 12. In some embodiments of the compound A-B, p is 0, 1, 2, 3, 4, 5, 6, 7 or 8. In some embodiments of the compound A-B, p is 0, 1, 2, 3, 4, 5 or 6. In some embodiments of the compound A-B, p is 0, 1, 2, 3 or 4. In some embodiments of the compound A-B, p is 0. In some embodiments of the compound A-B, p is 1. In some embodiments of the compound A-B, p is 2. In some embodiments of the compound A-B, p is 3. In some embodiments of the compound A-B, p is 4. In some embodiments of the compound A-B, p is 5. In some embodiments of the compound A-B, p is 6. In some embodiments of the compound A-B, p is 7. In some embodiments of the compound A-B, p is 8. In some embodiments of the compound A-B, p is 9. In some embodiments of the compound A-B, p is 10. In some embodiments of the compound A-B, p is 11. In some embodiments of the compound A-B, p is 12. In some embodiments of the compound A-B, p is 13. In some embodiments of the compound A-B, p is 14. In some embodiments of the compound A-B, p is 15. In some embodiments of the compound A-B, p is 16. In some embodiments of the compound A-B, p is 17. In some embodiments of the compound A-B, p is 18. In some embodiments of the compound A-B, p is 19. In some embodiments of the compound A-B, p is 20.

In some embodiments of the compound A-B, at least one group of formula R$_1$, R$_2$, R$_3$, R$_4$, R$_5$, R$_6$, R$_7$, R$_8$, R$_9$, R$_{10}$, R$_{12}$, R$_{13}$, R$_{14}$, R$_{20}$ or R$_{21}$ comprises at least one fluorine atom. In some embodiments of the compound A-B, at least one group of formula R$_8$, R$_9$, R$_{10}$, R$_{20}$ or R$_{21}$ comprises at least one fluorine atom. In some embodiments of the compound A-B, at least one group of formula R$_8$, R$_9$ or R$_{10}$, comprises at least one fluorine atom. In some embodiments of the compound A-B, at least one R$_8$ and R$_9$, of a group of the formula —(CR$_8$R$_9$)—, —(CR$_8$R$_9$) or —(CR$_8$R$_9$R$_{10}$), taken together form a 3-, 4-, 5-, 6- or 7-membered carbocyclic or heterocyclic ring. In some embodiments of the compound A-B, at least one of R$_8$ and R$_9$, of a group of the formula —(CR$_8$R$_9$) or —(CR$_8$R$_9$R$_{10}$), taken together form a 3-, 4-, 5-, 6- or 7-membered carbocyclic or heterocyclic ring. In some embodiments of the compound A-B, each R$_8$ and R$_9$, of a group of the formula —(CR$_8$R$_9$), taken together forms a 3-, 4-, 5-, 6- or 7-membered carbocyclic or heterocyclic ring.

In some embodiments, the compound A-B has the formula referred to herein as Compound X:

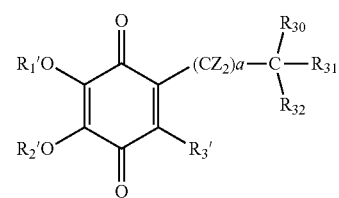

wherein, each of R$_1$' and R$_2$' is independently C$_1$-C$_3$ alkyl; R$_3$' is H, D, F, —CH$_3$, —CF$_3$, —OCH$_3$ or —OCF$_3$; each Z is independently H, D or F; a is 1, 2, 3, 4, 5, 6, 7, 9 or 9; and each of R$_{30}$, R$_{31}$ and R$_{32}$ is independently H, D or F, provided however, that at least one of R$_{30}$, R$_{31}$ or R$_{32}$ is F. In some embodiments of Compound X, each of R$_1$' and R$_2$' is methyl. In some embodiments of Compound X, each of R$_1$' and R$_2$' is ethyl. In some embodiments of Compound X, R$_3$' is H or —CH$_3$. In some embodiments of Compound X, R$_3$' is —CH$_3$. In some embodiments of Compound X, a is 3, 4, 5, 6, 7 or 8. In some embodiments of Compound X, a is 3, 4, 5, 6, or 7. In some embodiments of Compound X, a is 4, 5, 6, 7, 8 or 9. In some embodiments of Compound X, a is 4, 5, 6, 7 or 8. In some embodiments of Compound X, a is 4, 5, 6 or 7. In some embodiments of Compound X, a is 1. In some embodiments of Compound X, a is 2. In some embodiments of Compound X, a is 3. In some embodiments of Compound X, a is 4. In some embodiments of Compound X, a is 5. In some embodiments of Compound X, a is 6. In some embodiments of Compound X, a is 7. In some embodiments of Compound X, a is 8. In some embodiments of Compound X, a is 9. In some embodiments of Compound X, each Z is H. In some embodiments of Compound X, each of $R_{30}$, $R_{31}$ and $R_{32}$ is F.

In some embodiments, the compound A-B has the formula referred to herein as Y:

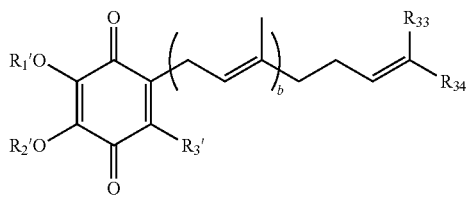

wherein, each of $R_1'$ and $R_2'$ is independently $C_1$-$C_3$ alkyl; $R_3'$ is H, D, F, —$CH_3$, —$CF_3$, —$OCH_3$ or —$OCF_3$; b is 1, 2, or 3; and each of $R_{33}$ and $R_{34}$ is independently H, D, F, —$CH_3$, —$CH_2F$, —$CHF_2$, or —$CHF_3$, provided however, that at least one of $R_{33}$ and $R_{34}$ is selected from F, —$CH_2F$, —$CHF_2$, and —$CF_3$. In some embodiments of Compound Y, each of $R_1'$ and $R_2'$ is methyl. In some embodiments of Compound Y, each of $R_1'$ and $R_2'$ is ethyl. In some embodiments of Compound Y, $R_3'$ is H or —$CH_3$. In some embodiments of Compound Y, b is 1. In some embodiments of Compound Y, b is 2. In some embodiments of Compound Y, b is 3. In some embodiments of Compound Y, each Z is H. In some embodiments of Compound Y, each of $R_{33}$ and $R_{34}$ is F.

In some embodiments, the compound A-B has the formula referred to herein as Z:

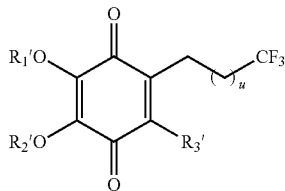

wherein, each of $R_1'$ and $R_2'$ is independently $C_1$-$C_3$ alkyl; $R_3'$ is H, D, F, —$CH_3$, —$CF_3$, —$OCH_3$ or —$OCF_3$; and u is 1, 2, 3, 4, 5, 6, 7 or 8. In some embodiments, each of $R_1'$ and $R_2'$ is independently —$CH_3$ or —$CH_2CH_3$ and $R_3'$ is H or —$CH_3$. In some embodiments, each of $R_1'$, $R_2'$ and $R_3'$ is —$CH_3$. In some embodiments, u is 1, 2, 3, 4, 5, 6, or 7. In some embodiments, u is 1, 2, 3, 4, 5 or 6. In some embodiments, u is 2, 3, 4, 5, 6, 7, or 8. In some embodiments, u is 2, 3, 4, 5, 6 or 7. In some embodiments, u is 3, 4, 5, 6 or 7. In some embodiments, u is 3, 4, 5 or 6. In some embodiments, u is 4, 5, 6 or 7. In some embodiments, u is 1. In some embodiments, u is 2. In some embodiments of Z, u is 3. In some embodiments, u is 4. In some embodiments, u is 5. In some embodiments, u is 6. In some embodiments, u is 7. In some embodiments, u is 8. In some embodiments, each of $R_1'$ and $R_2'$ is independently —$CH_3$ or —$CH_2CH_3$, $R_3'$ is —$CH_3$, u is 2, 3, 4, 5, 6, 7 or 8 and Z has a calculated Log D of 2 to 7, inclusive.

In some embodiments, the compound A-B has the formula referred to herein as Compound B:

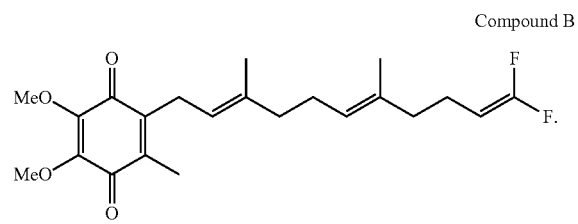 [SMILES: COC1=C(OC)C(=O)C(C/C=C(\C)CC/C=C(\C)CCC=C(F)F)=C(C)C1=O]

In some embodiments, the compound A-B has the formula referred to herein as Compound C:

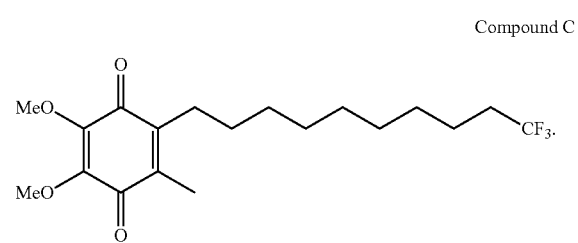 [SMILES: COC1=C(OC)C(=O)C(CCCCCCCCCC(F)(F)F)=C(C)C1=O]

In some embodiments, the compound A-B has the formula referred to herein as Compound E:

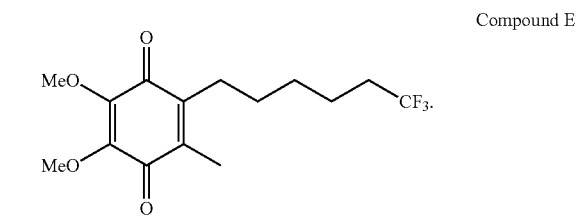 [SMILES: COC1=C(OC)C(=O)C(CCCCCC(F)(F)F)=C(C)C1=O]

In some embodiments, the compound A-B has the formula referred to herein as Compound F:

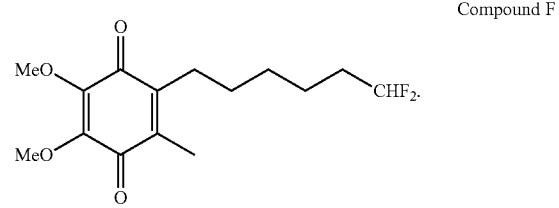 [SMILES: COC1=C(OC)C(=O)C(CCCCCC(F)F)=C(C)C1=O]

In some embodiments, the compound A-B has the formula referred to herein as Compound G:

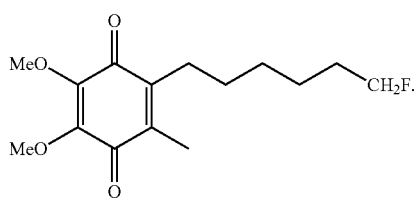

Compound G

In some embodiments, the compound A-B has the formula referred to herein as Compound I:

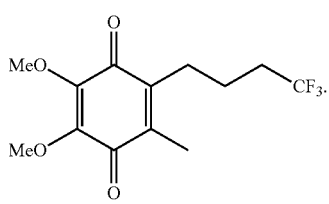

Compound I

In some embodiments, the compound A-B has the formula referred to herein as Compound J:

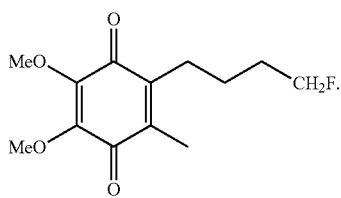

Compound J

In some embodiments, the compound A-B has the formula referred to herein as Compound K:

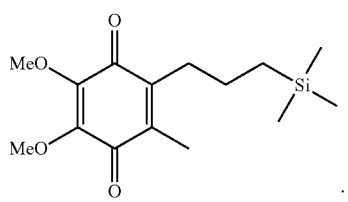

Compound K

In some embodiments, the compound A-B has the formula referred to herein as Compound M:

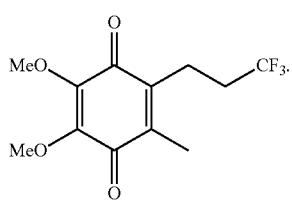

Compound M

In some embodiments, the compound A-B has the formula referred to herein as Compound N:

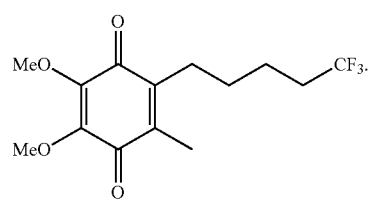

Compound N

In some embodiments, the compound A-B has the formula referred to herein as Compound O:

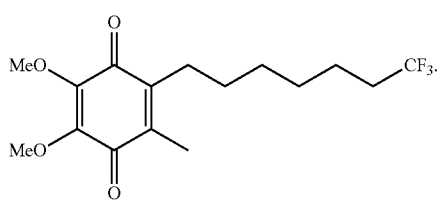

Compound O

In some embodiments, the compound A-B has the formula referred to herein as Compound P:

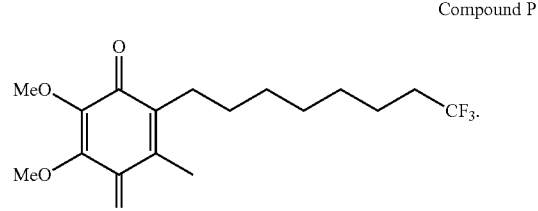

Compound P

In some embodiments, the compound A-B has the formula referred to herein as Compound Q:

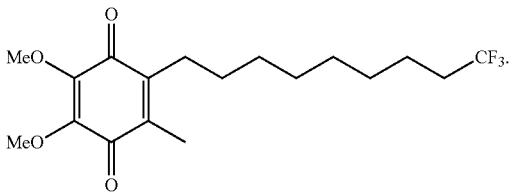

Compound Q

As illustrated in Examples 12-15 and Table 1, below, certain compounds disclosed herein exhibit a significant degree of potency in the BSO Assay (Example 12) and in the Rotenone ATP Assay (Example 13) and/or alternatively the Rotenone Oxygraph Assay (Example 15; each of the Rotenone ATP and Rotenone Oxygraph Assays providing information as to whether or not the compound being studied possesses Complex I by-pass capacity). For example, the potency and efficacy of Compound C, disclosed herein, is similar to that of Vatiquinone with respect to ameliorating the effects of Friedreich's ataxia in a cell-based assay (See: Example 12; BSO Assay). However, Compound C, unlike Vatiquinone, is also effective in rescuing cells exhibiting an induced Complex I deficiency in the Rotenone ATP Assay (Example 13) and the Rotenone Oxygraph Assay (Example 15). Indeed, by comparison, while several currently available therapeutics such as Vatiquinone, Idebenone or Omaveloxolone may exhibit good or fair activity in one or the other of the BSO Assay or the Rotenone ATP (or Rotenone Oxygraph Assays; See: Table 1, below), none of them are active in both assays, thereby suggesting that many compounds disclosed herein (e.g. Compounds B-I and K) may be superior therapeutics as compared with compounds currently being evaluated as therapeutic agents for treatment of mitochondrial disease (e.g. Friedreich's ataxia) in clinical trials. Thus, it is believed that the therapeutic compounds disclosed herein may prove to be superior agents for the treatment of mitochondrial diseases, such as Friedreich's ataxia. The aforementioned compounds can be used in the preparation of compositions, such as medicaments. Said compounds (e.g. Compounds B-I and K) or compositions thereof can thus be used in the treatment or prevention of mitochondrial disease, such as Friedreich's ataxia.

It is noteworthy that Compound J (calculated Log D of 1.79) is not that effective in any of the BSO Assay, the Rotenone ATP or the Rotenone Oxygraph Assays; See: Table 1, below. It is noteworthy however that according to: Erb et al, *Features of Idebenone and Related Short-Chain Quinones that Rescue ATP Levels under Conditions of Imparted Mitochondrial Complex I*, PLoSOne, (April, 2012) 7(4): e36153, quinone compounds with a calculated Log D value of less than 1.9 were poor at rescuing ATP levels in Complex I compromised cells and proposed a calculated Log D window of 2 to 7, inclusive, as being preferred. This Log D value may also explain the poor performance of Compound J in the BSO assay.

(b) Other Derivatives/Therapeutic Agents

In some embodiments, this application further provides therapeutic compounds of formula C-B (defined below), that can be prepared by reduction of the therapeutic compounds of formula A-B. Such reduced versions of compounds of formula A-B are believed to also be suitable for use in the treatment of mitochondrial disease, such as Friedreich's ataxia or other ataxia's (such as Ataxia with vitamin E deficiency (AVED)) because other compounds that have a hydroquinone structure, such are vitamin E, have also been shown to be clinically linked with ataxia (See: Imounan et al., Clinical and Genetic Study of Friedreich's ataxia and Ataxia with Vitamin E Deficiency in 44 Moroccan Families, World Journal of Neuroscience, 2014, 4, 299-305; and Abeti et al., Calcium Deregulation: Novel Insights to Understand Friedreich's ataxia Pathophysiology, Frontiers in Cellular Neuroscience: doi: 10.3398/fncel.2018.00264). For example, it is believed that the therapeutic compounds of formula C-B can themselves be considered therapeutic agents or alternatively as prodrug forms of the therapeutic agents of formula A-B. Specifically, therapeutic compounds of formula A-B are believed to be active in the processes affecting the in vivo concentration (e.g, the internal and external mitochondrial concentration) of reactive oxygen species (ROS) and indeed may actively cycle, in vivo, between the reduced form (compounds of formula C-B) and the oxidized form (compounds of formula A-B); Indeed, such cycling is discussed in the literature, for example in Erb et al., PLoSone (April, 2012) 7(4): e36153. Compounds of the formula A-B can, for example, be converted to compounds of the formula C-B as described below in Examples 11A and 11B, below. Alternatively, compounds of formula C—B are provided as intermediates to the production of compounds of formula A-B, as described in, for example, Examples 1-10, below.

Thus, in some embodiments, the present application pertains to compounds represented by the formula C-B, or pharmaceutically acceptable salts, stereoisomers, mixtures of stereoisomers, tautomers, hydrates, and/or solvates thereof, wherein C is a head-group of formula 13 or 14:

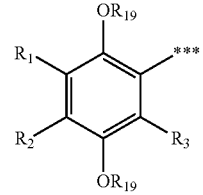

13

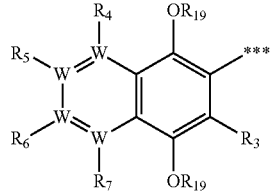

14 and B is a tail-group of formula 3, 4, 5, 6, 7, 8, 9, 10 or 11:

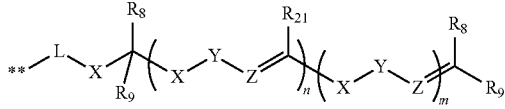

3

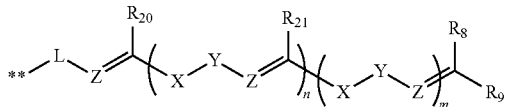

4

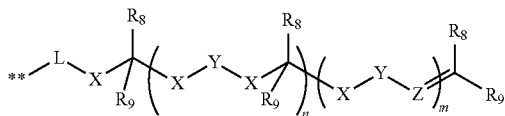

5

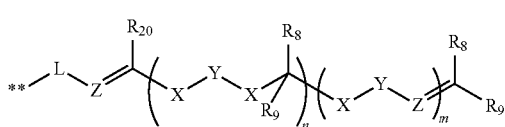

6

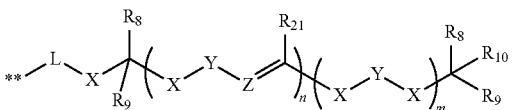

7

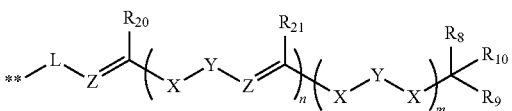

8

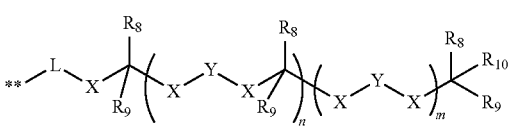

9

-continued

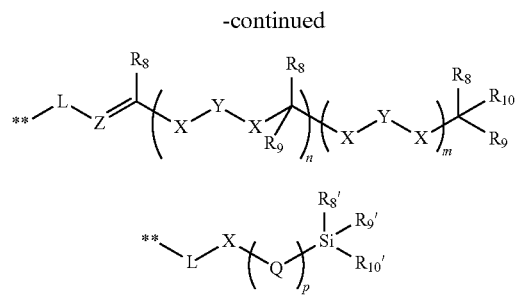

wherein, each Q is independently a group of formula —(CR$_{12}$R$_{13}$)—, O or Si(CH$_3$)$_2$, provided that each O and each Si(CH$_3$)$_2$ is not directly bonded to O or Si(CH$_3$)$_2$; each of R$_1$ and R$_2$ is independently H, D, or C$_1$-C$_6$ alkyl, or R$_1$ and R$_2$ together form a 5-membered heterocyclic ring or a 6-membered heterocyclic ring; R$_3$ is independently H, D, F, Cl, Br, I, C$_1$-C$_6$ alkyl or C$_1$-C$_6$ alkoxy; each W is independently C (carbon) or N (nitrogen) and wherein for each use of W≠W, the bond between each W can be a single bond or double bond and further provided that if a single bond, each C (carbon) atom will have a hydrogen atom linked hereto in addition to one of R$_4$, R$_5$, R$_6$ or R$_7$; and where (i) if W is C (carbon), each of R$_4$, R$_5$, R$_6$ and R$_7$ attached thereto is independently H, D, F, Cl, Br, I, C$_1$-C$_6$ alkyl or C$_1$-C$_6$ alkoxy, and (ii) if W is N (nitrogen), each of R$_4$, R$_5$, R$_6$ and R$_7$ attached thereto is independently absent or selected from H, D or C$_1$-C$_6$ alkyl; L is absent or —(CR$_{12}$R$_{13}$)—; each X is independently a group of formula —(CR$_{12}$R$_{13}$)—; each Y is independently absent or a group of formula —(CR$_{12}$R$_{13}$)—; each Z is independently a group of formula —(CR$_{14}$)—; each of R$_8$ and R$_9$ is independently H, D, F, Cl, Br, I, C$_1$-C$_4$ alkyl or C$_1$-C$_8$ alkoxy, or taken together, the R$_8$ and R$_9$, of a group of the formula —(CR$_8$R$_9$)—, —(CR$_8$R$_9$) or —(CR$_8$R$_9$R$_{10}$), form a 3-, 4-, 5-, 6- or 7-membered carbocyclic or heterocyclic ring; each R$_8$', R$_9$' and R$_{10}$' is independently Cl, Br, I, C$_1$-C$_4$ alkyl or C$_1$-C$_4$ alkoxy, or taken together R$_8$' and R$_9$' form a 3-, 4-, 5-, 6- or 7-membered carbocyclic or heterocyclic ring; R$_{10}$ is H, D, F, Cl, Br, I, C$_1$-C$_6$ alkyl or C$_1$-C$_6$ alkoxy; each R$_{12}$, R$_{13}$ and R$_{14}$ is independently H, D, F, Cl, Br, I, C$_1$-C$_8$ alkyl, C$_1$-C$_8$ alkoxy, C$_3$-C$_6$ cycloalkyl, C$_1$-C$_6$ alkenyl, C$_1$-C$_6$ alkynyl, C$_1$-C$_6$ heteroalkyl, C$_6$-C$_{14}$ aryl or —NR$_{22}$R$_{23}$, or taken together, the R$_{12}$ and R$_{13}$, of a group of formula —(CR$_{12}$R$_{13}$)—, form a 3-, 4-, 5-, 6- or 7-membered carbocyclic or heterocyclic ring; each R$_{19}$ is independently H, C$_1$-C$_4$ alkyl, (unsubstituted or substituted) benzyl, R$_{24}$C(O)—, R$_{24}$OC(O)—, R$_{24}$R$_{25}$NC(O)—, or (R$_{24}$O)(R$_{25}$O)P(O)—; R$_{20}$ is H, D, F, C$_1$-C$_{12}$ alkyl or C$_3$-C$_6$ cycloalkyl; each R$_{21}$ is independently H, D, F, Cl, Br, I, or C$_1$-C$_4$ alkyl; each of R$_{22}$ and R$_{23}$ is independently H, D, C$_1$-C$_4$ alkyl; or taken together, the R$_{22}$ and R$_{23}$, of the group of formula —NR$_{22}$R$_{23}$, form a 3-, 4-, 5-, 6- or 7-membered carbocyclic or heterocyclic ring; each of R$_{24}$ and R$_{25}$ is independently H, D, alkyl, alkenyl, alkynyl, heteroalkyl, cycloalkyl, aryl, arylalkyl, heteroaryl, arylheteroalkyl, heteroarylheteroalkyl or T, wherein T is —(CH$_3$)$_w$—(O)$_x$—[(CH$_2$CH$_2$)—O]$_q$—R$_{26}$; R$_{26}$ is H, methyl, ethyl, isopropyl, or tert-butyl; m is 0 or 1; n is an integer from 0 to 12 (i.e., 0, 1, 2, 3, 4, 5, 6, 7, 8, 9, 10, 11, or 12), inclusive; p is an integer from 0 to 20, inclusive (i.e., 0, 1, 2, 3, 4, 5, 6, 7, 8, 9, 10, 11, 12, 13, 14, 15, 16, 17, 18, 19 or 20); q is 0, 1, 2, 3, 4, or 5; x is 0 or 1; w is 0, 1 or 2; provided that if x is 0, then w is 0; and if w is 0, then x is 0; and * indicates the point of attachment of C to B and  indicates the point of attachment of B to C; and further provided that: (i) at least one of R$_8$, R$_9$, or R$_{10}$: (a) is F, or (b) is a group that comprises at least one fluorine atom; or (ii) at least one R$_8$ and R$_9$, of a group of the formula —(CR$_8$R$_9$)—, —(CR$_8$R$_9$) or —(CR$_8$R$_9$R$_{10}$), taken together forms a 3-, 4-, 5-, 6- or 7-membered carbocyclic or heterocyclic ring; or (iii) the compound of formula C—B is the hydroquinone form of a corresponding quinone that has a calculated Log D of 2 to 7, inclusive; or (iv) at least one R$_{19}$ is R$_{24}$C(O)—, R$_{24}$OC(O)—, R$_{24}$R$_{25}$NC(O)—, or (R$_{24}$O)(R$_{25}$O)P(O)—. In some embodiments, if B is 7, then n cannot be 0. In some embodiments, B is 9, each of m and n is independently 0 or 1, provided that if m+n=2, then L absent, and at least one of R$_8$, R$_9$, or R$_{10}$ is F. In some embodiments, B is 9, m+n=0, 1 or 2, provided that if m+n=2, then L is absent and each of R$_8$, R$_9$, and R$_{10}$ is F.

Any combination of head-group 13 and 14 (i.e. "C") with tail-group 3, 4, 5, 6, 7, 8, 9, 10, or 11 (i.e. "B") is permissible. In some embodiments, C is 13 and B is 3, 4, 9 or 10. In some embodiments, C is 13 and B is 5, 6, 7 or 8. In some embodiments, C is 13 and B is 3, 5, 7 or 9. In some embodiments, C is 13 and B is 4, 6, 8 or 10. In some embodiments, C is 13 and B is 11. In some embodiments, C is 14 and B is 3, 4, 9 or 10. In some embodiments, C is 14 and B is 5, 6, 7 or 8. In some embodiments, C is 14 and B is 3, 5, 7 or 9. In some embodiments, C is 14 and B is 4, 6, 8 or 10. In some embodiments, C is 14 and B is 11. In some embodiments, C is 13 and B is 3. In some embodiments, C is 13 and B is 4. In some embodiments, C is 13 and B is 5. In some embodiments, C is 13 and B is 6. In some embodiments, C is 13 and B is 7. In some embodiments, C is 13 and B is 8. In some embodiments, C is 13 and B is 9. In some embodiments, C is 13 and B is 10. In some embodiments, C is 13 and B is 11. In some embodiments, C is 14 and B is 3. In some embodiments, C is 14 and B is 4. In some embodiments, C is 14 and B is 5. In some embodiments, C is 14 and B is 6. In some embodiments, C is 14 and B is 7. In some embodiments, C is 14 and B is 8. In some embodiments, C is 14 and B is 9. In some embodiments, C is 14 and B is 10. In some embodiments, C is 14 and B is 11.

Generally for the compound C-B, any combination of head-group 1 with tail-group 3, 4, 5, 6, 7, 8, 9, 10, or 11, in combination with any possible value for m and n is permissible; provided that: (i) if B is 3, one of m or n is 1; (ii) if B is 5, m is not 0; (iii) if B is 7, then n is not 0; (iv) if B is 9, then m+n=0 or 1; and in some embodiments, R$_8$, R$_9$ and R$_{10}$ are selected from H, D, F, —CH$_3$, CH$_2$F, CHF$_2$ and CF$_3$. For example, in some embodiments, C is 13, B is 3, m is 1 and n is 0, or C is 13, B is 3, m is 0 and n is 1, or C is 13, B is 3, m is 1 and n is 1. In some embodiments, C is 13, B is 4, m is 0 and n is 0, or C is 13, B is 4, m is 1 and n is 0, or C is 13, B is 4, m is 1 and n is 1, or C is 13, B is 4, m is 0 and n is 1. In some embodiments, C is 13, B is 5, m is 1 and n is 0, or C is 13, B is 5, m is 1 and n is 1. In some embodiments, C is 13, B is 6, m is 0 and n is 0, or C is 13, B is 6, m is 1 and n is 0, or C is 13, B is 6, m is 1 and n is 1, or C is 13, B is 6, m is 0 and n is 1. In some embodiments, C is 13, B is 7, m is 0 and n is 1, or C is 13, B is 7, m is 1 and n is 1. In some embodiments, C is 13, B is 8, m is 0 and n is 0, or C is 13, B is 8, m is 1 and n is 0, or C is 13, B is 8, m is 1 and n is 1, or C is 13, B is 8, m is 0 and n is 1. In some embodiments, C is 13, B is 9, m is 0 and n is 0, or C is 13, B is 9, m is 1 and n is 0, or C is 13, B is 9, m is 0 and n is 1. In some embodiments, C is 13, B is 10, m is 0 and n is 0, or C is 13, B is 10, m is 1 and n is 0, or C is 13, B is 10, m is 1 and n is 1, or C is 13, B is 10, m is 0 and n is 1.

In some embodiments (i.e. any of the forgoing recited embodiments of C-B), the group represented by L is absent. In some embodiments (i.e. any of the forgoing recited embodiments of C-B), the group represented by L is —(CR$_{12}$R$_{13}$)—. In some embodiments, L is —(CH$_2$)—, —(CD$_2$)-, —(CHF)—, —(CF$_2$)—, —(CH(CH$_3$))—, —(CD(CD$_3$))-, —(CF(CH$_3$))—, —(CH(CF$_3$))—, —(CF(CF$_3$))—, —(C(CH$_3$)$_2$)—, —(C(CD$_3$)$_2$)-, —(C(CF$_3$)$_2$)—, —(CH(OCH$_3$))—, —(CD(OCD$_3$))-, —(CF(OCH$_3$))—, —(CH(OCF$_3$))—, —(CF(OCF$_3$))—, —(C(OCH$_3$)$_2$)—, —(C(OCD$_3$)$_2$)-, —(C(OCF$_3$)$_2$)—, —(C(CH$_3$)(CF$_3$))—, —(C(CD$_3$)(CF$_3$))—, —(CH(CH$_2$CH$_3$))—, —(CD(CD$_2$CD$_3$))-, —(CF(CH$_2$CH$_3$))—, —(CH(CH$_2$CF$_3$))—, —(CH(CF$_2$CF$_3$))—, —(CF(CF$_2$CF$_3$))—, —(C(CH$_2$CH$_3$)$_2$)—, —(C(CD$_2$CD$_3$)$_2$)— or —(C(CF$_2$CF$_3$)$_2$)—. In some embodiments, L is —(CH$_2$)—, —(CD$_2$)-, —(CF$_2$)—, —(CH(CH$_3$))—, —(CD(CD$_3$))-, —(CF(CF$_3$))—, —(C(CH$_3$)$_2$)—, —(C(CD$_3$)$_2$)-, —(C(CF$_3$)$_2$)—, —(CH(OCH$_3$))—, —(CD(OCD$_3$))-, —(CF(OCF$_3$))— or —(C(OCH$_3$)$_2$)—. In some embodiments, L is —(CH$_2$)—, —(CD$_2$)-, —(CHF)—, —(CF$_2$)—, —(CH(CH$_3$))—, —(CF(CF$_3$))—, —(C(CH$_3$)$_2$)— or —(C(CF$_3$)$_2$)—. In some embodiments, L is —(CH$_2$)—, —(CD$_2$)- or —(CF$_2$)—. In some embodiments, L is —(CH$_2$)—. In some embodiments, L is —(CD$_2$)-. In some embodiments, L is —(CF$_2$)—. In some embodiments, L is —(CHF)—. In some embodiments, L is —(CR$_{12}$R$_{13}$)— and wherein taken together R$_{12}$ and R$_{13}$ form a 3-, 4-, 5-, 6- or 7-membered carbocyclic or heterocyclic ring.

In some embodiments of the compound represented by C-B, each X and each Y is independently —(CH$_2$)—, —(CD$_2$)-, —(CHF)—, —(CF$_2$)—, —(CH(CH$_3$))—, —(CD(CD$_3$))-, —(CF(CH$_3$))—, —(CH(CF$_3$))—, —(CF(CF$_3$))—, —(C(CH$_3$)$_2$)—, —(C(CD$_3$)$_2$)-, —(C(CF$_3$)$_2$)—, —(CH(OCH$_3$))—, —(CD(OCD$_3$))-, —(CF(OCH$_3$))—, —(CH(OCF$_3$))—, —(CF(OCF$_3$))—, —(C(OCH$_3$)$_2$)—, —(C(OCD$_3$)$_2$)-, —(C(OCF$_3$)$_2$)—, —(C(CH$_3$)(CF$_3$))—, —(C(CD$_3$)(CF$_3$))—, —(CH(CH$_2$CH$_3$))—, —(CD(CD$_2$CD$_3$))-, —(CF(CH$_2$CH$_3$))—, —(CH(CH$_2$CF$_3$))—, —(CH(CF$_2$CF$_3$))—, —(CF(CF$_2$CF$_3$))—, —(C(CH$_2$CH$_3$)$_2$)—, —(C(CD$_2$CD$_3$)$_2$)— or —(C(CF$_2$CF$_3$)$_2$)—. In some embodiments, each X and each Y is independently —(CH$_2$)—, —(CD$_2$)-, —(CF$_2$)—, —(CH(CH$_3$))—, —(CD(CD$_3$))-, —(CF(CF$_3$))—, —(C(CH$_3$)$_2$)—, —(C(CD$_3$)$_2$)-, —(C(CF$_3$)$_2$)—, —(CH(OCH$_3$))—, —(CD(OCD$_3$))-, —(CF(OCF$_3$))— or —(C(OCH$_3$)$_2$)—. In some embodiments, each X and each Y is independently —(CH$_2$)—, —(CD$_2$)-, —(CHF)—, —(CF$_2$)—, —(CH(CH$_3$))—, —(CF(CF$_3$))—, —(C(CH$_3$)$_2$)— or —(C(CF$_3$)$_2$)—. In some embodiments, each X and each Y is independently —(CH$_2$)—, —(CD$_2$)- or —(CF$_2$)—. In some embodiments, each X and each Y is —(CH$_2$)—. In some embodiments, each X and each Y is —(CD$_2$)-. In some embodiments, each X and each Y is —(CF$_2$)—. In some embodiments, each X and each Y is —(CHF)—. In some embodiments, at least one of X and Y is —(CR$_{12}$R$_{13}$)—, wherein taken together R$_{12}$ and R$_{13}$ form a 3-, 4-, 5-, 6- or 7-membered carbocyclic or heterocyclic ring. In some embodiments, each X and each Y is —(CR$_{12}$R$_{13}$)—, wherein taken together each R$_{12}$ and R$_{13}$, with respect to each group of formula —(CR$_{12}$R$_{13}$)—, form a 3-, 4-, 5-, 6- or 7-membered carbocyclic or heterocyclic ring.

In some embodiments of the compound represented by C-B, each X is —(CH$_2$)—. In some embodiments, each X is —(CD$_2$)-. In some embodiments, each X is —(CF$_2$)—. In some embodiments, each X is —(CHF)—. In some embodiments, each Y is —(CH$_2$)—. In some embodiments, each Y is —(CD$_2$)-. In some embodiments, each Y is —(CF$_2$)—. In some embodiments, each Y is —(CHF)—. In some embodiments, at least one X is —(CD$_2$)-, —(CF$_2$)— or —(CHF)—. In some embodiments, at least one X or one Y is —(CD$_2$)-, —(CF$_2$)— or —(CHF)—.

In some embodiments of the compound represented by C-B, each Z is independently —(CH)—, —(CD)-, —(CF)— or —(C(CH$_3$))—. In some embodiments, each Z is —(CH)—. In some embodiments, each Z is —(CD)-. In some embodiments, each Z is —(CF)—. In some embodiments, each Z is —(C(CH$_3$))—. In some embodiments, at least one Z is —(CD)- or —(CF)—.

In some embodiments of the compound represented by C-B, each Q is a group of formula —(CR$_{12}$R$_{13}$)—. In some embodiments, each Q is a group of formula —(CH$_2$)—. In some embodiments, p is >2 and at least one Q is O and the other Qs are —(CH$_2$)—. In some embodiments, p is >2 and the group represented by -(Q)$_p$- comprises at least one ethylene glycol moiety (i.e. at least one group of formula —OCH$_2$CH$_2$—). In some embodiments, p is >3 and the group represented by -(Q)$_p$- comprises at least one propylene glycol moiety (i.e. at least one group of formula —OCH$_2$CH$_2$CH$_2$—). In some embodiments, the group represented by -(Q)$_p$- is a group of formula —(OCH$_2$CH$_2$)$_s$—, wherein s is 1, 2, 3, 4, 5 or 6. In some embodiments, the group represented by -(Q)$_p$- is a group of formula —(OCH$_2$CH$_2$CH$_2$)$_t$—, wherein t is 1, 2, 3, or 4.

In some embodiments of the compound represented by C-B, wherein C is 13, each of R$_1$ and R$_2$ is independently H, D, —CH$_3$, —CD$_3$, —CH$_2$F, —CHF$_2$, —CF$_3$, —CH$_2$CH$_3$, —CH(CH$_3$)$_2$, —CD$_2$CD$_3$, —CD(CD$_3$)$_2$, —CF$_2$CH$_3$, —CF(CH$_3$)$_2$, —CH$_2$CF$_3$, —CH(CF$_3$)$_2$, —CF$_2$CF$_3$, —CF(CF$_3$)$_2$, —C(CH$_3$)$_3$, —C(CD$_3$)$_3$, —C(CF$_3$)$_3$, —C(CH$_3$)$_2$(CF$_3$), —C(CH$_3$)(CF$_3$)$_2$, —CH$_2$CH$_2$CH$_3$, —CH(CH$_2$CH$_3$)$_2$, —CD$_2$CD$_2$CD$_3$, —CD(CD$_2$CD$_3$)$_2$, —CF$_2$CH$_2$CH$_3$, —CF(CH$_2$CH$_3$)$_2$, —CH$_2$CF$_2$CF$_3$, —CH(CF$_2$CF$_3$)$_2$, —CF$_2$CF$_2$CF$_3$, —CF(CF$_2$CF$_3$)$_2$, or —OCH$_2$CH$_2$CH$_3$; and R$_3$ is H, D, Cl, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, —CH(CH$_3$)$_2$, —CD$_2$CD$_3$, —CD(CD$_3$)$_2$, —CF$_2$CH$_3$, —CF(CH$_3$)$_2$, —CH$_2$CF$_3$, —CH(CF$_3$)$_2$, —CF$_2$CF$_3$, —CF(CF$_3$)$_2$, —C(CH$_3$)$_3$, —C(CD$_3$)$_3$, —C(CF$_3$)$_3$, —OCH$_2$CH$_3$, —OCH(CH$_3$)$_2$, —OCD$_2$CD$_3$, —OCD(CD$_3$)$_2$, —OCF$_2$CH$_3$, —OCF(CH$_3$)$_2$, —OCH$_2$CF$_3$, —OCF$_2$CF$_3$, —OCH(CF$_3$)$_2$, —OCF$_2$(CF$_3$), —OCF(CF$_3$)$_2$, —OC(CH$_3$)$_3$, —OC(CD$_3$)$_3$, —OC(CF$_3$)$_3$, —C(CH$_3$)$_2$(CF$_3$), —C(CH$_3$)(CF$_3$)$_2$, —OC(CH$_3$)$_2$(CF$_3$), —OC(CH$_3$)(CF$_3$)$_2$, —CH$_2$CH$_2$CH$_3$, —CH(CH$_2$CH$_3$)$_2$, —CD$_2$CD$_2$CD$_3$, —CD(CD$_2$CD$_3$)$_2$, —CF$_2$CH$_2$CH$_3$, —CF(CH$_2$CH$_3$)$_2$, —CH$_2$CF$_2$CF$_3$, —CH(CF$_2$CF$_3$)$_2$, —CF$_2$CF$_2$CF$_3$, —CF(CF$_2$CF$_3$)$_2$, —OCH$_2$CH$_2$CH$_3$, —OCH(CH$_2$CH$_3$)$_2$, —OCD$_2$CD$_2$CD$_3$, —OCD(CD$_2$CD$_3$)$_2$, —OCF$_2$CH$_2$CH$_3$, —OCF(CH$_2$CH$_3$)$_2$, —OCH$_2$CF$_2$CF$_3$, —OCH(CF$_2$CF$_3$)$_2$, —OCF$_2$CF$_2$CF$_3$ or —OCF(CF$_2$CF$_3$)$_2$. In some embodiments wherein C is 13, each of R$_1$ and R$_2$ is independently H, D, —CH$_3$, —CD$_3$, —CH$_2$F, —CHF$_2$, —CF$_3$, —C(CH$_3$)$_3$, —C(CD$_3$)$_3$, —C(CF$_3$)$_3$, —CH$_2$CH$_3$, or —CH(CH$_3$)$_2$; and R$_3$ is H, D, Cl, F, —CH$_3$, —OCH$_3$, —CD$_3$, —OCD$_3$, —CH$_2$F, —CHF$_2$, —CF$_3$, —OCF$_3$, —C(CH$_3$)$_3$, —C(CD$_3$)$_3$, —C(CF$_3$)$_3$, —OC(CH$_3$)$_3$, —OC(CD$_3$)$_3$, —OC(CF$_3$)$_3$, —CH$_2$CH$_3$, —OCH$_2$CH$_3$, or —CH(CH$_3$)$_2$. In some embodiments, wherein C is 13, each of R$_1$ and R$_2$ is independently and H, —CH$_3$, —CH$_2$F, —CHF$_2$, —CF$_3$, —C(CH$_3$)$_3$, —C(CF$_3$)$_3$, —CH$_2$CH$_3$, or —CH(CH$_3$)$_2$; and R$_3$ is H, F, —CH$_3$, —OCH$_3$, —CH$_2$F, —CHF$_2$, —CF$_3$, —OCF$_3$, —C(CH$_3$)$_3$, —C(CF$_3$)$_3$, —CH$_2$CH$_3$, —OCH$_2$CH$_3$, or —CH(CH$_3$)$_2$. In some embodiments wherein C is 13, each of R$_1$ and R$_2$ is H, —CH$_3$, or —CF$_3$;

and $R_3$ is H, F, —$CH_3$, —$OCH_3$, —$CF_3$ or —$OCF_3$. In some embodiments wherein C is 13, each of $R_1$ and $R_2$ is —$CH_3$ or —$CH_2CH_3$; and $R_3$ is H, F, or —$CH_3$. In some embodiments wherein C is 13, each of $R_1$ and $R_2$ is —$CH_3$; and $R_3$ is H. In some embodiments wherein C is 13, each of $R_1$ and $R_2$ is —$CH_3$; and $R_3$ is F. In some embodiments wherein C is 13, each of $R_1$ and $R_2$ is —$CH_3$; and $R_3$ is —$CH_3$. In some embodiments wherein C is 13, each of $R_1$ and $R_2$ is —$CH_3$; and $R_3$ is —$OCH_3$. In some embodiments wherein C is 13, at least one of $R_1$, $R_2$ and $R_3$ comprises at least one fluorine atom. In some embodiments wherein C is 13, each of $R_1$ and $R_2$ is —$CH_3$; $R_3$ is H, F, $CH_3$ or —$OCH_3$ and at least one of $R_8$ and $R_9$ comprises a fluorine atom. In some embodiments wherein C is 13, each of $R_1$ and $R_2$ is —$CH_3$; $R_3$ is H, F, $CH_3$ or —$OCH_3$ and each of $R_8$ and $R_9$ comprises a fluorine atom. In some embodiments wherein C is 13, each of $R_1$ and $R_2$ is —$CH_3$; $R_3$ is H, F, $CH_3$ or —$OCH_3$ and each of $R_8$, $R_9$ and $R_{10}$ comprises a fluorine atom. In some embodiments wherein C is 13: (i) at least one of $R_1$, $R_2$ and $R_3$ comprises at least one fluorine atom; and/or (ii) at least one of $R_8$ and $R_9$ comprises a fluorine atom. In some embodiments wherein C is 13, each of $R_1$ and $R_2$ is —$CH_3$; $R_3$ is H, F, $CH_3$ or —$OCH_3$ and each of $R_8$ and $R_9$ is a fluorine atom. In some embodiments wherein C is 13, each of $R_1$ and $R_2$ is —$CH_3$; $R_3$ is H, F, $CH_3$ or —$OCH_3$ and each of $R_8$, $R_9$ and $R_{10}$ is a fluorine atom. In some embodiments wherein C is 13, each of $R_1$ and $R_2$ is —$CH_3$; $R_3$ is H, F, $CH_3$ or —$OCH_3$ and one of $R_8$, $R_9$ and $R_{10}$ is a fluorine atom and the others are hydrogen atoms. In some embodiments wherein C is 13, each of $R_1$ and $R_2$ is —$CH_3$; $R_3$ is H, F, $CH_3$ or —$OCH_3$ and two of $R_8$, $R_9$ and $R_{10}$ are a fluorine atoms and the other(s) is/are a hydrogen atom. In some embodiments wherein C is 13, each of $R_1$ and $R_2$ is —$CH_3$; $R_3$ is H, F, $CH_3$ or —$OCH_3$ and each $R_8$, $R_9$ and $R_{10}$ is a fluorine atom.

In some embodiments of the compound represented by C-B, wherein C is 13, (i) $R_3$ is H, D, Cl, F, —$CH_3$, —$OCH_3$, —$CD_3$, —$OCD_3$, —$CF_3$, —$OCF_3$, —$C(CH_3)_3$, —$C(CD_3)_3$, —$C(CF_3)_3$, —$OC(CH_3)_3$, —$OC(CD_3)_3$, —$OC(CF_3)_3$, —$CH_2CH_3$, —$OCH_2CH_3$, or —$CH(CH_3)_2$; and (ii) $R_1$ and $R_2$ taken together form a 5-, or 6-membered carbocyclic or heterocyclic ring. In some embodiments wherein C is 13, (i) $R_3$ is H, D, F, —$CH_3$, —$OCH_3$, —$CF_3$ or —$OCF_3$; and (ii) $R_1$ and $R_2$ taken together form a 5-, or 6-membered carbocyclic or heterocyclic ring. In some embodiments wherein C is 13; (i) $R_3$ is H, F, —$CH_3$, or —$OCH_3$, and (ii) $R_1$ and $R_2$ taken together form a 5-, or 6-membered carbocyclic or heterocyclic ring. In some embodiments of the compound represented by C-B, wherein C is 13; (i) $R_3$ is H; and (ii) $R_1$ and $R_2$ taken together form a 5-, or 6-membered carbocyclic or heterocyclic ring. In some embodiments of the compound represented by C-B, wherein C is 13; (i) $R_3$ is —$CH_3$; and (ii) $R_1$ and $R_2$ taken together form a 5-, or 6-membered carbocyclic or heterocyclic ring. In some embodiments of the compound represented by C-B, wherein C is 13; (i) $R_3$ is —$OCH_3$; and (ii) $R_1$ and $R_2$ taken together form a 5-, or 6-membered carbocyclic or heterocyclic ring. In some embodiments of the compound represented by C-B, wherein C is 13; (i) $R_3$ is F; and (ii) $R_1$ and $R_2$ taken together form a 5-, or 6-membered carbocyclic or heterocyclic ring.

In some embodiments of the compound represented by C-B, C is a head-group of formula 13A or 13B:

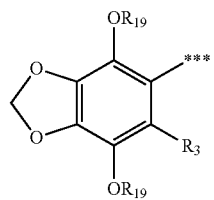

13A

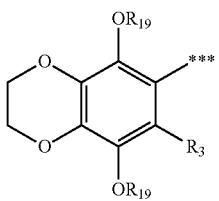

13B

In some embodiments of 13A or 13B, $R_3$ is H, F, —$CH_3$ or —$OCH_3$. In some embodiments of 13A or 13B, $R_3$ is H. In some embodiments of 13A or 13B, $R_3$ is F. In some embodiments of 13A or 13B, $R_3$ is —$CH_3$. In some embodiments of 13A or 13B, $R_3$ is —$OCH_3$.

In some embodiments of the compound represented by C-B, wherein C is 14, $R_3$ is H, D, F, Cl, —$CH_3$, —$OCH_3$, —$CD_3$, —$OCD_3$, —$CH_2F$, —$OCH_2F$, —$CHF_2$, —$OCHF_2$, —$CF_3$, —$OCF_3$, —$CH_2CH_3$, —$CH(CH_3)_2$, —$CD_2CD_3$, —$CD(CD_3)_2$, —$CF_2CH_3$, $CF(CH_3)_2$, —$CH_2CF_3$, —$CH(CF_3)_2$, —$CF_2CF_3$, —$CF(CF_3)_2$, —$C(CH_3)_3$, —$C(CD_3)_3$, —$C(CF_3)_3$, —$OCH_2CH_3$, —$OCH(CH_3)_2$, —$OCD_2CD_3$, —$OCD(CD_3)_2$, —$OCF_2CH_3$, —$OCF(CH_3)_2$, —$OCH_2CF_3$, —$OCF_2CF_3$, —$OCH(CF_3)_2$, —$OCF_2(CF_3)$, —$OCF(CF_3)_2$, —$OC(CH_3)_3$, —$OC(CD_3)_3$, —$OC(CF_3)_3$, —$C(CH_3)_2(CF_3)$, —$C(CH_3)(CF_3)_2$, —$OC(CH_3)_2(CF_3)$, —$OC(CH_3)(CF_3)_2$, —$CH_2CH_2CH_3$, —$CH(CH_2CH_3)_2$, —$CD_2CD_2CD_3$, —$CD(CD_2CD_3)_2$, —$CF_2CH_2CH_3$, —$CF(CH_2CH_3)_2$, —$CH_2CF_2CF_3$, —$CH(CF_2CF_3)_2$, —$CF_2CF_2CF_3$, —$CF(CF_2CF_3)_2$, —$OCH_2CH_2CH_3$, —$OCH(CH_2CH_3)_2$, —$OCD_2CD_2CD_3$, —$OCD(CD_2CD_3)_2$, —$OCF_2CH_2CH_3$, —$OCF(CH_2CH_3)_2$, —$OCH_2CF_2CF_3$, —$OCH(CF_2CF_3)_2$, —$OCF_2CF_2CF_3$ or —$OCF(CF_2CF_3)_2$; and where if W is C (carbon), each of $R_4$, $R_5$, $R_6$ and $R_7$ attached thereto can be independently H, D, F, Cl, Br, I, —$CH_3$, —$OCH_3$, —$CD_3$, —$OCD_3$, —$CH_2F$, —$OCH_2F$, —$CHF_2$, —$OCHF_2$, —$CF_3$, —$OCF_3$, —$CH_2CH_3$, or —$CH(CH_3)_2$, and where if W is N (nitrogen), each of $R_4$, $R_5$, $R_6$ and $R_7$ attached thereto can be independently absent or is H, D, methyl, ethyl, isopropyl or t-butyl. In some embodiments wherein C is 14, $R_3$ is H, D, Cl, F, —$CH_3$, —$OCH_3$, —$CD_3$, —$OCD_3$, —$CH_2F$, —$CHF_2$, —$CF_3$, —$OCF_3$, —$C(CH_3)_3$, —$C(CD_3)_3$, —$C(CF_3)_3$, —$OC(CH_3)_3$, —$OC(CD_3)_3$, —$OC(CF_3)_3$, —$CH_2CH_3$, —$OCH_2CH_3$, or —$CH(CH_3)_2$; and where if W is C (carbon), each of $R_4$, $R_5$, $R_6$ and $R_7$ attached thereto is independently H, D, F, Cl, —$CH_3$, —$OCH_3$, —$CH_2F$, —$CHF_2$, —$CF_3$, —$OCF_3$, —$CH_2CH_3$, or —$CH(CH_3)_2$, and where if W is N (nitrogen), each of $R_4$, $R_5$, $R_6$ and $R_7$ attached thereto is independently absent or is H, D, methyl or ethyl. In some embodiments wherein C is 14, $R_3$ is H, F, —$CH_3$, —$OCH_3$, —$CF_3$, or —$OCF_3$; and where if W is C (carbon), each of $R_4$, $R_5$, $R_6$ and $R_7$ attached thereto is independently H, F, —$CH_3$, —$OCH_3$, —$CF_3$, or —$OCF_3$, and where if W is N (nitrogen), each of $R_4$, $R_5$, $R_6$ and $R_7$ attached thereto is independently absent or is H, or methyl. In some embodiments wherein C is 14, each W is C (carbon) and each of $R_4$, $R_5$, $R_6$ and $R_7$ is independently H, D, Cl, F, —$CH_3$, —$OCH_3$, —$CH_2F$, —$CHF_2$, —$CF_3$ or —$OCF_3$. In some embodiments wherein C is 14, each W is C (carbon) and each of $R_4$, $R_5$, $R_6$ and $R_7$ is independently H, F, —$CH_3$, —$OCH_3$, —$CF_3$ or —$OCF_3$. In some embodiments wherein C is 14, each W is C (carbon) and each of $R_4$, $R_5$, $R_6$ and $R_7$ is independently H, F, —$CH_3$, or —$OCH_3$. In some embodiments wherein C is 14, each W is C (carbon) and each of $R_4$, $R_5$, $R_6$ and $R_7$ is H. In some embodiments wherein C is 14, each W is C (carbon) and each of $R_4$, $R_5$, $R_6$ and $R_7$ is F. In some embodiments wherein C is 14, each W is C (carbon) and each of $R_4$, $R_5$, $R_6$ and $R_7$ is —$CH_3$.

In some embodiments of the compound represented by C-B, each $R_8$ and $R_9$ is independently H, D, F, Cl, Br, I, —$CH_3$, —$CD_3$, —$CH_2F$, —$CHF_2$, —$CF_3$, —$CH_2CH_3$, —$CH(CH_3)_2$, —$CD_2CD_3$, —$CD(CD_3)_2$, —$CF_2CH_3$, —$CF(CH_3)_2$, —$CH_2CF_3$, —$CH(CH_2F)_2$, —$CH(CF_3)_2$, —$CF_2CF_3$, —$CF(CF_3)_2$, —$C(CH_3)_3$, —$C(CD_3)_3$, —$C(CF_3)_3$, —$C(CH_3)_2(CF_3)$, —$C(CH_3)(CF_3)_2$, —$CH_2CH_2CH_3$, —$CH(CH_2CH_3)_2$, —$CD_2CD_2CD_3$, —$CD(CD_2CD_3)_2$, —$CF_2CH_2CH_3$, —$CF(CH_2CH_3)_2$, —$CH_2CF_2CF_3$, —$CH(CF_2CF_3)_2$, —$CF_2CF_2CF_3$ or —$CF(CF_2CF_3)_2$. In some embodiments of the compound represented by C-B, each $R_8$ and $R_9$ is independently H, F, —$CH_3$, —$CH_2F$, —$CHF_2$, —$CF_3$, —$CH_2CH_3$, —$CH(CH_3)_2$, —$CF_2CH_3$, —$CH_2CF_3$, —$CH(CF_3)_2$, —$CF_2CF_3$, —$CF(CF_3)_2$, —$C(CH_3)_3$, —$C(CF_3)_3$, —$CH_2CH_2CH_3$, —$CH(CH_2F)_2$, —$CH(CH_2CH_3)_2$, —$CF_2CF_2CF_3$ or —$CF(CF_2CF_3)_2$. In some embodiments of the compound represented by C-B, each $R_8$ and $R_9$ is independently H, F, —$CH_3$, —$CF_3$, —$CH_2CH_3$, —$CH(CH_3)_2$, —$CH(CH_2F)_2$, —$CH(CF_3)_2$, —$CF_2CF_3$, —$CF(CF_3)_2$, —$C(CH_3)_3$ or —$C(CF_3)_3$. In some embodiments of the compound represented by C-B, each $R_8$ and $R_9$ is independently H, F, —$CH_3$, —$CF_3$, —$CH_2CH_3$ or —$CH(CH_2F)_2$. In some embodiments of the compound represented by C-B, each $R_8$ and $R_9$ is independently H, F, —$CH_3$, —$CH_2F$, —$CHF_2$, or —$CF_3$. In some embodiments of the compound represented by C-B, each $R_8$ and $R_9$ is H. In some embodiments of the compound represented by C-B, each $R_8$ and $R_9$ is F. In some embodiments of the compound represented by C-B, one of $R_8$ and $R_9$ is F and the other(s) of $R_8$ and $R_9$ is/are H. In some embodiments of the compound represented by C-B, each $R_8$ and $R_9$ is —$CH_3$. In some embodiments of the compound represented by C-B, each $R_8$ and $R_9$ is —$CH_2F$. In some embodiments of the compound represented by C-B, each $R_8$ and $R_9$ is —$CF_3$. In some embodiments of the compound represented by C-B, at least one of $R_8$ and $R_9$ is F. In some embodiments of the compound represented by C-B, at least one of $R_8$ and $R_9$ is —$CH_2F$.

In some embodiments of the compound represented by C-B, at least one $R_8$ and $R_9$, of a group of the formula —($CR_8R_9$)—, —($CR_8R_9$) or —($CR_8R_9R_{10}$), taken together form a 3-, 4-, 5-, 6- or 7-membered carbocyclic or heterocyclic ring selected from a group of formula 31, 32, 33, 34, 35, 36, 37, 38, 39, 40, 41, 42, 43, 44, 45, 46 and 47:

31

32

33

34

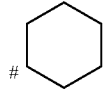

35

36

37

38

39

40

41

42

43

44

45

46

47

wherein # indicates the point of attachment of the carbocycle or heterocycle to the remainder of the compound. In some embodiments of the compound represented by C-B, each $R_8$ and $R_9$, of a group of the formula —($CR_8R_9$)—, —($CR_8R_9$) or —($CR_8R_9R_{10}$), taken together form a 3-, 4-, 5-, 6- or 7-membered carbocyclic or heterocyclic ring selected from a group of formula 31, 32, 33, 34, 35, 36, 37, 38, 39, 40, 41, 42, 43, 44, 45, 46 and 47:

31

32

33

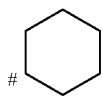
34

35

36

37

38

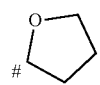
39

40

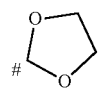
41

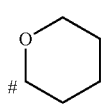
42

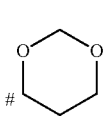
43

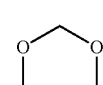
44

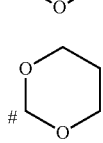
45

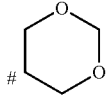
46

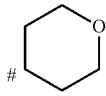
47 wherein # indicates the point of attachment of the carbocycle or heterocycle to the remainder of the compound. In some embodiments of the compound represented by C-B, each $R_8$ and $R_9$, of a group of the formula —$(CR_8R_9)$— or —$(CR_8R_9R_{10})$, taken together form a 3-, 4-, 5-, 6- or 7-membered carbocyclic or heterocyclic ring selected from a group of formula 31, 32, 33, 34, 35, 36, 37, 38, 39, 40, 41, 42, 43, 44, 45, 46 and 47:

31

32

33

34

35

36

37

38

39

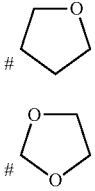
40

41

-continued

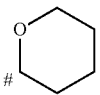
42

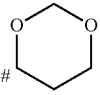
43

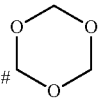
44

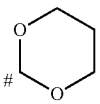
45

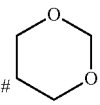
46

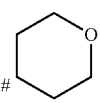
47 wherein # indicates the point of attachment of the carbocycle or heterocycle to the remainder of the compound.

In some embodiments, each $R_8'$, $R_9'$ and $R_{10}'$ is independently a $C_1$-$C_4$ alkyl. In some embodiments, each $R_8'$, $R_9'$ and $R_{10}'$ is independently a $C_1$-$C_4$ alkoxy. In some embodiments, each $R_8'$, $R_9'$ and $R_{10}'$ is independently methyl, ethyl or t-butyl. In some embodiments, each $R_8'$, $R_9'$ and $R_{10}'$ is methyl. In some embodiments, each $R_8'$, $R_9'$ and $R_{10}'$ is methoxy. In some embodiments, each $R_8'$, $R_9'$ and $R_{10}'$ is ethyl. In some embodiments, each $R_8'$, $R_9'$ and $R_{10}'$ is t-butyl. In some embodiments, taken together $R_8'$ and $R_9'$ form a 4-, 5-, or 6-membered carbocyclic or heterocyclic ring.

In some embodiments of the compound C-B, $R_{10}$ is H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, —CH(CH$_3$)$_2$, —CD$_2$CD$_3$, —CD(CD$_3$)$_2$, —CF$_2$CH$_3$, CF(CH$_3$)$_2$, —CH$_2$CF$_3$, —CH(CF$_3$)$_2$, —CF$_2$CF$_3$, —CF(CF$_3$)$_2$, —C(CH$_3$)$_3$, —C(CD$_3$)$_3$, —C(CF$_3$)$_3$, —OCH$_2$CH$_3$, —OCH(CH$_3$)$_2$, —OCD$_2$CD$_3$, —OCF$_2$CF$_3$, —OCD(CD$_3$)$_2$, —OCF$_2$(CF$_3$), —OCF(CF$_3$)$_2$, —OC(CH$_3$)$_3$, —OC(CD$_3$)$_3$, —OC(CF$_3$)$_3$, —C(CH$_3$)$_2$(CF$_3$), —C(CH$_3$)(CF$_3$)$_2$, —OC(CH$_3$)$_2$(CF$_3$), —OC(CH$_3$)(CF$_3$)$_2$, —CH$_2$CH$_2$CH$_3$, —CH(CH$_2$CH$_3$)$_2$, —CD$_2$CD$_2$CD$_3$, —CD(CD$_2$CD$_3$)$_2$, —CF$_2$CF$_2$CF$_3$, —CF(CF$_2$CF$_3$)$_2$, —C(CH$_2$CH$_3$)$_3$, —C(CD$_2$CD$_3$)$_3$, —C(CF$_2$CF$_3$)$_3$, —OCH$_2$CH$_2$CH$_3$, —OCH(CH$_2$CH$_3$)$_2$, —OCD$_2$CD$_2$CD$_3$, —OCD(CD$_2$CD$_3$)$_2$, —OCF$_2$CF$_2$CF$_3$ or —OCF(CF$_2$CF$_3$)$_2$. In some embodiments of the compound C-B, $R_{10}$ is H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$ or —CH(CH$_3$)$_2$. In some embodiments of the compound C-B, $R_{10}$ is H, D, F, —CH$_3$, —CH$_2$F, —CHF$_2$, or —CF$_3$. In some embodiments of the compound C-B, $R_{10}$ is $R_{10}$ is H, F, —CH$_3$, —OCH$_3$, —CF$_3$ or —OCF$_3$. In some embodiments of the compound C-B, $R_{10}$ is H, D or F. In some embodiments of the compound C-B, $R_{10}$ is —CH$_3$ or —CF$_3$. In some embodiments of the compound C-B, $R_{10}$ is —H or —CH$_3$. In some embodiments of the compound C-B, $R_{10}$ is H or —CF$_3$. In some embodiments of the compound C-B, $R_{10}$ is H. In some embodiments of the compound C-B, $R_{10}$ is D. In some embodiments of the compound C-B, $R_{10}$ is F. In some embodiments of the compound C-B, $R_{10}$ is —CH$_3$. In some embodiments of the compound C-B, $R_{10}$ is —OCH$_3$. In some embodiments of the compound C-B, $R_{10}$ is absent.

In some embodiments of the compound C-B, each instance of $R_{12}$, $R_{13}$ or $R_{14}$ is independently H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, —CH(CH$_3$)$_2$, —CH$_2$CH$_2$CH$_3$, —CH(CH$_2$CH$_3$)$_2$, —C(CH$_3$)$_3$, —OCH$_2$CH$_3$, —OCH(CH$_3$)$_2$, —OCH$_2$CH$_2$CH$_3$, —OCH(CH$_2$CH$_3$)$_2$, or —OC(CH$_3$)$_3$. In some embodiments of the compound C-B, each instance of $R_{12}$, $R_{13}$ or $R_{14}$ is independently H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$ or —CH(CH$_3$)$_2$. In some embodiments of the compound C-B, each instance of $R_{12}$, $R_{13}$ or $R_{14}$ is independently H, D, F, —CH$_3$, —OCH$_3$, —CD$_3$, —OCD$_3$, —CH$_2$F, —OCH$_2$F, —CHF$_2$, —OCHF$_2$, —CF$_3$ or —OCF$_3$. In some embodiments of the compound C-B, each instance of $R_{12}$, $R_{13}$ and $R_{14}$ is independently H, F, —CH$_3$, —OCH$_3$, —CF$_3$, —OCF$_3$, —CH$_2$CH$_3$ or —OCH$_2$CH$_3$. In some embodiments of the compound C-B, each instance of $R_{12}$, $R_{13}$ or $R_{14}$ is independently H, D, F, —CH$_3$, —CD$_3$ or —CF$_3$. In some embodiments of the compound C-B, each instance of $R_{12}$, $R_{13}$ or $R_{14}$ is independently H, D, F or —CH$_3$. In some embodiments of the compound C-B, each instance of $R_{12}$, $R_{13}$ or $R_{14}$ is independently H, or F. In some embodiments of the compound C-B, each instance of $R_{12}$, $R_{13}$ or $R_{14}$ is H. In some embodiments of the compound C-B, each instance of $R_{12}$, $R_{13}$ or $R_{14}$ is D. In some embodiments of the compound C-B, each instance of $R_{12}$, $R_{13}$ or $R_{14}$ is F. In some embodiments of the compound C-B, each instance of $R_{12}$, $R_{13}$ or $R_{14}$ is —CH$_3$. In some embodiments of the compound C-B, each $R_{12}$, $R_{13}$ and $R_{14}$ is independently H, F, —CH$_3$, —OCH$_3$, —CF$_3$, —OCF$_3$, —CH$_2$CH$_3$ or —OCH$_2$CH$_3$; provided however that for at least one group of formula —(CR$_{12}$R$_{13}$)—, taken together $R_{12}$ and $R_{13}$ form a 3-, 4-, 5-, 6- or 7-membered carbocyclic or heterocyclic ring.

In some embodiments of the compound C-B, at least one $R_{19}$ is H. In some embodiments of the compound C-B, each $R_{19}$ is H. In some embodiments of the compound C-B, at least one $R_{19}$ is —CH$_3$. In some embodiments of the compound C-B, each $R_{19}$ is —CH$_3$. In some embodiments of the compound C-B, at least one $R_{19}$ is a (unsubstituted or substituted) benzyl group. In some embodiments of the compound C-B, each $R_{19}$ is a (unsubstituted or substituted) benzyl group.

In some embodiments of the compound C-B, at least one $R_{19}$ is $R_{24}$C(O)— or $R_{24}$OC(O)—, wherein $R_{24}$ is H, —CH$_3$, —CD$_3$, —CF$_3$, —CH$_2$CH$_3$ or —CH(CH$_3$)$_2$. In some embodiments of the compound C-B, each $R_{19}$ is $R_{24}$C(O)— or $R_{24}$OC(O)—, wherein $R_{24}$ is H, —CH$_3$, —CD$_3$, —CF$_3$, —CH$_2$CH$_3$ or —CH(CH$_3$)$_2$. In some embodiments of the compound C-B, at least one $R_{19}$ is $R_{24}$C(O)— or $R_{24}$OC(O)—, wherein $R_{24}$ is T. In some embodiments of the compound C-B, wherein $R_{24}$ is T and T can be —(CH$_2$)$_0$—(O)$_0$—[(CH$_2$CH$_2$)—O]$_q$—R$_{26}$, —(CH$_2$)$_1$—(O)$_1$—[(CH$_2$CH$_2$)—O]$_q$—R$_{26}$, or —(CH$_2$)$_2$—(O)$_1$—[(CH$_2$CH$_2$)—O]$_q$—R$_{26}$, wherein $R_{26}$ is H, methyl, ethyl or tert-butyl. In some embodiments of the compound C-B, wherein $R_{24}$ is T, q is 1. In some embodiments of the compound C-B, wherein $R_{24}$ is T, q is 2. In some embodiments of the compound C-B, wherein $R_{24}$ is T, q is 3. In some embodiments of the compound C-B, wherein $R_{24}$ is T, q is 4. In some embodiments of the compound C-B, wherein $R_{24}$ is T, q is 5.

In some embodiments of the compound C-B, at least one $R_{19}$ is $R_{24}R_{25}NC(O)$— or $(R_{24}O)(R_{25}O)P(O)$—, wherein each of $R_{24}$ and $R_{25}$ is independently H, —$CH_3$, —$CD_3$, —$CF_3$, —$CH_2CH_3$ or —$CH(CH_3)_2$. In some embodiments of the compound C-B, each $R_{19}$ is $R_{24}R_{25}NC(O)$— or $(R_{24}O)(R_{25}O)P(O)$—, wherein each of $R_{24}$ and $R_{25}$ is independently H, —$CH_3$, —$CD_3$, —$CF_3$, —$CH_2CH_3$ or —$CH(CH_3)_2$. In some embodiments of the compound C-B, at least one $R_{19}$ is $R_{24}R_{25}NC(O)$— or $(R_{24}O)(R_{25}O)P(O)$—, wherein $R_{24}$ and $R_{25}$, taken together, form a 3-, 4-, 5-, 6- or 7-membered carbocyclic or heterocyclic ring. In some embodiments of the compound C-B, each $R_{19}$ is $R_{24}R_{25}NC(O)$— or $(R_{24}O)(R_{25}O)P(O)$—, wherein $R_{24}$ and $R_{25}$, taken together, form a 3-, 4-, 5-, 6- or 7-membered carbocyclic or heterocyclic ring.

In some embodiments of the compound C-B, at least one $R_{19}$ is $R_{24}R_{25}NC(O)$—, or $(R_{24}O)(R_{25}O)P(O)$— and wherein at least one of $R_{24}$ and $R_{25}$ is T. In some embodiments of the compound C-B, each $R_{19}$ is $R_{24}R_{25}NC(O)$—, or $(R_{24}O)(R_{25}O)P(O)$— and wherein at least one of $R_{24}$ and $R_{25}$ is T. In some embodiments of the compound C-B, at least one $R_{19}$ is $R_{24}R_{25}NC(O)$—, or $(R_{24}O)(R_{25}O)P(O)$— and wherein each of $R_{24}$ and $R_{25}$ is T. In some embodiments of the compound C-B, each $R_{19}$ is $R_{24}R_{25}NC(O)$—, or $(R_{24}O)(R_{25}O)P(O)$— and each of $R_{24}$ and $R_{25}$ is T. In some embodiments of the compound C-B, wherein one or more of $R_{24}$ and/or $R_{25}$ is T and T can be —$(CH_2)_0$—$(O)_0$—$[(CH_2CH_2)$—$O]_q$—$R_{26}$, —$(CH_2)_1$—$(O)_1$—$[(CH_2CH_2)$—$O]_q$—$R_{26}$, or —$(CH_2)_2$—$(O)_1$—$[(CH_2CH_2)$—$O]_q$—$R_{26}$, wherein $R_{26}$ is H, methyl, ethyl or tert-butyl. In some embodiments of the compound C-B, wherein at least one of $R_{24}$ and $R_{25}$ is T, for each T, q is 1. In some embodiments of the compound C-B, wherein at least one of $R_{24}$ and $R_{25}$ is T, for each T, q is 2. In some embodiments of the compound C-B, wherein at least one of $R_{24}$ and $R_{25}$ is T, for each T, q is 3. In some embodiments of the compound C-B, wherein at least one of $R_{24}$ and $R_{25}$ is T, for each T, q is 4. In some embodiments of the compound C-B, wherein at least one of $R_{24}$ and $R_{25}$ is T, for each T, q is 5.

In some embodiments of the compound C-B, $R_{20}$ is H, D, F, —$CH_3$, —$CD_3$, —$CH_2F$, —$CHF_2$, —$CF_3$, —$CH_2CH_3$, —$CH_2CH_2CH_3$, —$CH(CH_3)_2$, —$C(CH_3)_3$, —$CH_2CH_2CH_2CH_3$, —$CH_2CH_2CH_2CH_3$, —$CH_2CH_2CH_2CH_2CH_2CH_3$, —$CH_2CH_2CH_2CH_2CH_2CH_2CH_3$, —$CH_2CH_2CH_2CH_2CH_2CH_2CH_2CH_3$, —$CH_2CH_2CH_2CH_2CH_2CH_2CH_2CH_2CH_3$ or —$CH_2CH_2CH_2CH_2CH_2CH_2CH_2CH_2CH_2CH_3$. In some embodiments of the compound C-B, $R_{20}$ is H, D, F, —$CH_3$, —$CD_3$, —$CH_2F$, —$CHF_2$, —$CF_3$, —$CH_2CH_3$, —$CH_2CH_2CH_3$, —$CH(CH_3)_2$ or —$C(CH_3)_3$. In some embodiments of the compound C-B, $R_{20}$ is H, D, F, —$CH_3$, —$CD_3$, —$CH_2F$, —$CHF_2$ or —$CF_3$. In some embodiments of the compound C-B, $R_{20}$ is H, D, F, —$CH_3$, —$CD_3$, —$CH_2F$, —$CHF_2$ or —$CF_3$. In some embodiments of the compound C-B, $R_{20}$ is H, D, F, or —$CH_3$. In some embodiments of the compound C-B, $R_{20}$ is —$CH_3$, —$CD_3$, —$CH_2F$, —$CHF_2$ or —$CF_3$. In some embodiments of the compound C-B, $R_{20}$ is H, F or —$CH_3$. In some embodiments of the compound C-B, $R_{20}$ is H. In some embodiments of the compound C-B, $R_{20}$ is —$CH_3$. In some embodiments of the compound C-B, $R_{20}$ is —$CF_3$. In some embodiments of the compound C-B, $R_{20}$ is F.

In some embodiments of the compound C-B, each $R_{21}$ is independently H, D, F, —$CH_3$, —$CD_3$, —$CH_2F$, —$CHF_2$, —$CF_3$, —$CH_2CH_3$, —$CH_2CH_2CH_3$, —$CH(CH_3)_2$, —$CH_2CH_2CH_2CH_3$ or —$C(CH_3)_3$. In some embodiments of the compound C-B, each $R_{21}$ is independently H, D, F, —$CH_3$, —$CD_3$, —$CH_2F$, —$CHF_2$ or —$CF_3$. In some embodiments of the compound C-B, each $R_{21}$ is independently H, F, —$CH_3$ or —$CF_3$. In some embodiments of the compound C-B, each $R_{21}$ is independently H, F, or —$CH_3$. In some embodiments of the compound C-B, each $R_{21}$ is —$CH_3$. In some embodiments of the compound C-B, each $R_{21}$ is H. In some embodiments of the compound A-B, each $R_{21}$ is F.

In some embodiments of the compound C-B, $R_{27}$ is H. In some embodiments of the compound C-B, $R_{27}$ is methyl. In some embodiments of the compound C-B, $R_{27}$ is ethyl. In some embodiments of the compound C-B, $R_{27}$ is t-butyl.

In some embodiments of the compound C-B, m is 0. In some embodiments of the compound C-B, m is 1. In some embodiments of the compound C-B, n is 0. In some embodiments of the compound C-B, n is 1. In some embodiments of the compound C-B, both n and m are 0. In some embodiments of the compound C-B, one of n and m is 0 and the other is 1. In some embodiments of the compound C-B, both n and m are 1. In some embodiments of the compound C-B, (i) m is 0 and n is 0; (ii) m is 0 and n is 1, 2 or 3; or (iii) m is 1 and n is 0, 1, 2 or 3.

In some embodiments of the compound C-B, n is 0, 1, 2, 3, 4, 5, 6, 7 or 8. In some embodiments of the compound C-B, n is 0, 1, 2, 3, 4, 5 or 6. In some embodiments of the compound C-B, n is 0, 1, 2, 3 or 4. In some embodiments of the compound C-B, n is 2. In some embodiments of the compound C-B, n is 3. In some embodiments of the compound C-B, n is 4. In some embodiments of the compound C-B, n is 5. In some embodiments of the compound C-B, n is 6. In some embodiments of the compound D-B, n is 7. In some embodiments of the compound C-B, n is 8. In some embodiments of the compound C-B, n is 9. In some embodiments of the compound C-B, n is 10. In some embodiments of the compound C-B, n is 11. In some embodiments of the compound C-B, n is 12.

In some embodiments of the compound C-B, p is 0, 1, 2, 3, 4, 5, 6, 7, 8, 9, 10, 11, 12, 13, 14 or 15. In some embodiments of the compound C-B, p is 0, 1, 2, 3, 4, 5, 6, 7, 8, 9, 10, 11 or 12. In some embodiments of the c3,3ompound C-B, p is 0, 1, 2, 3, 4, 5, 6, 7 or 8. In some embodiments of the compound C-B, p is 0, 1, 2, 3, 4, 5 or 6. In some embodiments of the compound C-B, p is 0, 1, 2, 3 or 4. In some embodiments of the compound C-B, p is 0. In some embodiments of the compound C-B, p is 1. In some embodiments of the compound C-B, p is 2. In some embodiments of the compound C-B, p is 3. In some embodiments of the compound C-B, p is 4. In some embodiments of the compound C-B, p is 5. In some embodiments of the compound C-B, p is 6. In some embodiments of the compound C-B, p is 7. In some embodiments of the compound C-B, p is 8. In some embodiments of the compound C-B, p is 9. In some embodiments of the compound C-B, p is 10. In some embodiments of the compound C-B, p is 11. In some embodiments of the compound C-B, p is 12. In some embodiments of the compound C-B, p is 13. In some embodiments of the compound C-B, p is 14. In some embodiments of the compound C-B, p is 15. In some embodiments of the compound C-B, p is 16. In some embodiments of the compound C-B, p is 17. In some embodiments of the compound C-B, p is 18. In some embodiments of the compound C-B, p is 19. In some embodiments of the compound C-B, p is 20.

In some embodiments of the compound C-B, at least one group of formula $R_1$, $R_2$, $R_3$, $R_4$, $R_5$, $R_6$, $R_7$, $R_8$, $R_9$, $R_{10}$, $R_{12}$, $R_{13}$, $R_{14}$, $R_{20}$ or $R_{21}$ comprises at least one fluorine atom. In some embodiments of the compound C-B, at least one group of formula $R_8$, $R_9$, $R_{10}$, $R_{20}$ or $R_{21}$ comprises at least one fluorine atom. In some embodiments of the compound C-B, at least one group of formula $R_8$, $R_9$ or $R_{10}$, comprises at least one fluorine atom. In some embodiments of the compound C-B, at least one $R_8$ and $R_9$, of a group of the formula $-(CR_8R_9)-$, $-(CR_8R_9)$ or $-(CR_8R_9R_{10})$, taken together form a 3-, 4-, 5-, 6- or 7-membered carbocyclic or heterocyclic ring. In some embodiments of the compound C-B, at least one of $R_8$ and $R_9$, of a group of the formula $-(CR_8R_9)$ or $-(CR_8R_9R_{10})$, taken together forms a 3-, 4-, 5-, 6- or 7-membered carbocyclic or heterocyclic ring. In some embodiments of the compound C-B, each $R_8$ and $R_9$, of a group of the formula $-(CR_8R_9)$, taken together forms a 3-, 4-, 5-, 6- or 7-membered carbocyclic or heterocyclic ring. In some embodiments of the compound C-B, at least one $R_{19}$ is $R_{24}C(O)-$, $R_{24}OC(O)-$, $R_{24}R_{25}NC(O)-$, or $(R_{24}O)(R_{25}O)P(O)-$. In some embodiments of the compound C-B, at least one $R_{19}$ is $R_{24}C(O)-$. In some embodiments of the compound C-B, at least one $R_{19}$ is $R_{24}OC(O)-$. In some embodiments of the compound C-B, at least one $R_{19}$ is $R_{24}R_{25}NC(O)-$. In some embodiments of the compound C-B, at least one $R_{19}$ is $(R_{24}O)(R_{25}O)P(O)-$.

In some embodiments, the compound C-B has the formula referred to herein as Compound X':

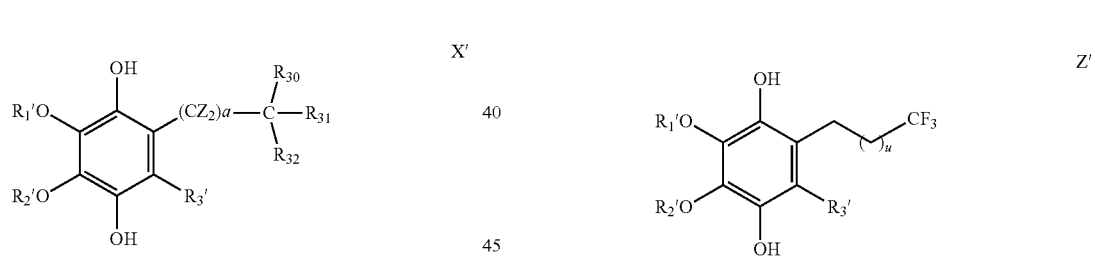

wherein, each of $R_1'$ and $R_2'$ is independently $C_1$-$C_3$ alkyl; $R_3'$ is H, D, F, $-CH_3$, $-CF_3$, $-OCH_3$ or $-OCF_3$; each Z is independently H, D or F; a is 1, 2, 3, 4, 5, 6 or 7; and each of $R_{30}$, $R_{31}$ and $R_{32}$ is independently H, D or F, provided however, that at least one of $R_{30}$, $R_{31}$ or $R_{32}$ is F. In some embodiments of Compound X', each of $R_1'$ and $R_2'$ is methyl. In some embodiments of Compound X', each of $R_1'$ and $R_2'$ is ethyl. In some embodiments of Compound X', $R_3'$ is H or $-CH_3$. In some embodiments of Compound X', a is 3, 4 or 5. In some embodiments of Compound X', a is 1. In some embodiments of Compound X', a is 2. In some embodiments of Compound X', a is 3. In some embodiments of Compound X', a is 4. In some embodiments of Compound X', a is 5. In some embodiments of Compound X', a is 6. In some embodiments of Compound X', a is 7. In some embodiments of Compound X', each Z is H. In some embodiments of Compound X', each of $R_{30}$, $R_{31}$ and $R_{32}$ is F.

In some embodiments, the compound C-B has the formula referred to herein as Z':

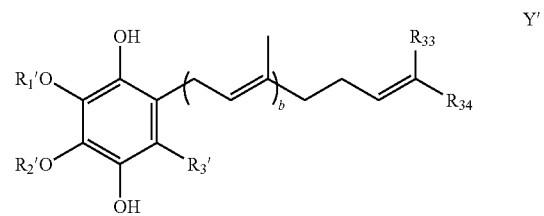

wherein, each of $R_1'$ and $R_2'$ is independently $C_1$-$C_3$ alkyl; $R_3'$ is H, D, F, $-CH_3$, $-CF_3$, $-OCH_3$ or $-OCF_3$; b is 1, 2, or 3; and each of $R_{33}$ and $R_{34}$ is independently H, D, F, $-CH_3$, $-CH_2F$, $-CHF_2$, or $-CHF_3$, provided, however, that at least one of $R_{33}$ and $R_{34}$ is selected from F, $-CH_2F$, $-CHF_2$, and $-CF_3$. In some embodiments of Compound Y', each of $R_1'$ and $R_2'$ is methyl. In some embodiments of Compound Y', each of $R_1'$ and $R_2'$ is ethyl. In some embodiments of Compound Y', $R_3'$ is H or $-CH_3$. In some embodiments of Compound Y', b is 1. In some embodiments of Compound Y', b is 2. In some embodiments of Compound Y', b is 3. In some embodiments of Compound Y', each Z is H. In some embodiments of Compound Y', each of $R_{33}$ and $R_{34}$ is F.

In some embodiments, the compound C-B has the formula referred to herein as Z':

wherein, each of $R_1'$ and $R_2'$ is independently $C_1$-$C_3$ alkyl; $R_3'$ is H, D, F, $-CH_3$, $-CF_3$, $-OCH_3$ or $-OCF_3$; and u is 1, 2, 3, 4, 5, 6, 7 or 8. In some embodiments, each of $R_1'$ and $R_2'$ is independently $-CH_3$ or $-CF_2CH_3$ and $R_3'$ is H or $-CH_3$. In some embodiments, each of $R_1'$, $R_2'$ and $R_3'$ is $-CH_3$. In some embodiments, u is 1, 2, 3, 4, 5, 6, or 7. In some embodiments, u is 1, 2, 3, 4, 5 or 6. In some embodiments, u is 2, 3, 4, 5, 6, 7, or 8. In some embodiments, u is 2, 3, 4, 5, 6 or 7. In some embodiments, u is 3, 4, 5, 6 or 7. In some embodiments, u is 3, 4, 5 or 6. In some embodiments, u is 4, 5, 6 or 7. In some embodiments, u is 1. In some embodiments, u is 2. In some embodiments of Z, u is 3. In some embodiments, u is 4. In some embodiments, u is 5. In some embodiments, u is 6. In some embodiments, u is 7. In some embodiments, u is 8. In some embodiments, each of $R_1'$ and $R_2'$ is independently $-CH_3$ or $-CF_2CH_3$, $R_3'$ is $-CH_3$, u is 2, 3, 4, 5, 6, 7 or 8 and Z has a calculated Log D of 2 to 7, inclusive.

In some embodiments of the compound C-B has the formula referred to herein as (22):

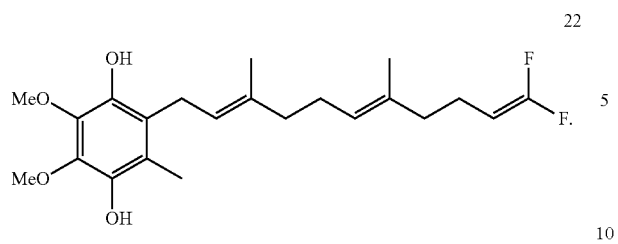

In some embodiments of the compound C-B has the formula referred to herein as (28):

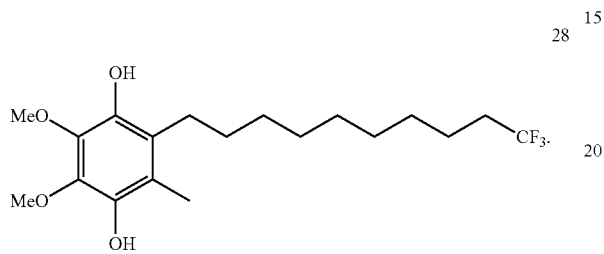

In some embodiments of the compound C-B has the formula referred to herein as (31):

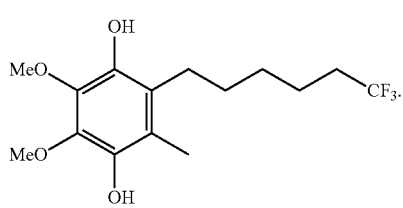

In some embodiments of the compound C-B has the formula referred to herein as (34):

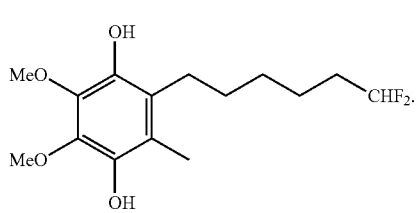

In some embodiments of the compound C-B has the formula referred to herein as (37):

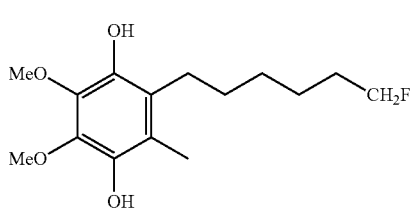

In some embodiments of the compound C-B has the formula referred to herein as (43):

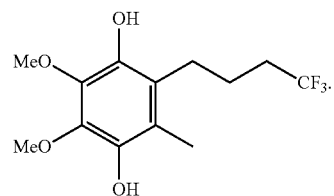

In some embodiments of the compound C-B has the formula referred to herein as (46):

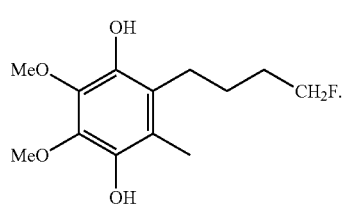

In some embodiments of the compound C-B has the formula referred to herein as (49):

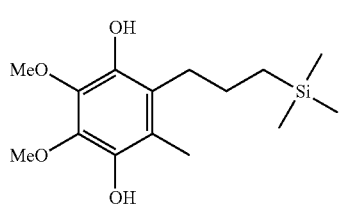

In some embodiments of the compound C-B has the formula referred to herein as (50):

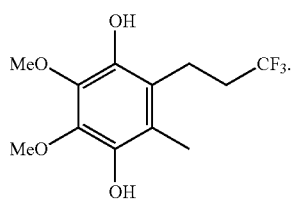

In some embodiments of the compound C-B has the formula referred to herein as (51):

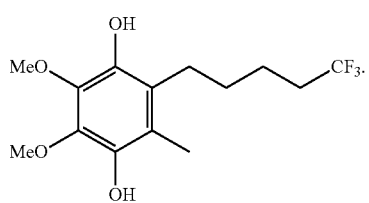

In some embodiments of the compound C-B has the formula referred to herein as (52):

52

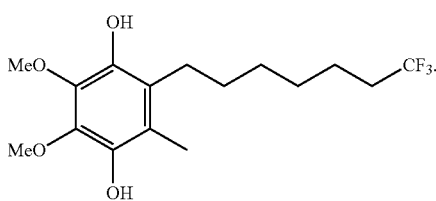

In some embodiments of the compound C-B has the formula referred to herein as (53):

53

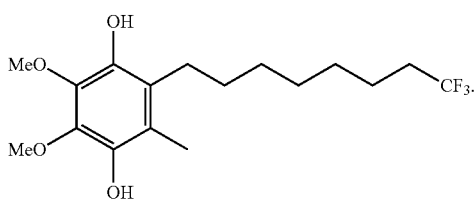

In some embodiments of the compound C-B has the formula referred to herein as (54):

54

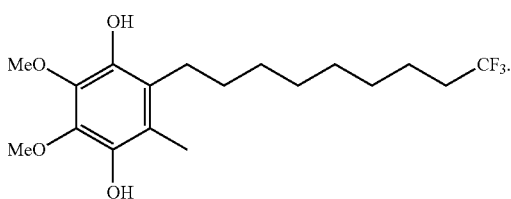

VI. Methods for Making Therapeutic Compounds and Related Intermediates

In some embodiments, the present application pertains to methods for the production of the novel compositions disclosed herein. Suitable methods are generically illustrated in the schemes provided in FIGS. 1A, 1B, 1C, 2A, 2B, 2C, 3A, 3B, 3C, 4A, 4B, 4C, 5A, 5B, 6A, 6B, 6C, 6D, 7A and 7B. Specific examples of the use of this methodology for the production of various intermediates and therapeutic compounds can be found in Examples 1-10, below. The generic synthetic scheme found in FIGS. 1A, 1B, 1C, 2A, 2B, 2C, 3A, 3B, 3C, 4A, 4B, 4C, 5A, 5B, 6A, 6B, 6C, 6D, 7A and 7B and the following description is in close alignment with Schemes 1-12 (Examples section, below), and the associated description in Examples 1-10. A general method for reducing certain of the therapeutic compounds of general formula A-B to compounds of general formula C—B can be found in Examples 11A and 11B. However, while these Examples demonstrate the ease of interconvertibility between oxidized and reduced forms, the reduced forms (i.e. compounds of general formula C-B) were already provided according to the disclosed methods of synthesis, whereby said reduced forms were converted to the oxidized forms (i.e. compounds of general formula A-B) as disclosed in Examples 1-10. Thus, the reduced forms (i.e. compounds of formula C-B) are more readily obtained as intermediates of the disclosed synthetic routes to the compounds of general formula A-B.

Figure 8:
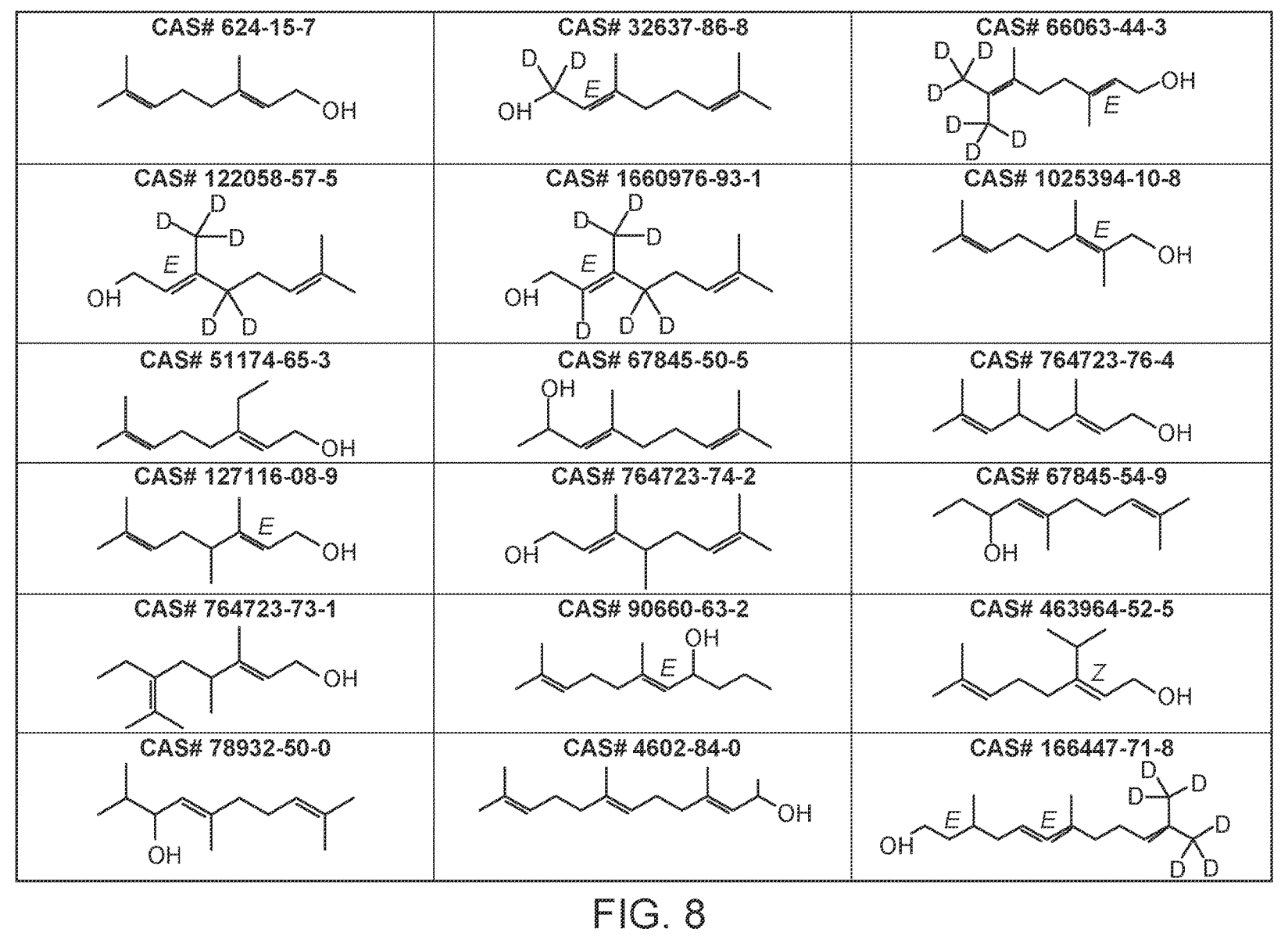
Figure 8:
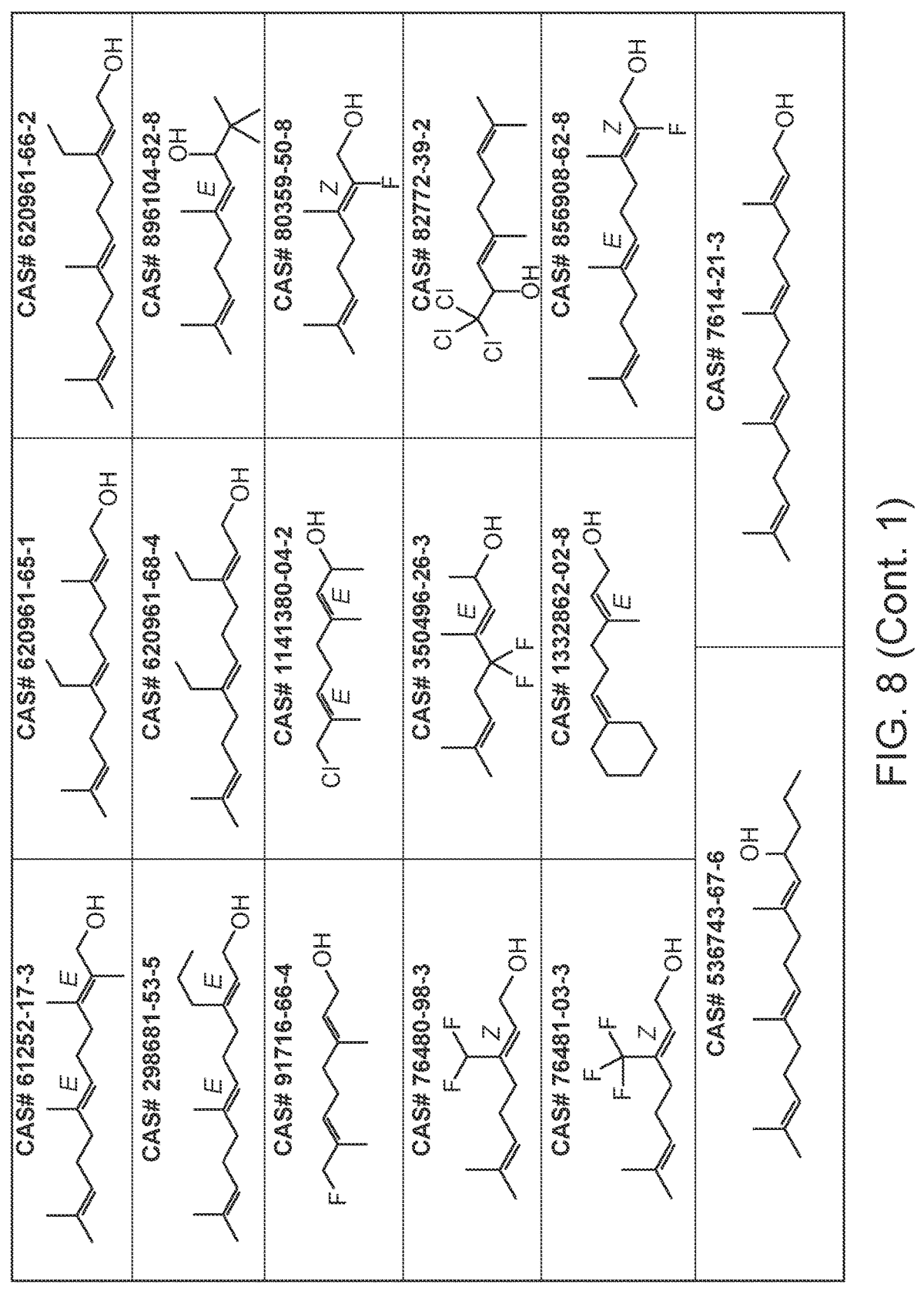
Figure 8:
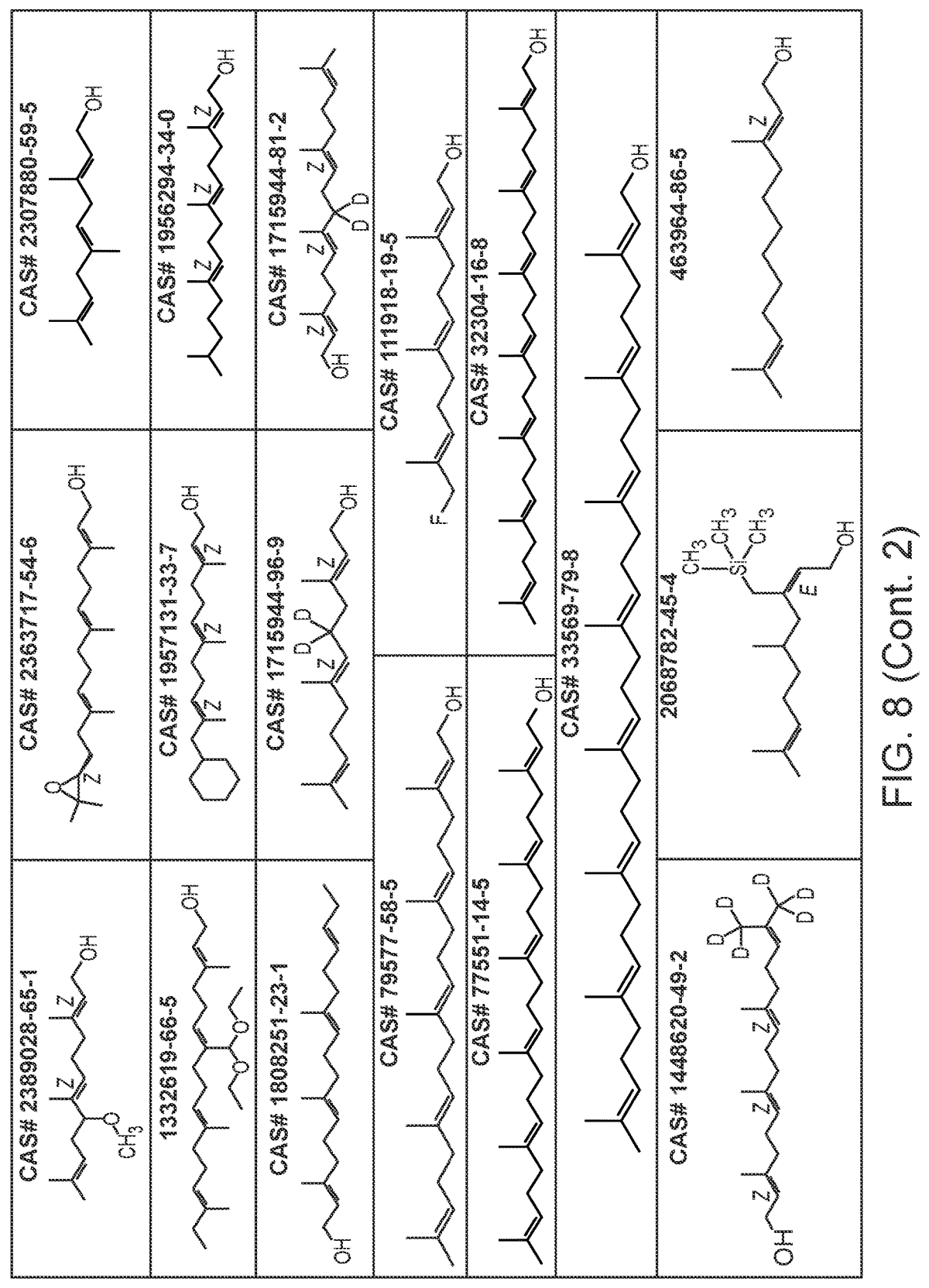
Figure 8:
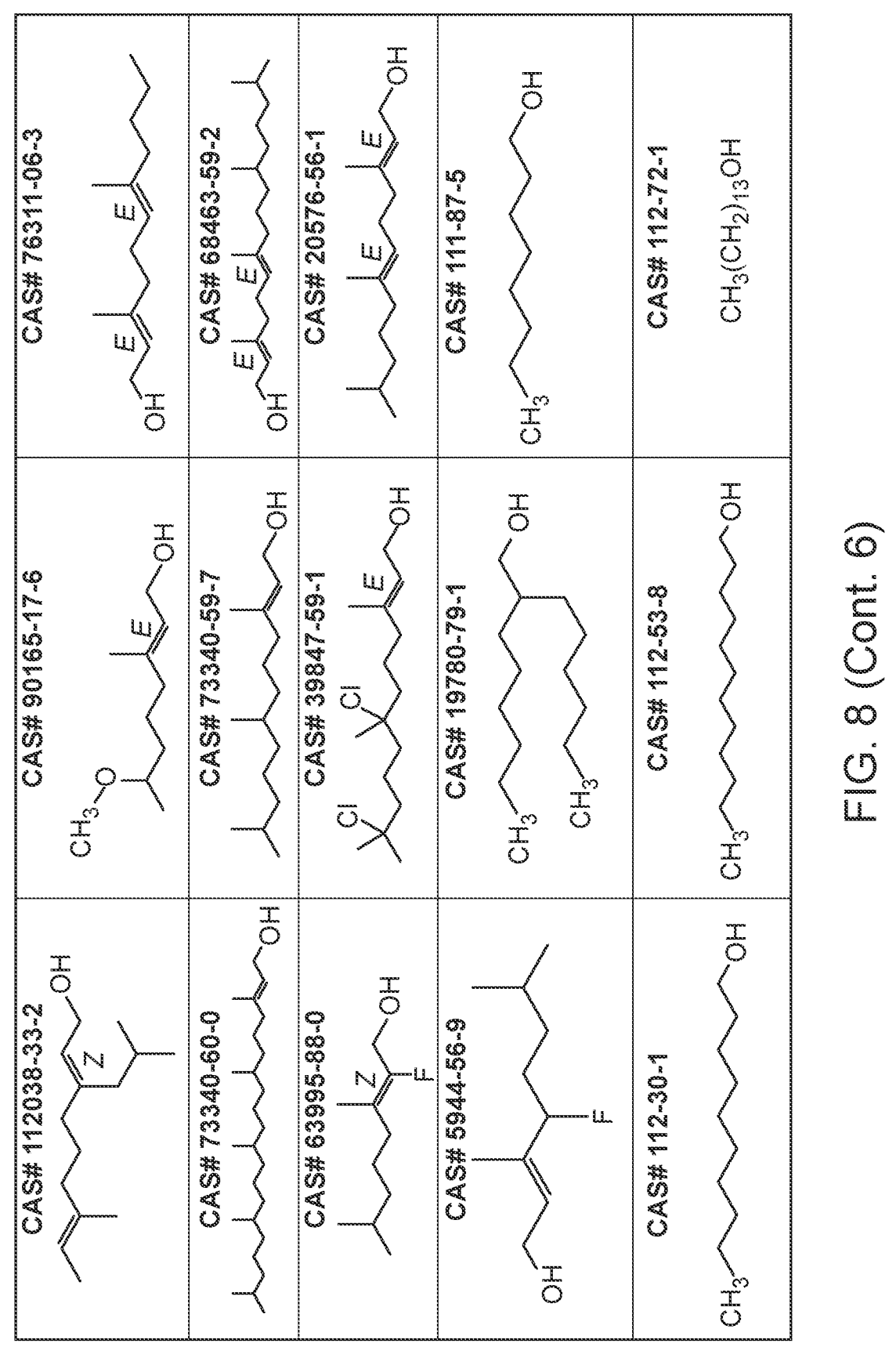
Figure 8:
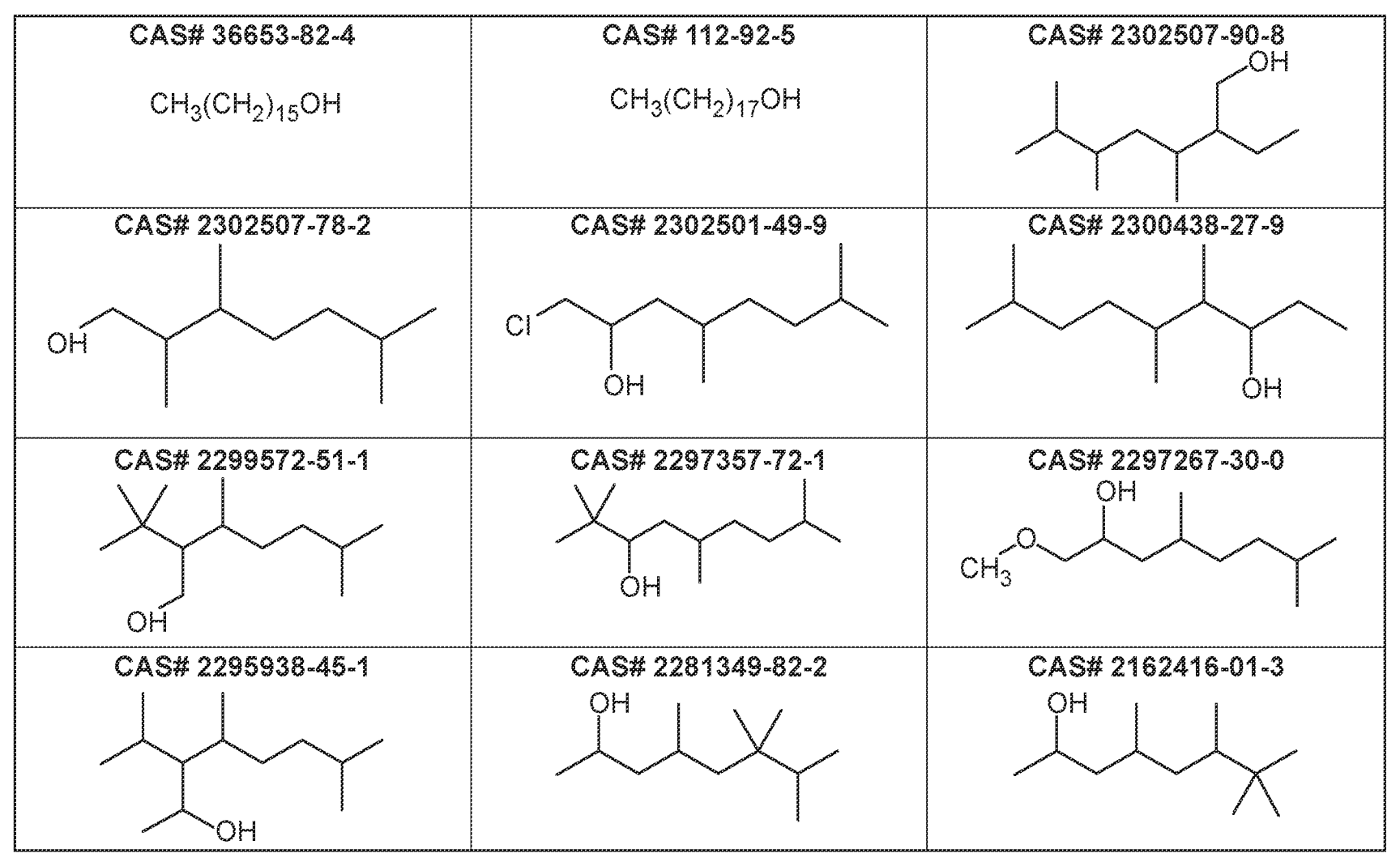
Figure 8:
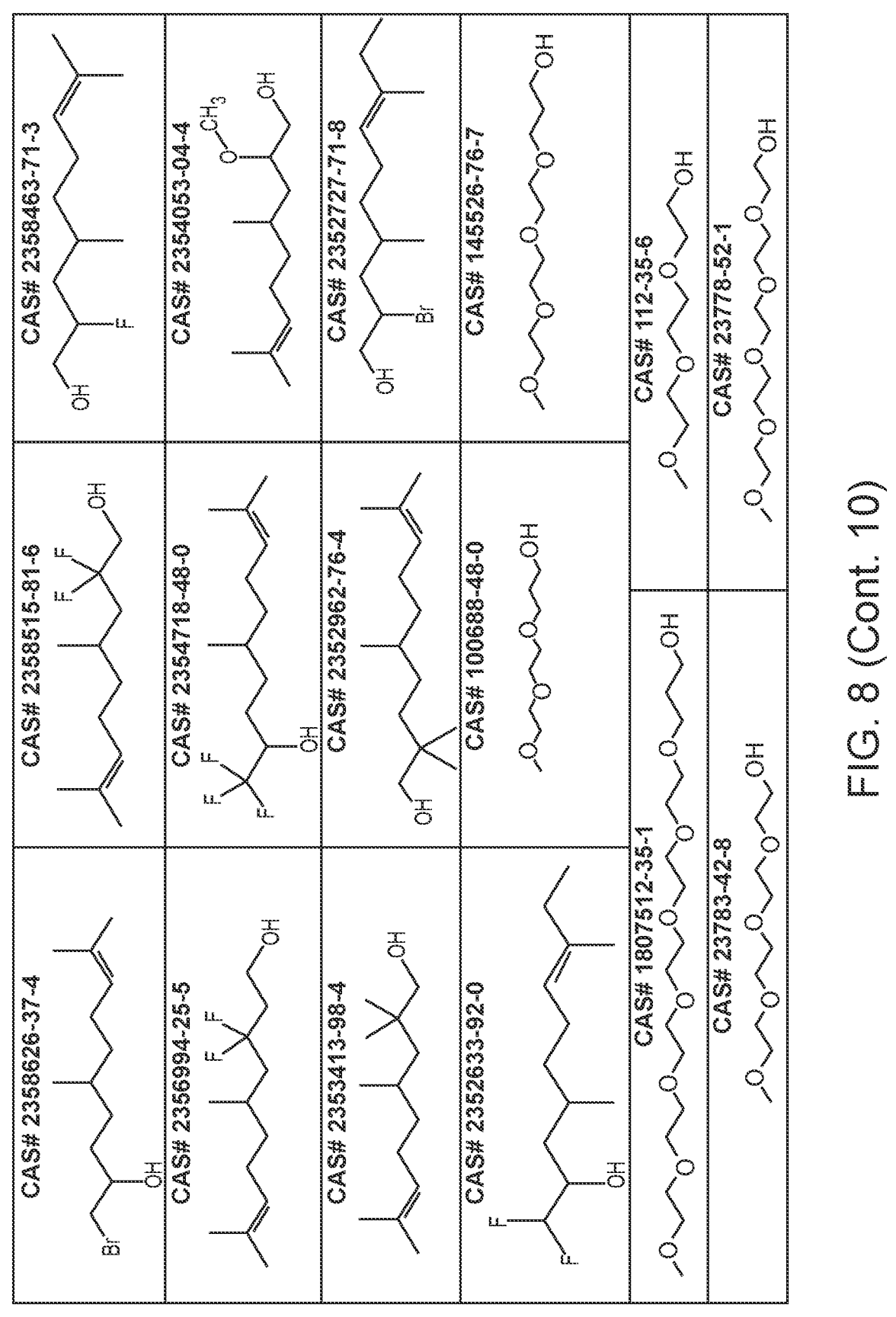

With reference to FIG. 1A, a compound of generic formula 201 is provided, wherein variables L, X, Y, Z, $R_{20}$, $R_{21}$ and n are previously defined herein. Representative known compounds of generic formula 201 can be found in FIG. 8 (the Chemical Abstracts Service (CAS) registration number is provided for each known composition that is illustrated) and the Examples. As illustrated in step a of FIG. 1A, 201 can be converted to a compound of generic formula 202 by protection of the hydroxyl group. Numerous hydroxyl protecting groups (abbreviated "Pg") are known in the art and many are discussed in Greene's "*Protective Groups in Organic Synthesis*", supra. The protecting group can be acid labile or base labile or otherwise labile under specified conditions. For example, the protecting group can be silyl-based (e.g. tert-butyldimethylsilyl or triisopropylsilyl) and therefore removed with fluoride ion (i.e. $F^-$). Conditions suitable for such conversion can be found, for example, in Example 1, infra, with respect to the conversion of (1) to (2) (See: Scheme 1, step a).

Next, with reference to FIG. 1A, as illustrated in step b, compounds of generic formula 202 can be converted to brominated compounds of generic formula 203. Said conversion can be performed, for example, by treating 202 with N-bromosuccinimide as described in Example 1, step, b, for the conversion of (2) to (3).

Again with reference to FIG. 1A, said brominated compounds of generic formula 203 can then be converted to an epoxide of generic formula 204 as illustrated in step c. For example, this conversion to 204 can be performed by treating the brominated compounds of generic formula 203 with an inorganic base, such as potassium carbonate, as described in Example 1, step c for the conversion of (3) to (4).

As illustrated in FIG. 1A, step d, compounds of generic formula 204 can be converted to compounds of generic formula 205. For example, this conversion of 204 to 205 can be performed by treating 204 with a mixture of sodium metaperiodate ($NaIO_4$) and periodic acid ($HIO_4$) as described in Example 1, step d for the conversion of (4) to (5a) and (5b). As described in Example 1, step d, a fraction of the tert-butyldimethylsilyl protecting group was removed from the hydroxyl group. This deprotected impurity could be easily re-protected as described in Example 1, step e (i.e. the (5b) was converted to (5a)). Alternatively, the deprotected material (5b) could be removed by performing a purification step (e.g. chromatography). As noted above however, silyl-based protection is not the only option and indeed other (more stable) forms of hydroxyl protection might be better suited for this process. Regardless, as shown in Example 1, the silyl protection will suffice to produce the desired bromo compound as illustrated in FIG. 1A, compound 209 and as exemplified in Example 1 by (9).

Next, as illustrated in FIG. 1A, step f., compounds of generic formula 205 can be converted to novel compounds of generic formula 207 by treatment with sodium 2-chloro-2,2-difluoroacetate (6) and triphenylphosphine as described in Example 1, step f for the conversion of (5) to (7). Compounds of generic formula 207 comprise a terminal bis-fluoro group and these are believed to be of novel structure and of particular use in preparing therapeutic compounds as disclosed herein. Hence, in some embodiments, this application is further directed to compounds of generic formula 207.

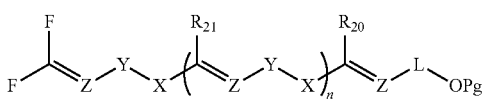

207 wherein L, X, Y, Z, $R_{20}$, $R_{21}$, n and Pg are previously defined.

Thereafter, the protecting group, Pg, of the compounds of generic formula 207 can be removed to thereby generate compounds of generic formula 208 as illustrated in FIG. 1A, step. g. The conversion of 207 to 208 can, for example, (for silyl-based protecting groups) be performed by treatment of 207 with tetra-n-butylammonium fluoride (TBAF) as described in Example 1, step, g for the conversion of (7) to (8). Compounds of generic formula 208 comprise a terminal bis-fluoro group and these are believed to be of novel structure and of particular use in preparing therapeutic compounds as disclosed herein. Hence, in some embodiments, this application is still further directed to compounds of generic formula 208.

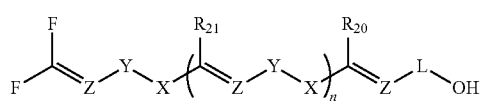

208 wherein L, X, Y, Z, $R_{20}$, $R_{21}$, and n are previously defined.

Finally, hydroxyl compounds of generic formula 208 can be converted to their bromo derivatives, 209 as illustrated in FIG. 1A, step h. For example, compounds of generic formula 208 can be converted to their bromides as described in Example 1, step h. for the conversion of (8) to (9), by treating 208 with phosphorus tribromide as described. Compounds of generic formula 209 comprise a terminal bis-fluoro group and these are believed to be of novel structure and of particular use in preparing therapeutic compounds as disclosed herein. Hence, in some embodiments, this application is also directed to compounds of generic formula 209.

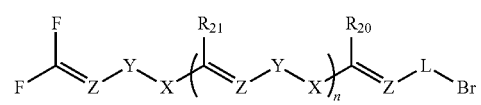

209 wherein L, X, Y, Z, $R_{20}$, $R_{21}$, and n are previously defined.

Figure 1B:
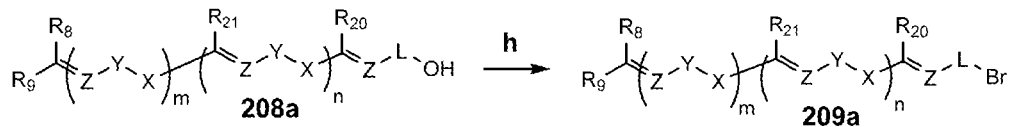
FIG. 1B is an illustration of a chemical scheme for the production of tail-group intermediates used in the production of the therapeutic compositions disclosed herein.

Similarly and with reference to FIG. 1B, hydroxyl compounds of generic formula 208a can be converted to their bromides of generic formula 209a. For example, compounds of generic formula 208a can be converted to their bromides (i.e. 209a) as described in Example 1, step h, for the conversion of (8) to (9), by treating 208a with phosphorus tribromide as described. Compounds of generic formula 208a differ from compounds of 208 in that compounds of generic formula 208a encompass compounds of generic formula 208, but compounds of generic formula 208a represent a larger group of compounds (at least in that they do not require a bis-terminal fluorine atoms). Several representative compounds of formula 208a can be found in FIG. 8.

Figure 1C:
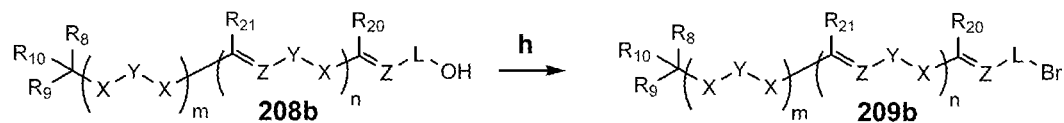
FIG. 1C is an illustration of a chemical scheme for the production of tail-group intermediates used in the production of the therapeutic compositions disclosed herein.

Furthermore and with reference to FIG. 1C, hydroxyl compounds of generic formula 208b can be converted to their bromides of generic formula 209b. For example, compounds of generic formula 208b can be converted to their bromides (i.e. 209b) as described in Example 1, step h, for the conversion of (8) to (9), by treating 208b with phosphorus tribromide as described. Compounds of generic formula 208b differ from compounds of generic formulas 208 and 208a in that compounds of generic formula 208b do not comprise a terminal alkene. Several representative compounds of formula 208b can be found in FIG. 8.

Figure 2A:
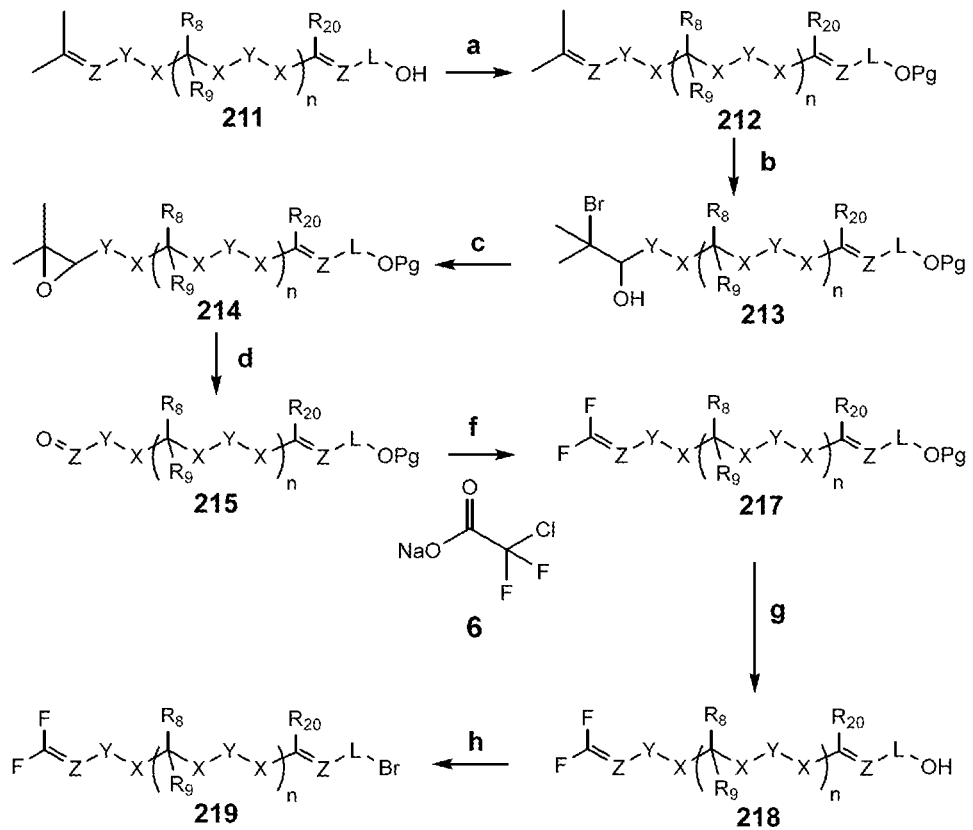
FIG. 2A is an illustration of a chemical scheme for the production of novel bis-fluorinated tail-group intermediates used in the production of the therapeutic compositions disclosed herein.

With reference to FIG. 2A and the discussion of FIG. 1A above, compounds of general formula 211 can be converted to compounds of the generic formula 219 though the multistep process illustrated in FIG. 2A, which process is almost identical in scheme to that of FIG. 1A and is exemplified in Example 1, Scheme 1 and the associated description of the conversion of (1) to (9). Thus, following the description above for FIG. 1A, with reference to the Examples and FIG. 2A, provides the necessary guidance to convert compounds of generic formula 211 to compounds of generic formula 219.

Compounds of generic formula 217 comprise a terminal bis-fluoro group and these are believed to be of novel structure and of particular use in preparing therapeutic compounds as disclosed herein. Hence, in some embodiments, this application is further directed to compounds of generic formula 217.

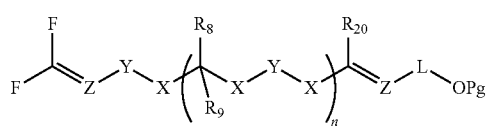

217 wherein L, X, Y, Z, $R_8$, $R_9$, $R_{20}$, n and Pg are previously defined.

Compounds of generic formula 218 comprise a terminal bis-fluoro group and these are believed to be of novel structure and of particular use in preparing therapeutic compounds as disclosed herein. Hence, in some embodiments, this application is further directed to compounds of generic formula 218.

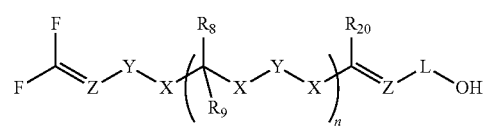

218 wherein L, X, Y, Z, $R_8$, $R_9$, $R_{20}$ and n are previously defined.

Compounds of generic formula 219 comprise a terminal bis-fluoro group and these are believed to be of novel structure and of particular use in preparing therapeutic compounds as disclosed herein. Hence, in some embodiments, this application is further directed to compounds of generic formula 219.

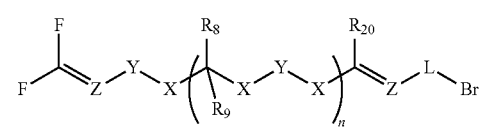

219 wherein L, X, Y, Z, $R_8$, $R_9$, $R_{20}$ and n are previously defined.

Figure 2B:
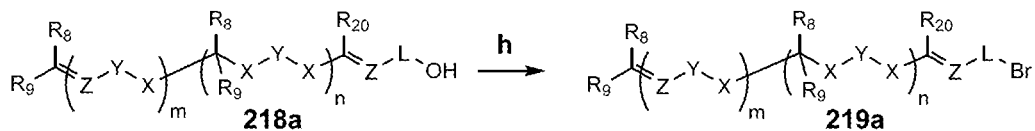
FIG. 2B is an illustration of a chemical scheme for the production of tail-group intermediates used in the production of the therapeutic compositions disclosed herein.
Figure 2C:
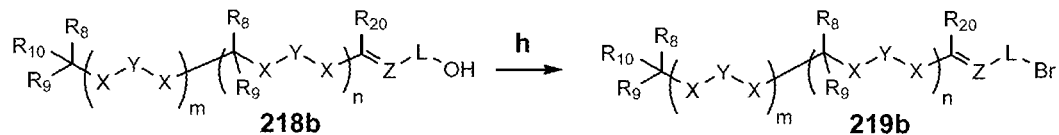
FIG. 2C is an illustration of a chemical scheme for the production of tail-group intermediates used in the production of the therapeutic compositions disclosed herein.

Similarly (as compared with FIG. 1B) and with reference to FIG. 2B, compounds of general formula 218a can be converted to compounds of general formula 219a by treatment with phosphorus tribromide as described in Example 1, step h for the conversion of (8) to (9). Similarly (as compared with FIG. 1C) and with reference to FIG. 2C, compounds of general formula 218b can be converted to compounds of general formula 219b by treatment with phosphorus tribromide as described in Example 1, step h for the conversion of (8) to (9). Representative compounds of general formula 211, 218a or 218b can be found in FIG. 8.

Figure 3A:
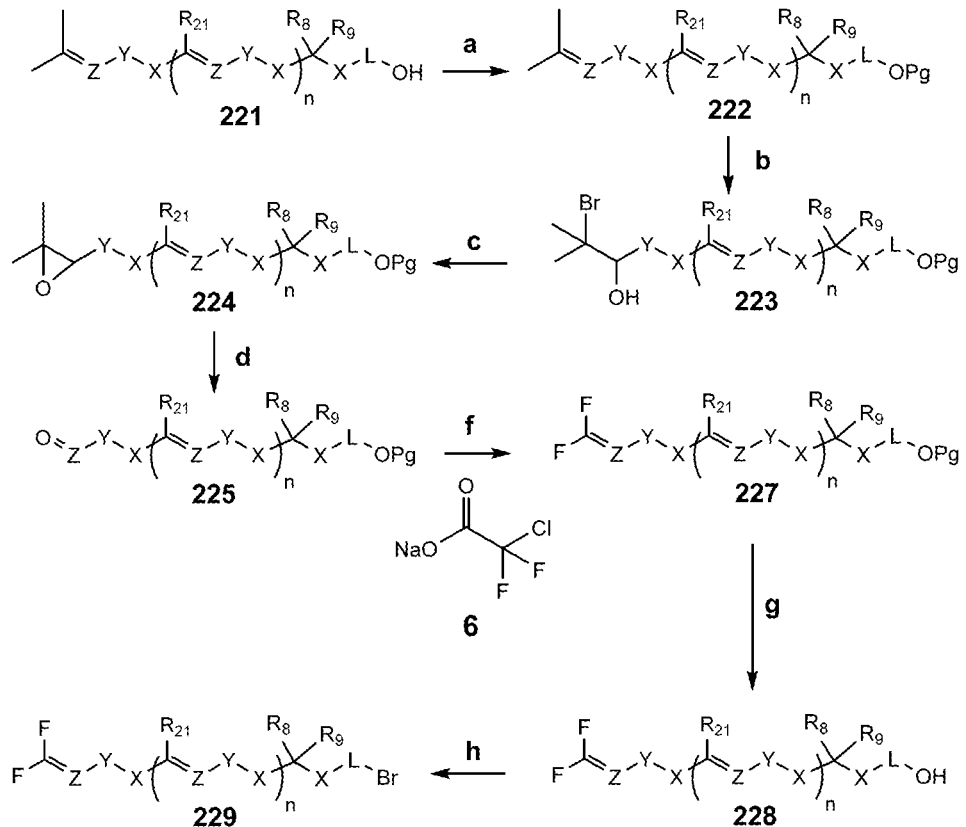
FIG. 3A is an illustration of a chemical scheme for the production of novel bis-fluorinated tail-group intermediates used in the production of the therapeutic compositions disclosed herein.

With reference to FIG. 3A and the discussion of FIG. 1A (and FIG. 2A) above, compounds of general formula 221 can be converted to compounds of the generic formula 229 though the multistep process illustrated in FIG. 3A, which process is almost identical in scheme to that of FIG. 1A (and FIG. 2A) and is exemplified by Example 1, Scheme 1 and the associated description of the conversion of (1) to (9). Thus, following the description above for FIG. 1A, with reference to the Examples and FIG. 3A, provides the necessary guidance to convert compounds of generic formula 221 to compounds of generic formula 229.

Compounds of generic formula 227 comprise a terminal bis-fluoro group and these are believed to be of novel structure and of particular use in preparing therapeutic compounds as disclosed herein. Hence, in some embodiments, this application is further directed to compounds of generic formula 227.

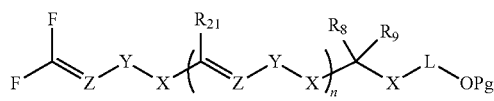

227 wherein L, X, Y, Z, $R_8$, $R_9$, $R_{21}$, n and Pg are previously defined.

Compounds of generic formula 228 comprise a terminal bis-fluoro group and these are believed to be of novel structure and of particular use in preparing therapeutic compounds as disclosed herein. Hence, in some embodiments, this application is further directed to compounds of generic formula 228.

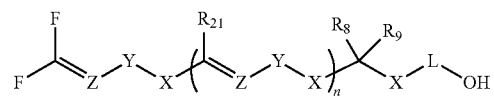

228 wherein L, X, Y, Z, $R_8$, $R_9$, $R_{21}$ and n are previously defined.

Compounds of generic formula 229 comprise a terminal bis-fluoro group and these are believed to be of novel structure and of particular use in preparing therapeutic compounds as disclosed herein. Hence, in some embodiments, this application is further directed to compounds of generic formula 229.

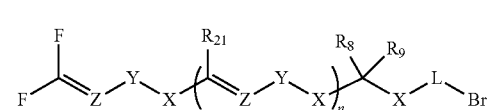

229 wherein L, X, Y, Z, $R_8$, $R_9$, $R_{21}$ and n are previously defined.

Figure 3B:
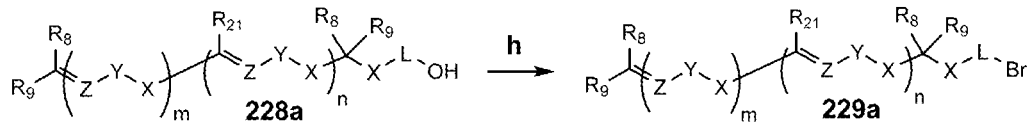
FIG. 3B is an illustration of a chemical scheme for the production of tail-group intermediates used in the production of the therapeutic compositions disclosed herein.
Figure 3C:
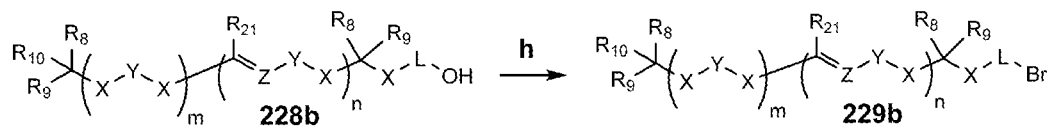
FIG. 3C is an illustration of a chemical scheme for the production of tail-group intermediates used in the production of the therapeutic compositions disclosed herein.

Similarly (as compared with FIG. 1B and FIG. 2B) and with reference to FIG. 3B, compounds of general formula 228a can be converted to compounds of general formula 229a by treatment with phosphorus tribromide as described in Example 1, step h for the conversion of (8) to (9). Similarly (as compared with FIG. 1C and FIG. 2C) and with reference to FIG. 3C, compounds of general formula 228b can be converted to compounds of general formula 229b by treatment with phosphorus tribromide as described in Example 1, step h for the conversion of (8) to (9). Representative compounds of general formula 221, 228a or 228b can be found in FIG. 8.

Figure 4A:
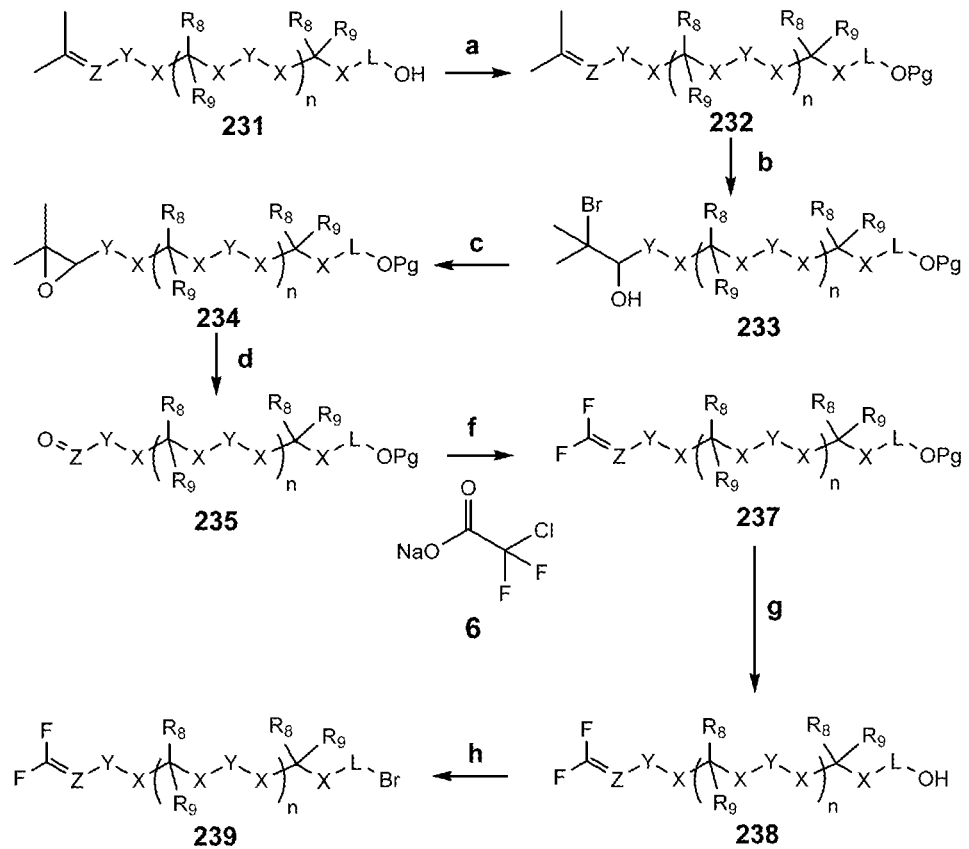
FIG. 4A is an illustration of a chemical scheme for the production of novel bis-fluorinated tail-group intermediates used in the production of the therapeutic compositions disclosed herein.

With reference to FIG. 4A and the discussion of FIG. 1A (and FIG. 2A and FIG. 3A) above, compounds of general formula 231 can be converted to compounds of the generic formula 239 though the multistep process illustrated in FIG. 4A, which process is almost identical in scheme to that of FIG. 1A (and FIG. 2A & FIG. 3A) and is exemplified by Example 1, Scheme 1 and the associated description of the conversion of (1) to (9). Thus, the following the description above for FIG. 1A, with reference to the Examples, FIG. 4A provides the necessary guidance to convert compounds of generic formula 231 to compounds of generic formula 239.

Compounds of generic formula 237 comprise a terminal bis-fluoro group and these are believed to be of novel structure and of particular use in preparing therapeutic compounds as disclosed herein. Hence, in some embodiments, this application is further directed to compounds of generic formula 237.

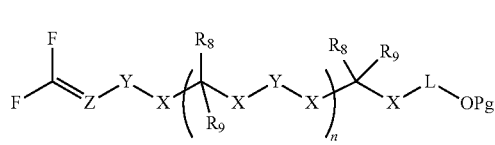

237 wherein L, X, Y, Z, $R_8$, $R_9$, n and Pg are previously defined.

Compounds of generic formula 238 comprise a terminal bis-fluoro group and these are believed to be of novel structure and of particular use in preparing therapeutic compounds as disclosed herein. Hence, in some embodiments, this application is further directed to compounds of generic formula 238.

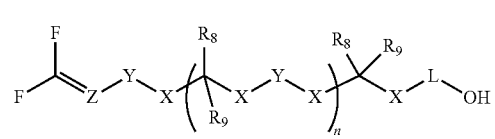

238 wherein L, X, Y, Z, $R_8$, $R_9$ and n are previously defined.

Compounds of generic formula 239 comprise a terminal bis-fluoro group and these are believed to be of novel structure and of particular use in preparing therapeutic compounds as disclosed herein. Hence, in some embodiments, this application is further directed to compounds of generic formula 239.

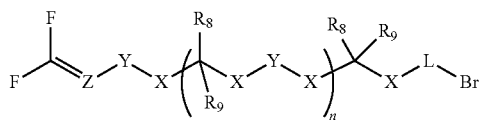

239 wherein L, X, Y, Z, $R_8$, $R_9$ and n are previously defined.

Figure 4B:
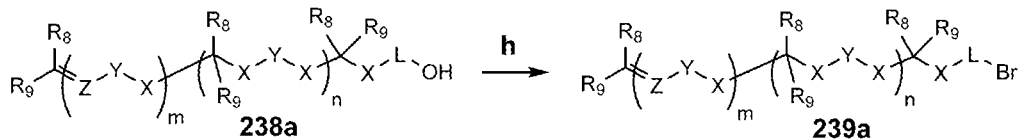
FIG. 4B is an illustration of a chemical scheme for the production of tail-group intermediates used in the production of the therapeutic compositions disclosed herein.
Figure 4C:
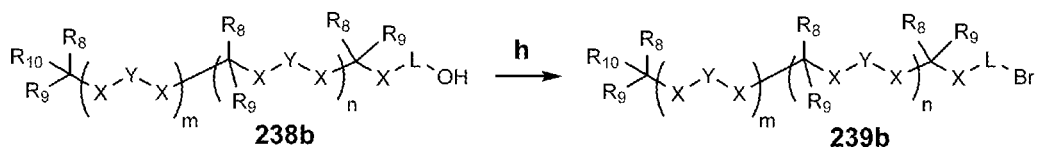
FIG. 4C is an illustration of a chemical scheme for the production of tail-group intermediates used in the production of the therapeutic compositions disclosed herein.

Similarly (as compared with FIG. 1B, FIG. 2B and FIG. 3B) and with reference to FIG. 4B, compounds of general formula 238a can be converted to compounds of general formula 239a by treatment with phosphorus tribromide as described in Example 1, step h for the conversion of (8) to (9). Similarly (as compared with FIG. 1C, FIG. 2C and FIG. 3C) and with reference to FIG. 4C, compounds of general formula 238b can be converted to compounds of general formula 239b by treatment with phosphorus tribromide as described in Example 1, step h for the conversion of (8) to (9). Representative compounds of general formula 231, 238a or 238b can be found in FIG. 8.

Figure 5A:
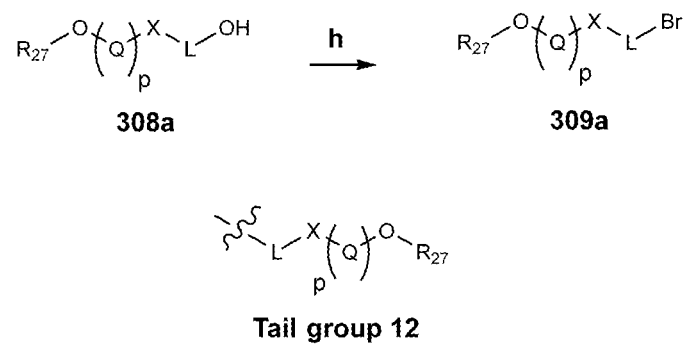
FIG. 5A is an illustration of a chemical scheme for the production of tail-group intermediates (in this case the "tail group" is tail group 12, as illustrated) used in the production of the therapeutic compositions disclosed herein.
Figure 5B:
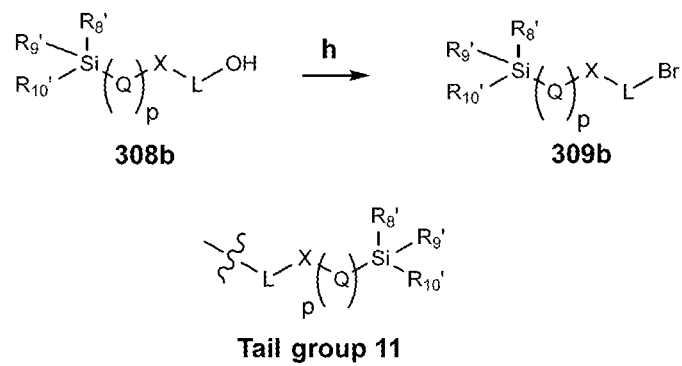
FIG. 5B is an illustration of a chemical scheme for the production of tail-group intermediates (in this case the "tail group" is tail group H, as illustrated) used in the production of the therapeutic compositions disclosed herein.

Additionally with reference to FIGS. 5A and 5B, compounds of general formula 308a and 308b can be converted to compounds of general formula 309a and 309b, respectively by treatment of 308a or 308b with phosphorus tribromide as described in Example 1, step h for the conversion of (8) to (9). Compounds of general formula 308a include, for example, alcohols that contain ethers, silyl ethers, polyethylene glycols (PEGs) other substituted alkyl groups that terminate with an ether. Compounds of general formula 308b include, for example, alcohols that contain ethers, silyl ethers, polyethylene glycols (PEGs) and other substituted alkyl groups that terminate with a trialkylsilyl moiety. Representative compounds of general formula 308a and 308b can be found in FIG. 8.

The bromides of general formula represented by 209, 209a, 209b, 219, 219a, 219b, 229, 229a, 229b, 239, 239a, 239b, 309a and 309b discussed above (with reference to FIGS. 1A, 1B, 1C, 2A, 2B, 2C, 3A, 3B, 3C, 4A, 4B, 4C, 5A and 5B), can be described as tail-group intermediates and these tail-group intermediates can be used in the processes described below for making the therapeutic compounds disclosed herein. Before doing so however, the preparation of certain head-group intermediates used in such process will be described.

Figure 6A:
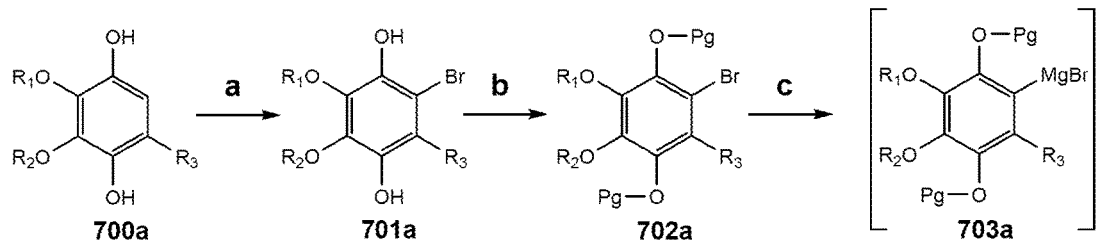
FIG. 6A is an illustration of a chemical scheme for the production of head-group intermediates used in the production of the therapeutic compositions disclosed herein.
Figure 9:
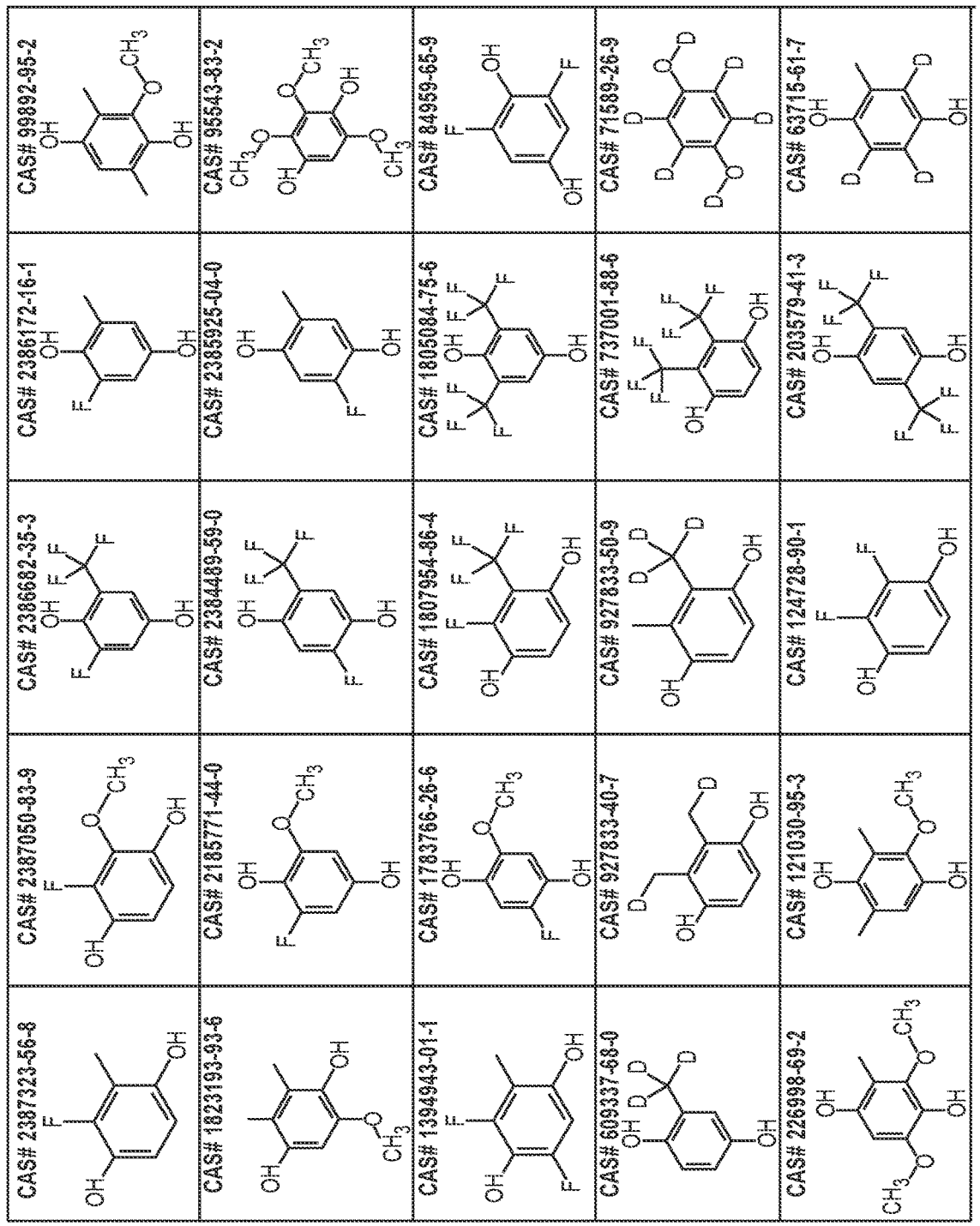
FIG. 9 is a listing of various possible known compounds illustrated by general formula 700a and useful in the production of Grignard or lithiated reagents described in FIGS. 6A and 6B and illustrated by general formula 703a and 705a, 703b.

With reference to FIG. 6A, the process for preparing the Grignard reagent of the protected head-group intermediate of general formula 703a is described starting from the compound of general formula 700a, wherein variables $R_1$, $R_2$ and $R_3$ are previously defined. Representative compounds of formula 700a can be found in FIG. 9. This process is exemplified in Examples 1 and 2 described below for the production of Grignard reagents (13) and (20), respectively (see Schemes 2 and 3, respectively). Again with reference to FIG. 6A, compound of general formula 700a is brominated, for example, by treatment with bromine (as described in Examples 1 and 2, Schemes 2 and 3, step a) to thereby produce the brominated hydroquinone 701a. Compounds of general formula 701a are exemplified by (11) and (18) in the Examples. Next, the phenolic —OH groups of the compound of general formula 701a are protected with a protecting group ("Pg"). As the Grignard reaction is very basic, base labile hydroxyl/phenoxyl protecting groups are generally avoided. Thus, acid labile and/or Grignard stable protecting groups can be used. Hence, the the compound of general formula 701a can be converted to the protected compound of general formula 702a by treatment with an appropriate protecting group. In Examples 1 and 2, step b, the methoxymethyl ether (MOM) protecting group (prepared from chloromethyl methyl ether) was selected to thereby produce (12) and (19), respectively (see Schemes 2 and 3, respectively). Now properly protected, compounds of general formula 702a can be converted to the Grignard reagent of general formula 703a by reaction with magnesium in a dry ether-based solvent. Grignard reagents of the general formula 703a are exemplified by (13) and (20) in Examples 1 and 2, step c, respectively (see Schemes 2 and 3, respectively).

Figure 6B:
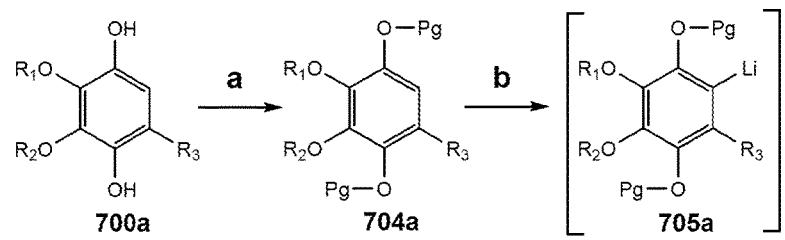
FIG. 6B is an illustration of a chemical scheme for the production of head-group intermediates used in the production of the therapeutic compositions disclosed herein.
Figure 6C:
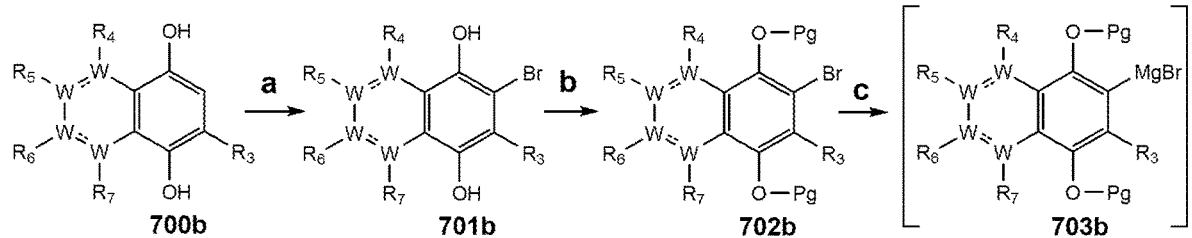
FIG. 6C is an illustration of a chemical scheme for the production of head-group intermediates used in the production of the therapeutic compositions disclosed herein.
Figure 6D:
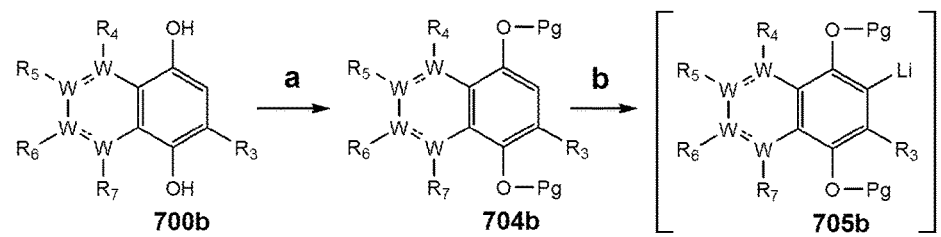
FIG. 6D is an illustration of a chemical scheme for the production of head-group intermediates used in the production of the therapeutic compositions disclosed herein.

Similarly and with reference to FIG. 6C, this process described in FIG. 6A (i.e. steps a-c) can be used to convert the compound of general formula 700b to the Grignard reagent of general formula 703b. Grignard reagents (head-group intermediates) of general formula 703a and 703b can be reacted with the bromides (tail-group intermediates) of general formula 209, 209a, 209b, 219, 219a, 219b, 229, 229a, 229b, 239, 239a, 239b, 309a and 309b (prepared as described above) to thereby produce intermediates and the therapeutic compounds described herein. This process is described in more detail below with respect to FIG. 7A.

Alternatively, and with reference to FIG. 6B, the scheme for producing a lithiated compound of general formula 705a from compounds of general formula 700a is illustrated. This process is exemplified in Examples 3-9, Schemes 4-10, and the related description. In general, the bis-phenol of general formula 700a is protected to produce the bis-protected (for example bis-methoxy methyl (MOM) protected or bis-THP (bis-tetra-hydropyranyl) derivative) derivative 704a as illustrated FIG. 6C, step a (See: Example 3, Scheme 4, step a). Compound 704a is exemplified by (24) in Examples 3-9. The bis-protected derivative of general formula 704a can then be lithiated (for example by treatment with n-butyl lithium as described in Example 3, Scheme 4, step b) to produce the lithiated intermediate 705a. Compound 705a is exemplified by (25) in Examples 3-9. Similarly and with reference to FIG. 6D, this process described in FIG. 6B (i.e. steps a-b) can be used to convert the compounds of general formula 700b to the lithiated intermediates of general formula 705b. Lithiated intermediates of general formula 705a and 705b (head-group intermediates) can be reacted with the bromides (tail-group intermediates) of general formula 209, 209a, 209b, 219, 219a, 219b, 229, 229a, 229b, 239, 239a, 239b, 309a and 309b (prepared as described above) to thereby produce intermediates used to produce the therapeutic compounds described herein. This process is described in more detail below with respect to FIG. 7B.

Figure 7A:
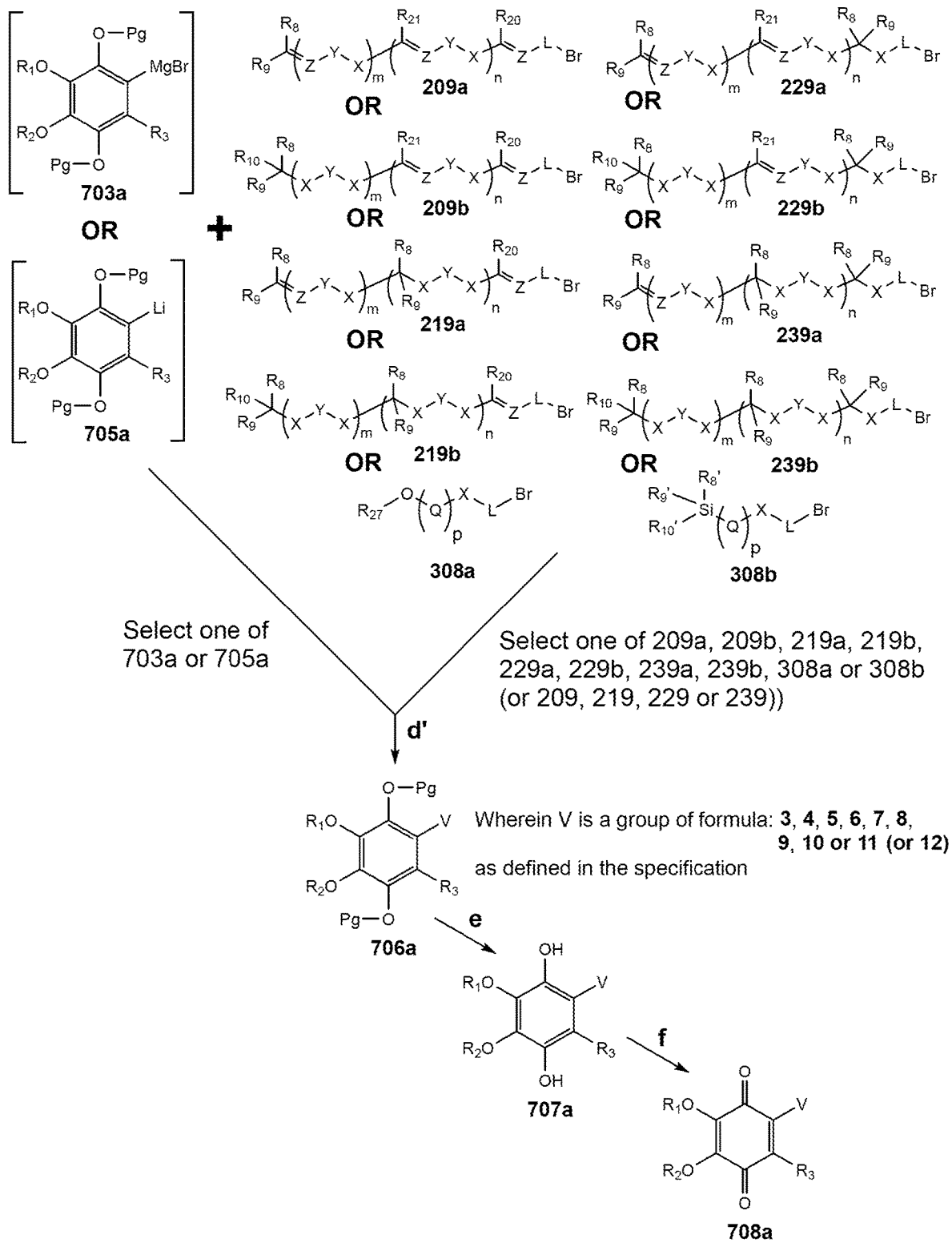
FIG. 7A is an illustration of a chemical scheme for the production of various compounds some of which are intermediates used in the production of the therapeutic compositions disclosed herein and some of which are therapeutic compositions disclosed herein.

With reference to FIG. 7A, the scheme for reacting the Grignard reagent 703a or lithiated intermediate 705a (the "head-group intermediates") with one of the bromides (the "tail-group intermediates") of general formula 209, 209a, 209b, 219, 219a, 219b, 229, 229a, 229b, 239, 239a, 239b, 309a and 309b to produce therapeutic agents of formula (707a) and quinone (708a) is described. This process is exemplified in Examples 1-3. Again with reference to FIG. 7A, one of the Grignard reagent (703a) or lithiated intermediate (705a) is selected and reacted with one of the bromides selected from 209, 209a, 209b, 219, 219a, 219b, 229, 229a, 229b, 239, 239a, 239b, 309a and 309b (209, 219, 229 and 239 are omitted to simplify the figure but nevertheless would react as indicated) to thereby produce bis-protected hydroquinone compounds of general formula 706a as illustrated in step d', wherein V is a tail-group of formula 3, 4, 5, 6, 7, 8, 9, 10 or 11 (or 12) as described above. This reaction could proceed as described in Schemes 2-3, step d, Scheme 4, step c, and Schemes 5-9, step b, and the related Examples. Compounds of general formula 706a are examples of protected compounds of formula C-B, described above. These bis-protected compounds of general formula 706a can then be deprotected to produce the compounds of general formula 707a (also compounds of formula C-B) as illustrated in Schemes 2-3, step e, Scheme 4, step d, and Schemes 5-9, step c, and the related Examples. Compounds of general formula 707a are examples of compounds of formula C-B, described above. Finally the compounds of general formula 707a can be converted to the compounds of general formula 708a as illustrated in Schemes 2-3, step f, Scheme 4, step e, and Schemes 5-9, step d, and the related Examples. Compounds of general formula 708a are examples of compounds of formula A-B, described above. Thus, any specific alcohol listed in FIG. 8 can be used to produce its corresponding (tail-group) bromide as illustrated in FIGS. 1A, 1B, 1C, 2A, 2B, 2C, 3A, 3B, 3C, 4A, 4B, 4C, 5A and 5B, which bromide can then be reacted with a head-group Grignard or lithiated reagent prepared from any of the compounds listed in FIG. 9 to thereby yield a specific therapeutic agent illustrated by the general formula 707a or 708a, wherein the specific structure is dictated by the particular alcohol selected from FIG. 8 and the specific compound selected from FIG. 9. All the possible combinations of the reagents illustrated in FIG. 8 and FIG. 9 and produced according to the foregoing described methodology are contemplated by this application.

Figure 7B:
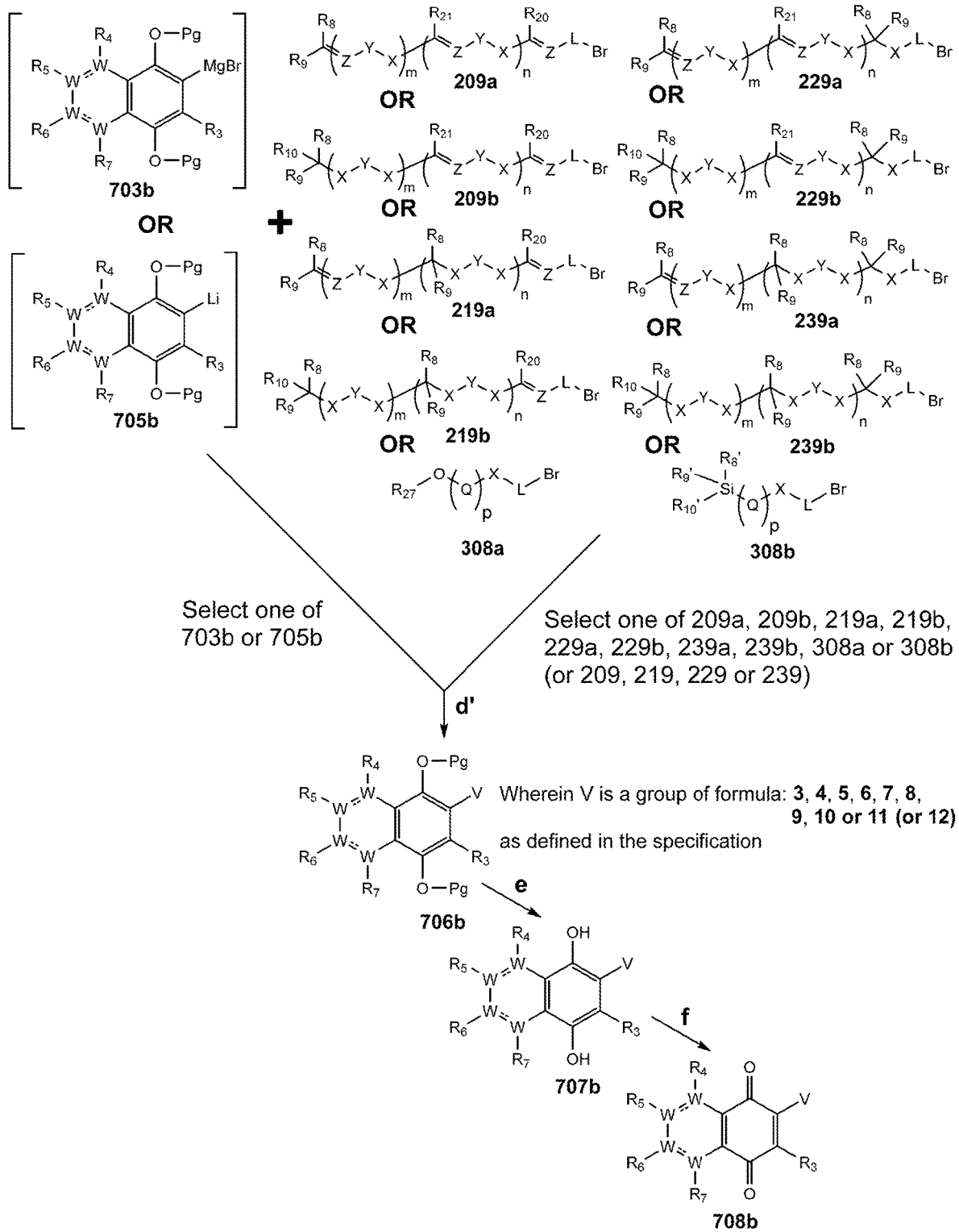
FIG. 7B is an illustration of a chemical scheme for the production of various compounds some of which are intermediates used in the production of the therapeutic compositions disclosed herein and some of which are therapeutic compositions disclosed herein.

Similarly and with reference to FIG. 7B, the scheme for reacting the Grignard reagent 703b or lithiated intermediate 705b (the "head-group intermediates") with one of the bromides (the "tail-group intermediates") of general formula 209, 209a, 209b, 219, 219a, 219b, 229, 229a, 229b, 239, 239a, 239b, 309a and 309b (209, 219, 229 and 239 are omitted to simplify the figure but nevertheless would react as indicated) to produce therapeutic agents of formula (707b) and quinone (708b) is described. This process is exemplified in Examples 1-10. Again with reference to FIG. 7B, one of the Grignard reagent (703b) or lithiated intermediate (705b) is selected and reacted with one of the bromides selected from 209, 209a, 209b, 219, 219a, 219b, 229, 229a, 229b, 239, 239a, 239b, 309a and 309b to thereby produce bis-protected hydroquinone compounds of general formula 706b as illustrated in step d wherein Visa tail-group of formula 3, 4, 5, 6, 7, 8, 9, 10 or 11 (or 12) as described above. This reaction could proceed as described in Schemes 2-3, step d, Scheme 4, step c, and Schemes 5-9, step b, and the related Examples. Compounds of general formula 706b are examples of compounds of formula C-B, described above. These bis-protected compounds of general formula 706b can then be deprotected to produce the compounds of general formula 707b as illustrated in Schemes 2-3, step e, Scheme 4, step d, and Schemes 5-9, step c, and the related Examples. Compounds of general formula 707b are examples of compounds of formula C-B, described above. Finally the compounds of general formula 707b can be converted to the compounds of general formula 708b as illustrated in Schemes 2-3, step f, Scheme 4, step e, and Schemes 5-9, step d, and the related Examples. Compounds of general formula 708b are examples of compounds of formula A-B, described above.

EXAMPLES

Example 1: Synthesis of 2-((2E,6E)-11,11-difluoro-3,7-dimethylundeca-2,6,10-trien-1-yl)-3,5,6-trimethylcyclohexa-2,5-diene-1,4-dione (Compound A)

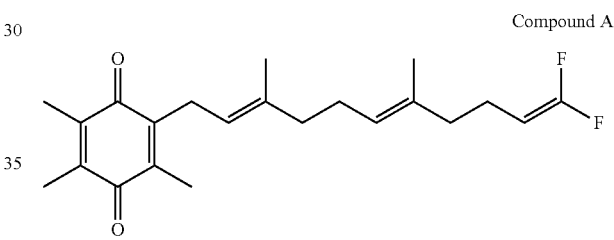

Compound A

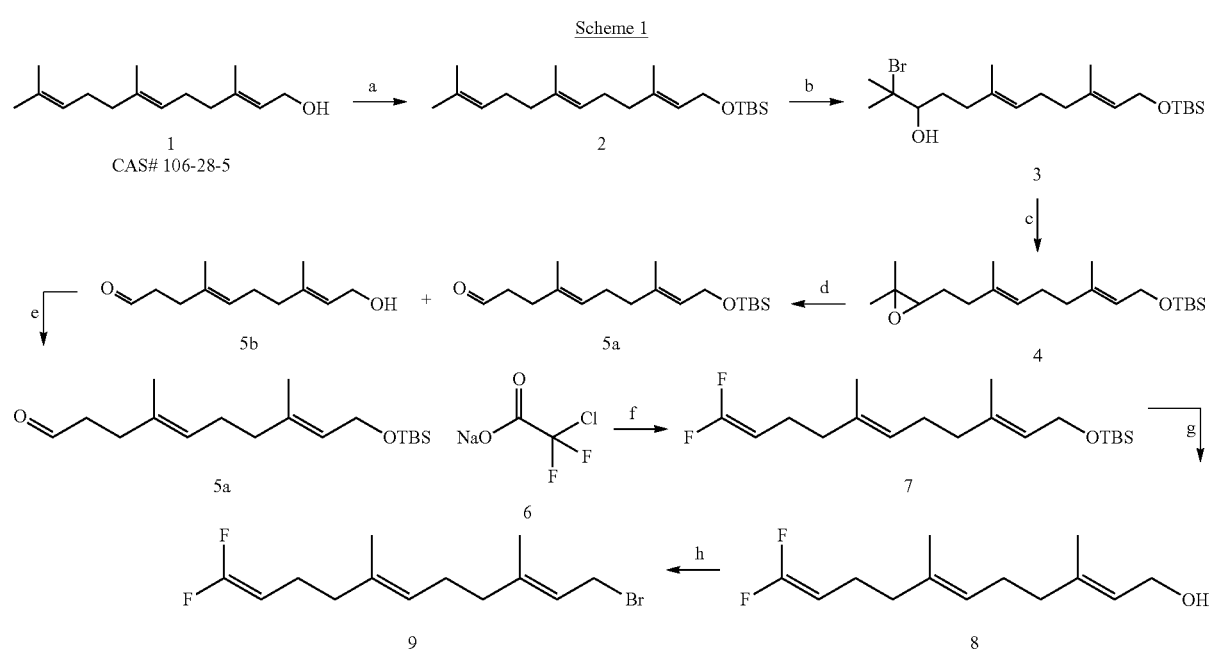

Scheme 1

1) Synthesis of (5E,9E)-11-bromo-1,1-difluoro-5,9-dimethylundeca-1,5,9-triene (9)

Step a. Synthesis of tert-butyldimethyl(((2E,6E)-3,7,11-trimethyldodeca-2,6,10-trien-1-yl)oxy)silane (2)

To a solution of trans,trans-Farnesol (1, 3.30 g, 14.84 mmol) and imidazole (1.52 g, 22.26 mmol) in dry dichloromethane (DCM, 38 mL) was added tert-butyldimethylsilyl chloride (TBSCl, 3.70 g, 20.78 mmol) and the reaction mixture was stirred at room temperature (r.t.) for 4 hours (hrs.). Then, the reaction mixture was diluted with DCM (22 mL) and water (60 mL) and stirred at r.t. for 15 minutes (min.). The aqueous phase was separated and the organic phase was washed with water (3×60 mL) and brine (30 mL), dried over anhydrous (anh.) $Na_2SO_4$, and concentrated under reduced pressure. The crude product was purified by silica gel column flash chromatography ($SiO_2$, hexane-ethyl acetate (EtOAc, 5:1, $R_f$(PR) 0.3)) to yield 2 (4.75 g, 95%) as colorless oil.

$^1$H-NMR (300 MHz, $CDCl_3$) δ: 5.36-5.27 (m, 1H), 5.17-5.04 (m, 2H), 4.20 (d, J=6.8 Hz, 2H), 2.16-1.91 (m, 8H), 1.68 (s, 3H), 1.63 (s, 3H), 1.60 (s, 6H), 0.91 (s, 9H), 0.07 (s, 6H).

Step b. Synthesis of (6E,10E)-2-bromo-12-((tert-butyldimethylsilyl)oxy)-2,6,10-trimethyldodeca-6,10-dien-3-ol (3)

To a solution of 2 (4.75 g, 14.11 mmol) in tetrahydrofuran (THF, 160 mL) and $H_2O$ (77 mL) at 0° C., dropwise was added solution of A-bromosuccinimide (2.76 g, 15.52 mmol) in THF (30 mL). After the reaction mixture was stirred for 2 hrs. at 0° C., the reaction mixture was quenched by the addition of $Et_2O$ (200 mL) and water (100 mL) and the resulting mixture was stirred at r.t. for 15 min. The organic phase was separated and the aqueous phase was washed with brine (100 mL) and dried over anh. $Na_2SO_4$. After evaporation of the solvent under reduced pressure, crude product was purified by silica gel column flash chromatography ($SiO_2$, hexane-EtOAc (3:1, $R_f$(PR) 0.3)) to yield 3 (3.90 g, 64%) as colourless oil.

$^1$H-NMR (300 MHz, $CDCl_3$) δ: 5.36-5.25 (m, 1H), 5.25-5.14 (m, 1H), 4.19 (d, J=6.3 Hz, 2H), 3.97 (dd, 7=11.3, 1.9 Hz, 1H), 2.38-2.26 (m, 1H), 2.19-1.90 (m, 7H), 1.88-1.69 (m, 1H), 1.62 (s, 3H), 1.59 (s, 3H), 1.34 (s, 3H), 1.33 (s, 3H), 0.90 (s, 9H), 0.07 (s, 6H).

Step c. Synthesis of tert-butyl(((2E,6E)-9-(3,3-dimethyloxiran-2-yl)-3,7-dimethylnona-2,6-dien-1-yl)oxy)dimethylsilane (4)

To a solution of 3 (3.90 g, 9.0 mmol) in methanol (MeOH, 81 mL) was added $K_2CO_3$ (2.49 g, 18.0 mmol) and the resulting mixture was stirred at r.t. for 1.5 hrs. Then, the reaction mixture was quenched by the addition of water (100 mL), and the resulting aqueous phase was extracted with $Et_2O$ (3×150 mL). The combined organic phases were washed with brine (80 mL), dried over anh. $Na_2SO_4$, and concentrated under reduced pressure to give crude 4 (3.0 g, 95%) as colourless oil, which was used in the next step without further purification.

$^1$H-NMR (300 MHz, $CDCl_3$) δ: 5.34-5.27 (m, 1H), 5.20-5.12 (m, 1H), 4.19 (d, J=6.3 Hz, 2H), 2.70 (t, J=6.2 Hz, 1H), 2.24-1.95 (m, 6H), 1.73-1.51 (m, 2H), 1.62 (s, 3H), 1.30 (s, 3H), 1.26 (s, 3H), 0.90 (s, 9H), 0.07 (s, 6H).

Step d. Synthesis of a mixture of (4E,8E)-10-((tert-butyldimethylsilyl)oxy)-4,8-dimethyldeca-4,8-dienal (5a) and (4E,8E)-10-hydroxy-4,8-dimethyldeca-4,8-dienal (5b)

A stirred mixture of 4 (3.0 g, 8.51 mmol), THF (54 mL), and water (10 mL) at 0° C. was sequentially treated with $NaIO_4$ (1.09 g, 5.10 mmol) and $HIO_4$ (2.13 g, 9.36 mmol). The resulting mixture was stirred at 0° C. for 10 min. and, then, warmed to r.t. After 1 hour, the reaction mixture was quenched by the addition of sat. $NaHCO_3$ solution (100 mL) and the resulting mixture was stirred at r.t. for 5 min. The biphasic layers were separated and the aqueous layer was extracted with diethyl ether (3×200 mL). The combined organic layers were washed with brine (80 mL), dried over anh. $Na_2SO_4$, filtered and concentrated under reduced pressure. The crude mixture of 5a and 5b (2 g) was used in the next step without further purification.

Step e. Synthesis of (4E,8E)-10-((tert-butyldimethylsilyl)oxy)-4,8-dimethyldeca-4,8-dienal (5a)

To a solution of crude mixture of 5a and 5b (8.51 mmol) and imidazole (869 mg, 12.77 mmol) in dry DCM (21 mL) was added TBSCl (2.12 g, 11.91 mmol) and the reaction mixture was stirred at r.t. for 4 hrs. Then, the reaction mixture was diluted with DCM (19 mL) and water (40 mL) and stirred at r.t. for 15 min. The aqueous phase was separated and the organic phase was washed with water (3×40 mL) and brine (20 mL), dried over anh. $Na_2SO_4$, and concentrated under reduced pressure. The crude product was purified by silica gel column flash chromatography ($SiO_2$, hexane-EtOAc (4:1, $R_f$(PR) 0.3)) to yield 5a (2.52 g, 95% over 2 steps) as colorless oil.

$^1$H-NMR (300 MHz, $CDCl_3$) δ: 9.75 (t, J=1.9 Hz, 1H), 5.34-5.24 (m, 1H), 5.19-5.09 (m, 1H), 4.18 (d, 7=6.3 Hz, 2H), 2.55-2.45 (m, 2H), 2.31 (t, 7=7.4 Hz, 2H), 2.16-1.95 (m, 4H), 1.61 (s, 6H), 0.90 (s, 9H), 0.07 (s, 6H).

Step f Synthesis of tert-butyl(((2E,6E)-11,11-difluoro-3,7-dimethylundeca-2,6,10-trien-1-yl)oxy)dimethylsilane (7)

To a mixture of 5a (2.52 g, 8.11 mmol), sodium 2-chloro-2,2-difluoroacetate (6, 2.47 g, 16.22 mmol), and triphenylphosphine ($PPh_3$, 4.25 g, 16.22 mmol) under argon was added dry N,N'-diethylformamide (DMF, 16 mL) and the reaction mixture was stirred at 105° C. for 2 hrs. After cooling in an ice bath, water (20 mL) was added slowly. Then, the resulting mixture was diluted by water (80 mL) and $Et_2O$ (400 mL) and stirred at r.t. for 5 min. The aqueous phase was separated and the organic phase was washed with water (2×100 mL) and brine (100 mL). After drying over anh. $Na_2SO_4$, the volatile matters were removed under reduced pressure and the crude product was purified by silica gel column flash chromatography ($SiO_2$, hexane-EtOAc (20:1, $R_f$(PR) 0.5)) to yield 7 (1.58 g, 56% (discounting $PPh_3$ impurity)) as colorless oil.

$^1$H-NMR (300 MHz, $CDCl_3$) δ: 5.38-5.26 (m, 1H), 5.18-5.08 (m, 1H), 4.20 (d, J=6.3 Hz, 2H), 4.10 (dtd, J=25.8, 7.6, 2.6 Hz, 1H), 2.18-1.97 (m, 8H), 1.63 (s, 3H), 1.60 (s, 3H), 0.91 (s, 9H), 0.08 (s, 6H).

Step g. Synthesis of (2E,6E)-11,11-difluoro-3,7-dimethylundeca-2,6,10-trien-1-ol (8)

To a solution of 7 (1.58 g, 4.58 mmol) in dry THF (7 mL) was added tetra-n-butylammonium fluoride (TBAF, 6.9 mL, 6.87 mmol, 1M in THF) dropwise. The reaction mixture was stirred at r.t. for 2 hrs. After completion of the reaction (TLC control), the reaction mixture was quenched by the addition of $Et_2O$ (25 mL) and water (25 mL) and the resulting mixture was stirred at r.t. for 5 min. Then, the organic phase was separated and the aqueous phase was extracted with $Et_2O$ (2×25 mL). The combined organic phases were washed with brine (25 mL), dried over anh. $Na_2SO_4$, and concentrated under reduced pressure. The crude product was purified by silica gel flash column chromatography ($SiO_2$, hexane-EtOAc (4:1, $R_f$(PR) 0.3)) to yield 8 (905 mg, 86%) as colorless oil.

$^1$H-NMR (300 MHz, $CDCl_3$) δ: 5.48-5.34 (m, 1H), 5.15-5.07 (m, 1H), 4.15 (d, J=6.8 Hz, 2H), 4.13-4.00 (m, 1H), 2.20-1.96 (m, 8H), 1.68 (s, 3H), 1.59 (s, 3H), 1.29 (s, 1H).

Step h. Synthesis of (5E,9E)-11-bromo-1,1-difluoro-5,9-dimethylundeca-f 5,9-triene (9)

To a cooled (0° C.) solution of 8 (400 mg, 1.74 mmol) in dry diethyl ether ($Et_2O$, 6 mL) dropwise was added phosphorus tribromide ($PBr_3$, 0.20 mL, 2.08 mmol, d=2.85) and the reaction mixture was stirred at 0° C. for 1 hour (hr.). The reaction mixture was poured on ice (2 g) and extracted with $Et_2O$ (3×15 mL). The combined organic phases were dried over anh. $Na_2SO_4$ and concentrated under reduced pressure to give 9 (504 mg, 99%) as slightly yellowish oil.

$^1$H-NMR (300 MHz, $CDCl_3$) δ: 5.58-5.48 (m, 1H), 5.13-5.04 (m, 1H), 4.18-4.05 (m, 1H), 4.02 (d, J=8.4 Hz, 2H), 2.18-1.98 (m, 8H), 1.73 (s, 3H), 1.59 (s, 3H).

2) Synthesis of 2-((2E,6E)-11,11-difluoro-3,7-dimethylundeca-2,6,10-trien-1-yl)-3,5,6-trimethylcyclohexa-2,5-diene-1,4-dione (Compound A)

temp. The resulting mixture was stirred at r.t. for 2 hrs., then quenched by the addition of water (40 mL) and extracted with DCM (20 mL). Organic phase was additionally washed with 5% $Na_2S_2O_3$ water solution (20 mL) and brine (20 mL), dried on $Na_2SO_4$, filtered and evaporated to yield 11 (2.24 g, 97%) as brown solid which used further without additional purification.

Step b: Synthesis of 1-bromo-2,5-bis (methoxymethoxy)-3,4,6-trimethylbenzene (12)

To a solution of 11 (2.24 g, 9.70 mmol) in dry acetonitrile (MeCN, 40 mL) was added $K_2CO_3$ (5.36 g, 38.8 mmol) and chloromethyl methyl ether (MOMCl, 2.2 mL, 29.1 mmol) and allowed to stir at r.t. for 24 hrs. To reaction mixture was added EtOAc (100 mL) and water (100 mL). The organic phase was separated and additionally washed with brine (40 mL), dried on $Na_2SO_4$, filtered and evaporated. Crude product was purified by flash column chromatography ($SiO_2$, hexane-EtOAc (5:1, $R_f$(PR) 0.3)) to yield 12 as a slightly yellow solid (1.48, 48%).

$^1$H-NMR (300 MHz, $CDCl_3$) δ: 5.00 (s, 2H), 4.88 (s, 2H), 3.65 (s, 3H), 3.61 (s, 3H), 2.37 (s, 3H), 2.25 (s, 3H), 2.18 (s, 3H).

Step c and d: Synthesis of 1-((2E,6E)-11,11-difluoro-3,7-dimethylundeca-2,6,10-trien-1-yl)-2,5-bis (methoxymethoxy)-3,4,6-trimethylbenzene (14)

12 (326 mg, 1.02 mmol) was reacted with magnesium (49 mg, 2.05 mmol) in THF (4 mL), at 40° C. for one hour, in presence of pinch of iodine and 1,2-dibromoethane, to form the Grignard reagent 13 (completion of the reaction was confirmed by LC/MS). To cooled (0-5° C.) reaction mixture was added CuCl (68 mg, 0.682 mmol) and mixture was stirred at room temperature for 1 hr., followed by dropwise addition of a solution of 9 (200 mg, 0.682 mmol, prepared as described above) in THF (2 mL). The reaction mixture was stirred for 16 hours, quenched by adding it to saturated (sat.) aqueous (aq.) $NH_4Cl$ (5 mL) and extracted in $Et_2O$ (15

Scheme 2

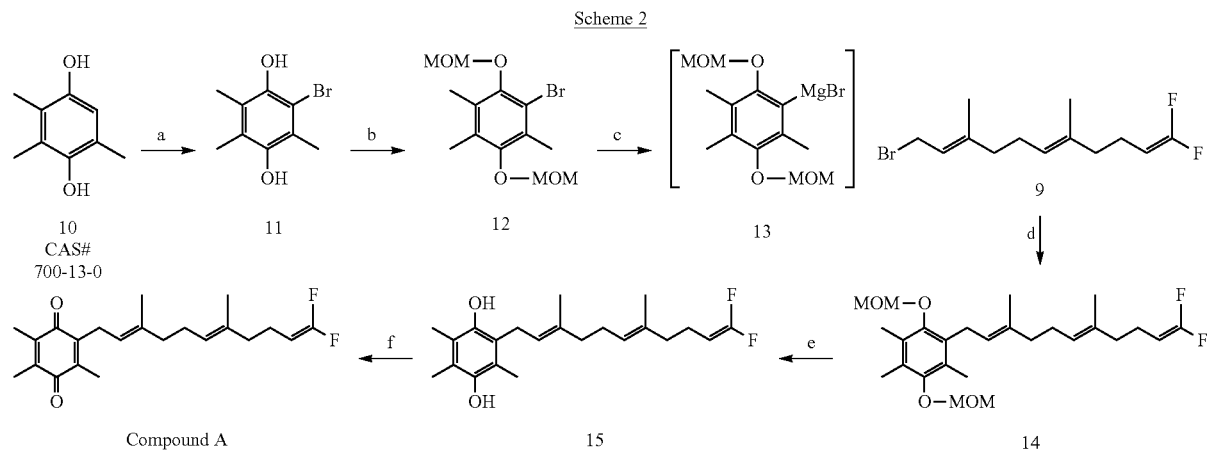

Step a: Synthesis of 2-bromo-3,5,6-trimethylbenzene-1,4-diol (11)

To a solution of 2,3,5-trimethyl-benzene-1,4-diol (10, 1.52 mg, 10.0 mmol) in DCM (20 mL) was added a solution of bromine (1.60 g, 10.0 mmol) in DCM (5 mL) at room mL). The organic phase was additionally washed with water (10 mL) and brine (10 mL), dried on $Na_2SO_4$, filtered and evaporated. Crude product was purified by flash column chromatography ($SiO_2$, hexane-$Et_2O$ (5:1, $R_f$(PR) 0.4)) to yield 14 as a colorless oil (212 mg, 69%, contains 10-15% of impurity).

$^1$H-NMR (300 MHz, CDCl$_3$) δ: 5.12-5.00 (m, 2H), 4.88 (s, 2H), 4.86 (s, 2H), 4.07 (dtd, J=25.6, 7.3, 2.6 Hz, 1H), 3.61 (s, 3H), 3.59 (s, 3H), 3.38 (d, J=6.2 Hz, 2H), 2.19 (s, 6H), 2.18 (s, 3H), 2.15-1.94 (m, 8H), 1.75 (s, 3H), 1.56 (s, 3H).

Step e and f: Synthesis of 2-((2E,6E)-11,11-difluoro-3,7-dimethylundeca-2,6,10-trien-1-yl)-3,5,6-trimethylcyclohexa-2,5-diene-1,4-dione (Compound A)

To a solution of 14 (212 mg, 0.468 mmol) in MeOH (8 mL) was added 7 drops of concentrated (conc.) hydrochloric acid (HCl) at room temp and the reaction was stirred for 16 hrs. After evaporation, crude hydroquinone, 2-((2E,6E)-11,11-difluoro-3,7-dimethylundeca-2,6,10-trien-1-yl)-3,5,6-trimethylbenzene-1,4-diol (15), was dissolved in mixture of isopropyl alcohol (z-PrOH, 2.3 mL) and water (0.12 mL) and treated with FeCl$_3$ (304 mg, 1.87 mmol) for 3 hours at r.t. To the reaction mixture was added water (10 mL) and Et$_2$O (10 mL). The organic phase was separated and additionally washed with brine (10 mL), dried on Na$_2$SO$_4$, filtered and evaporated. Crude product was purified by flash column chromatography (SiO$_2$, hexane-Et$_2$O (5:1, R$_f$(PR) 0.7)) to yield 78 mg (46%) of Compound A as a yellow oil (HPLC purity 96.4%).

$^1$H-NMR (400 MHz, CDCl$_3$) δ: 5.09-5.01 (m, 1H), 4.99-4.89 (m, 1H), 4.06 (dtd, J=25.7, 7.5, 2.6 Hz, 1H), 3.20 (d, J=7.0 Hz, 2H), 2.11-1.92 (m, 8H), 2.02 (s, 1H), 2.01 (s, 6H), 1.74 (s, 3H), 1.56 (s, 3H). MS (M+H$^+$): 363.2.

Example 2: Synthesis of 2-((2E,6E)-11,11-difluoro-3,7-dimethylundeca-2,6,10-trien-1-yl)-5,6-dimethoxy-3-methylcyclohexa-2,5-diene-1,4-dione (Compound B)

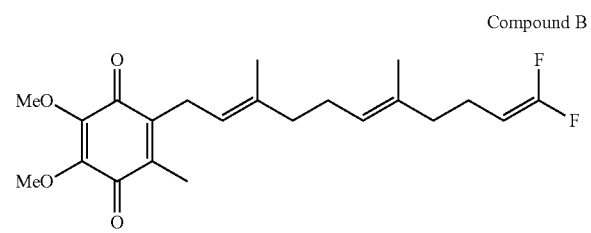 [SMILES: COC1=C(OC)C(=O)C(C/C=C(\C)CC/C=C(\C)CCC=C(F)F)=C(C)C1=O]

Compound B

Step a: Synthesis of 2-bromo-5,6-dimethoxy-3-methylbenzene-1,4-diol (18)

To a solution of 2,3-dimethoxy-5-methyl-benzene-1,4-diol (17, 822 mg, 4.46 mmol) in DCM (10 mL) was added solution of bromine (714 mg, 4.46 mmol) in DCM (2 mL) at room temperature. The resulting mixture was stirred at room temperature for 2 hr., then quenched in water (20 mL) and extracted with DCM (10 mL). The organic phase was additionally washed with 5% Na$_2$S$_2$O$_3$ water solution (10 mL) and brine (10 mL), dried on Na$_2$SO$_4$, filtered and evaporated to yield 18 (1.17 g, 99%) as yellow solid which used further without additional purification.

$^1$H-NMR (300 MHz, CDCl$_3$) δ: 5.49 (s, 1H), 5.46 (s, 1H), 3.93 (s, 3H), 3.91 (s, 3H), 2.29 (s, 3H).

Step b: Synthesis of 1-bromo-3,4-dimethoxy-2,5-bis(methoxymethoxy)-6-methylbenzene (19)

To a solution of 18 (1.17 g, 4.46 mmol) in dry MeCN (22 mL) was added K$_2$CO$_3$ (2.47 g, 17.84 mmol) and MOMCl (1.0 mL, 13.38 mmol) and the reaction was allowed to stir at r.t. for 24 hrs. To the reaction mixture was added EtOAc (50 mL) and water (50 mL). The organic phase was separated and additionally washed with brine (20 mL), dried on Na$_2$SO$_4$, filtered and evaporated. Crude product was purified by flash column chromatography (SiO$_2$, hexane-EtOAc (5:1, R$_f$(PR) 0.3)) to yield 19 as a colorless oil (862 mg, 55%).

$^1$H-NMR (300 MHz, CDCl$_3$) δ: 5.14 (s, 2H), 5.06 (s, 2H), 3.87 (s, 6H), 3.67 (s, 3H), 3.59 (s, 3H), 2.36 (s, 3H).

Step c and d: Synthesis of 1-((2E,6E)-11,11-difluoro-3,7-dimethylundeca-2,6,10-trien-1-yl)-3,4-dimethoxy-2,5-bis(methoxymethoxy)-6-methylbenzene (21)

Compound 19 (358 mg, 1.02 mmol) was reacted with magnesium (49 mg, 2.05 mmol) in THF (4 mL), at ambient temperature for 2 hours in presence of pinch of iodine and 1,2-dibromoethane, to form the Grignard reagent 20 (the completion of reaction confirmed by LC/MS). To the cooled (0-5° C.) reaction mixture was added CuCl (68 mg, 0.682 mmol) and mixture was stirred at r.t. for 1 hr., followed by dropwise addition of a solution of 9 (200 mg, 0.682 mmol) in THF (2 mL). The reaction mixture was stirred for 16 hrs., quenched quenched by the addition of sat. aq. NH$_4$Cl (5 mL)

Scheme 3

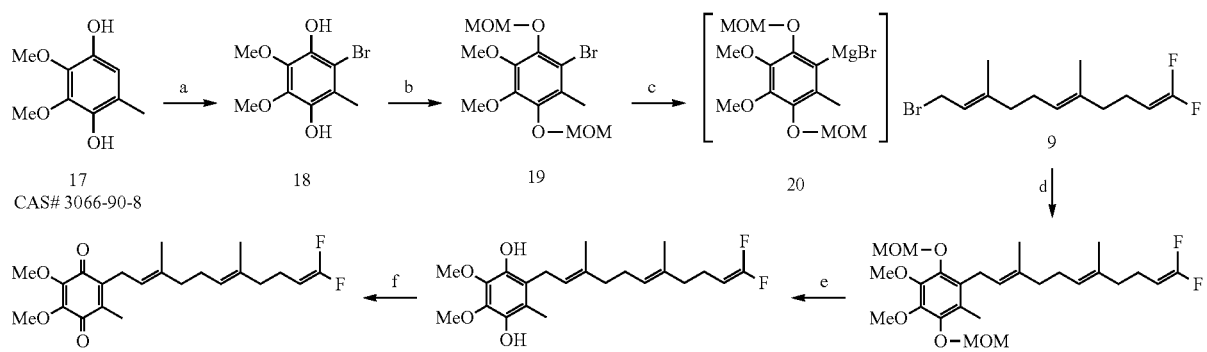

and extracted in Et$_2$O (15 mL). The organic phase was additionally washed with water (10 mL) and brine (10 mL), dried on Na$_2$SO$_4$, filtered and evaporated. Crude product was purified by flash column chromatography (SiO$_2$, hexane-Et$_2$O (5:1, R$_f$(PR) 0.4)) to yield 21 as a colorless oil (269 mg, 81%, contains 10-15% of impurity).

$^1$H-NMR (300 MHz, CDCl$_3$) δ: 5.11-5.02 (m, 2H), 5.05 (s, 2H), 5.04 (s, 2H), 4.07 (dtd, J=26.0, 7.3, 2.8 Hz, 1H), 3.86 (s, 6H), 3.59 (s, 3H), 3.58 (s, 3H), 3.37 (d, J=6.3 Hz, 2H), 2.17 (s, 3H), 2.15-1.94 (m, 8H), 1.75 (s, 3H), 1.57 (s, 3H).

Step e and f: Synthesis of 2-((2E,6E)-11,11-difluoro-3,7-dimethylundeca-2,6,10-trien-1-yl)-5,6-dimethoxy-3-methylcyclohexa-2,5-diene-1,4-dione (Compound B)

To a solution of 21 (269 mg, 0.555 mmol) in MeOH (10 mL) was added 8 drops of conc. HCl at r.t. and the reaction was stirred for 16 hrs. After evaporation, crude hydroquinone, 2-((2E,6E)-11,11-difluoro-3,7-dimethylundeca-2,6,10-trien-1-yl)-5,6-dimethoxy-3-methylbenzene-1,4-diol (22), was dissolved in mixture of i-PrOH (2.8 mL) and water (0.14 mL) and treated with FeCl$_3$ (360 mg, 2.22 mmol) for 3 hrs. at r.t. To the reaction mixture was added water (10 mL) and Et$_2$O (10 mL). The organic phase was separated and additionally washed with brine (10 mL), dried on Na$_2$SO$_4$, filtered and evaporated. Crude product was purified by flash column chromatography (Si O2, hexane-Et$_2$O (5:1, R$_f$(PR) 0.3)) to yield 110 mg (50%) of Compound B as a reddish-orange oil (HPLC purity 99.2%).

$^1$H-NMR (400 MHz, CDCl$_3$) δ: 5.09-5.00 (m, 1H), 4.98-4.88 (m, 1H), 4.07 (dtd, J=25.7, 7.5, 2.6 Hz, 1H), 3.99 (s, 3H), 3.97 (s, 3H), 3.18 (d, J=7.0 Hz, 2H), 2.10-1.94 (m, 8H), 2.01 (s, 3H), 1.73 (s, 3H), 1.56 (s, 3H). MS (M+H$^+$): 395.3.

Example 3: Synthesis of 2,3-dimethoxy-5-methyl-6-(10,10,10-trifluorodecyl)cyclohexa-2,5-diene-1,4-dione (Compound C)

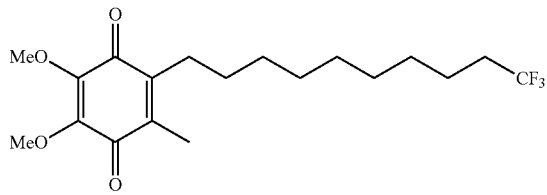

Compound C

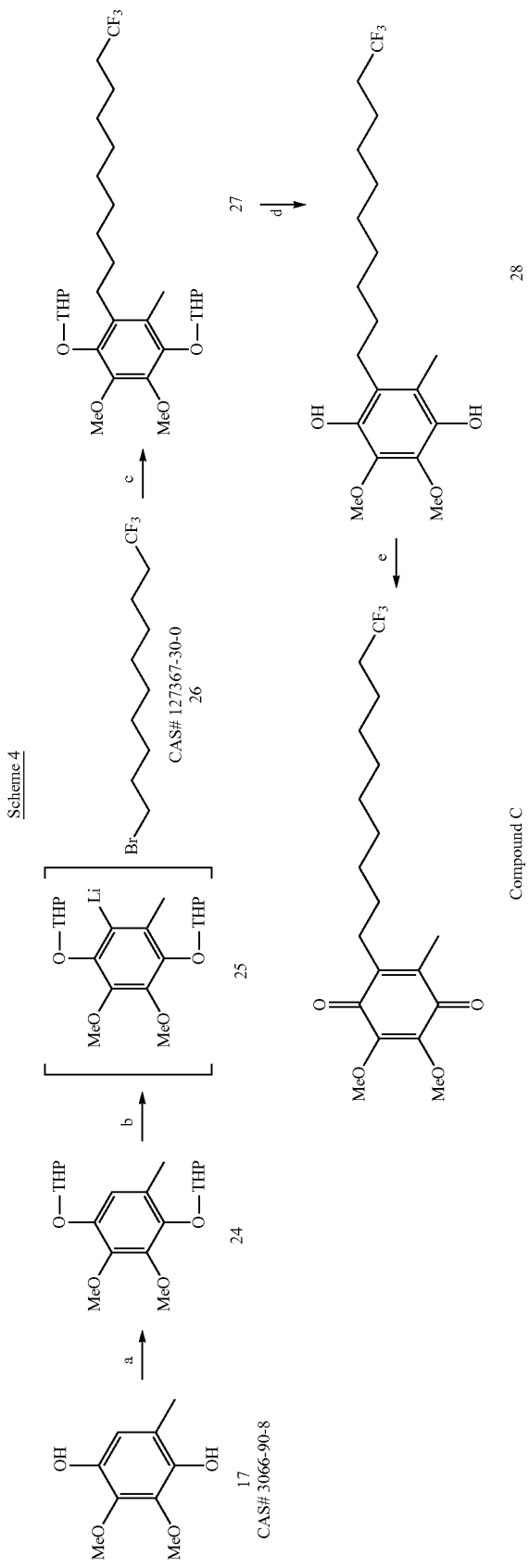

Step a: Synthesis of 2N'-((2,3-dimethoxy-5-methyl-1,4-phenylene)bis(oxy))bis(tetrahydro-2H-pyran) (24)

To a solution of 2,3-dimethoxy-5-methylbenzene-1,4-diol (17, 970 mg, 11.52 mmol) and 3,4-dihydropyran (3.16 mL, 34.56 mmol, d=0.920) in dry DCM (9 mL) was added pyridinium p-toluenesulfonate (29 mg, 0.115 mmol) and this mixture was allowed to stir at r.t. for 48 hrs. To the reaction mixture was added EtOAc (20 mL) and washed first with sat. aq. NaHCO$_3$ solution (20 mL) and then brine (20 mL). The organic phase was separated, dried on Na$_2$SO$_4$, filtered and evaporated. Crude product was purified by flash column chromatography (SiO$_2$, hexane-EtOAc (4:1, R$_f$(PR) 0.3)) to yield 24 (2.56 g, 63%) as a colorless oil.

$^1$H-NMR (300 MHz, CDCl$_3$) δ: 6.69 (d, J=2.1 Hz, 1H), 5.34 (q, J=3.3 Hz, 1H), 5.12 (t, J=3.6 Hz, 1H), 4.16-4.06 (m, 1H), 4.06-3.90 (m, 1H), 3.87 (s, 3H), 3.86 (d, J=2.8 Hz, 3H), 3.67-3.50 (m, 2H), 2.25 (s, 3H), 2.06-1.83 (m, 6H), 1.74-1.51 (m, 6H).

Step b and c: Synthesis of 2,2'-((2,3-dimethoxy-5-methyl-6-(10,10,10-trifluorodecyl)-1,4-phenylene)bis(oxy))bis(tetrahydro-2H-pyran) (27)

To a solution of 24 (556 mg, 1.578 mmol) in dry THF (14 mL) at 0° C. was added n-butyl lithium (n-BuLi, 1.03 mL, 2.367 mmol, 2.3 M in hexane). The solution was allowed to warm to r.t. and stirred for 1 hr. The mixture was re-cooled to 0° C. and was treated with hexamethylphosphoramide (HMPA, 0.41 mL, 2.367 mmol, d=1.03) followed by addition of 10-bromo-1,1,1,-trifluorodecane (26, 521 mg, 1.893 mmol) dissolved in THF (2 mL). The solution was allowed warm to room temperature and stirred for 24 hrs. The reaction was quenched by the addition of sat. aq. NH$_4$Cl solution, and then extracted with EtOAc (20 mL). The organic phase was dried over Na$_2$SO$_4$, filtered and concentrated under reduced pressure. The crude product was purified by column chromatography (SiO$_2$, hexane-Et$_2$O (4:1, R$_f$(PR) 0.3)) to yield 27 (298 mg, 35%) as a colorless oil.

$^1$H-NMR (300 MHz, CDCl$_3$) δ:5.18-5.07 (m, 2H), 4.20-4.00 (m, 2H), 3.84 (s, 3H), 3.82 (d, J=1.4 Hz, 3H), 3.61-3.50 (m, 2H), 2.81-2.47 (m, 2H), 2.21 (d, J=1.4 Hz, 3H), 2.13-1.85 (m, 8H), 1.71-1.22 (m, 20H).

Step d and e: Synthesis of 2,3-dimethoxy-5-methyl-6-(10,10,10-trifluorodecyl)cyclohexa-2,5-diene-1,4-dione (Compound C)

To a solution of 27 (298 mg, 0.545 mmol) in MeOH (10 mL) was added 8 drops of conc. HCl at r.t. and the reaction was stirred for 16 hrs. After evaporation, crude hydroquinone, 2,3-dimethoxy-5-methyl-6-(10,10,10-trifluorodecyl)benzene-1,4-diol (28), was dissolved in mixture of i-PrOH (2.7 mL) and water (0.14 mL) and treated with FeCl$_3$ (354 mg, 2.18 mmol) for 3 hours at room temperature. To the reaction mixture was added water (10 mL) and Et$_2$O (10 mL). The organic phase was separated and additionally washed with brine (10 mL), dried on Na$_2$SO$_4$, filtered and evaporated. Crude product purified by flash column chromatography (SiO$_2$, hexane-Et$_2$O (5:1, R$_f$(PR) 0.3)) to yield 115 mg (56%) of Compound C as a reddish-orange oil (HPLC purity 96.9%).

$^1$H-NMR (400 MHz, CDCl$_3$) δ: 3.98 (s, 3H), 3.98 (s, 3H), 2.47-2.40 (m, 2H), 2.11-1.97 (m, 2H), 2.00 (s, 3H), 1.59-1.47 (m, 2H), 1.41-1.25 (m, 12H). MS (M+H$^+$): 377.3.
Compound D (CAS #55486-00-5) was purchased from Cayman Chemical Company, Ann Arbor, Michigan (21027). LCMS analysis confirmed identity and purity of approximately 98%. This Compound D was used as received without purification.

Compound D

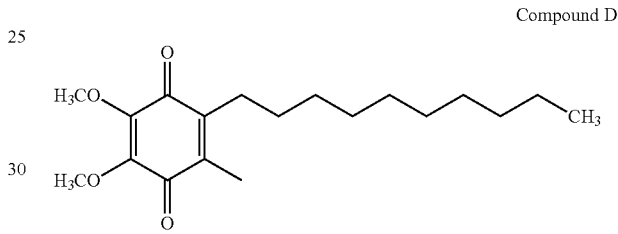

Example 4: Synthesis of 2,3-dimethoxy-5-methyl-6-(6,6,6-trifluorohexyl)cyclohexa-2,5-diene-1,4-dione (Compound E)

Compound E

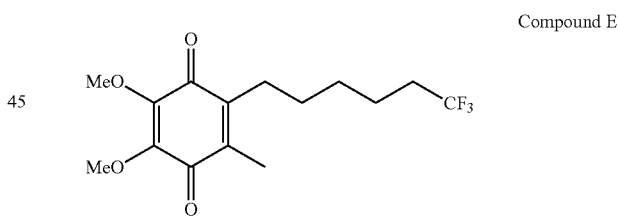

Scheme 5

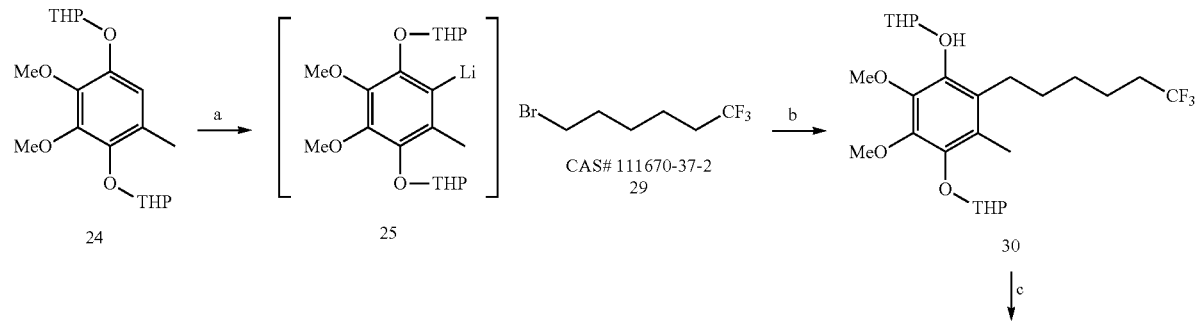

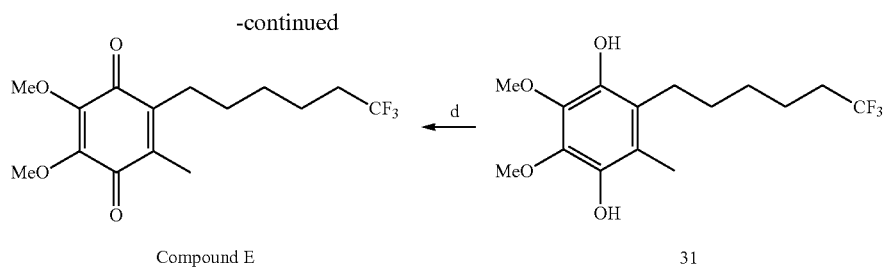

Compound E                                                                 31

Steps a and b: Synthesis of 2,2'-((2,3-dimethoxy-5-methyl-6-(6,6,6-trifluorohexyl)-1,4-phenylene)bis(oxy))bis(tetrahydro-2H-pyran) (30)

To a solution of 24 (801 mg, 2.3 mmol) in dry hexane (3.8 mL) at 0° C. under gentle argon flow dry N,N,N',N'-tetramethylethylenediamine (TMEDA) (0.37 mL, 2.5 mmol, d=0.775) was added, followed by the drop-wise addition of n-BuLi (1.5 mL, 3.5 mmol, 2.3 M in hexane). The solution was allowed to warm to RT and stirred for 30 min, the formation of yellow precipitates was observed. To mixture was added dry THF (5 mL) and reaction mixture was cooled to 0° C. (orange solution). To the reaction mixture was rapidly added a solution of dry HMPA (0.43 mL, 2.5 mmol, d=1.03) and 6-bromo-1,1,1-trifluorohexane (29, 767 g, 3.5 mmol) dissolved in dry THF (5 mL). The solution was allowed to warm to RT and stirred for 4 h. The reaction was quenched by the addition of sat. aq. $NH_4Cl$ solution, and then extracted with EtOAc (50 mL), dried over $Na_2SO_4$, filtered and concentrated under reduced pressure. The crude product was purified by flash chromatography ($SiO_2$, hexane-$Et_2O$ (4:1, $R_f$(PR) 0.3)) to yield 30 (630 mg, 56%). This material was used in the next reaction without further purification.

Steps c and d: Synthesis of 2,3-dimethoxy-5-methyl-6-(6,6,6-trifluorohexyl)cyclohexa-2,5-diene-1,4-dione (Compound E)

Note: The product is light sensitive so this reaction and product isolation should be performed in the dark. To a solution of 30 (630 mg, 1.28 mmol) in methanol (21 mL) was added 0.21 mL of conc. hydrochloric acid at room temp and the mixture was stirred for 16 hours. After evaporation, crude hydroquinone (2,3-dimethoxy-5-methyl-6-(6,6,6-trifluorohexyl)benzene-1,4-diol (31)) was dissolved in a mixture of i-PrOH (6.9 mL) and water (0.34 mL) and treated with $FeCl_3$ (892 mg, 5.5 mmol) for 3 hours at RT. To reaction mixture was added water (20 mL) and $Et_2O$ (40 mL). The organic phase was separated and additionally washed with brine (20 mL), dried on $Na_2SO_4$, filtered and evaporated. Crude product was first purified by flash column chromatography ($SiO_2$, hexane-$Et_2O$ (5:1, $R_f$(PR) 0.3)) and then by reversed phase flash chromatography (KP-C-18-HS, (MeCN/MeOH, 70/30)/$H_2O$) to yield Compound E (205 mg, 49%, HPLC purity 96.23%).

$^1$H-NMR (400 MHz, $CDCl_3$) δ: 3.99 (s, 3H), 3.99 (s, 3H), 2.48-2.45 (m, 2H), 2.13-2.03 (m, 2H), 2.01 (s, 3H), 1.62-1.57 (m, 2H), 1.44-1.41 (m, 4H).

Example 5: Synthesis of 2-(6,6-difluorohexyl)-5,6-dimethoxy-3-methylcyclohexa-2,5-diene-1,4-dione (Compound F)

Compound F

Scheme 6

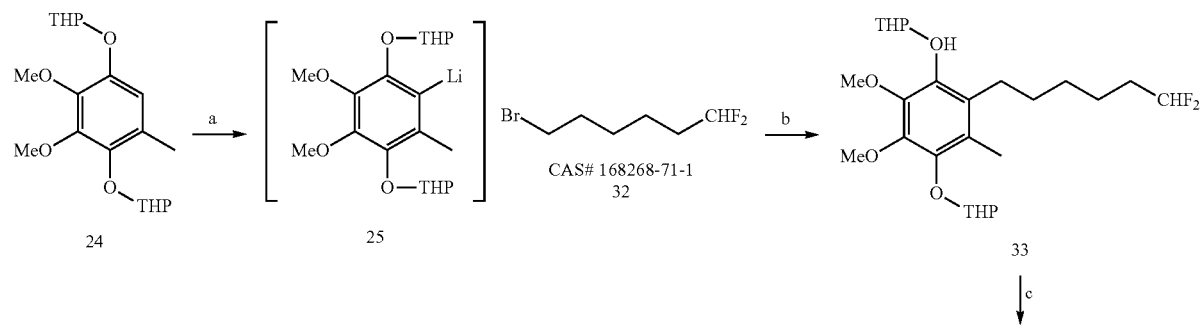

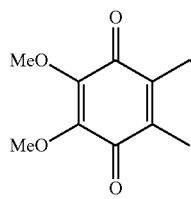

Compound F

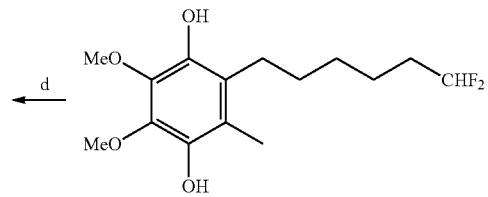

34

Steps a and b: Synthesis of 2N'-((2-(6,6-difluorohexyl)-5,6-dimethoxy-3-methyl-1,4-phenylene)bis(oxy))bis(tetrahydro-2H-pyran) (33)

To a solution of 24 (1.0 g, 2.83 mmol) in dry hexane (10 mL) at 0° C. under gentle argon flow was added first TMEDA (0.46 mL, 3.12 mmol, d=0.775), followed by the drop-wise addition of n-BuLi (1.8 mL, 4.25 mmol, 2.3 M in hexane). The solution was allowed to warm to RT and stirred for 30 min. Formation of yellow precipitates was observed. The mixture was re-cooled to 0° C. and treated with HMPA (0.74 mL, 4.255 mmol, d=1.03) followed by addition of 6-bromo-1,1-difluorohexane (32, 0.68 g, 3.4 mmol) dissolved in THF (4 mL). The solution was allowed to warm to RT and stirred for 4 h. The reaction was quenched by the addition of sat. aq. $NH_4Cl$ solution, and then extracted with EtOAc (250 mL), dried over $Na_2SO_4$, filtered and concentrated under reduced pressure. The crude product was purified by column chromatography ($SiO_2$, hexane-$Et_2O$ (25:1)) to yield 33 (317 mg, 23%) as colorless oil. This material was used in the next reaction without further purification.

$^1$H-NMR (400 MHz, $CDCl_3$) δ: 5.80 (tt; J=57.0; 4.5 Hz; 1H), 5.13-5.11 (m, 2H), 4.15-4.04 (m, 2H), 3.82 (s, 3H), 3.81 (s, 3H), 3.59-3.52 (m, 2H), 2.77-2.70 (m, 1H), 2.61-2.55 (m, 1H), 2.21 (s, 3H), 2.01-1.78 (m, 8H), 1.67-1.57 (m, 6H), 1.53-1.41 (m, 6H).

Steps c and d; Synthesis of 2-(6,6-difluorohexyl)-5,6-dimethoxy-3-methylcyclohexa-2,5-diene-1,4-dione (Compound F)

Note: The product is light sensitive so this reaction and product isolation should be performed in the dark. To a solution of 33 (0.31 g, 0.66 mmol) in methanol (15 mL) was added 10 drops of conc. hydrochloric acid at RT and the mixture was stirred for 16 hours. After evaporation, crude hydroquinone (2-(6,6-difluorohexyl)-5,6-dimethoxy-3-methylbenzene-1,4-diol (34)) was dissolved in a mixture of i-PrOH (5 mL) and water (0.3 mL) and treated with $FeCl_3$ (520 mg) for 3 hours at RT. To the reaction mixture water (10 mL) and $Et_2O$ (250 mL) were added. The organic phase was separated and additionally washed with brine (70 mL), dried on $Na_2SO_4$, filtered and evaporated. Crude product was first purified by flash column chromatography ($SiO_2$, hexane-$Et_2O$ (25:1)) and then re-purified by reversed phase flash chromatography ((MeCN/MeOH)/$H_2O$; 70-85%) to give Compound F (61 mg, 30%, HPLC purity 99.62%).

$^1$H-NMR (400 MHz, $CDCl_3$) δ: 5.79 (tt; J=57.0; 4.5 Hz; 1H), 3.99 (s, 3H), 3.99 (s, 3H), 2.48-2.44 (m, 2H), 2.01 (s, 3H), 1.89-1.75 (m, 2H), 1.50-1.39 (m, 6H).

Example 6: Synthesis of 2-(6-fluorohexyl)-5,6-dimethoxy-3-methylcyclohexa-2,5-diene-1,4-dione (Compound G)

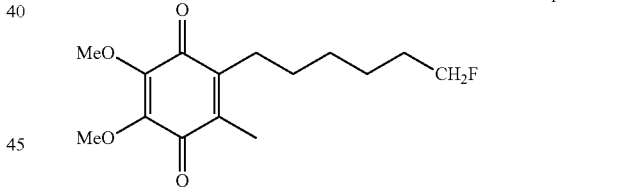

Compound G

Scheme 7

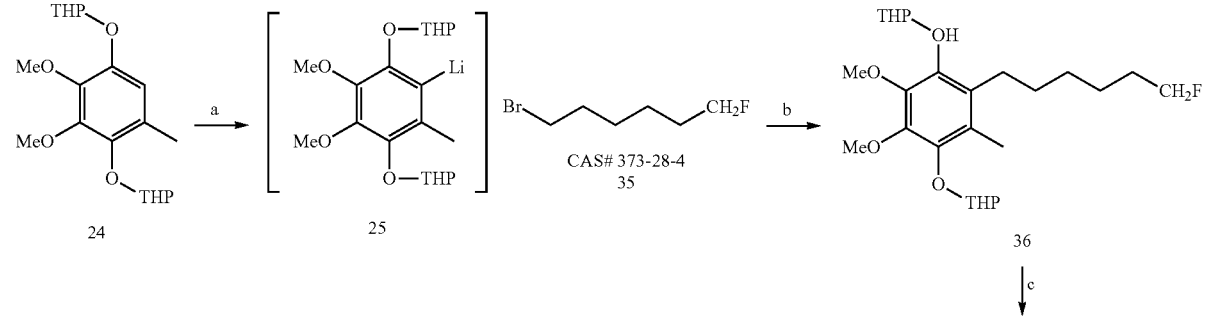

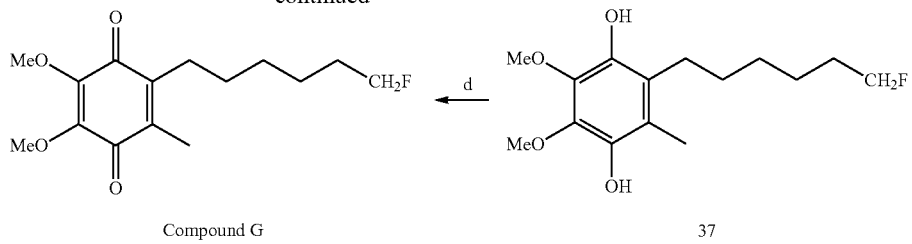

Compound G    37

Steps a and b: Synthesis of 2N'-((2-(6-fluorohexyl)-5,6-dimethoxy-3-methyl-1,4-phenylene)bis(oxy))bis(tetrahydro-2H-pyran) (36)

To a solution of 24 (1.0 g, 2.83 mmol) in dry hexane (10 mL) at 0° C. under gentle argon flow was added first TMEDA (0.46 mL, 3.12 mmol, d=0.775), and then dropwise n-BuLi (1.8 mL, 4.25 mmol, 2.3 M in hexane). The solution was allowed to warm to RT and stirred for 30 min. Formation of yellow precipitates was observed. The mixture was re-cooled to 0° C. and treated with HMPA (0.41 mL, 2.367 mmol, d=1.03) followed by addition of 1-bromo-6-fluorohexane (35, 0.62 g, 3.4 mmol) dissolved in THF (4 mL). The solution was allowed to warm to RT and stirred for 4 h. The reaction was quenched by the addition of sat. aq. NH$_4$Cl solution, and then extracted with EtOAc (200 mL), dried over Na$_2$SO$_4$, filtered and concentrated under reduced pressure. The crude product was purified by flash chromatography (SiO$_2$, hexane-Et$_2$O (23:1) to yield 36 (350 mg, 27%) as colorless oil. This material was used in the next reaction without further purification.

$^1$H-NMR (400 MHz, CDCl$_3$) δ: 5.13-5.11 (m, 2H), 4.52-4.48 (m, 1H), 4.40-4.37 (m, 1H), 4.14-4.05 (m, 2H), 3.82 (s, 3H), 3.81 (s, 3H), 3.59-3.53 (m, 2H), 2.21 (s, 3H), 2.01-1.89 (m, 6H), 1.76-1.58 (m, 9H), 1.52-1.41 (m, 6H).

Steps c and d: Synthesis of 2-(6-fluorohexyl)-5,6-dimethoxy-3-methylcyclohexa-2,5-diene-1,4-dione (Compound G)

Note: The product is light sensitive so this reaction and product isolation should be performed in the dark. To a solution of 36 (0.35 g, 0.77 mmol) in methanol (15 mL) was added 8 drops of conc. hydrochloric acid at RT and the mixture was stirred for 16 hours. After evaporation, crude hydroquinone (2-(6-fluorohexyl)-5,6-dimethoxy-3-methylbenzene-1,4-diol (37)) was dissolved in mixture of i-PrOH (3 mL) and water (0.2 mL) and treated with FeCl$_3$ (415 mg) for 3 hours at RT. To reaction mixture was added water (10 mL) and Et$_2$O (100 mL). The organic phase was separated and additionally washed with brine (50 mL), dried over Na$_2$SO$_4$, filtered and evaporated. Crude product was purified by flash column chromatography (SiO$_2$, hexane-Et$_2$O (5:1) to yield Compound G (133 mg, 60%, HPLC purity 98.0%).

$^1$H-NMR (400 MHz, CDCl$_3$) δ: 4.51-4.48 (m, 1H), 4.39-4.36 (m, 1H), 3.98 (s, 3H), 3.98 (s, 3H), 2.48-2.44 (m, 2H), 2.01 (s, 3H), 1.75-1.63 (m, 2H), 1.46-1.36 (m, 6H).

Example 7: Synthesis of 2-heptyl-5,6-dimethoxy-3-methylcyclohexa-2,5-diene-1,4-dione (Compound H)

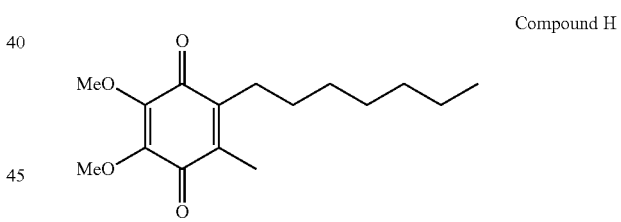

Compound H

Scheme 8

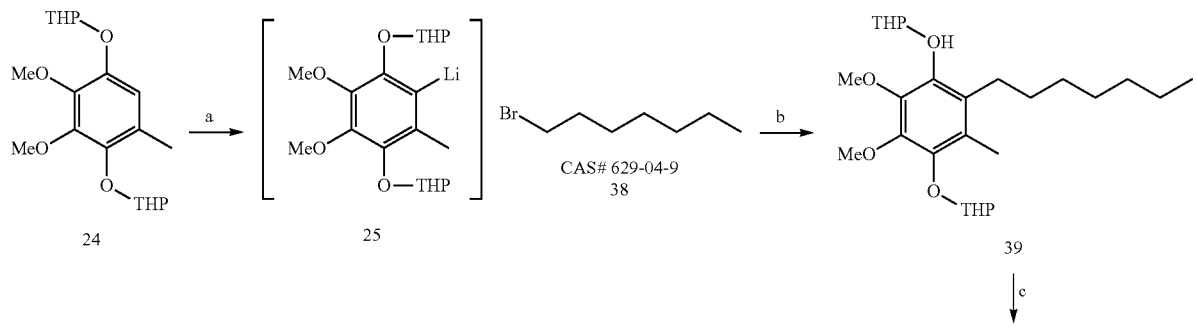

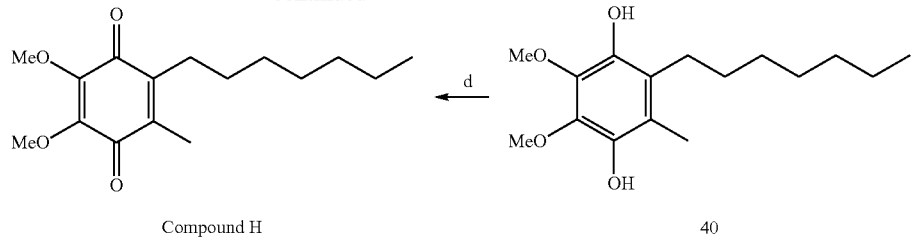

Compound H      40

Step a and b: Synthesis of 2,2'-((2-heptyl-5,6-dimethoxy-3-methyl-1,4-phenylene)bis(oxy))bis(tetrahydro-2H-pyran) (39)

To a solution of 24 (1.0 g, 2.83 mmol) in dry hexane (10 mL) at 0° C. under gentle argon flow was added first TMEDA (0.46 mL, 3.12 mmol, d=0.775), and then dropwise n-BuLi (1.8 mL, 4.25 mmol, 2.3 M in hexane). The solution was allowed to warm to room temperature and stirred for 30 min. Formation of yellow precipitates was observed. The mixture was re-cooled to 0° C. and treated with HMPA (0.41 mL, 2.367 mmol, d=1.03) followed by addition of 1-bromoheptane (38, 0.74 ml, 3.4 mmol) dissolved in THF (4 mL). The solution was allowed to warm to RT and stirred for 4 h. The reaction was quenched by addition of sat. aq. NH$_4$Cl solution, and then extracted with EtOAc (200 mL), dried over Na$_2$SO$_4$, filtered and concentrated under reduced pressure. The crude product was purified by column chromatography (SiO$_2$, hexane-Et$_2$O (20:1)) to yield 39 (310 mg, 24%) as colorless oil. This material was used in the next reaction without further purification.

$^1$H-NMR (400 MHz, CDCl$_3$) δ: 5.15-5.11 (m, 2H), 4.16-4.07 (m, 2H), 3.82 (s, 3H), 3.81 (s, 3H), 3.60-3.54 (m, 2H), 2.74-2.67 (m, 1H), 2.60-2.53 (m, 1H), 2.21 (s, 3H), 2.01-1.89 (m, 5H), 1.69-1.59 (m, 5H), 1.52-1.44 (m, 2H), 1.41-1.24 (m, 8H), 0.9-0.87 (m, 3H).

Steps c and d: Synthesis of 2-heptyl-5,6-dimethoxy-3-methylcyclohexa-2,5-diene-1,4-dione (Compound H)

Note: The product is light sensitive so this reaction and product isolation should be performed in the dark. To a solution of 39 (0.31 g, 0.69 mmol) in methanol (15 mL) was added 8 drops of conc. hydrochloric acid at RT and the mixture was stirred for 16 hours. After evaporation, crude hydroquinone (2-heptyl-5,6-dimethoxy-3-methylbenzene-1,4-diol (40)) was dissolved in mixture of i-PrOH (3 mL) and water (0.2 mL) and treated with FeCl$_3$ (430 mg) for 3 hours. To the reaction mixture was added water (10 mL) and Et$_2$O (200 mL). The organic phase was separated and additionally washed with brine (70 mL), dried over Na$_2$SO$_4$, filtered and evaporated. Crude product purified by flash column chromatography (SiO$_2$, hexane-Et$_2$O (5:1)) to yield Compound H (140 mg, 72%, HPLC purity 98.8%).

$^1$H-NMR (400 MHz, CDCl$_3$) δ: 3.99 (s, 3H), 3.98 (s, 3H), 2.46-2.43 (m, 2H), 2.01 (s, 3H), 1.40-1.27 (m, 10H), 0.89-0.86 (m, 3H).

Example 8: Synthesis of 2,3-dimethoxy-5-methyl-6-(4,4,4-trifluorobutyl)cyclohexa-2,5-diene-1,4-dione (Compound I)

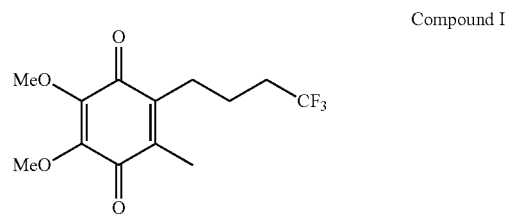 [SMILES: COC1=C(OC)C(=O)C(CCCC(F)(F)F)=C(C)C1=O]

Compound I

Scheme 9

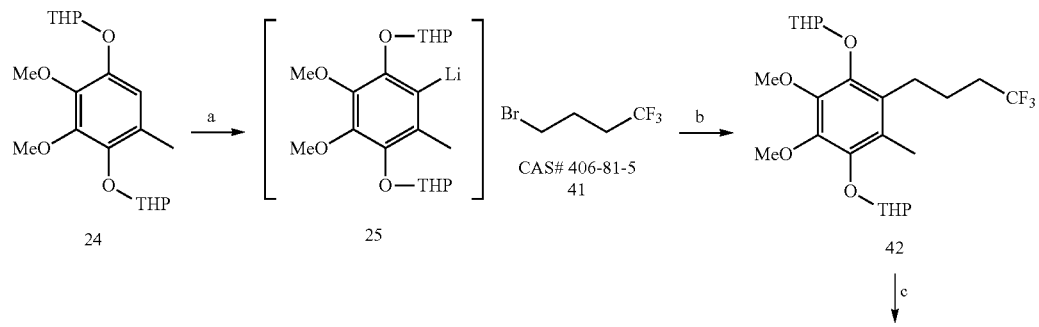

Steps a and b. Synthesis of 2N'-((2,3-dimethoxy-5-methyl-6-(4,4,4-trifluorobutyl)-1,4-phenylene)bis(oxy))bis(tetrahydro-2H-pyran) (42)

To a solution of 24 (801 mg, 2.3 mmol) in dry hexane (3.8 mL) at 0° C. under gentle argon flow was added dry TMEDA (0.37 mL, 2.5 mmol, d=0.775), followed by the drop-wise addition of n-BuLi (1.5 mL, 3.5 mmol, 2.3 M in hexane). The solution was allowed to warm to RT and stirred for 30 min. Formation of yellow precipitates was observed. To mixture was added dry THF (5 mL) and the reaction mixture was cooled to 0° C. (orange solution). To the reaction mixture was rapidly added a solution of dry HMPA (0.43 mL, 2.5 mmol, d=1.03) and 4-bromo-1,1,1-trifluorobutane (41, 668 g, 3.5 mmol) dissolved in dry THF (5 mL). The solution was allowed to warm to RT and stirred for 4 h. The reaction was quenched by the addition of sat. aq. NH$_4$Cl solution, and then extracted with EtOAc (50 mL), dried over Na$_2$SO$_4$, filtered and concentrated under reduced pressure. The crude product was purified by column chromatography (SiO$_2$, hexane-Et$_2$O (4:1, R$_f$(PR) 0.3)) to yield 42 (441 mg, 39%). This material was used in the next reaction without further purification.

Steps c and d: Synthesis of 2,3-dimethoxy-5-methyl-6-(4,4,4-trifluorobutyl)cyclohexa-2,5-diene-1,4-dione (Compound I)

Note: The product is light sensitive so this reaction and product isolation should be performed in the dark. To a solution of 42 (441 mg, 0.95 mmol) in methanol (15 mL) was added 0.15 mL of conc. hydrochloric acid at RT and stirred for 16 hours. After evaporation, crude hydroquinone (2,3-dimethoxy-5-methyl-6-(4,4,4-trifluorobutyl)benzene-1,4-diol (43)) was dissolved in mixture of i-PrOH (5.0 mL) and water (0.26 mL) and treated with FeCl$_3$ (662 mg, 4.08 mmol) for 3 hours. To the reaction mixture was added water (20 mL) and Et$_2$O (40 mL). The organic phase was separated and additionally washed with brine (20 mL), dried on Na$_2$SO$_4$, filtered and evaporated. Crude product purified first by flash column chromatography (SiO$_2$, hexane-Et$_2$O (5:1, R$_f$(PR) 0.3)), then by reversed-phase flash chromatography (KP-C-18-HS, (MeCN/MeOH, 70/30)/H$_2$O) to yield Compound I (66 mg, 24%, HPLC purity 95.66%) as a reddish-orange oil.

$^1$H-NMR (400 MHz, CDCl$_3$) δ: 4.00 (s, 3H), 3.99 (s, 3H), 2.56-2.52 (m, 2H), 2.20-2.07 (m, 2H), 2.03 (s, 3H), 1.71-1.63 (m, 2H).

Example 9: Synthesis of 2-(4-fluorobutyl)-5,6-dimethoxy-3-methylcyclohexa-2,5-diene-1,4-dione (Compound J)

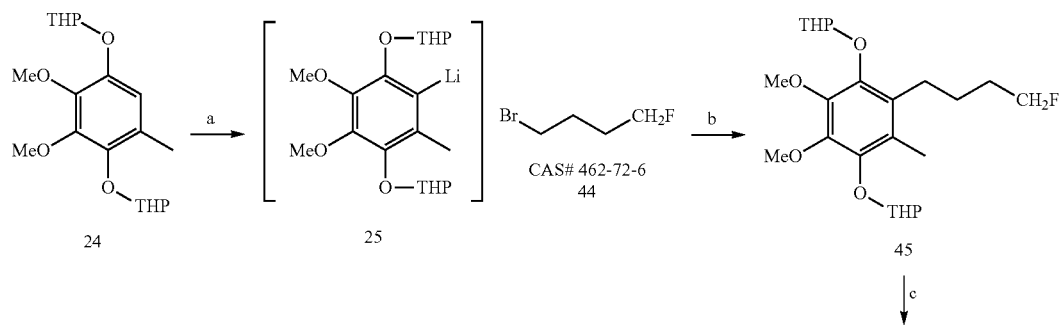

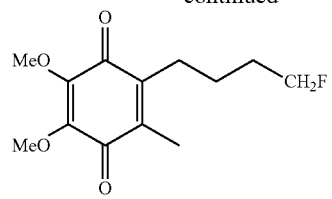

Compound J

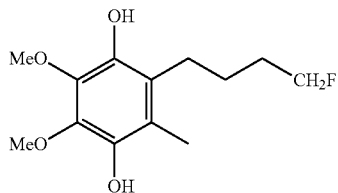

46

Steps a and b: Synthesis of 2N'-((2-(4-fluorobutyl)-5,6-dimethoxy-3-methyl-1,4-phenylene)bis(oxy))bis(tetrahydro-2H-pyran) (45)

To a solution of 24 (1.0 g, 2.83 mmol) in dry hexane (10 mL) at 0° C. under gentle argon flow was added first TMEDA (0.46 mL, 3.12 mmol, d=0.775), and then was added drop-wise n-BuLi (1.8 mL, 4.25 mmol, 2.3 M in hexane). The solution was allowed to warm to RT and stirred for 30 min. Formation of yellow precipitates was observed. The mixture was re-cooled to 0° C. and was treated with HMPA (0.74 mL, 4.255 mmol, d=1.03) followed by addition of 1-bromo-4-fluorobutane (44, 0.74 mL, 4.2 mmol) solution in THF (5 mL). The solution was allowed to warm to RT and stirred for 3 h. The reaction was quenched by the addition of sat. aq. $NH_4Cl$ solution, and then extracted with EtOAc (250 mL), dried over $Na_2SO_4$, filtered and concentrated under reduced pressure. The crude product was purified by column chromatography ($SiO_2$, hexane-$Et_2O$ (25:1) to yield 45 (250 mg, 21%) as colorless oil. This material was used in the next reaction without further purification.

Steps c and d: Synthesis of 2-(4-fluorobutyl)-5,6-dimethoxy-3-methylcyclohexa-2,5-diene-1,4-dione (Compound J)

Note: The product is light sensitive so this reaction and product isolation should be performed in the dark. To a solution of 45 (0.25 g, 0.58 mmol) in methanol (10 mL) was added 7 drops of conc. hydrochloric acid at RT and the mixture was stirred for 16 hours. After evaporation, crude hydroquinone (2-(4-fluorobutyl)-5,6-dimethoxy-3-methylbenzene-1,4-diol (46)) was dissolved in a mixture of i-PrOH (4 mL) and water (0.2 mL) and treated with $FeCl_3$ (420 mg) for 3 hours. To the reaction mixture was added water (10 mL) and $Et_2O$ (250 mL). The organic phase was separated and additionally washed with brine (70 mL), dried over $Na_2SO_4$, filtered and evaporated. Crude product was first purified by flash column chromatography ($SiO_2$, hexane-$Et_2O$ (30:1) and re-purified by reversed phase flash chromatography ((MeCN/MeOEQ/ELO; 65-75%) to give Compound J (48 mg, 32%, HPLC purity 99.4%).

$^1$H-NMR (400 MHz, $CDCl_3$) δ: 4.52 (t; J=5.9 Hz; 1H), 4.40 (t; J=5.9 Hz; 1H), 3.99 (s, 3H), 3.99 (s, 3H), 2.53-2.49 (m, 2H), 2.03 (s, 3H), 1.81-1.68 (m, 2H), 1.57-1.49 (m, 2H).

Example 10: Synthesis of 2,3-dimethoxy-5-methyl-6-(3-(trimethylsilyl)propyl)cyclohexa-2,5-diene-1,4-dione (Compound K)

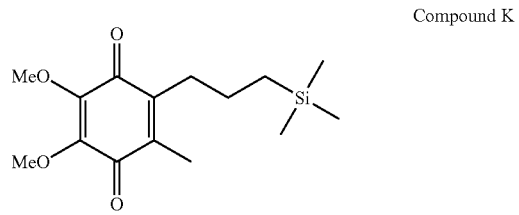 [SMILES: COC1=C(OC)C(=O)C(CCC[Si](C)(C)C)=C(C)C1=O]

Compound K

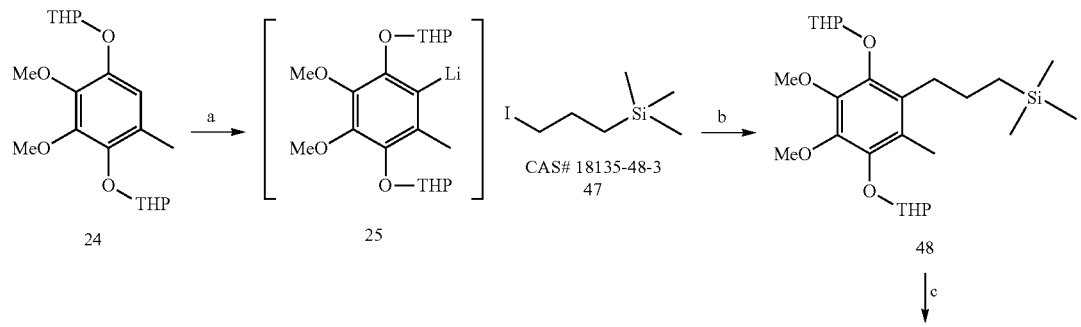

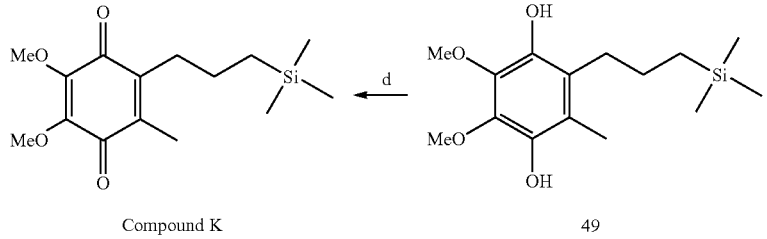

Compound K            49

Steps a and b: Synthesis of (3-(3,4-dimethoxy-6-methyl-2,5-bis((tetrahydro-2H-pyran-2-yl)oxy)phenyl)propyl)trimethylsilane (48)

To a solution of 24 (1.0 g, 2.83 mmol) in dry hexane (10 mL) at 0° C. under gentle argon flow was first added TMEDA (0.46 ml, 3.12 mmol, d=0.775), and then drop-wise n-BuLi (1.8 mL, 4.25 mmol, 2.3 M in hexane). The solution was allowed to warm to RT and stirred for 30 min. Formation of yellow precipitates was observed. The mixture was re-cooled to 0° C. and was treated with HMPA (0.74 mL, 4.255 mmol, d=1.03) followed by addition of (3-iodopropyl) trimethylsilane (47, 0.82 g, 3.4 mmol) dissolved in THF (4 mL). The solution was allowed warm to RT and stirred for 4 h. The reaction was quenched by the addition of sat. aq. $NH_4Cl$ solution, and then extracted with EtOAc (250 mL), dried over $Na_2SO_4$, filtered and concentrated under reduced pressure. The crude product was purified by column chromatography ($SiO_2$, hexane-$Et_2O$ (20:1) to yield 48 (510 mg, 39%) as colorless oil. This material was used in the next reaction without further purification.

Steps c and d: Synthesis of 2,3-dimethoxy-5-methyl-6-(3-(trimethylsilyl)propyl)cyclohexa-2,5-diene-1,4-dione (Compound K)

Note: The product is light sensitive so this reaction and product isolation should be performed in the dark. To a solution of 48 (0.31 g, 0.66 mmol) in methanol (15 mL) was added 10 drops of conc. hydrochloric acid at RT and stirred for 16 hours. After evaporation, crude hydroquinone (2,3-dimethoxy-5-methyl-6-(3-(trimethylsilyl)propyl)benzene-1,4-diol (49)) was dissolved in a mixture of i-PrOH (5 mL) and water (0.3 mL) and treated with $FeCl_3$ (530 mg) for 3 hours. To the reaction mixture was added water (10 mL) and $Et_2O$ (250 mL). The organic phase was separated and additionally washed with brine (70 mL), dried over $Na_2SO_4$, filtered and evaporated. Crude product was purified by flash column chromatography ($SiO_2$, hexane-$Et_2O$ (25:1) and re-purified by reversed phase flash chromatography ((MeCN/MeOH)/$H_2O$; 65-75%) to yield Compound K (241 mg, 74%, HPLC purity 99.44%).

$^1$H-NMR (400 MHz, $CDCl_3$) δ: 3.99 (s, 3H), 3.98 (s, 3H), 2.49-2.46 (m, 2H), 2.01 (s, 3H), 1.44-1.36 (m, 2H), 0.58-0.53 (m, 2H), −0.03 (s, 9H).

Example 11A: Preparation of Reduced Form of Compound C (prophetic)

Compound C (20 mg) is dissolved in mixture of MeOH/THF (1 mL+1 mL) under an argon atmosphere. Then $NaBH_4$ (3 mg) is added and the reaction mixture is stirred at r.t. for 1 hr. Next, the reaction mixture is quenched by the addition of $Et_2O$ (30 mL) and aq. $NH_4Cl$ (10 mL) with stirring at r.t. for 2 min. The aqueous phase is separated and the organic phase is washed with brine (10 mL), dried over anhydrous $Na_2SO_4$ and concentrated under reduced pressure. The crude product is purified by column chromatography to yield 28 (i.e. the reduced form of Compound C—which compound can also be isolated as 28 from Example 3).

Example 11B: Preparation of Reduced Form of Vatiquinone ("Vatiquinone-R")

Scheme 12

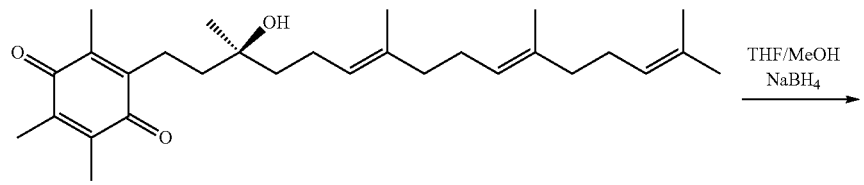

Vatiquinone

-continued

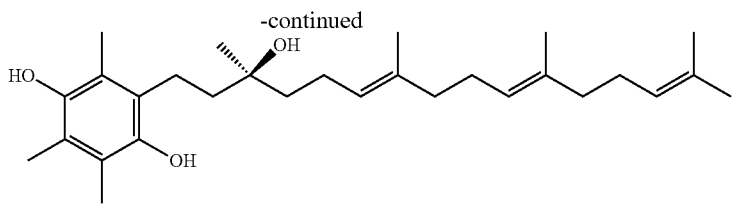

Vatiquinone-R

Vatiquinone (20 mg) was dissolved in mixture of MeOH/THF (1 mL+1 mL) under an argon atmosphere. Then NaBH4 (3 mg) was added and the reaction mixture was stirred at r.t. for 1 hr. Next, the reaction mixture was quenched by the addition of Et$_2$O (30 mL) and aq. NH$_4$C$_1$ (10 mL) with stirring at r.t. for 2 min. The aqueous phase was separated and organic phase was washed with brine (10 mL), dried over anhydrous Na$_2$SO$_4$ and concentrated under reduced pressure. The crude product was purified by column chromatography to yield 0.015 g (74% yield) of reduced vatiquinone (Vatiquinone-R).

$^1$H-NMR (CDCl3, 400 MHz): δ=5.17-5.08 (m, 3H), 2.74-2.71 (m, 2H), 2.19-2.16 (m, 9H), 2.11-1.96 (m, 11H), 1.71-1.68 (m, 5H), 1.62-1.56 (m, 11H), 1.25 (s, 4H).

$^{13}$C-NMR (101 MHz, Chloroform-d) δ=145.9, 145.5, 136.1, 135.3, 131.4, 125.9, 124.5, 124.2, 124.0, 121.8, 120.7, 119.1, 74.0, 41.9, 41.0, 40.0, 30.5, 26.9, 26.7, 26.7, 25.8, 23.0, 20.7, 17.8, 16.2, 16.2, 12.5, 12.4, 12.2.

HRMS, [M+H]: $C_{29}H_{47}O_3$ (calculated: 443.3525). Found: 443.3516.

Example 12: Frataxin Deficient Fibroblast Viability Assay (the "BSO Assay")

Reference: Matthias L. Jauslin, Thomas Wirth, Thomas Meier and Fabrice Schoumacher, A cellular model for Friederichs Ataxia reveals small-molecule glutathione peroxidase mimetics as novel treatment strategy, Human Molecular Genetics, 2002, Vol. 11 (24): 3055-3063.

This Example was used to evaluate the various new compositions for their potential efficacy in the treatment of Friedreich's Ataxia (FA or FRDA)—substantially as described in the above cited Reference (Matthias et al.). This data can be used to select candidates for further testing, including animal studies directed to development of active therapeutic agents.

Introduction:

The assay utilizes frataxin deficient fibroblasts (i.e., fibroblasts from Friedreich's ataxia (FRDA) patient material) as a means to assay cell viability by determining how compounds of interest can potentially inhibit/delay/prevent L-buthionine-sulfoximine-induced (BSO-induced) cell death in diseased and control (healthy) cells.

Test Articles:

The stock solutions of the test articles (and control compounds) were prepared in dimethyl sulfoxide (DMSO at 10 mM), Working stock solutions (2 times concentrated) were prepared on the day of the experiment in respective cell culture medium to be used for assay (detailed medium description below). A listing of compounds used as test articles in this Example 12 are found in Table 1, below.

Assay Experimental:

A patient derived frataxin deficient fibroblast cell line was obtained from Coriell Institute. More specifically, the following cell lines/DNA samples were obtained from the NIGMS Human Genetic Cell Repository at the Coriell Institute for Medical Research: GM03665. To evaluate importance of various growth conditions on cell susceptibility to BSO toxicity cells were grown on:

MEM (Sigma-Aldrich) 15% Fetal Bovine Serum (FBS) without growth factors;

MEM (Sigma-Aldrich) 15% FBS with growth factors (Catalogue number 100-18B, Recombinant Human FGF-basic (154 a.a.) and catalogue number AF-100-15, Animal-Free Recombinant Human EGF from Peprotech);

MEM199/MEM EBS (Bioconcept Ltd.) 10% FBS, insulin 10 μg/ml, L-glutamine 2 mM with growth factors (Catalogue number 100-18B, Recombinant Human FGF-basic (154 a.a.) and catalogue number AF-100-15, Animal-Free Recombinant Human EGF from Peprotech).

To conduct an experiment, fibroblast cells (from all growth conditions) were seeded (100 μL (cells 3×10^3/well) on 96-well plates in MEM199/MEM EBS medium 10% FBS, insulin 10 μg/mL, L-glutamine 2 mM with growth factors and allowed to grow on plate for 24 hrs. After 24 hrs., media was removed and then test compounds of interest were added (100 μL, 2 times concentrated stock) to 96-well plates (end DM80 concentration not exceeding 0.5%) and incubated for 24 hours. Then L-buthionine-sulfoximine (BSO, from Acros Organics, Cat. No. 235520010) was added (100 μL, 2 times concentrated stock) at end concentrations ranging from 1 to 10 mM. Both test compounds and BSO were dissolved in MEM199/MEM EBS medium 10% FBS, insulin 10 μg/mL, L-glutamine 2 mM with growth factors. Cell viability was monitored and either after 24- or 48-hours cell viability was assayed by MTT (Thiazolyl blue tetrazolium bromide) assay. For the MTT assay, media was removed and 100 μL of MTT 1 mg/mL was added, incubated for 2 hours at +37° C., then medium was removed and 100 μL of isopropanol added to dissolve sediment. Absorption was measured at 570 (OD570) and 650 (QD650) nm wavelengths. Control cells (vehicle instead of BSO and compound) and vehicle control (with BSO, but vehicle instead of test compound) were treated in the same manner as ceils with BSO and compound. All cell media contained penicillin and streptomycin 100 U/mL each.

Calculations:

Absorption readouts were processed as follows: Value$_A$=Value$_{OD570}$−Value$_{OD650}$ and the obtained values were used to calculate cell viability as % of control cell (i.e., no BSO, no compound, just vehicle) viability.

Replicates:

Except as otherwise indicated in Table 1, all samples were run in at least 3 replicates for test compounds and at least 8 replicates for controls (i.e., both control (no BSO, no compound) and vehicle control (i.e., with BSO, no compound). Exact N per data points are indicated in the figures/table legends. Results for the compounds (test articles and controls) tested are listed in Table 1, below.

Discussion:

This is a cell-based assay measuring cytotoxicity which results from oxidative stress subsequent to depletion of endogenous glutathione defense mechanisms. The cells were primary Friedreich Ataxia (FA) patient fibroblasts which were incubated for 48 hrs. in BSO, an inhibitor of gamma glutamyl synthetase, an enzyme required for glutathione production. Relative to healthy control fibroblasts, FA patient fibroblasts are more susceptible to the BSO induced cell death due to the loss of frataxin and subsequent accumulation of cytosolic iron, which accelerates the process of ROS driven lipid peroxidation. In the assay, cells were pretreated with drug at decreasing doses from 250 nM down to 6.125 nM the day before the BSO was added at a fixed dose of 10 mM. Cytotoxicity was measured with MTT assay 48 hrs. later and reported as the percent of MTT absorbance normalized to cells grown in media without BSO for 48 hrs. Unless otherwise indicated, each data point was performed in triplicate wells of a 96 well plate. Data obtained is presented below in Table 1. In summary, all compounds tested (i.e. Compounds A-I and K), except for Compound J, were protective against BSO induced cell death in the assay, though in all cases, the test compounds were not as protective as Vatiquinone. The best of the test compounds were Compounds A and C. Omaveloxolone was roughly equivalent in protection as compared with Vatiquinone but Idebenone was not really very protective at all in this assay.

Example 13: Rotenone ATP Assay (a Complex I by-Pass Assay)

Introduction

This assay has been adapted from Haefeli R H, Erb M, Gemperli A C, Robay D, Courdier Fruh I, et al. (2011) NQO1-Dependent Redox Cycling of Idebenone: Effects on Cellular Redox Potential and Energy Levels. PLoS ONE 6(3): e17963. HepG2 human hepatocarcinoma cells are co-incubated with the electron transport chain complex I toxin rotenone +/− compounds of interest and the corresponding effect on ATP synthesis is measured with a bioluminescent substrate. The assay is useful in identifying compounds which can "by-pass" the rotenone induced block of complex I, which significantly impairs mitochondrial respiration and results in a net reduction of ATP generated from endogenous substrates.

Test Articles:

The stock solutions of the test articles (See Table 1, below for a list of the test articles examined using this assay) were prepared in dimethyl sulfoxide (DMSO at 10 mM). Working stock solutions were prepared on the day of the experiment in glucose free, serum free Dulbecco's modified Eagles medium (DMEM) supplemented with 50 micromolar rotenone.

Assay Experimental:

In brief, HepG2 cells were plated at 25,000 cells per well in low glucose (1 gram/Liter) DMEM medium+10% fetal calf serum and incubated for 24 hours. The following day, the media was decanted and subsequently replaced with glucose free/serum free DMEM which has been supplemented with 50 micromolar rotenone and compound of interest. Serial dilutions of compound were prepared in 3× dilutions beginning at 25 micromolar. The cells were incubated for 60 minutes in a humidified tissue culture incubator. Following incubation, ATP levels were quantified via bioluminescent assay (Promega TiterMax Glo Assay kit) and readings were captured on a standard microplate reader.

Calculations:

ATP bioluminescence is plotted versus the log of compound of interest and data are used to generate EC50 values. Curve fitting is performed using a sigmoidal dose response curve fit function (GraphPad Prism software).

Replicates:

EC50 values were derived from seven-point dose response curves performed on n=3 technical replicates per dose. Robustness of curve fit was assessed as a quality control measure, with an R squared value of at least 0.80 being required for a successful curve fit. Compounds of interest showing an increase in ATP bioluminescence relative to vehicle control were verified in an independent biological replicate of n=3 technical replicates per dose.

Discussion:

This assay is a direct measure of the ability of compounds of interest to restore ATP production under conditions of inhibition of Complex I of the mitochondrial electron transport chain. As the majority of ATP produced via the electron transport chain is thought to derive from Complex I activity, significant impairment in Complex I function has dire biological consequences. Of note, Complex I mutations are thought to drive pathophysiology in multiple mitochondrial diseases, including Leigh syndrome and Leber's Hereditary Optic Neuropathy (LHON), while diminished Complex I activity and the resultant attenuation of ATP production has been shown in neurodegenerative diseases, including Friedreich's Ataxia, Parkinson's Disease and Huntington's Disease. Data are presented in Table 1 below. In brief, most compounds were tested in the Rotenone Oxygraph Assay instead of this assay but only Idebenone was active amongst Omaveloxolone, Idebenone and Vatiquinone. Compounds B and C were also tested and exhibited complex I by-pass activity that was comparable to that of Idebenone.

Example 14: RSL-3 Toxicity Assay (RSL-3 Assay)

This assay has been adapted from: Hinman, A., Holst, C. R., Latham, J. C., Bruegger, J. J., Ulas, G., McCusker, K. P., Amagata, A., Davis, D., Hoff, K. G., Kahn-Kirby, A. H., Kim, V., Kosaka, Y., Lee, E., Malone, S. A., Mei, J. J., Richards, S. J., Rivera, V., Miller, G., Trimmer, J. K., Shrader, W. D., "Vitamin E hydroquinone is an endogenous regulator of ferroptosis via redox control of 15-lipoxygenase", (2018) PLoS ONE 13(8): e0201369. This assay is designed to determine if the novel compounds disclosed herein exhibit protective effects when fibroblasts from a subject with Friedreich's ataxia are subjected to the toxic effects of RSL-3, a known inducer of the iron and lipid peroxidation catalyzed process of regulated cell death known as ferroptosis.

In brief, GM03665 cells (Coriell Institute) were seeded in 96-well plates (Sarstedt) in DMEM cell culture media containing 10% Fetal Bovine serum and 1% Penicillin-Streptomycin (Pen-Strep) antibiotic mix at the amount of $2 \times 10^4$/mL (100 μL or $2 \times 10^3$ cells per well). Cells were left to rest overnight at 37° C. in a humidified atmosphere with 5% $CO_2$ to allow attachment of the cells to the culture plate. Test compounds were prepared as DMSO stocks (10 mM) and were serially diluted in cell culture media to obtain 2× working solutions. Cell media was discarded and replaced by 50 µL of test compound solutions or cell media with vehicle for control wells. Within 15 minutes, 2× working solution (4 µM) of 1S,3R-RSL-3 (CAS #1219810-16-8, Sigma-Aldrich) (diluted from 5 mM DMSO stock in cell culture media) was added. Final reaction volume was 100 µL and final DMSO concentration in reaction was kept below 0.2% (v/v) and equal in all wells. Final RSL-3 concentration was 2 µM and test compound final concentrations in reaction were up to 1000 nM. After 24 hours of incubation cell viability was assessed by MTT test. MTT (Sigma-Aldrich) solution 1 mg/mL in IX PBS (pH=7.4) was prepared 1 hour before the assay and filtered through Filtropur S 0.2 filters (Sarstedt). Cell media with test compounds was discarded and 100 µL of MTT solution was added to cells. The plates were incubated for 2 hours at +37° C. Thereafter, the MTT solution was removed and 100 µL of isopropanol was added to dissolve sediment. Absorption at 570 and 650 nm was measured using Hidex Sense microplate reader. Obtained data were analyzed using GraphPad Prism software to calculate $EC_{50}$ values that are reported in Table 1, below.

Compounds A and B and idebenone were not examined in this assay. The data presented in Table 1 indicates omaveloxolone was not active in this assay but that vatiquinone was active. Of Compounds C-K that were tested, only Compound J was essentially inactive, though none of the test compounds were quite as active as vatiquinone. In summary, vatiquinone and Compounds C-I and K were found to be protective of the Friedreich's ataxia fibroblasts when exposed to the toxic effects of RSL-3.

Discussion—Both BSO and RSL-3 are frequently utilized to induce the regulated cell death pathway known as ferroptosis. Ferroptosis is thought to require the joint activity of iron catalyzed oxidative stress and lipid peroxidation and has been described in cell and animal models of multiple neurodegenerative diseases, including Friedreich's Ataxia, Huntington Disease, Parkinson Disease and Alzheimer's Disease. Compounds active in both assays should in theory possess strong anti-ferroptotic activity. Surprisingly, the reference compound omaveloxolone displayed anti-ferroptotic activity in the BSO assay, but not the RSL-3 assay. These data suggest that the downstream mechanisms of ferroptosis may be differentially regulated based upon the experimental insult and some compounds—such as omaveloxolone—may not be effective in all contexts. Of note, the results for Compounds C-I and K were favorable with respect to inhibition of ferroptotic cell death when either BSO or RSL3 were used as initiating stimulus, differentiating these compounds from omaveloxolone and idebenone.

Example 15: Rotenone Oxygraph Assay (High-Resolution Respirometry of Intact HepG2 Cells)

The Oxygraph-2k (O2k, OROBOROS INSTRUMENTS, Austria) was used for measurements of respiration of intact cells. The respirometry was performed in Dulbecco's Modified Eagle Medium (DMEM) high glucose without supplements. All experiments were performed at 37° C.

HepG2 cells (ATCC collection code HB-8065™) were cultured in 10 $cm^2$ culture dishes in DMEM high glucose medium supplemented with 10% fetal bovine serum (FBS) and 100 units/mL penicillin and 100 µg/mL streptomycin until approximately 90% confluence was reached. Immediately prior to performing the respirometric assay, the cells were washed with media without FBS, trypsinized and resuspended in DMEM high glucose without FBS.

The final concentration of intact cells in the O2k-chamber was $0.5-10^6$/mL. After stabilization of respiration, the Complex I inhibitor, rotenone, at 1 µM final concentration was added to inhibit electron flux via Complex I. Then, compound to be tested was added at 10 µM final concentration, and the change in respiration rate of intact cells was monitored. The increase in respiration rate indicates that Complex I by-pass is occurring.

The data presented in Table 1 indicates that all of Compounds C-K were active in this assay, though Compound J was least active. Compounds B-C were active in the Rotenone ATP Assay. Vatiquinone and Omaveloxolone were inactive in this assay and the Rotenone ATP assay—thereby indicating that Vatiquinone and Omaveloxolone do not possess Complex I bypass capacity. Idebenone was active (and had the highest score) in this assay but was only very weakly active in the BSO assay—specifically, an EC50 could not be calculated as 50% rescue was achieved even at the highest doses assessed (3 µM). In summary, all of the novel test compounds examined in this assay, except Compound A—which was not tested in either Complex I by-pass assay, were found to exhibit reasonably strong to marginal Complex I by-pass activity.

Discussion of Significance to High Scores in Both the BSO Assay (or RSL-3 Assay) and Either Complex I by-Pass Assay (i.e. the Rotenone ATP Assay or the Rotenone Oxygraph Assay):

Compounds with activity in both the BSO (or RSL-3) ferroptosis assay and a complex I by-pass assay (i.e. Rotenone ATP Assay or Rotenone Oxygraph Assay) are thought to possess polypharmacology which is uniquely efficacious. Benchmark compounds (i.e. Idebenone, Vatiquinone or Omaveloxolone) assessed in our screening assays appear to possess either the ability to circumvent BSO induced cell death (vatiquinone, omaveloxolone) or the ability to restore ATP production when complex I is inhibited (idebenone). However, these benchmark compounds do not possess both activities. Significantly, we have discovered and characterized multiple compounds which possess both activities (e.g. Compounds B-I and K (and, in view of the trends in the data in Table 1, expect that closely related analogs thereof such as Compounds M, N, O, P and Q will possess similar polypharmacology)), and we believe these compounds will provide superior efficacy over therapeutic approaches which target one pathway alone in indications in which ferroptosis/lipid peroxidation driven cell death co-exists with bioenergetic impairment due to dysfunctional complex I activity (e.g. Friedreich's ataxia).

TABLE 1

| Structure | Compound ID | Log D[1] | BSO Assay EC50 (nM) | ATP Rotenone Assay EC50 (nM) | RSL-3 Assay EC50 (nM) | Rotenone Oxygraph Assay % Increase |
|---|---|---|---|---|---|---|
| 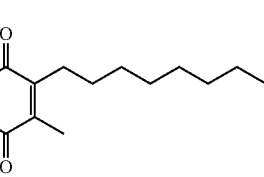 | Omaveloxolone | 3.98 | 148.6+/−10.5[2] | Inactive | Inactive | Inactive |
| 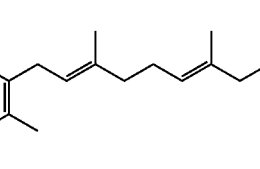 | Idebenone | 3.57 | >1000 nM | 1561+/−910 | Not Done | 70.2+/−15 |
| 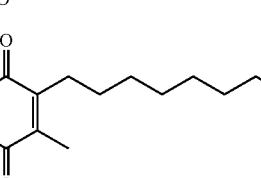 | Vatiquinone | 7.81 | 44.3+/−17.5 | Inactive | 56.0+/−25.5 | Inactive |
| 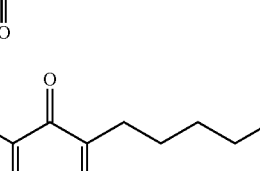 | Compound A | 6.69 | 67.1 (n = 1) | Not Done | Not Done | Not Done |
| 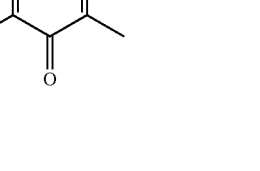 | Compound B | 5.09 | 199.3 (n = 1) | 1025+/−24.04 | Not Done | Not Done |
| 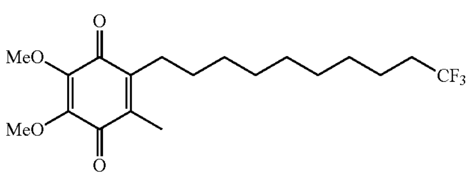 [SMILES: COC1=C(OC)C(=O)C(CCCCCCCCCC(F)(F)F)=C(C)C1=O] | Compound C | 5.19 | 128.5+/−18.8 | 1435+/−172.43 | 109.7+/−80.55 | 63.91+/−11.69 |
| 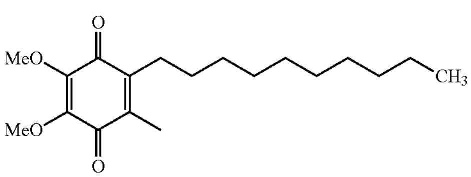 [SMILES: CCCCCCCCCCC1=C(C)C(=O)C(OC)=C(OC)C1=O] | Compound D | 5.00 | 159+/−44 | Not Done | 70+/−26 | 30.0+/−9.0 |
| 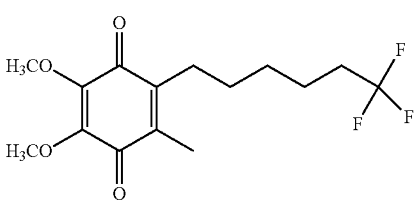 [SMILES: COC1=C(OC)C(=O)C(CCCCCC(F)F)=C(C)C1=O] | Compound E | 3.42 | 359+/−40 | Not Done | 135+/−5 | 49.0+/−7.1 |

TABLE 1-continued

| Structure | Compound ID | Log D[1] | BSO Assay EC50 (nM) | ATP Rotenone Assay EC50 (nM) | RSL-3 Assay EC50 (nM) | Rotenone Oxygraph Assay % Increase |
|---|---|---|---|---|---|---|
| 2,3-dimethoxy-5-methyl-6-(6,6-difluorohexyl)-1,4-benzoquinone | Compound F | 2.72 | 689+/−101 | Not Done | 146+/−17 | 44.7+/−8.0 |
| 2,3-dimethoxy-5-methyl-6-(6-fluorohexyl)-1,4-benzoquinone | Compound G | 2.68 | 555+/−83 | Not Done | 205+/−69 | 42.7+/−8.5 |
| 2,3-dimethoxy-5-methyl-6-hexyl-1,4-benzoquinone | Compound H | 3.67 | 241+/−30 | Not Done | 56+/−26 | 41.8+/−13.3 |
| 2,3-dimethoxy-5-methyl-6-(4,4,4-trifluorobutyl)-1,4-benzoquinone | Compound I | 2.53 | 772+/−71 | Not Done | 479+/−144 | 37.8+/−9.2 |
| 2,3-dimethoxy-5-methyl-6-(4-fluorobutyl)-1,4-benzoquinone | Compound J | 1.79 | >1000 nM | Not Done | >1000 nM | 21.8+/−8.6 |
| 2,3-dimethoxy-5-methyl-6-(3-(trimethylsilyl)propyl)-1,4-benzoquinone | Compound K | 2.21 | 343+/−63 | Not Done | 75+/−21 | 41.4+/−16.1 |

1. Calculated by CDD Vault software
2. Omaveloxolone is toxic to cells at doses higher than 330 nM Example 16: Determining Log D at pH 7.4 ("Log D")

The octanol/buffer distribution coefficient at pH 7.4 ("Log D") may be measured as follows. A pH 7.4 phosphate buffer will be prepared by combining 50 mL of 0.2 M solution of $KH_2PO_4$ with 150 mL of distilled $H_2O$, and then adjusting to pH 7.4 with 1ON NaOH. In triplicate incubations for each compound of interest, 15 μL of a 10 mM DMSO solution of the compound will be added to test tubes which contain 0.75 mL of n-octanol and 0.75 mL of pH 7.4 phosphate buffer. These samples will be gently mixed on a benchtop rotator for 1 hour at room temperature (23° C.). The tubes will then be removed from the rotator and the aqueous and organic phases will be allowed to separate for 1 hour. The concentration of compound (both ionized and non-ionized) will be determined for the aqueous phase and for the organic phase for each incubation and the log D value calculated therefrom, where the final log D for the particular compound will be the average log D of the three log D values.

EQUIVALENTS

The present application is not to be limited in terms of the particular embodiments described in this application, which are intended as single illustrations of individual aspects of the present technology. Many modifications and variations of the present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present application is to be limited only by the terms of the appended claims, along with the full scope of equivalents to which such claims are entitled. It is to be understood that the present application is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible sub-ranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A compound of formula X, or a pharmaceutically acceptable salt, hydrate, and/or solvate thereof:

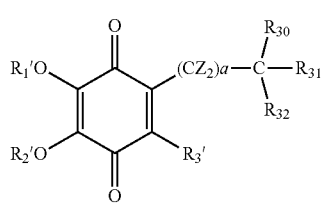

X wherein,
each of $R_1'$ and $R_2'$ is independently $C_1$-$C_3$ alkyl;
$R_3'$ is H, D, F, —$CH_3$, —$CF_3$, —$OCH_3$ or —$OCF_3$;
each Z is independently H, D or F;
a is 4, 5, 6, 7, 8 or 9; and
each of $R_{30}$, $R_{31}$ and $R_{32}$ is independently H, D or F, provided, however, that at least two of $R_{30}$, $R_{31}$ or $R_{32}$ is F.

2. The compound of claim 1, having the formula of Compound C, Compound E, Compound F, or a pharmaceutically acceptable salt, hydrate, and/or solvate thereof:

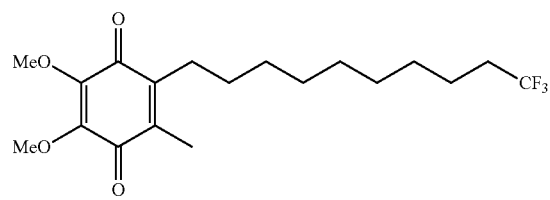

Compound C

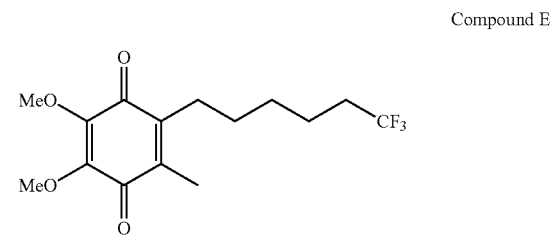

Compound E

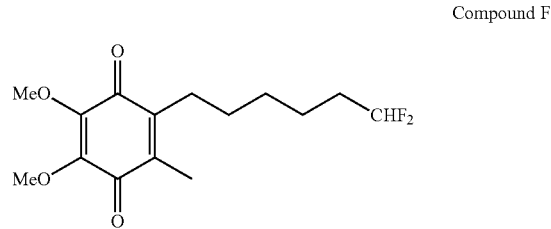

Compound F

3. The compound of claim 1, having the formula of Compound C or a pharmaceutically acceptable salt, hydrate, and/or solvate thereof:

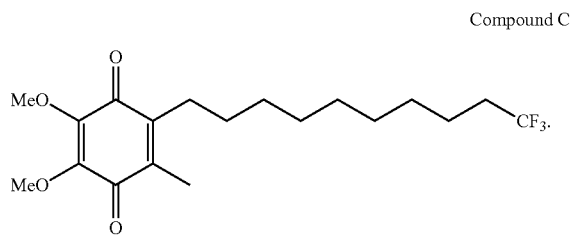 [SMILES: COC1=C(OC)C(=O)C(CCCCCCCCCC(F)(F)F)=C(C)C1=O]

Compound C

4. The compound of claim 1, having the formula of Compound E or a pharmaceutically acceptable salt, hydrate, and/or solvate thereof:

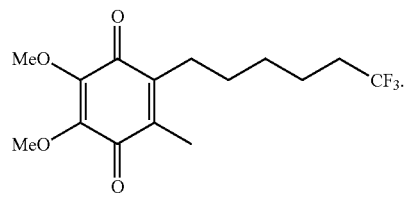
Compound E
5. The compound of claim 1, having the formula of Compound F or a pharmaceutically acceptable salt, hydrate, and/or solvate thereof:
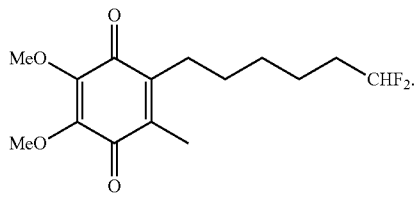
Compound F
6. The compound of claim 1 or a pharmaceutically acceptable salt, hydrate, and/or solvate thereof, wherein each of $R_{30}$, $R_{31}$ and $R_{32}$ is independently F.
* * * * *